(12) United States Patent
Verbruggen

(10) Patent No.: US 7,253,338 B2
(45) Date of Patent: Aug. 7, 2007

(54) GENES INVOLVED IN TOLERANCE TO ENVIRONMENTAL STRESS

(75) Inventor: Nathalie Verbruggen, Ixelles (BE)

(73) Assignee: Cropdesign N.V. (BE)

( * ) Notice: Subject to any disclaimer, the term of this patent is extended or adjusted under 35 U.S.C. 154(b) by 417 days.

(21) Appl. No.: 10/342,224

(22) Filed: Jan. 13, 2003

(65) Prior Publication Data

US 2003/0162294 A1    Aug. 28, 2003

Related U.S. Application Data

(63) Continuation of application No. 09/762,154, filed as application No. PCT/EP99/05652 on Aug. 4, 1999, now abandoned.

(51) Int. Cl.
    *C12N 15/82*    (2006.01)
(52) U.S. Cl. ...................................... 800/289; 800/287
(58) Field of Classification Search ................ 800/289; 435/468
    See application file for complete search history.

(56) References Cited

OTHER PUBLICATIONS

Van Camp W. et al. Enhancement of oxidative stress tolerance in transgenic tobacco plants overproducing Fe-superoxide dismutase in chloroplasts. Plant Physiol. Dec. 1996;112(4):1703-14.*
Broun P et al. Catalytic plasticity of fatty acid modification enzymes underlying chemical diversity of plant lipids. Science. Nov. 13, 1998;282(5392):1315-7.*
Schena M. et al. The HAT4 gene of *Arabidopsis* encodes a developmental regulator. Genes Dev. 1993 7: 367-379.*

* cited by examiner

*Primary Examiner*—Cynthia Collins
(74) *Attorney, Agent, or Firm*—Lahive & Cockfield, LLP; Maria Laccotripe Zacharakis; Jill A. Mello

(57) ABSTRACT

The present invention relates to a method for obtaining polynucleic acids comprising coding sequences and/or genes involved in environmental stress resistance in plants, comprising the preparation of a cDNA library comprising coding sequences from siliques, introducing said coding sequences in yeast cells in a functional format and screening for polynucleic acids leading to an enhanced tolerance or resistance to environmental stress conditions in said transformed yeast cells. The present invention further relates to an isolated polynucleic acid obtainable by such a method as listed in Table 1 as well as recombinant polynucleic acid comprising the same. The present invention further relates to an isolated polypeptide encoded by a polynucleic acid of the invention. The present invention also relates to a method for producing a plant with enhanced tolerance or resistance to environmental stress, said method comprising introducing into a plant cell a recombinant DNA comprising a polynucleic acid as defined which when expressed in a plant cell enhances the tolerances or induces resistance to environmental stress conditions of said plant. The present invention particularly relates to plant cells, plants or harvestable parts or propagation material thereof transformed with a recombinant polynucleic acid as defined above.

10 Claims, 15 Drawing Sheets

```
At-DBF2  ..........MAGNMSCLSTDGHGTPGGSHFPNQNLTKRRTRPAGINDSPSPVKCFFFPYEDTSNTSLKEVSQPTKYSSNSPPVSPAIFYERATSWCT  89
         :||||  || || :|||||| |:||| |||| |||||||||||||||||||||||||||| |: |||  ||| || ||:|||||||||||| |
DBF2     MLSKSEKNVDLLAGNMSNLSFDGHGTPGGTGLFPNQNITKRRTRPAGINDSPSPVKPSFFPYEDTSNMDIDEVSQPDMDVSNSPKKLPPKFYERATSNKT  100
                                                                                   *  *
                                                                                       I
At-DBF2  QRVVSGRAMYFLEYYCDMFDYVISRRQRTKQVLEYLQQQSQLPNSDQIKLNEEWSSYLQREHQVLSKRRLKPKNRDFEMITQVGQGGYGHVYLARKKDTK  189
         |||| |  ||||| |||||||||||||||||||||:||||||||||||||||||||||||:||||||||||||||||||||||||||| ||||||||||
DBF2     QRVVSVCKMYFLEHYCDMFDYVISRRQRTKQVLEYLQQQSQLPNSDQIKLNEEWSSYLQREHQVLRKRRLKPKNRDFEMITQVGQGGYGQVYLARKKDTK  200
                   II                         III                           V
                    *                          *
At-DBF2  EVCALKILNKKLGFKLNGTCHVLTERQSLTTTRSETMVKLLSGTTPVGSRGMAIESELGGDFRTESIGRRCLKSGHARFYISEMFCAVNEKHLLSKT...  287
         ||||||||||| ||||| |:|||| |||||||||||:||||||||||||||| ||| |||||:|||||||||||||||||||||||:|| |:||:||
DBF2     EVCALKILNKKLLFKLNETKHVLTERDILTTTRSEWLVKLLYAFQDLQSLYLAMEFVPGGDFRTLLINTRCLKSGHARFYISEMFCAVNALHDLGYTHRD  300
                                   IV                                                              IX
                                                                                                       *
At-DBF2  ..........DSTISNEEDSSINIRLEKFKDLGYPALSEKSIEDRRKLY.........TCPNSMVGSPDYIALEVLRGKRYEYTVDYWS  356
                   ||:| |  |||||| :|:||| ||||||||||:| |||||||| |||||||||:||||::|:|||||||||||||
DBF2     LKPENFLIDAKGHIKLTDFGLAAGTISNERIESMKIRLEKIKDLEFPAFTEKSIEDRRKMYNQLREKEINYANSMVGSPDYMALEVLEGKKYDFTVDYWS  400
                            VI                       VII                          VIII
                            *                         *                            * **
At-DBF2  LGCMLFESLVGYTPFSGSSTNETYAISRSHKQTLNRARHEDGRAAFYNRTWDLITRHRADLSTRTRSFEHEVKMSYFADILFKALRSIIPPFTPQLDSET  456
         ||||||||||||||||||||||||  |||:|||:|:|:|||||||| |:| |||||||||| ::||| ||||:|||||||| |:|||:||||||||||
DBF2     LGCMLFESLVGYTPFSGSSTNETYDNLRRWKQTLRRPRQSDGRAAFSDRTWDLITRLIADPINRLRSFEHVKRMSYFADINFSTLRSMIPPFTPQLDSET  500
                                            X                     XI
                                                                   *
At-DBF2  DAGYFDDFWNEADIAKYADVFNSQCCRTALVDDSAVSSKLVGFTFRHRNGKQGSSGMLFNGLEHSDPFSTFY  528
         |||||||| : |||||||||||||:||   ||:||||||||||||||||||||||:|||||||||||||||
DBF2     DAGYFDDFTSEADMAKYADVFKRQDKLTAMVDDSAVSSKLVGFTFRHRNGKQGSSGILFNGLEHSDPFSTFY  572
```

FIGURE 1 A

SEQUENCE LISTING

<160> NUMBER OF SEQ ID NOS: 123

<210> SEQ ID NO 1
<211> LENGTH: 1909
<212> TYPE: DNA
<213> ORGANISM: Arabidopsis thaliana
<220> FEATURE:
<221> NAME/KEY: CDS
<222> LOCATION: (40)...(1623)

<400> SEQUENCE: 1

```
cggtagcctg actgctggat tggcctgctg ctgacaatt atg gcg ggt aac atg      54
                                              Met Ala Gly Asn Met
                                                1               5 tcg tgt tta agc acg gac gga cac ggg acc cct ggc ggt tca ggg cat    102
Ser Cys Leu Ser Thr Asp Gly His Gly Thr Pro Gly Gly Ser Gly His
             10                  15                  20 ttc ccc aat cag aac cta acg aaa aga aga acg cgt cca gcg ggt atc    150
Phe Pro Asn Gln Asn Leu Thr Lys Arg Arg Thr Arg Pro Ala Gly Ile
         25                  30                  35 aac gac tcg cct tcg ccg gtg aaa tgc ttt ttt ttc ccc tat gaa gac    198
Asn Asp Ser Pro Ser Pro Val Lys Cys Phe Phe Phe Pro Tyr Glu Asp
     40                  45                  50 acc tcc aac acg tca tta aag gaa gtg tcc cag ccc acg aaa tac agt    246
Thr Ser Asn Thr Ser Leu Lys Glu Val Ser Gln Pro Thr Lys Tyr Ser
 55                  60                  65 tcc aat tcc cct cca gtc agc ccg gca att ttt tat gag agg gcg acg    294
Ser Asn Ser Pro Pro Val Ser Pro Ala Ile Phe Tyr Glu Arg Ala Thr
 70                  75                  80                  85 tcg tgg tgc acg caa agg gtg gtg agt ggg agg gca atg tac ttt cta    342
Ser Trp Cys Thr Gln Arg Val Val Ser Gly Arg Ala Met Tyr Phe Leu
                 90                  95                 100 gaa tat tat tgc gat atg ttc gat tat gta att agc agg aga caa cgc    390
Glu Tyr Tyr Cys Asp Met Phe Asp Tyr Val Ile Ser Arg Arg Gln Arg
            105                 110                 115 acg aaa cag gtc cta gag tat ctg cag cag caa agc caa ctt ccg aat    438
Thr Lys Gln Val Leu Glu Tyr Leu Gln Gln Gln Ser Gln Leu Pro Asn
        120                 125                 130 tct gac cag atc aag ctc aac gaa gag tgg tcc tcc tat tta cag aga    486
Ser Asp Gln Ile Lys Leu Asn Glu Glu Trp Ser Ser Tyr Leu Gln Arg
```

|     |     |     |     |     |     |     |     |     |     |     |     |     |     |     |     |     |
|---|---|---|---|---|---|---|---|---|---|---|---|---|---|---|---|---|
|     |     |     | 135 |     |     |     |     | 140 |     |     |     |     | 145 |     |     |     |
| gag | cat | cag | gtt | ttg | tcg | aaa | aga | agg | ttg | aag | cca | aaa | aac | aga | gac | 534 |
| Glu | His | Gln | Val | Leu | Ser | Lys | Arg | Arg | Leu | Lys | Pro | Lys | Asn | Arg | Asp |     |
| 150 |     |     |     |     | 155 |     |     |     |     | 160 |     |     |     |     | 165 |     |
| ttt | gaa | atg | att | aca | caa | gta | ggt | caa | ggt | ggt | tat | ggg | cat | gtt | tat | 582 |
| Phe | Glu | Met | Ile | Thr | Gln | Val | Gly | Gln | Gly | Gly | Tyr | Gly | His | Val | Tyr |     |
|     |     |     |     | 170 |     |     |     |     | 175 |     |     |     |     | 180 |     |     |
| tta | gcc | aga | aag | aaa | gac | aca | aaa | gag | gtg | tgc | gcc | tta | aaa | att | ttg | 630 |
| Leu | Ala | Arg | Lys | Lys | Asp | Thr | Lys | Glu | Val | Cys | Ala | Leu | Lys | Ile | Leu |     |
|     |     |     |     | 185 |     |     |     |     | 190 |     |     |     |     | 195 |     |     |
| aat | aag | aag | cta | ggt | ttc | aaa | ctt | aat | ggt | aca | tgc | cat | gtt | ttg | acc | 678 |
| Asn | Lys | Lys | Leu | Gly | Phe | Lys | Leu | Asn | Gly | Thr | Cys | His | Val | Leu | Thr |     |
|     |     |     |     | 200 |     |     |     |     | 205 |     |     |     |     | 210 |     |     |
| gag | agg | cag | agt | ctg | act | aca | acg | aga | tcc | gag | acg | atg | gtg | aag | ctc | 726 |
| Glu | Arg | Gln | Ser | Leu | Thr | Thr | Thr | Arg | Ser | Glu | Thr | Met | Val | Lys | Leu |     |
|     |     |     |     | 215 |     |     |     |     | 220 |     |     |     |     | 225 |     |     |
| cta | agt | ggg | acg | acc | ccc | gta | ggc | agt | agg | ggg | atg | gcg | ata | gaa | agt | 774 |
| Leu | Ser | Gly | Thr | Thr | Pro | Val | Gly | Ser | Arg | Gly | Met | Ala | Ile | Glu | Ser |     |
| 230 |     |     |     |     | 235 |     |     |     |     | 240 |     |     |     |     | 245 |     |
| gag | cta | ggc | ggt | gac | ttc | cgt | aca | gaa | agt | ata | gga | cgt | aga | tgc | ttg | 822 |
| Glu | Leu | Gly | Gly | Asp | Phe | Arg | Thr | Glu | Ser | Ile | Gly | Arg | Arg | Cys | Leu |     |
|     |     |     |     | 250 |     |     |     |     | 255 |     |     |     |     | 260 |     |     |
| aaa | agt | ggc | cat | gcg | aga | ttc | tat | att | agc | gaa | atg | ttc | tgt | gcc | gtc | 870 |
| Lys | Ser | Gly | His | Ala | Arg | Phe | Tyr | Ile | Ser | Glu | Met | Phe | Cys | Ala | Val |     |
|     |     |     |     | 265 |     |     |     |     | 270 |     |     |     |     | 275 |     |     |
| aac | gag | aaa | cat | ctt | tta | agt | aaa | acg | gac | agc | aca | atc | tcc | aac | gaa | 918 |
| Asn | Glu | Lys | His | Leu | Leu | Ser | Lys | Thr | Asp | Ser | Thr | Ile | Ser | Asn | Glu |     |
|     |     |     |     | 280 |     |     |     |     | 285 |     |     |     |     | 290 |     |     |
| gaa | gat | agt | agc | atc | aac | ata | agg | tta | gaa | aaa | ttc | aaa | gac | ctt | ggg | 966 |
| Glu | Asp | Ser | Ser | Ile | Asn | Ile | Arg | Leu | Glu | Lys | Phe | Lys | Asp | Leu | Gly |     |
|     |     |     |     | 295 |     |     |     |     | 300 |     |     |     |     | 305 |     |     |
| tac | cca | gcg | ttg | agc | gag | aaa | tct | atc | gag | gac | agg | agg | aag | ttg | tac | 1014 |
| Tyr | Pro | Ala | Leu | Ser | Glu | Lys | Ser | Ile | Glu | Asp | Arg | Arg | Lys | Leu | Tyr |     |
| 310 |     |     |     |     | 315 |     |     |     |     | 320 |     |     |     |     | 325 |     |
| acc | tgt | ccg | aac | tcc | atg | gtt | ggg | tct | ccg | gac | tac | ata | gcc | tta | gaa | 1062 |
| Thr | Cys | Pro | Asn | Ser | Met | Val | Gly | Ser | Pro | Asp | Tyr | Ile | Ala | Leu | Glu |     |
|     |     |     |     | 330 |     |     |     |     | 335 |     |     |     |     | 340 |     |     |
| gtc | ttg | aga | gga | aag | agg | tac | gag | tat | acc | gta | gac | tat | tgg | tcg | ttg | 1110 |
| Val | Leu | Arg | Gly | Lys | Arg | Tyr | Glu | Tyr | Thr | Val | Asp | Tyr | Trp | Ser | Leu |     |
|     |     |     |     | 345 |     |     |     |     | 350 |     |     |     |     | 355 |     |     |
| ggt | tgt | atg | ctg | ttt | gag | agc | ttg | gtc | ggc | tac | acc | ccc | ttc | agt | ggc | 1158 |
| Gly | Cys | Met | Leu | Phe | Glu | Ser | Leu | Val | Gly | Tyr | Thr | Pro | Phe | Ser | Gly |     |
|     |     |     |     | 360 |     |     |     |     | 365 |     |     |     |     | 370 |     |     |
| tcg | tcg | acc | aac | gaa | acg | tat | gcg | atc | agt | cgt | agc | tgg | aaa | cag | acg | 1206 |
| Ser | Ser | Thr | Asn | Glu | Thr | Tyr | Ala | Ile | Ser | Arg | Ser | Trp | Lys | Gln | Thr |     |
|     |     |     |     | 375 |     |     |     |     | 380 |     |     |     |     | 385 |     |     |
| ttg | aat | aga | gcg | aga | cac | gag | gat | ggg | agg | gcg | gcg | ttt | tac | aat | agg | 1254 |
| Leu | Asn | Arg | Ala | Arg | His | Glu | Asp | Gly | Arg | Ala | Ala | Phe | Tyr | Asn | Arg |     |
| 390 |     |     |     |     | 395 |     |     |     |     | 400 |     |     |     |     | 405 |     |
| acg | tgg | gac | ttg | att | acc | aga | cac | agg | gcc | gac | cta | agc | acg | cgg | acg | 1302 |
| Thr | Trp | Asp | Leu | Ile | Thr | Arg | His | Arg | Ala | Asp | Leu | Ser | Thr | Arg | Thr |     |
|     |     |     |     | 410 |     |     |     |     | 415 |     |     |     |     | 420 |     |     |
| aga | tcc | ttt | gag | cac | gag | gta | aag | atg | agc | tac | ttc | gcg | gac | atc | ttg | 1350 |
| Arg | Ser | Phe | Glu | His | Glu | Val | Lys | Met | Ser | Tyr | Phe | Ala | Asp | Ile | Leu |     |
|     |     |     |     | 425 |     |     |     |     | 430 |     |     |     |     | 435 |     |     |
| ttt | aag | gcc | tta | aga | tcg | ata | att | cca | cct | ttc | aca | ccc | caa | cta | gac | 1398 |
| Phe | Lys | Ala | Leu | Arg | Ser | Ile | Ile | Pro | Pro | Phe | Thr | Pro | Gln | Leu | Asp |     |
|     |     |     |     | 440 |     |     |     |     | 445 |     |     |     |     | 450 |     |     |
| agc | gag | acc | gat | gcc | ggt | tat | ttc | gat | gac | ttt | tgg | aat | gag | gct | gac | 1446 |

-continued

```
Ser Glu Thr Asp Ala Gly Tyr Phe Asp Asp Phe Trp Asn Glu Ala Asp
    455                 460                 465 ata gcc aaa tac gct gac gtc ttt aat agt cag tgc tgc cgt acg gct      1494
Ile Ala Lys Tyr Ala Asp Val Phe Asn Ser Gln Cys Cys Arg Thr Ala
470                 475                 480                 485 tta gtc gac gat tct gct gtt tct tct aaa ctt gtt ggg ttc acc ttc      1542
Leu Val Asp Asp Ser Ala Val Ser Ser Lys Leu Val Gly Phe Thr Phe
            490                 495                 500 cga cac aga aat ggt aaa cag ggt tcc agt ggt atg tta ttc aac ggg      1590
Arg His Arg Asn Gly Lys Gln Gly Ser Ser Gly Met Leu Phe Asn Gly
        505                 510                 515 cta gaa cac tca gac ccc ttc tca acc ttt tac tagtaatcgg cagcctgcag   1643
Leu Glu His Ser Asp Pro Phe Ser Thr Phe Tyr
        520                 525 cctgcccagc tgccagcctg ccctcgcctg acgcctgccc aggatgcct  ctcctttgga    1703 taacatgccc tgctccccca tgccttgctg cctcgcagcc tgaacgcctg ccagagctcg    1763
ccagcctgcc cagcctttcg ccccagcctg ccagcctttt tttaaacgct gaaaaacgcc    1823 taaaaaatc gaactttaaa cgcttttaaa acggctgccc ataaaaaaaa aggttttta      1883 ataaaaaatc gtaaaaaaaa aaacgt                                          1909
```

<210> SEQ ID NO 2
<211> LENGTH: 528
<212> TYPE: PRT
<213> ORGANISM: Arabidopsis thaliana

<400> SEQUENCE: 2

```
Met Ala Gly Asn Met Ser Cys Leu Ser Thr Asp Gly His Gly Thr Pro
1               5                   10                  15

Gly Gly Ser Gly His Phe Pro Asn Gln Asn Leu Thr Lys Arg Arg Thr
            20                  25                  30

Arg Pro Ala Gly Ile Asn Asp Ser Pro Ser Val Lys Cys Phe Phe
        35                  40                  45

Phe Pro Tyr Glu Asp Thr Ser Asn Thr Ser Leu Lys Glu Val Ser Gln
    50                  55                  60

Pro Thr Lys Tyr Ser Ser Asn Ser Pro Val Ser Pro Ala Ile Phe
65                  70                  75                  80

Tyr Glu Arg Ala Thr Ser Trp Cys Thr Gln Arg Val Val Ser Gly Arg
                85                  90                  95

Ala Met Tyr Phe Leu Glu Tyr Tyr Cys Asp Met Phe Asp Tyr Val Ile
            100                 105                 110

Ser Arg Arg Gln Arg Thr Lys Gln Val Leu Glu Tyr Leu Gln Gln Gln
        115                 120                 125

Ser Gln Leu Pro Asn Ser Asp Gln Ile Lys Leu Asn Glu Glu Trp Ser
    130                 135                 140

Ser Tyr Leu Gln Arg Glu His Gln Val Leu Ser Lys Arg Leu Lys
145                 150                 155                 160

Pro Lys Asn Arg Asp Phe Glu Met Ile Thr Gln Val Gly Gln Gly Gly
                165                 170                 175

Tyr Gly His Val Tyr Leu Ala Arg Lys Lys Asp Thr Lys Glu Val Cys
            180                 185                 190

Ala Leu Lys Ile Leu Asn Lys Lys Leu Gly Phe Lys Leu Asn Gly Thr
        195                 200                 205

Cys His Val Leu Thr Glu Arg Gln Ser Leu Thr Thr Thr Arg Ser Glu
    210                 215                 220
```

```
      Thr Met Val Lys Leu Leu Ser Gly Thr Thr Pro Val Gly Ser Arg Gly
      225                 230                 235                 240

Met Ala Ile Glu Ser Glu Leu Gly Gly Asp Phe Arg Thr Glu Ser Ile
                      245                 250                 255

Gly Arg Arg Cys Leu Lys Ser Gly His Ala Arg Phe Tyr Ile Ser Glu
                  260                 265                 270

Met Phe Cys Ala Val Asn Glu Lys His Leu Leu Ser Lys Thr Asp Ser
              275                 280                 285

Thr Ile Ser Asn Glu Glu Asp Ser Ser Ile Asn Ile Arg Leu Glu Lys
          290                 295                 300

Phe Lys Asp Leu Gly Tyr Pro Ala Leu Ser Glu Lys Ser Ile Glu Asp
      305                 310                 315                 320

Arg Arg Lys Leu Tyr Thr Cys Pro Asn Ser Met Val Gly Ser Pro Asp
                      325                 330                 335

Tyr Ile Ala Leu Glu Val Leu Arg Gly Lys Arg Tyr Glu Tyr Thr Val
                  340                 345                 350

Asp Tyr Trp Ser Leu Gly Cys Met Leu Phe Glu Ser Leu Val Gly Tyr
              355                 360                 365

Thr Pro Phe Ser Gly Ser Thr Asn Glu Thr Tyr Ala Ile Ser Arg
          370                 375                 380

Ser Trp Lys Gln Thr Leu Asn Arg Ala Arg His Glu Asp Gly Arg Ala
      385                 390                 395                 400

Ala Phe Tyr Asn Arg Thr Trp Asp Leu Ile Thr Arg His Arg Ala Asp
                      405                 410                 415

Leu Ser Thr Arg Thr Arg Ser Phe Glu His Glu Val Lys Met Ser Tyr
                  420                 425                 430

Phe Ala Asp Ile Leu Phe Lys Ala Leu Arg Ser Ile Ile Pro Pro Phe
              435                 440                 445

Thr Pro Gln Leu Asp Ser Glu Thr Asp Ala Gly Tyr Phe Asp Asp Phe
          450                 455                 460

Trp Asn Glu Ala Asp Ile Ala Lys Tyr Ala Asp Val Phe Asn Ser Gln
      465                 470                 475                 480

Cys Cys Arg Thr Ala Leu Val Asp Asp Ser Ala Val Ser Ser Lys Leu
                      485                 490                 495

Val Gly Phe Thr Phe Arg His Arg Asn Gly Lys Gln Gly Ser Ser Gly
                  500                 505                 510

Met Leu Phe Asn Gly Leu Glu His Ser Asp Pro Phe Ser Thr Phe Tyr
              515                 520                 525

<210> SEQ ID NO 3
<211> LENGTH: 695
<212> TYPE: DNA
<213> ORGANISM: Arabidopsis thaliana
<220> FEATURE:
<221> NAME/KEY: CDS
<222> LOCATION: (94)...(564)

<400> SEQUENCE: 3
tattaagctt ggtaccgagc tcggatccac tagtaacggc cgccagtgtg ctggaattcg      60
gcacgagcaa gaaagttaac acaacagcta aga atg gat ttg gag ttt gga agg     114
                                    Met Asp Leu Glu Phe Gly Arg
                                      1               5 ttt cca ata ttt tca atc ctc gaa gac atg ctt gaa gcc cct gaa gaa      162
Phe Pro Ile Phe Ser Ile Leu Glu Asp Met Leu Glu Ala Pro Glu Glu
            10                  15                  20 caa acc gag aag act cgt aac aac cct tca aga gct tac atg cga gac      210
```

```
Gln Thr Glu Lys Thr Arg Asn Asn Pro Ser Arg Ala Tyr Met Arg Asp
        25                  30                  35 gca aag gca atg gct gct aca cca gct gac gtt atc gag cac ccg gat      258
Ala Lys Ala Met Ala Ala Thr Pro Ala Asp Val Ile Glu His Pro Asp
 40                  45                  50                  55 gcg tac gtt ttc gcc gtg gac atg cct gga atc aaa gga gat gag att      306
Ala Tyr Val Phe Ala Val Asp Met Pro Gly Ile Lys Gly Asp Glu Ile
                 60                  65                  70 cag gtc cag ata gag aac gag aac gtg ctt gtg gtg agt ggc aaa aga      354
Gln Val Gln Ile Glu Asn Glu Asn Val Leu Val Val Ser Gly Lys Arg
                     75                  80                  85 cag agg gac aac aag gag aat gaa ggt gtg aag ttt gtg agg atg gag      402
Gln Arg Asp Asn Lys Glu Asn Glu Gly Val Lys Phe Val Arg Met Glu
         90                  95                 100 agg agg atg ggg aag ttt atg agg aag ttt cag tta cct gat aat gca      450
Arg Arg Met Gly Lys Phe Met Arg Lys Phe Gln Leu Pro Asp Asn Ala
        105                 110                 115 gat ttg gag aag atc tct gcg gct tgt aat gac ggt gtg ttg aaa gtg      498
Asp Leu Glu Lys Ile Ser Ala Ala Cys Asn Asp Gly Val Leu Lys Val
120                 125                 130                 135 act att ccg aaa ctt cct cct cct gag cca aag aaa cca aag act ata      546
Thr Ile Pro Lys Leu Pro Pro Pro Glu Pro Lys Lys Pro Lys Thr Ile
                140                 145                 150 caa gtt caa gtc gct tga gtttgtttgt gatccgtgtt tttgtgtttt             594
Gln Val Gln Val Ala  *
                155 aatgaatgta atcgataagc aactacctct tggtgttcgt tgtaaaatga aataaaaata    654 gttttctctg ttcataaaaa aaaaaaaaaa aaaactcgag c                        695

<210> SEQ ID NO 4
<211> LENGTH: 156
<212> TYPE: PRT
<213> ORGANISM: Arabidopsis thaliana

<400> SEQUENCE: 4

Met Asp Leu Glu Phe Gly Arg Phe Pro Ile Phe Ser Ile Leu Glu Asp
 1               5                  10                  15

Met Leu Glu Ala Pro Glu Glu Gln Thr Glu Lys Thr Arg Asn Asn Pro
                 20                  25                  30

Ser Arg Ala Tyr Met Arg Asp Ala Lys Ala Met Ala Ala Thr Pro Ala
             35                  40                  45

Asp Val Ile Glu His Pro Asp Ala Tyr Val Phe Ala Val Asp Met Pro
         50                  55                  60

Gly Ile Lys Gly Asp Glu Ile Gln Val Gln Ile Glu Asn Glu Asn Val
 65                  70                  75                  80

Leu Val Val Ser Gly Lys Arg Gln Arg Asp Asn Lys Glu Asn Glu Gly
                 85                  90                  95

Val Lys Phe Val Arg Met Glu Arg Arg Met Gly Lys Phe Met Arg Lys
            100                 105                 110

Phe Gln Leu Pro Asp Asn Ala Asp Leu Glu Lys Ile Ser Ala Ala Cys
        115                 120                 125

Asn Asp Gly Val Leu Lys Val Thr Ile Pro Lys Leu Pro Pro Pro Glu
130                 135                 140

Pro Lys Lys Pro Lys Thr Ile Gln Val Gln Val Ala
145                 150                 155

<210> SEQ ID NO 5
```

-continued

```
<211> LENGTH: 1311
<212> TYPE: DNA
<213> ORGANISM: Arabidopsis thaliana
<220> FEATURE:
<221> NAME/KEY: CDS
<222> LOCATION: (133)...(1083)

<400> SEQUENCE: 5
cggcacgagt ccacatgaaa ttcgattctc acatttcttc tatttaattc gaatttcaaa      60
ttgccatttc tcagattccg ggaaagaaa aaaaaaacct agaaaagtgt tttctccgtt      120
ttccaatcat cc atg agt ccg gac aat aaa ctg ctt ccg aag cgg atc atc    171
              Met Ser Pro Asp Asn Lys Leu Leu Pro Lys Arg Ile Ile
                1               5                   10 ctt gta cgg cac ggt gaa tcg gaa ggg aat ctc gac acg gcg gcg tat    219
Leu Val Arg His Gly Glu Ser Glu Gly Asn Leu Asp Thr Ala Ala Tyr
 15                  20                  25 aca acg acg ccg gat cat aag atc cag tta acg gat tcc ggt ttg ctt    267
Thr Thr Thr Pro Asp His Lys Ile Gln Leu Thr Asp Ser Gly Leu Leu
 30                  35                  40                  45 cag gcg cag gaa gcc gga gct cgt ctc cac gct ttg atc tct tct aat    315
Gln Ala Gln Glu Ala Gly Ala Arg Leu His Ala Leu Ile Ser Ser Asn
             50                  55                  60 cct tct tca ccg gag tgg cgt gtg tac ttc tac gtt tcg ccg tac gat    363
Pro Ser Ser Pro Glu Trp Arg Val Tyr Phe Tyr Val Ser Pro Tyr Asp
         65                  70                  75 cgg act cga tct acg ctc cgg gag atc gga cgg tcg ttc tcg cgt cgc    411
Arg Thr Arg Ser Thr Leu Arg Glu Ile Gly Arg Ser Phe Ser Arg Arg
     80                  85                  90 cgt gtg att ggt gtt cgc gaa gaa tgt cgg att agg gaa cag gat ttt    459
Arg Val Ile Gly Val Arg Glu Glu Cys Arg Ile Arg Glu Gln Asp Phe
 95                 100                 105 ggg aat ttt cag gtt aaa gag cga atg aga gca acg aaa aag gtc aga    507
Gly Asn Phe Gln Val Lys Glu Arg Met Arg Ala Thr Lys Lys Val Arg
110                 115                 120                 125 gag aga ttt ggc cgc ttt ttt tac cgg ttc ccg gag gga gaa tcc gcc    555
Glu Arg Phe Gly Arg Phe Phe Tyr Arg Phe Pro Glu Gly Glu Ser Ala
                130                 135                 140 gcc gat gtc ttc gat cgc gtc tcc agt ttt ctc gag tct cta tgg aga    603
Ala Asp Val Phe Asp Arg Val Ser Ser Phe Leu Glu Ser Leu Trp Arg
            145                 150                 155 gac att gac atg aac aga ctg cac atc aac ccg tct cat gag cta aac    651
Asp Ile Asp Met Asn Arg Leu His Ile Asn Pro Ser His Glu Leu Asn
        160                 165                 170 ttt gtg att gtc tca cat ggc tta aca tcg cgt gtg ttt ctg atg aaa    699
Phe Val Ile Val Ser His Gly Leu Thr Ser Arg Val Phe Leu Met Lys
    175                 180                 185 tgg ttt aag tgg tca gtg gaa cag ttc gag gga cta aac aat cca ggg    747
Trp Phe Lys Trp Ser Val Glu Gln Phe Glu Gly Leu Asn Asn Pro Gly
190                 195                 200                 205 aac agt gag atc aga gtg atg gaa tta gga caa ggc ggt gat tac agc    795
Asn Ser Glu Ile Arg Val Met Glu Leu Gly Gln Gly Gly Asp Tyr Ser
                210                 215                 220 ttg gcg att cat cac aca gag gaa gag tta gcc aca tgg gga ctg tca    843
Leu Ala Ile His His Thr Glu Glu Glu Leu Ala Thr Trp Gly Leu Ser
            225                 230                 235 cca gag atg att gca gat caa aag tgg cgg gct aac gcg cat aaa ggc    891
Pro Glu Met Ile Ala Asp Gln Lys Trp Arg Ala Asn Ala His Lys Gly
        240                 245                 250 gaa tgg aaa gaa gat tgt aag tgg tat ttt ggt gat ttc ttc gac cat    939
Glu Trp Lys Glu Asp Cys Lys Trp Tyr Phe Gly Asp Phe Phe Asp His
```

```
                255                 260                 265
atg gca gat tcc gat aaa gag tgc gag act gag gcc act gaa gat aga       987
Met Ala Asp Ser Asp Lys Glu Cys Glu Thr Glu Ala Thr Glu Asp Arg
270             275                 280                 285 gaa gaa gaa gaa gaa gaa gag ggg aaa agg gta aat ctg cta acg agt      1035
Glu Glu Glu Glu Glu Glu Gly Lys Arg Val Asn Leu Leu Thr Ser
                290                 295                 300 tca gaa tat agc aat gag cca gag tta tac aat gga caa tgc tgc tga      1083
Ser Glu Tyr Ser Asn Glu Pro Glu Leu Tyr Asn Gly Gln Cys Cys *
            305                 310                 315 tactatttta cagaacaaaa gcatacatga aagaaacgt ttaactaaag aattcagaag     1143
atttgatttt gataaaaact tgtaccaatt tactgattaa gctttctggt gtcttagttt    1203
gtagcttttg gtttgtggaa aagtgttgta cacatcgtta taacaccagg aaacattaca    1263
ggaaatttga aagattcatt ttattgtgac aaaaaaaaaa aaaaaaa                  1311
```

<210> SEQ ID NO 6
<211> LENGTH: 316
<212> TYPE: PRT
<213> ORGANISM: Arabidopsis thaliana

<400> SEQUENCE: 6

```
Met Ser Pro Asp Asn Lys Leu Leu Pro Lys Arg Ile Ile Leu Val Arg
1               5                   10                  15

His Gly Glu Ser Glu Gly Asn Leu Asp Thr Ala Ala Tyr Thr Thr Thr
            20                  25                  30

Pro Asp His Lys Ile Gln Leu Thr Asp Ser Gly Leu Leu Gln Ala Gln
        35                  40                  45

Glu Ala Gly Ala Arg Leu His Ala Leu Ile Ser Ser Asn Pro Ser Ser
    50                  55                  60

Pro Glu Trp Arg Val Tyr Phe Tyr Val Ser Pro Tyr Asp Arg Thr Arg
65                  70                  75                  80

Ser Thr Leu Arg Glu Ile Gly Arg Ser Phe Ser Arg Arg Val Ile
                85                  90                  95

Gly Val Arg Glu Glu Cys Arg Ile Arg Glu Gln Asp Phe Gly Asn Phe
            100                 105                 110

Gln Val Lys Glu Arg Met Arg Ala Thr Lys Lys Val Arg Glu Arg Phe
        115                 120                 125

Gly Arg Phe Phe Tyr Arg Phe Pro Glu Gly Glu Ser Ala Ala Asp Val
    130                 135                 140

Phe Asp Arg Val Ser Ser Phe Leu Glu Ser Leu Trp Arg Asp Ile Asp
145                 150                 155                 160

Met Asn Arg Leu His Ile Asn Pro Ser His Glu Leu Asn Phe Val Ile
                165                 170                 175

Val Ser His Gly Leu Thr Ser Arg Val Phe Leu Met Lys Trp Phe Lys
            180                 185                 190

Trp Ser Val Glu Gln Phe Glu Gly Leu Asn Asn Pro Gly Asn Ser Glu
        195                 200                 205

Ile Arg Val Met Glu Leu Gly Gln Gly Gly Asp Tyr Ser Leu Ala Ile
    210                 215                 220

His His Thr Glu Glu Leu Ala Thr Trp Gly Leu Ser Pro Glu Met
225                 230                 235                 240

Ile Ala Asp Gln Lys Trp Arg Ala Asn Ala His Lys Gly Glu Trp Lys
                245                 250                 255

Glu Asp Cys Lys Trp Tyr Phe Gly Asp Phe Phe Asp His Met Ala Asp
```

|  |  |  | 260 |  |  |  | 265 |  |  |  | 270 |  |
|---|---|---|---|---|---|---|---|---|---|---|---|---|

Ser Asp Lys Glu Cys Glu Thr Glu Ala Thr Glu Asp Arg Glu Glu Glu
           275                    280                  285

Glu Glu Glu Gly Lys Arg Val Asn Leu Leu Thr Ser Ser Glu Tyr
    290                    295                    300

Ser Asn Glu Pro Glu Leu Tyr Asn Gly Gln Cys Cys
305                    310                    315

<210> SEQ ID NO 7
<211> LENGTH: 863
<212> TYPE: DNA
<213> ORGANISM: Arabidopsis thaliana
<220> FEATURE:
<221> NAME/KEY: CDS
<222> LOCATION: (19)...(837)

<400> SEQUENCE: 7

```
agagacagta aacctaaa atg gcg aac tca gac aaa aga tta ttc gag aag         51
                    Met Ala Asn Ser Asp Lys Arg Leu Phe Glu Lys
                      1               5                  10 gta gct ata ata acc gga gga gca aga ggg ata gga gcg gcc acg gcg         99
Val Ala Ile Ile Thr Gly Gly Ala Arg Gly Ile Gly Ala Ala Thr Ala
             15                  20                  25 aga ttg ttc aca gag aat ggc gcg tat gtg ata gtc gcg gat atc ctt        147
Arg Leu Phe Thr Glu Asn Gly Ala Tyr Val Ile Val Ala Asp Ile Leu
         30                  35                  40 gat aat gaa ggc atc ctt gtg gcg gaa tcg atc ggt ggg tgt tac gtt        195
Asp Asn Glu Gly Ile Leu Val Ala Glu Ser Ile Gly Gly Cys Tyr Val
 45                  50                  55 cat tgt gac gta tcg aag gag gct gat gtt gag gcg gca gtg gag cta        243
His Cys Asp Val Ser Lys Glu Ala Asp Val Glu Ala Ala Val Glu Leu
 60                  65                  70                  75 gca atg aga cgt aaa ggt aga cta gat gtg atg ttc aac aat gcc ggg        291
Ala Met Arg Arg Lys Gly Arg Leu Asp Val Met Phe Asn Asn Ala Gly
                 80                  85                  90 atg tcg ctt aac gaa ggt agt atc atg ggg atg gac gtg gac atg gtt        339
Met Ser Leu Asn Glu Gly Ser Ile Met Gly Met Asp Val Asp Met Val
             95                 100                 105 aac aaa ctt gtc tcg gtt aat gtc aat ggt gtt ttg cat ggt atc aaa        387
Asn Lys Leu Val Ser Val Asn Val Asn Gly Val Leu His Gly Ile Lys
         110                 115                 120 cat gcc gct aag gcc atg atc aaa ggg gga cga gga ggc tcg ata ata        435
His Ala Ala Lys Ala Met Ile Lys Gly Gly Arg Gly Gly Ser Ile Ile
 125                 130                 135 tgc aca tcg agc tca tca ggg cta atg gga gga ctt gga gga cat gcg        483
Cys Thr Ser Ser Ser Ser Gly Leu Met Gly Gly Leu Gly Gly His Ala
140                 145                 150                 155 tat acg ctc tcc aaa gga ggc atc aac ggg gtg gtg agg aca acg gag        531
Tyr Thr Leu Ser Lys Gly Gly Ile Asn Gly Val Val Arg Thr Thr Glu
                 160                 165                 170 tgc gag ctt ggg tct cac ggc atc cgt gtg aat agc atc tct cct cat        579
Cys Glu Leu Gly Ser His Gly Ile Arg Val Asn Ser Ile Ser Pro His
             175                 180                 185 gga gtt ccc act gac atc ttg gtt aat gcg tac cgt aag ttc ctt aac        627
Gly Val Pro Thr Asp Ile Leu Val Asn Ala Tyr Arg Lys Phe Leu Asn
         190                 195                 200 aat gac aaa ctc aac gtc gct gag gtc acc gac att att gct gag aaa        675
Asn Asp Lys Leu Asn Val Ala Glu Val Thr Asp Ile Ile Ala Glu Lys
 205                 210                 215 ggg agt ttg ctg acc gga aga gcc ggt act gtg gag gac gta gct caa        723
Gly Ser Leu Leu Thr Gly Arg Ala Gly Thr Val Glu Asp Val Ala Gln
```

```
Gly Ser Leu Leu Thr Gly Arg Ala Gly Thr Val Glu Asp Val Ala Gln
220                 225                 230                 235 gca gct ttg ttt ctt gca agc caa gaa tcg tcg ggg ttc att acc gga      771
Ala Ala Leu Phe Leu Ala Ser Gln Glu Ser Ser Gly Phe Ile Thr Gly
                240                 245                 250 cat aac ttg gtt gtt gat ggt ggt tac aca tct gcc act agt act atg      819
His Asn Leu Val Val Asp Gly Gly Tyr Thr Ser Ala Thr Ser Thr Met
                255                 260                 265 aga ttt atc tac aac tag ttttcgtttg gtggtgtttc cttttc                 863
Arg Phe Ile Tyr Asn *
                270

<210> SEQ ID NO 8
<211> LENGTH: 272
<212> TYPE: PRT
<213> ORGANISM: Arabidopsis thaliana

<400> SEQUENCE: 8

Met Ala Asn Ser Asp Lys Arg Leu Phe Glu Lys Val Ala Ile Ile Thr
 1               5                  10                  15

Gly Gly Ala Arg Gly Ile Gly Ala Ala Thr Ala Arg Leu Phe Thr Glu
            20                  25                  30

Asn Gly Ala Tyr Val Ile Val Ala Asp Ile Leu Asp Asn Glu Gly Ile
        35                  40                  45

Leu Val Ala Glu Ser Ile Gly Gly Cys Tyr Val His Cys Asp Val Ser
    50                  55                  60

Lys Glu Ala Asp Val Glu Ala Ala Val Glu Leu Ala Met Arg Arg Lys
65                  70                  75                  80

Gly Arg Leu Asp Val Met Phe Asn Asn Ala Gly Met Ser Leu Asn Glu
                85                  90                  95

Gly Ser Ile Met Gly Met Asp Val Asp Met Val Asn Lys Leu Val Ser
            100                 105                 110

Val Asn Val Asn Gly Val Leu His Gly Ile Lys His Ala Ala Lys Ala
        115                 120                 125

Met Ile Lys Gly Gly Arg Gly Gly Ser Ile Ile Cys Thr Ser Ser Ser
    130                 135                 140

Ser Gly Leu Met Gly Gly Leu Gly Gly His Ala Tyr Thr Leu Ser Lys
145                 150                 155                 160

Gly Gly Ile Asn Gly Val Val Arg Thr Thr Glu Cys Glu Leu Gly Ser
                165                 170                 175

His Gly Ile Arg Val Asn Ser Ile Ser Pro His Gly Val Pro Thr Asp
            180                 185                 190

Ile Leu Val Asn Ala Tyr Arg Lys Phe Leu Asn Asn Asp Lys Leu Asn
        195                 200                 205

Val Ala Glu Val Thr Asp Ile Ile Ala Glu Lys Gly Ser Leu Leu Thr
    210                 215                 220

Gly Arg Ala Gly Thr Val Glu Asp Val Ala Gln Ala Leu Phe Leu
225                 230                 235                 240

Ala Ser Gln Glu Ser Ser Gly Phe Ile Thr Gly His Asn Leu Val Val
                245                 250                 255

Asp Gly Gly Tyr Thr Ser Ala Thr Ser Thr Met Arg Phe Ile Tyr Asn
            260                 265                 270

<210> SEQ ID NO 9
<211> LENGTH: 3107
<212> TYPE: DNA
<213> ORGANISM: Arabidopsis thaliana
```

-continued

```
<220> FEATURE:
<221> NAME/KEY: CDS
<222> LOCATION: (20)...(34)
<220> FEATURE:
<221> NAME/KEY: CDS
<222> LOCATION: (958)...(1054)
<220> FEATURE:
<221> NAME/KEY: CDS
<222> LOCATION: (1209)...(1486)
<220> FEATURE:
<221> NAME/KEY: CDS
<222> LOCATION: (1578)...(2354)
<220> FEATURE:
<221> NAME/KEY: CDS
<222> LOCATION: (2440)...(2529)
<220> FEATURE:
<221> NAME/KEY: CDS
<222> LOCATION: (2629)...(2790)
<220> FEATURE:
<221> NAME/KEY: CDS
<222> LOCATION: (2884)...(2943)

<400> SEQUENCE: 9
tcaaccttct atcatcacc atg gat cct tac aag gtatcttcga tcatattctt          54
                     Met Asp Pro Tyr Lys
                      1               5 cttactttt ctttgttttt gtgtggtgta tgtgtatctt aattagaatt aggttcaact       114
atatatgctc gttttctaaa ctatttttta attggattga tgttcttaaa tcttaagggt       174
caaaatactt tttatgctca aaaacttact taaattctgt gatcgcttga acctaagtgg       234
atgatgtgga tttcctgttt tggctgccta tctttaagta aaacgtttaa cccactgcgt       294
gagaaagaca cgccacatgt ggttttgtt gttttttcc ttagattaga agttattttg        354
ttgttgtttt ttttttata gtatgacaca catgtgttct aaaaatcgga cgttcaaatg       414
atataatcga ttgtttagac gtccgaccgt atattatttt agtgatatca gccaaatcag       474
attaagtaat catcaacaaa atgattgatc agatctatca atacaagtgt attttttttt       534
cacatacaaa aaaattatct caccgacgaa aaaaaaataa aaaattatta tgtagatcca       594
tcgaacaaaa ggcttgaata tcggaagtca cttaaaagtg taataatcga ataaatatta       654
gtggataaaa tgaaatttat ctacaaccct actctccgac atgttactgt ttgcgtcatc       714
aaatctaaag ccttttttggc aaataatggt cggaagacta ctcgtgtcgg gatggaccac       774
ccggatccga tcaggaaacg ggttttgata tgtttcgggt tacgacaaaa aattagggct       834
ttttatcaaa tcaatcagtt ggtagtaaaa ttttgtggat tgttcttgtc gattccgttt       894
gattgttgac caaatttctt cctaggattt tgttgataat cgatcgtata atggtgattg       954 cag tat cgt cct tca agc gcg tac aac gcc cca ttc tac acc aca aac      1002
Tyr Arg Pro Ser Ser Ala Tyr Asn Ala Pro Phe Tyr Thr Thr Asn
         10                  15                  20 ggt ggt gct cca gtc tcc aac aac atc tct tcc ctc acc atc gga gaa      1050
Gly Gly Ala Pro Val Ser Asn Asn Ile Ser Ser Leu Thr Ile Gly Glu
        25                  30                  35 aga g gtatcgtaac cctgaatttc aagagtctat caataagaat cggaacttgt         1104
Arg tggatttatg aaagagataa aactgagata tagagtctaa gctgagatct gttcgtgaag     1164
cgtgatgtga ttatttttaa catgtgttac ttcgtaatgg gcag gt ccg gtt ctt      1219
                                               Gly Pro Val Leu
                                                        40 ctt gag gat tat cat ttg atc gag aag gtt gct aat ttc acc aga gag      1267
Leu Glu Asp Tyr His Leu Ile Glu Lys Val Ala Asn Phe Thr Arg Glu
    45                  50                  55
```

```
agg atc cct gag aga gtg gtt cat gct aga gga atc agt gct aag ggt      1315
Arg Ile Pro Glu Arg Val Val His Ala Arg Gly Ile Ser Ala Lys Gly
         60                  65                  70 ttc ttt gaa gtc acc cat gac att tca aac ctc act tgt gct gat ttt      1363
Phe Phe Glu Val Thr His Asp Ile Ser Asn Leu Thr Cys Ala Asp Phe
 75                  80                  85 ctc aga gcc cct ggt gtt caa act ccg gtt att gtc cgt ttc tca acg      1411
Leu Arg Ala Pro Gly Val Gln Thr Pro Val Ile Val Arg Phe Ser Thr
 90                  95                 100                 105 gtt gtt cac gga cgt gcc agt cct gaa acc atg agg gat att cgt ggt      1459
Val Val His Gly Arg Ala Ser Pro Glu Thr Met Arg Asp Ile Arg Gly
                110                 115                 120 ttt gct gtc aag ttt tac acc aga gag gtataagaaa gattcaaagt            1506
Phe Ala Val Lys Phe Tyr Thr Arg Glu
                125                 130 ttccattttt aatcgtcttt tagcttcttt agaatcagga ctgattttg tcttgttact     1566 gttatgatca g gga aac ttt gat ctt gtt ggg aac aac act ccg gtg ttc     1616
             Gly Asn Phe Asp Leu Val Gly Asn Asn Thr Pro Val Phe
                                 135                 140 ttc atc cgt gat ggg att cag ttc ccg gat gtt gtc cac gcg ttg aaa      1664
Phe Ile Arg Asp Gly Ile Gln Phe Pro Asp Val Val His Ala Leu Lys
145                 150                 155 cct aac cga aaa aca aac atc caa gag tac tgg agg att ctg gac tac      1712
Pro Asn Arg Lys Thr Asn Ile Gln Glu Tyr Trp Arg Ile Leu Asp Tyr
160                 165                 170                 175 atg tcc cac ttg cct gag agt ttg ctc aca tgg tgc tgg atg ttt gat      1760
Met Ser His Leu Pro Glu Ser Leu Leu Thr Trp Cys Trp Met Phe Asp
                180                 185                 190 gat gtt ggt att cca caa gat tac agg cat atg gag ggt ttc ggt gtc      1808
Asp Val Gly Ile Pro Gln Asp Tyr Arg His Met Glu Gly Phe Gly Val
                195                 200                 205 cac acc tac act ctt att gcc aaa tct gga aaa gtt ctc ttt gtg aag      1856
His Thr Tyr Thr Leu Ile Ala Lys Ser Gly Lys Val Leu Phe Val Lys
        210                 215                 220 ttc cac tgg aaa cca act tgt ggg atc aag aat ctg act gat gaa gag      1904
Phe His Trp Lys Pro Thr Cys Gly Ile Lys Asn Leu Thr Asp Glu Glu
225                 230                 235 gcc aag gtt gtt gga gga gcc aat cac agc cac gcc act aag gat ctc      1952
Ala Lys Val Val Gly Gly Ala Asn His Ser His Ala Thr Lys Asp Leu
240                 245                 250                 255 cac gat gcc att gca tct ggc aac tac ccc gag tgg aaa ctt ttc atc      2000
His Asp Ala Ile Ala Ser Gly Asn Tyr Pro Glu Trp Lys Leu Phe Ile
                260                 265                 270 cag acc atg gat cct gca gat gag gat aag ttt gac ttt gac cca ctt      2048
Gln Thr Met Asp Pro Ala Asp Glu Asp Lys Phe Asp Phe Asp Pro Leu
                275                 280                 285 gat gtg acc aag atc tgg cct gag gat att ttg cct ctg caa ccg gtt      2096
Asp Val Thr Lys Ile Trp Pro Glu Asp Ile Leu Pro Leu Gln Pro Val
        290                 295                 300 ggt cgc ttg gtt ctg aac agg acc att gac aac ttc ttc aat gaa act      2144
Gly Arg Leu Val Leu Asn Arg Thr Ile Asp Asn Phe Phe Asn Glu Thr
305                 310                 315 gag cag ctt gcg ttc aac ccg ggt ctt gtg gtt cct gga atc tac tac      2192
Glu Gln Leu Ala Phe Asn Pro Gly Leu Val Val Pro Gly Ile Tyr Tyr
320                 325                 330                 335 tca gac gac aag ctg ctc cag tgt agg atc ttt gct tat ggt gac act      2240
Ser Asp Asp Lys Leu Leu Gln Cys Arg Ile Phe Ala Tyr Gly Asp Thr
                340                 345                 350 cag aga cat cgc ctt gga ccg aat tat ttg cag ctt cca gtc aat gct      2288
Gln Arg His Arg Leu Gly Pro Asn Tyr Leu Gln Leu Pro Val Asn Ala
```

```
                Gln Arg His Arg Leu Gly Pro Asn Tyr Leu Gln Leu Pro Val Asn Ala
                            355                 360                 365 ccc aaa tgt gct cac cac aac aat cac cat gaa ggt ttt atg aac ttc                2336
Pro Lys Cys Ala His His Asn Asn His His Glu Gly Phe Met Asn Phe
        370                 375                 380 atg cac aga gat gag gag gtacgtctta gtacaccact tgagctacca                       2384
Met His Arg Asp Glu Glu
        385 ttgttagtct ttttacttgg aatcaaaatt ctcatttggt ttgtactttt tacag atc               2442
                                                                  Ile
                                                                  390 aat tac tac ccc tca aag ttt gat cct gtc cgc tgc gct gag aaa gtt               2490
Asn Tyr Tyr Pro Ser Lys Phe Asp Pro Val Arg Cys Ala Glu Lys Val
                395                 400                 405 ccc acc cct aca aac tcc tac act gga att cga aca aag gtccgattcc                 2539
Pro Thr Pro Thr Asn Ser Tyr Thr Gly Ile Arg Thr Lys
        410                 415 tgccatgcct tctctaaatc ttcaaatcct aaactcaagt ttattagaat attggtgcta              2599
agaaaacctt ttaattgcta atgttgcag tgc gtc atc aag aaa gag aac aac                2652
                                 Cys Val Ile Lys Lys Glu Asn Asn
                                             420                 425 ttc aaa cag gct gga gac agg tac aga tca tgg gca cca gac agg caa                2700
Phe Lys Gln Ala Gly Asp Arg Tyr Arg Ser Trp Ala Pro Asp Arg Gln
        430                 435                 440 gac agg ttt gtt aag aga tgg gtg gag att cta tcg gag cca cgt ctc                2748
Asp Arg Phe Val Lys Arg Trp Val Glu Ile Leu Ser Glu Pro Arg Leu
        445                 450                 455 acc cac gag atc cgc ggc atc tgg acc tct tac tgg ctc aag                        2790
Thr His Glu Ile Arg Gly Ile Trp Thr Ser Tyr Trp Leu Lys
460             465                 470 gtcagaacca aaaaacact cggtcaaatt tctacgtcct ttttaccaag tttcagcaaa               2850
ctaaaacatt atttatctct ctgtatctct cag gct gat cga tcc ttg gga cag               2904
                                   Ala Asp Arg Ser Leu Gly Gln
                                               475                 480 aaa ctc gca agc cgt ctg aac gtg agg cca agc atc tag aggccaatct                 2953
Lys Leu Ala Ser Arg Leu Asn Val Arg Pro Ser Ile *
        485                 490 ccatataagc tcagtctatg tgaggtacaa tcaatctcat cgatctatca tcgcttggtc              3013
gttaaatccg tcaaaagat aatcacatgt gttgttgttt cttgtctata taataataat              3073
gcttgtaatc ccaaaaactc atgtttcctt cctt                                          3107

<210> SEQ ID NO 10
<211> LENGTH: 492
<212> TYPE: PRT
<213> ORGANISM: Arabidopsis thaliana

<400> SEQUENCE: 10

Met Asp Pro Tyr Lys Tyr Arg Pro Ser Ser Ala Tyr Asn Ala Pro Phe
1               5                   10                  15

Tyr Thr Thr Asn Gly Gly Ala Pro Val Ser Asn Asn Ile Ser Ser Leu
                20                  25                  30

Thr Ile Gly Glu Arg Gly Pro Val Leu Leu Glu Asp Tyr His Leu Ile
            35                  40                  45

Glu Lys Val Ala Asn Phe Thr Arg Glu Arg Ile Pro Glu Arg Val Val
        50                  55                  60

His Ala Arg Gly Ile Ser Ala Lys Gly Phe Phe Glu Val Thr His Asp
65                  70                  75                  80
```

```
Ile Ser Asn Leu Thr Cys Ala Asp Phe Leu Arg Ala Pro Gly Val Gln
                 85                  90                  95
Thr Pro Val Ile Val Arg Phe Ser Thr Val His Gly Arg Ala Ser
            100                 105                 110
Pro Glu Thr Met Arg Asp Ile Arg Gly Phe Ala Val Lys Phe Tyr Thr
            115                 120                 125
Arg Glu Gly Asn Phe Asp Leu Val Gly Asn Asn Thr Pro Val Phe Phe
    130                 135                 140
Ile Arg Asp Gly Ile Gln Phe Pro Asp Val Val His Ala Leu Lys Pro
145                 150                 155                 160
Asn Arg Lys Thr Asn Ile Gln Glu Tyr Trp Arg Ile Leu Asp Tyr Met
                165                 170                 175
Ser His Leu Pro Glu Ser Leu Leu Thr Trp Cys Trp Met Phe Asp Asp
            180                 185                 190
Val Gly Ile Pro Gln Asp Tyr Arg His Met Glu Gly Phe Gly Val His
            195                 200                 205
Thr Tyr Thr Leu Ile Ala Lys Ser Gly Lys Val Leu Phe Val Lys Phe
    210                 215                 220
His Trp Lys Pro Thr Cys Gly Ile Lys Asn Leu Thr Asp Glu Glu Ala
225                 230                 235                 240
Lys Val Val Gly Gly Ala Asn His Ser His Ala Thr Lys Asp Leu His
                245                 250                 255
Asp Ala Ile Ala Ser Gly Asn Tyr Pro Glu Trp Lys Leu Phe Ile Gln
            260                 265                 270
Thr Met Asp Pro Ala Asp Glu Asp Lys Phe Asp Phe Asp Pro Leu Asp
            275                 280                 285
Val Thr Lys Ile Trp Pro Glu Asp Ile Leu Pro Leu Gln Pro Val Gly
    290                 295                 300
Arg Leu Val Leu Asn Arg Thr Ile Asp Asn Phe Phe Asn Glu Thr Glu
305                 310                 315                 320
Gln Leu Ala Phe Asn Pro Gly Leu Val Val Pro Gly Ile Tyr Tyr Ser
                325                 330                 335
Asp Asp Lys Leu Leu Gln Cys Arg Ile Phe Ala Tyr Gly Asp Thr Gln
            340                 345                 350
Arg His Arg Leu Gly Pro Asn Tyr Leu Gln Leu Pro Val Asn Ala Pro
            355                 360                 365
Lys Cys Ala His His Asn Asn His His Glu Gly Phe Met Asn Phe Met
    370                 375                 380
His Arg Asp Glu Glu Ile Asn Tyr Tyr Pro Ser Lys Phe Asp Pro Val
385                 390                 395                 400
Arg Cys Ala Glu Lys Val Pro Thr Pro Thr Asn Ser Tyr Thr Gly Ile
                405                 410                 415
Arg Thr Lys Cys Val Ile Lys Lys Glu Asn Asn Phe Lys Gln Ala Gly
            420                 425                 430
Asp Arg Tyr Arg Ser Trp Ala Pro Asp Arg Gln Asp Arg Phe Val Lys
    435                 440                 445
Arg Trp Val Glu Ile Leu Ser Glu Pro Arg Leu Thr His Glu Ile Arg
    450                 455                 460
Gly Ile Trp Thr Ser Tyr Trp Leu Lys Ala Asp Arg Ser Leu Gly Gln
465                 470                 475                 480
Lys Leu Ala Ser Arg Leu Asn Val Arg Pro Ser Ile
                485                 490
```

```
<210> SEQ ID NO 11
<211> LENGTH: 2687
<212> TYPE: DNA
<213> ORGANISM: Arabidopsis thaliana
<220> FEATURE:
<221> NAME/KEY: CDS
<222> LOCATION: (67)...(204)
<220> FEATURE:
<221> NAME/KEY: CDS
<222> LOCATION: (521)...(661)
<220> FEATURE:
<221> NAME/KEY: CDS
<222> LOCATION: (745)...(1026)
<220> FEATURE:
<221> NAME/KEY: CDS
<222> LOCATION: (1114)...(2667)

<400> SEQUENCE: 11
aagttccaaa ttttctctta gcattctctt tcgtttctcg ttttcgttga atcaaagttc      60 gttgcg atg gcg gat gtt cag atg gct gat gca gaa act ttt gct ttc       108
       Met Ala Asp Val Gln Met Ala Asp Ala Glu Thr Phe Ala Phe
         1               5                  10 caa gct gag att aac cag ctt ctt agc ttg atc atc aac acg ttc tac      156
Gln Ala Glu Ile Asn Gln Leu Leu Ser Leu Ile Ile Asn Thr Phe Tyr
 15                  20                  25                  30 agc aac aaa gaa atc ttc ctc cgt gag ctc atc agt aac tct tct gat      204
Ser Asn Lys Glu Ile Phe Leu Arg Glu Leu Ile Ser Asn Ser Ser Asp
             35                  40                  45 gtaagtttcc cttcaaatct ctctctgact cggtgtgact cgtccgcttc ctattttctt      264
gactgttgtt tgttctttaa ttcctggatt cgttgatagc gttggattcg taggtttagc      324
gttgtgattg cttattcaaa taaatcgtga tttggcttgt gcatcacgtt aagtttagaa      384
ttcttagctt gtgctcgatc ttcatgtgtt gtagttacat atatagaacg gttcttgctt      444
cgatgtagtt tttgatttac cctagaggat tgagtaaagc ttctgattat ctttgtttat      504
atgaacggtt ttgtag gct ctt gac aag att cga ttt gag agc tta acg gat     556
               Ala Leu Asp Lys Ile Arg Phe Glu Ser Leu Thr Asp
                                50                  55 aag agc aag ctc gat gga cag cct gaa ctc ttc att aga ttg gtt cct      604
Lys Ser Lys Leu Asp Gly Gln Pro Glu Leu Phe Ile Arg Leu Val Pro
 60                  65                  70 gac aag cct aat aag acg ctc tca att att gac agt ggt att ggc atg      652
Asp Lys Pro Asn Lys Thr Leu Ser Ile Ile Asp Ser Gly Ile Gly Met
 75                  80                  85                  90 acc aaa gca ggtaacgaat caatgcctaa taatctctcg ttggtgagat                701
Thr Lys Ala gtttagtgta tgtgctgtgg ttatgactct ctattatttt tca gat ttg gtg aac       756
                                                Asp Leu Val Asn
                                                         95 aac ttg gga acc att gcg agg tct gga aca aaa gag ttt atg gag gcg      804
Asn Leu Gly Thr Ile Ala Arg Ser Gly Thr Lys Glu Phe Met Glu Ala
         100                 105                 110 ctt caa gct gga gct gat gta agc atg ata gga caa ttt ggt gtt ggt      852
Leu Gln Ala Gly Ala Asp Val Ser Met Ile Gly Gln Phe Gly Val Gly
 115                 120                 125 ttc tac tct gct tat ctt gtt gca gag aag gtt gtt gtc act aca aag      900
Phe Tyr Ser Ala Tyr Leu Val Ala Glu Lys Val Val Val Thr Thr Lys
130                 135                 140                 145 cac aat gat gat gaa caa tac gtt tgg gag tct caa gct ggt ggt tcc      948
His Asn Asp Asp Glu Gln Tyr Val Trp Glu Ser Gln Ala Gly Gly Ser
             150                 155                 160
```

```
ttc act gtc act agg gat gtg gat ggg gaa cca ctt ggt aga gga act      996
Phe Thr Val Thr Arg Asp Val Asp Gly Glu Pro Leu Gly Arg Gly Thr
            165                 170                 175 aag atc agc ctc ttc ctt aag gac gat cag gtaaggaatc gtagctttga       1046
Lys Ile Ser Leu Phe Leu Lys Asp Asp Gln
        180                 185 gtgttttggg ggatgttctt ttcttttggt gttttctgtg ttcttacaag tgtgtttatt   1106 catgcag ctt gaa tac ttg gag gag agg aga ctc aaa gac ttg gtg aag     1155
        Leu Glu Tyr Leu Glu Glu Arg Arg Leu Lys Asp Leu Val Lys
                    190                 195                 200 aag cac tct gag ttc atc agt tac cct atc tac ctt tgg acc gag aaa     1203
Lys His Ser Glu Phe Ile Ser Tyr Pro Ile Tyr Leu Trp Thr Glu Lys
                205                 210                 215 acc acc gag aag gag atc agt gac gat gag gat gaa gat gaa cca aag     1251
Thr Thr Glu Lys Glu Ile Ser Asp Asp Glu Asp Glu Asp Glu Pro Lys
                220                 225                 230 aaa gaa aac gaa ggt gag gtt gaa gaa gtt gat gag aag aag gag aaa     1299
Lys Glu Asn Glu Gly Glu Val Glu Glu Val Asp Glu Lys Lys Glu Lys
            235                 240                 245 gat ggt aaa aag aag aag aaa atc aag gaa gtc tct cac gag tgg gaa     1347
Asp Gly Lys Lys Lys Lys Lys Ile Lys Glu Val Ser His Glu Trp Glu
250                 255                 260                 265 ctc atc aac aag cag aaa ccg atc tgg ttg agg aag cca gaa gag atc     1395
Leu Ile Asn Lys Gln Lys Pro Ile Trp Leu Arg Lys Pro Glu Glu Ile
                270                 275                 280 act aag gaa gag tat gct gct ttc tac aag agc ttg acc aat gac tgg     1443
Thr Lys Glu Glu Tyr Ala Ala Phe Tyr Lys Ser Leu Thr Asn Asp Trp
            285                 290                 295 gaa gat cac tta gcc gtg aaa cac ttc tca gtg gag ggt cag cta gaa     1491
Glu Asp His Leu Ala Val Lys His Phe Ser Val Glu Gly Gln Leu Glu
            300                 305                 310 ttc aag gcc att ctc ttt gta cca aag aga gct ccg ttt gat ctc ttt     1539
Phe Lys Ala Ile Leu Phe Val Pro Lys Arg Ala Pro Phe Asp Leu Phe
        315                 320                 325 gac acg agg aag aag ttg aat aac atc aag ctt tat gtc agg agg gtg     1587
Asp Thr Arg Lys Lys Leu Asn Asn Ile Lys Leu Tyr Val Arg Arg Val
330                 335                 340                 345 ttc att atg gac aac tgt gaa gag cta atc cca gag tac ctc agc ttt     1635
Phe Ile Met Asp Asn Cys Glu Glu Leu Ile Pro Glu Tyr Leu Ser Phe
                350                 355                 360 gtg aaa ggt gtt gtt gac tct gat gac ttg cca ctc aac atc tct cgt    1683
Val Lys Gly Val Val Asp Ser Asp Asp Leu Pro Leu Asn Ile Ser Arg
            365                 370                 375 gag acg ctt caa cag aac aag atc ctt aag gtg atc agg aag aat cta     1731
Glu Thr Leu Gln Gln Asn Lys Ile Leu Lys Val Ile Arg Lys Asn Leu
        380                 385                 390 gtg aag aag tgc att gag atg ttc aac gag att gct gag aac aaa gag     1779
Val Lys Lys Cys Ile Glu Met Phe Asn Glu Ile Ala Glu Asn Lys Glu
        395                 400                 405 gac tac acc aaa ttc tat gag gct ttc tcc aag aat ctc aaa ttg ggt     1827
Asp Tyr Thr Lys Phe Tyr Glu Ala Phe Ser Lys Asn Leu Lys Leu Gly
410                 415                 420                 425 atc cat gaa gac agt cag aac agg gga aag att gct gat ctt cta cgg    1875
Ile His Glu Asp Ser Gln Asn Arg Gly Lys Ile Ala Asp Leu Leu Arg
                430                 435                 440 tac cac tcc aca aag agt ggt gat gaa atg acg agc ttc aaa gat tac    1923
Tyr His Ser Thr Lys Ser Gly Asp Glu Met Thr Ser Phe Lys Asp Tyr
            445                 450                 455 gtc aca agg atg aag gaa ggt caa aag gac att ttc tac atc act ggt    1971
Val Thr Arg Met Lys Glu Gly Gln Lys Asp Ile Phe Tyr Ile Thr Gly
```

```
                                                                                      -continued
Val Thr Arg Met Lys Glu Gly Gln Lys Asp Ile Phe Tyr Ile Thr Gly
            460                 465                 470 gaa agc aaa aag gcg gtg gag aat tcc ttc ttg gag agg ctg aag aag        2019
Glu Ser Lys Lys Ala Val Glu Asn Ser Phe Leu Glu Arg Leu Lys Lys
    475                 480                 485 aga ggc tac gag gta ctt tac atg gtg gat gcg att gac gaa tac gct        2067
Arg Gly Tyr Glu Val Leu Tyr Met Val Asp Ala Ile Asp Glu Tyr Ala
490                 495                 500                 505 gtt gga caa ttg aag gag tat gac ggt aag aaa ctt gtt tct gcg act        2115
Val Gly Gln Leu Lys Glu Tyr Asp Gly Lys Lys Leu Val Ser Ala Thr
                510                 515                 520 aaa gaa ggc ctc aaa ctt gaa gat gag acc gaa gaa gag aag aaa aag        2163
Lys Glu Gly Leu Lys Leu Glu Asp Glu Thr Glu Glu Glu Lys Lys Lys
525                 530                 535 agg gaa gag aag aag aag tcc ttc gag aat ctc tgc aag acg att aag        2211
Arg Glu Glu Lys Lys Lys Ser Phe Glu Asn Leu Cys Lys Thr Ile Lys
        540                 545                 550 gaa att ctc ggg gac aag gtt gag aag gtt gtg gtc tca gac agg att        2259
Glu Ile Leu Gly Asp Lys Val Glu Lys Val Val Val Ser Asp Arg Ile
    555                 560                 565 gtg gac tct ccc tgc tgt cta gta act ggt gaa tat gga tgg act gca        2307
Val Asp Ser Pro Cys Cys Leu Val Thr Gly Glu Tyr Gly Trp Thr Ala
570                 575                 580                 585 aat atg gag agg att atg aag gca cag gcc ttg aga gat agc agc atg        2355
Asn Met Glu Arg Ile Met Lys Ala Gln Ala Leu Arg Asp Ser Ser Met
                590                 595                 600 agt ggt tac atg tcg agc aag aaa aca atg gag atc aac ccc gac aac        2403
Ser Gly Tyr Met Ser Ser Lys Lys Thr Met Glu Ile Asn Pro Asp Asn
            605                 610                 615 ggt ata atg gag gac ctc agg aag aga gct gaa gca gac aag aat gac        2451
Gly Ile Met Glu Asp Leu Arg Lys Arg Ala Glu Ala Asp Lys Asn Asp
        620                 625                 630 aag tct gtt aaa gat ctt gtc atg ttg ctg tat gag aca gct ttg ttg        2499
Lys Ser Val Lys Asp Leu Val Met Leu Leu Tyr Glu Thr Ala Leu Leu
    635                 640                 645 acg tct gga ttt agt ctt gat gaa ccg aac act ttt gct gct agg att        2547
Thr Ser Gly Phe Ser Leu Asp Glu Pro Asn Thr Phe Ala Ala Arg Ile
650                 655                 660                 665 cac agg atg ttg aag ttg ggt ctg agt att gat gag gat gag aac gtt        2595
His Arg Met Leu Lys Leu Gly Leu Ser Ile Asp Glu Asp Glu Asn Val
                670                 675                 680 gag gaa gat ggt gat atg cct gag ttg gag gag gac gct gct gaa gag        2643
Glu Glu Asp Gly Asp Met Pro Glu Leu Glu Glu Asp Ala Ala Glu Glu
            685                 690                 695 agc aag atg gag gaa gtc gac taa gagatgaaga aattgctctt                  2687
Ser Lys Met Glu Glu Val Asp  *
        700

<210> SEQ ID NO 12
<211> LENGTH: 704
<212> TYPE: PRT
<213> ORGANISM: Arabidopsis thaliana

<400> SEQUENCE: 12

Met Ala Asp Val Gln Met Ala Asp Ala Glu Thr Phe Ala Phe Gln Ala
1               5                   10                  15

Glu Ile Asn Gln Leu Leu Ser Leu Ile Ile Asn Thr Phe Tyr Ser Asn
                20                  25                  30

Lys Glu Ile Phe Leu Arg Glu Leu Ile Ser Asn Ser Ser Asp Ala Leu
        35                  40                  45
```

```
Asp Lys Ile Arg Phe Glu Ser Leu Thr Asp Lys Ser Lys Leu Asp Gly
    50                  55                  60

Gln Pro Glu Leu Phe Ile Arg Leu Val Pro Asp Lys Pro Asn Lys Thr
65                  70                  75                  80

Leu Ser Ile Ile Asp Ser Gly Ile Gly Met Thr Lys Ala Asp Leu Val
                    85                  90                  95

Asn Asn Leu Gly Thr Ile Ala Arg Ser Gly Thr Lys Glu Phe Met Glu
                100                 105                 110

Ala Leu Gln Ala Gly Ala Asp Val Ser Met Ile Gly Gln Phe Gly Val
            115                 120                 125

Gly Phe Tyr Ser Ala Tyr Leu Val Ala Glu Lys Val Val Thr Thr
    130                 135                 140

Lys His Asn Asp Asp Glu Gln Tyr Val Trp Glu Ser Gln Ala Gly Gly
145                 150                 155                 160

Ser Phe Thr Val Thr Arg Asp Val Asp Gly Glu Pro Leu Gly Arg Gly
                165                 170                 175

Thr Lys Ile Ser Leu Phe Leu Lys Asp Asp Gln Leu Glu Tyr Leu Glu
                180                 185                 190

Glu Arg Arg Leu Lys Asp Leu Val Lys Lys His Ser Glu Phe Ile Ser
        195                 200                 205

Tyr Pro Ile Tyr Leu Trp Thr Glu Lys Thr Thr Glu Lys Glu Ile Ser
    210                 215                 220

Asp Asp Glu Asp Glu Asp Glu Pro Lys Lys Glu Asn Glu Gly Glu Val
225                 230                 235                 240

Glu Glu Val Asp Glu Lys Lys Glu Lys Asp Gly Lys Lys Lys Lys
                245                 250                 255

Ile Lys Glu Val Ser His Glu Trp Glu Leu Ile Asn Lys Gln Lys Pro
                260                 265                 270

Ile Trp Leu Arg Lys Pro Glu Glu Ile Thr Lys Glu Glu Tyr Ala Ala
        275                 280                 285

Phe Tyr Lys Ser Leu Thr Asn Asp Trp Glu Asp His Leu Ala Val Lys
    290                 295                 300

His Phe Ser Val Glu Gly Gln Leu Glu Phe Lys Ala Ile Leu Phe Val
305                 310                 315                 320

Pro Lys Arg Ala Pro Phe Asp Leu Phe Asp Thr Arg Lys Lys Leu Asn
                325                 330                 335

Asn Ile Lys Leu Tyr Val Arg Arg Val Phe Ile Met Asp Asn Cys Glu
                340                 345                 350

Glu Leu Ile Pro Glu Tyr Leu Ser Phe Val Lys Gly Val Val Asp Ser
            355                 360                 365

Asp Asp Leu Pro Leu Asn Ile Ser Arg Glu Thr Leu Gln Gln Asn Lys
    370                 375                 380

Ile Leu Lys Val Ile Arg Lys Asn Leu Val Lys Lys Cys Ile Glu Met
385                 390                 395                 400

Phe Asn Glu Ile Ala Glu Asn Lys Glu Asp Tyr Thr Lys Phe Tyr Glu
                405                 410                 415

Ala Phe Ser Lys Asn Leu Lys Leu Gly Ile His Glu Asp Ser Gln Asn
                420                 425                 430

Arg Gly Lys Ile Ala Asp Leu Leu Arg Tyr His Ser Thr Lys Ser Gly
            435                 440                 445

Asp Glu Met Thr Ser Phe Lys Asp Tyr Val Thr Arg Met Lys Glu Gly
    450                 455                 460
```

```
Gln Lys Asp Ile Phe Tyr Ile Thr Gly Glu Ser Lys Lys Ala Val Glu
465                 470                 475                 480

Asn Ser Phe Leu Glu Arg Leu Lys Lys Arg Gly Tyr Glu Val Leu Tyr
                485                 490                 495

Met Val Asp Ala Ile Asp Glu Tyr Ala Val Gly Gln Leu Lys Glu Tyr
            500                 505                 510

Asp Gly Lys Lys Leu Val Ser Ala Thr Lys Glu Gly Leu Lys Leu Glu
        515                 520                 525

Asp Glu Thr Glu Glu Lys Lys Arg Glu Glu Lys Lys Ser
    530                 535                 540

Phe Glu Asn Leu Cys Lys Thr Ile Lys Glu Ile Leu Gly Asp Lys Val
545                 550                 555                 560

Glu Lys Val Val Val Ser Asp Arg Ile Val Asp Ser Pro Cys Cys Leu
                565                 570                 575

Val Thr Gly Glu Tyr Gly Trp Thr Ala Asn Met Glu Arg Ile Met Lys
            580                 585                 590

Ala Gln Ala Leu Arg Asp Ser Ser Met Ser Gly Tyr Met Ser Ser Lys
        595                 600                 605

Lys Thr Met Glu Ile Asn Pro Asp Asn Gly Ile Met Glu Asp Leu Arg
    610                 615                 620

Lys Arg Ala Glu Ala Asp Lys Asn Asp Lys Ser Val Lys Asp Leu Val
625                 630                 635                 640

Met Leu Leu Tyr Glu Thr Ala Leu Leu Thr Ser Gly Phe Ser Leu Asp
                645                 650                 655

Glu Pro Asn Thr Phe Ala Ala Arg Ile His Arg Met Leu Lys Leu Gly
            660                 665                 670

Leu Ser Ile Asp Glu Asp Glu Asn Val Glu Glu Asp Gly Asp Met Pro
        675                 680                 685

Glu Leu Glu Glu Asp Ala Ala Glu Glu Ser Lys Met Glu Glu Val Asp
    690                 695                 700

<210> SEQ ID NO 13
<211> LENGTH: 2932
<212> TYPE: DNA
<213> ORGANISM: Arabidopsis thaliana
<220> FEATURE:
<221> NAME/KEY: CDS
<222> LOCATION: (18)...(2924)

<400> SEQUENCE: 13
ttgattgatc ggcgata atg gcg ggt cgg aac ata gag aag atg gca tct         50
                  Met Ala Gly Arg Asn Ile Glu Lys Met Ala Ser
                   1               5                  10 att gat gct cag ctt cgg caa ctc gtt cct gct aaa gtc agt gaa gac        98
Ile Asp Ala Gln Leu Arg Gln Leu Val Pro Ala Lys Val Ser Glu Asp
            15                  20                  25 gat aag ctt gtt gag tac gat gct ctt ctc ctt gat cgc ttt ctc gac       146
Asp Lys Leu Val Glu Tyr Asp Ala Leu Leu Leu Asp Arg Phe Leu Asp
        30                  35                  40 att ctc cag gat tta cac ggc gag gat ctc cgt gaa acg gtt caa gag       194
Ile Leu Gln Asp Leu His Gly Glu Asp Leu Arg Glu Thr Val Gln Glu
    45                  50                  55 tta tac gag ctt tct gct gag tat gaa ggg aag cgt gag cct agc aag       242
Leu Tyr Glu Leu Ser Ala Glu Tyr Glu Gly Lys Arg Glu Pro Ser Lys
60                  65                  70                  75 ctt gag gag cta ggg agt gtc cta acg agt ttg gat cct ggt gac tca       290
Leu Glu Glu Leu Gly Ser Val Leu Thr Ser Leu Asp Pro Gly Asp Ser
                80                  85                  90
```

-continued

| | |
|---|---|
| att gtt atc tcc aag gct ttc tct cac atg ctt aac tta gcc aat ttg<br>Ile Val Ile Ser Lys Ala Phe Ser His Met Leu Asn Leu Ala Asn Leu<br>                  95                          100                      105 | 338 |
| gct gag gag gtg cag att gct cac cgt cgc agg atc aag aag ctg aag<br>Ala Glu Glu Val Gln Ile Ala His Arg Arg Arg Ile Lys Lys Leu Lys<br>                110                      115                      120 | 386 |
| aaa ggt gat ttc gtt gat gag agt tct gca act act gaa tcc gat att<br>Lys Gly Asp Phe Val Asp Glu Ser Ser Ala Thr Thr Glu Ser Asp Ile<br>      125                      130                      135 | 434 |
| gaa gag act ttt aag agg ctc gtt tcg gat ctt ggt aag tct cct gaa<br>Glu Glu Thr Phe Lys Arg Leu Val Ser Asp Leu Gly Lys Ser Pro Glu<br>140                      145                      150                      155 | 482 |
| gag atc ttt gat gcc ttg aag aat cag act gtg gat ctg gtt ttg act<br>Glu Ile Phe Asp Ala Leu Lys Asn Gln Thr Val Asp Leu Val Leu Thr<br>                160                      165                      170 | 530 |
| gct cat cct act cag tct gtg cgt aga tca ttg ctt cag aag cat ggg<br>Ala His Pro Thr Gln Ser Val Arg Arg Ser Leu Leu Gln Lys His Gly<br>      175                      180                      185 | 578 |
| agg ata agg gac tgt ctt gct caa ctc tat gca aag gac att act cct<br>Arg Ile Arg Asp Cys Leu Ala Gln Leu Tyr Ala Lys Asp Ile Thr Pro<br>                190                      195                      200 | 626 |
| gat gac aag cag gag cta gat gag tct ctg caa aga gag att caa gct<br>Asp Asp Lys Gln Glu Leu Asp Glu Ser Leu Gln Arg Glu Ile Gln Ala<br>      205                      210                      215 | 674 |
| gca ttc cga aca gat gag att aga aga aca cct cca acc cca caa gat<br>Ala Phe Arg Thr Asp Glu Ile Arg Arg Thr Pro Pro Thr Pro Gln Asp<br>220                      225                      230                      235 | 722 |
| gaa atg aga gct gga atg agt tat ttc cac gag aca atc tgg aaa ggt<br>Glu Met Arg Ala Gly Met Ser Tyr Phe His Glu Thr Ile Trp Lys Gly<br>                240                      245                      250 | 770 |
| gtc ccc aag ttc ttg cgc cgt gtg gac aca gct ctg aaa aac att ggg<br>Val Pro Lys Phe Leu Arg Arg Val Asp Thr Ala Leu Lys Asn Ile Gly<br>      255                      260                      265 | 818 |
| att gat gaa cgt gtt cct tac aat gcc cca ttg att caa ttc tct tcg<br>Ile Asp Glu Arg Val Pro Tyr Asn Ala Pro Leu Ile Gln Phe Ser Ser<br>                270                      275                      280 | 866 |
| tgg atg ggc ggt gat cgt gat ggt aat ccg agg gtc aca cct gag gtc<br>Trp Met Gly Gly Asp Arg Asp Gly Asn Pro Arg Val Thr Pro Glu Val<br>      285                      290                      295 | 914 |
| act aga gat gtg tgc ttg ttg gct aga atg atg gct gcc aat ctc tac<br>Thr Arg Asp Val Cys Leu Leu Ala Arg Met Met Ala Ala Asn Leu Tyr<br>300                      305                      310                      315 | 962 |
| tat aac caa atc gag aat ctg atg ttt gag tta tct atg tgg cgt tgc<br>Tyr Asn Gln Ile Glu Asn Leu Met Phe Glu Leu Ser Met Trp Arg Cys<br>                320                      325                      330 | 1010 |
| act gat gaa ttc cgt gtg cgg gcg gat gaa ctg cac agg aac tca agg<br>Thr Asp Glu Phe Arg Val Arg Ala Asp Glu Leu His Arg Asn Ser Arg<br>      335                      340                      345 | 1058 |
| aaa gat gct gca aaa cat tac ata gaa ttc tgg aag aca att cct cca<br>Lys Asp Ala Ala Lys His Tyr Ile Glu Phe Trp Lys Thr Ile Pro Pro<br>                350                      355                      360 | 1106 |
| act gag cca tac cgt gtg att ctt ggt gat gtg agg gat aag ctg tat<br>Thr Glu Pro Tyr Arg Val Ile Leu Gly Asp Val Arg Asp Lys Leu Tyr<br>      365                      370                      375 | 1154 |
| cac aca cgt gag cgt tcc cgc caa ttg ctg agt aat gga atc tcg gat<br>His Thr Arg Glu Arg Ser Arg Gln Leu Leu Ser Asn Gly Ile Ser Asp<br>380                      385                      390                      395 | 1202 |
| att cct gaa gaa gct acc ttc act aat gtg gaa cag ttc ttg gag cct<br>Ile Pro Glu Glu Ala Thr Phe Thr Asn Val Glu Gln Phe Leu Glu Pro | 1250 |

-continued

```
                   400                 405                  410
ctt gag ctc tgt tac cga tca cta tgt tca tgt ggt gac agc ccg ata    1298
Leu Glu Leu Cys Tyr Arg Ser Leu Cys Ser Cys Gly Asp Ser Pro Ile
            415                 420                 425 gct gat gga agc ctt ctt gat ttc ttg agg caa gtc tct acc ttt gga    1346
Ala Asp Gly Ser Leu Leu Asp Phe Leu Arg Gln Val Ser Thr Phe Gly
            430                 435                 440 ctc tcc ctt gtg aga ctt gac atc agg caa gag tct gaa cgc cac aca    1394
Leu Ser Leu Val Arg Leu Asp Ile Arg Gln Glu Ser Glu Arg His Thr
            445                 450                 455 gat gtc ttg gat gct atc acc aag cac ttg gac atc ggt tcc tcc tat    1442
Asp Val Leu Asp Ala Ile Thr Lys His Leu Asp Ile Gly Ser Ser Tyr
460                 465                 470                 475 aga gac tgg tct gaa gaa ggc cga cag gaa tgg ctt ctt gct gaa cta    1490
Arg Asp Trp Ser Glu Glu Gly Arg Gln Glu Trp Leu Leu Ala Glu Leu
                480                 485                 490 agc ggc aaa cgt cca ctt ttc gga cct gat ctt ccc aaa acc gaa gaa    1538
Ser Gly Lys Arg Pro Leu Phe Gly Pro Asp Leu Pro Lys Thr Glu Glu
            495                 500                 505 att tct gat gtc ctg gac aca ttc aaa gtc ata tct gag ctg cct tca    1586
Ile Ser Asp Val Leu Asp Thr Phe Lys Val Ile Ser Glu Leu Pro Ser
            510                 515                 520 gat tgt ttt gga gct tat att atc tct atg gca act tca cct agt gat    1634
Asp Cys Phe Gly Ala Tyr Ile Ile Ser Met Ala Thr Ser Pro Ser Asp
525                 530                 535 gtg ctt gcg gtt gag ctt tta cag cgc gaa tgc cat gtg aaa aat cca    1682
Val Leu Ala Val Glu Leu Leu Gln Arg Glu Cys His Val Lys Asn Pro
540                 545                 550                 555 ctt aga gtt gtt cca ctc ttt gag aag cta gct gat ctt gaa gca gct    1730
Leu Arg Val Val Pro Leu Phe Glu Lys Leu Ala Asp Leu Glu Ala Ala
                560                 565                 570 cct gcc gct gtt gca aga ctc ttt tct ata gac tgg tac aaa aac cgt    1778
Pro Ala Ala Val Ala Arg Leu Phe Ser Ile Asp Trp Tyr Lys Asn Arg
            575                 580                 585 att aac ggt aaa caa gag gtt atg att ggt tac tca gat tca ggg aaa    1826
Ile Asn Gly Lys Gln Glu Val Met Ile Gly Tyr Ser Asp Ser Gly Lys
            590                 595                 600 gat gca ggg cgt ctc tca gct gct tgg gag cta tac aaa gct caa gaa    1874
Asp Ala Gly Arg Leu Ser Ala Ala Trp Glu Leu Tyr Lys Ala Gln Glu
605                 610                 615 gag ctt gtg aag gtt gct aag aaa tat gga gtg aag cta act atg ttc    1922
Glu Leu Val Lys Val Ala Lys Lys Tyr Gly Val Lys Leu Thr Met Phe
620                 625                 630                 635 cat ggc cgt ggt ggc aca gtc gga aga gga ggt ggt cct act cat ctt    1970
His Gly Arg Gly Gly Thr Val Gly Arg Gly Gly Gly Pro Thr His Leu
                640                 645                 650 gct ata ttg tct cag cca cca gat aca gtt aat ggc tct ctt cga gtc    2018
Ala Ile Leu Ser Gln Pro Pro Asp Thr Val Asn Gly Ser Leu Arg Val
            655                 660                 665 acg gtt cag ggt gaa gtc att gag caa tca ttt ggg gag gca cac tta    2066
Thr Val Gln Gly Glu Val Ile Glu Gln Ser Phe Gly Glu Ala His Leu
            670                 675                 680 tgc ttt aga aca ctt caa cgt ttc aca gca gct act cta gag cac gga    2114
Cys Phe Arg Thr Leu Gln Arg Phe Thr Ala Ala Thr Leu Glu His Gly
685                 690                 695 atg aac cct ccg att tca cca aaa ccc gag tgg cgt gct ttg ctt gat    2162
Met Asn Pro Pro Ile Ser Pro Lys Pro Glu Trp Arg Ala Leu Leu Asp
700                 705                 710                 715 gaa atg gcg gtt gtt gca act gag gaa tac cga tct gtc gtt ttc caa    2210
Glu Met Ala Val Val Ala Thr Glu Glu Tyr Arg Ser Val Val Phe Gln
```

```
                Glu Met Ala Val Val Thr Glu Glu Tyr Arg Ser Val Val Phe Gln
                            720                 725                 730 gaa cct cga ttc gtc gag tat ttc cgc ctc gct act ccg gag ctg gag          2258
Glu Pro Arg Phe Val Glu Tyr Phe Arg Leu Ala Thr Pro Glu Leu Glu
            735                 740                 745 tat gga cgt atg aat att gga agt aga cct tca aag cga aaa cca agc          2306
Tyr Gly Arg Met Asn Ile Gly Ser Arg Pro Ser Lys Arg Lys Pro Ser
        750                 755                 760 ggt ggg atc gaa tct ctc cgt gca atc cca tgg atc ttt gct tgg acg          2354
Gly Gly Ile Glu Ser Leu Arg Ala Ile Pro Trp Ile Phe Ala Trp Thr
    765                 770                 775 caa aca aga ttc cat ctt cct gta tgg tta ggt ttc gga gca gca ttt          2402
Gln Thr Arg Phe His Leu Pro Val Trp Leu Gly Phe Gly Ala Ala Phe
780                 785                 790                 795 agg tat gcg atc aag aag gat gtg aga aac ctt cac atg ctg caa gat          2450
Arg Tyr Ala Ile Lys Lys Asp Val Arg Asn Leu His Met Leu Gln Asp
                800                 805                 810 atg tat aaa caa tgg ccc ttt ttc cga gtc acc atc gat cta att gaa          2498
Met Tyr Lys Gln Trp Pro Phe Phe Arg Val Thr Ile Asp Leu Ile Glu
            815                 820                 825 atg gtg ttc gcc aag gga gac ccc ggg atc gct gct ttg tac gac aaa          2546
Met Val Phe Ala Lys Gly Asp Pro Gly Ile Ala Ala Leu Tyr Asp Lys
        830                 835                 840 ctt ctt gtc tca gaa gat tta tgg gct ttt gga gag aaa ctc aga gcc          2594
Leu Leu Val Ser Glu Asp Leu Trp Ala Phe Gly Glu Lys Leu Arg Ala
    845                 850                 855 aac ttt gat gaa acc aag aac ctc gtc ctc cag act gct gga cat aaa          2642
Asn Phe Asp Glu Thr Lys Asn Leu Val Leu Gln Thr Ala Gly His Lys
860                 865                 870                 875 gac ctt ctt gaa gga gat cct tac ttg aaa cag aga cta agg cta cgt          2690
Asp Leu Leu Glu Gly Asp Pro Tyr Leu Lys Gln Arg Leu Arg Leu Arg
                880                 885                 890 gac tct tac att acg acc ctc aac gtt tgc caa gcc tac aca ttg aag          2738
Asp Ser Tyr Ile Thr Thr Leu Asn Val Cys Gln Ala Tyr Thr Leu Lys
            895                 900                 905 agg atc cgt gat gca aac tac aat gtg act ctg cga cca cac att tct          2786
Arg Ile Arg Asp Ala Asn Tyr Asn Val Thr Leu Arg Pro His Ile Ser
        910                 915                 920 aaa gag atc atg caa tca agc aaa tca gca caa gag ctc gtc aag ctt          2834
Lys Glu Ile Met Gln Ser Ser Lys Ser Ala Gln Glu Leu Val Lys Leu
    925                 930                 935 aac ccc acg agt gaa tac gcg cct gga ctt gag gac aca ctt atc tta          2882
Asn Pro Thr Ser Glu Tyr Ala Pro Gly Leu Glu Asp Thr Leu Ile Leu
940                 945                 950                 955 acc atg aag ggt att gct gca gga ttg caa aac acc ggt taa                  2924
Thr Met Lys Gly Ile Ala Ala Gly Leu Gln Asn Thr Gly  *
                960                 965 gtgagtca                                                                 2932

<210> SEQ ID NO 14
<211> LENGTH: 968
<212> TYPE: PRT
<213> ORGANISM: Arabidopsis thaliana

<400> SEQUENCE: 14

Met Ala Gly Arg Asn Ile Glu Lys Met Ala Ser Ile Asp Ala Gln Leu
 1               5                  10                  15

Arg Gln Leu Val Pro Ala Lys Val Ser Glu Asp Asp Lys Leu Val Glu
            20                  25                  30
```

Tyr Asp Ala Leu Leu Leu Asp Arg Phe Leu Asp Ile Leu Gln Asp Leu
          35                  40                  45

His Gly Glu Asp Leu Arg Glu Thr Val Gln Glu Leu Tyr Glu Leu Ser
    50                  55                  60

Ala Glu Tyr Glu Gly Lys Arg Glu Pro Ser Lys Leu Glu Glu Leu Gly
65                  70                  75                  80

Ser Val Leu Thr Ser Leu Asp Pro Gly Asp Ser Ile Val Ile Ser Lys
                85                  90                  95

Ala Phe Ser His Met Leu Asn Leu Ala Asn Leu Ala Glu Glu Val Gln
            100                 105                 110

Ile Ala His Arg Arg Ile Lys Lys Leu Lys Lys Gly Asp Phe Val
            115                 120                 125

Asp Glu Ser Ser Ala Thr Thr Glu Ser Asp Ile Glu Glu Thr Phe Lys
    130                 135                 140

Arg Leu Val Ser Asp Leu Gly Lys Ser Pro Glu Glu Ile Phe Asp Ala
145                 150                 155                 160

Leu Lys Asn Gln Thr Val Asp Leu Val Leu Thr Ala His Pro Thr Gln
                165                 170                 175

Ser Val Arg Arg Ser Leu Leu Gln Lys His Gly Arg Ile Arg Asp Cys
            180                 185                 190

Leu Ala Gln Leu Tyr Ala Lys Asp Ile Thr Pro Asp Asp Lys Gln Glu
            195                 200                 205

Leu Asp Glu Ser Leu Gln Arg Glu Ile Gln Ala Ala Phe Arg Thr Asp
    210                 215                 220

Glu Ile Arg Arg Thr Pro Pro Thr Pro Gln Asp Glu Met Arg Ala Gly
225                 230                 235                 240

Met Ser Tyr Phe His Glu Thr Ile Trp Lys Gly Val Pro Lys Phe Leu
                245                 250                 255

Arg Arg Val Asp Thr Ala Leu Lys Asn Ile Gly Ile Asp Glu Arg Val
            260                 265                 270

Pro Tyr Asn Ala Pro Leu Ile Gln Phe Ser Ser Trp Met Gly Gly Asp
    275                 280                 285

Arg Asp Gly Asn Pro Arg Val Thr Pro Glu Val Thr Arg Asp Val Cys
    290                 295                 300

Leu Leu Ala Arg Met Met Ala Ala Asn Leu Tyr Tyr Asn Gln Ile Glu
305                 310                 315                 320

Asn Leu Met Phe Glu Leu Ser Met Trp Arg Cys Thr Asp Glu Phe Arg
                325                 330                 335

Val Arg Ala Asp Glu Leu His Arg Asn Ser Arg Lys Asp Ala Ala Lys
            340                 345                 350

His Tyr Ile Glu Phe Trp Lys Thr Ile Pro Pro Thr Glu Pro Tyr Arg
            355                 360                 365

Val Ile Leu Gly Asp Val Arg Asp Lys Leu Tyr His Thr Arg Glu Arg
    370                 375                 380

Ser Arg Gln Leu Leu Ser Asn Gly Ile Ser Asp Ile Pro Glu Glu Ala
385                 390                 395                 400

Thr Phe Thr Asn Val Glu Gln Phe Leu Glu Pro Leu Glu Leu Cys Tyr
                405                 410                 415

Arg Ser Leu Cys Ser Cys Gly Asp Ser Pro Ile Ala Asp Gly Ser Leu
            420                 425                 430

Leu Asp Phe Leu Arg Gln Val Ser Thr Phe Gly Leu Ser Leu Val Arg
            435                 440                 445

Leu Asp Ile Arg Gln Glu Ser Glu Arg His Thr Asp Val Leu Asp Ala

-continued

```
            450                 455                 460
Ile Thr Lys His Leu Asp Ile Gly Ser Ser Tyr Arg Asp Trp Ser Glu
465                 470                 475                 480

Glu Gly Arg Gln Glu Trp Leu Leu Ala Glu Leu Ser Gly Lys Arg Pro
                485                 490                 495

Leu Phe Gly Pro Asp Leu Pro Lys Thr Glu Ile Ser Asp Val Leu
            500                 505                 510

Asp Thr Phe Lys Val Ile Ser Glu Leu Pro Ser Asp Cys Phe Gly Ala
                515                 520                 525

Tyr Ile Ile Ser Met Ala Thr Ser Pro Ser Asp Val Leu Ala Val Glu
            530                 535                 540

Leu Leu Gln Arg Glu Cys His Val Lys Asn Pro Leu Arg Val Val Pro
545                 550                 555                 560

Leu Phe Glu Lys Leu Ala Asp Leu Glu Ala Pro Ala Ala Val Ala
                565                 570                 575

Arg Leu Phe Ser Ile Asp Trp Tyr Lys Asn Arg Ile Asn Gly Lys Gln
                580                 585                 590

Glu Val Met Ile Gly Tyr Ser Asp Ser Gly Lys Asp Ala Gly Arg Leu
                595                 600                 605

Ser Ala Ala Trp Glu Leu Tyr Lys Ala Gln Glu Glu Leu Val Lys Val
            610                 615                 620

Ala Lys Lys Tyr Gly Val Lys Leu Thr Met Phe His Gly Arg Gly Gly
625                 630                 635                 640

Thr Val Gly Arg Gly Gly Pro Thr His Leu Ala Ile Leu Ser Gln
                645                 650                 655

Pro Pro Asp Thr Val Asn Gly Ser Leu Arg Val Thr Val Gln Gly Glu
                660                 665                 670

Val Ile Glu Gln Ser Phe Gly Glu Ala His Leu Cys Phe Arg Thr Leu
                675                 680                 685

Gln Arg Phe Thr Ala Ala Thr Leu Glu His Gly Met Asn Pro Pro Ile
                690                 695                 700

Ser Pro Lys Pro Glu Trp Arg Ala Leu Leu Asp Glu Met Ala Val Val
705                 710                 715                 720

Ala Thr Glu Glu Tyr Arg Ser Val Val Phe Gln Glu Pro Arg Phe Val
                725                 730                 735

Glu Tyr Phe Arg Leu Ala Thr Pro Glu Leu Glu Tyr Gly Arg Met Asn
                740                 745                 750

Ile Gly Ser Arg Pro Ser Lys Arg Lys Pro Ser Gly Gly Ile Glu Ser
                755                 760                 765

Leu Arg Ala Ile Pro Trp Ile Phe Ala Trp Thr Gln Thr Arg Phe His
770                 775                 780

Leu Pro Val Trp Leu Gly Phe Gly Ala Ala Phe Arg Tyr Ala Ile Lys
785                 790                 795                 800

Lys Asp Val Arg Asn Leu His Met Leu Gln Asp Met Tyr Lys Gln Trp
                805                 810                 815

Pro Phe Phe Arg Val Thr Ile Asp Leu Ile Glu Met Val Phe Ala Lys
                820                 825                 830

Gly Asp Pro Gly Ile Ala Ala Leu Tyr Asp Lys Leu Leu Val Ser Glu
                835                 840                 845

Asp Leu Trp Ala Phe Gly Glu Lys Leu Arg Ala Asn Phe Asp Glu Thr
            850                 855                 860

Lys Asn Leu Val Leu Gln Thr Ala Gly His Lys Asp Leu Leu Glu Gly
865                 870                 875                 880
```

```
Asp Pro Tyr Leu Lys Gln Arg Leu Arg Leu Arg Asp Ser Tyr Ile Thr
            885                 890                 895

Thr Leu Asn Val Cys Gln Ala Tyr Thr Leu Lys Arg Ile Arg Asp Ala
        900                 905                 910

Asn Tyr Asn Val Thr Leu Arg Pro His Ile Ser Lys Glu Ile Met Gln
        915                 920                 925

Ser Ser Lys Ser Ala Gln Glu Leu Val Lys Leu Asn Pro Thr Ser Glu
        930                 935                 940

Tyr Ala Pro Gly Leu Glu Asp Thr Leu Ile Leu Thr Met Lys Gly Ile
945                 950                 955                 960

Ala Ala Gly Leu Gln Asn Thr Gly
                965

<210> SEQ ID NO 15
<211> LENGTH: 271
<212> TYPE: DNA
<213> ORGANISM: Arabidopsis thaliana
<220> FEATURE:
<221> NAME/KEY: CDS
<222> LOCATION: (17)...(259)

<400> SEQUENCE: 15
tcgattcagg ttaagg atg tcg aga gct aca tac att atc ggt gcc ctt gcg      52
               Met Ser Arg Ala Thr Tyr Ile Ile Gly Ala Leu Ala
                 1               5                  10 gga tct gcg gta gta gct tac gtg tgt gac aaa gtt att tct gat gat       100
Gly Ser Ala Val Val Ala Tyr Val Cys Asp Lys Val Ile Ser Asp Asp
         15                  20                  25 aag ctt ttt gga ggt act aca cca gga act att act aac aag gaa tgg      148
Lys Leu Phe Gly Gly Thr Thr Pro Gly Thr Ile Thr Asn Lys Glu Trp
     30                  35                  40 ggt gct gcg act gaa gag aga tta caa gca tgg cca aga gtt gct ggt      196
Gly Ala Ala Thr Glu Glu Arg Leu Gln Ala Trp Pro Arg Val Ala Gly
 45                  50                  55                  60 cct ccc gtc gtc atg aac cct atc agt cgc cag aat ttc atc gtc aag      244
Pro Pro Val Val Met Asn Pro Ile Ser Arg Gln Asn Phe Ile Val Lys
                 65                  70                  75 tca cgt cct gaa taa cttttgatgc ct                                    271
Ser Arg Pro Glu *
         80

<210> SEQ ID NO 16
<211> LENGTH: 80
<212> TYPE: PRT
<213> ORGANISM: Arabidopsis thaliana

<400> SEQUENCE: 16

Met Ser Arg Ala Thr Tyr Ile Ile Gly Ala Leu Ala Gly Ser Ala Val
  1               5                  10                  15

Val Ala Tyr Val Cys Asp Lys Val Ile Ser Asp Asp Lys Leu Phe Gly
             20                  25                  30

Gly Thr Thr Pro Gly Thr Ile Thr Asn Lys Glu Trp Gly Ala Ala Thr
         35                  40                  45

Glu Glu Arg Leu Gln Ala Trp Pro Arg Val Ala Gly Pro Pro Val Val
     50                  55                  60

Met Asn Pro Ile Ser Arg Gln Asn Phe Ile Val Lys Ser Arg Pro Glu
 65                  70                  75                  80

<210> SEQ ID NO 17
```

-continued

```
<211> LENGTH: 2580
<212> TYPE: DNA
<213> ORGANISM: Arabidopsis thaliana
<220> FEATURE:
<221> NAME/KEY: CDS
<222> LOCATION: (30)...(143)
<220> FEATURE:
<221> NAME/KEY: CDS
<222> LOCATION: (295)...(417)
<220> FEATURE:
<221> NAME/KEY: CDS
<222> LOCATION: (582)...(632)
<220> FEATURE:
<221> NAME/KEY: CDS
<222> LOCATION: (1179)...(1245)
<220> FEATURE:
<221> NAME/KEY: CDS
<222> LOCATION: (1334)...(1383)
<220> FEATURE:
<221> NAME/KEY: CDS
<222> LOCATION: (1497)...(1577)
<220> FEATURE:
<221> NAME/KEY: CDS
<222> LOCATION: (1661)...(1740)
<220> FEATURE:
<221> NAME/KEY: CDS
<222> LOCATION: (1882)...(1984)
<220> FEATURE:
<221> NAME/KEY: CDS
<222> LOCATION: (2370)...(2564)

<400> SEQUENCE: 17
tcttcacaaa tcctaaacga gtaggagct atg gct gca ccg att gtt gat gcg       53
                                Met Ala Ala Pro Ile Val Asp Ala
                                 1               5 gag tac ttg aaa gag atc act aag gct cgc cgt gag ctc cgt tct ctc      101
Glu Tyr Leu Lys Glu Ile Thr Lys Ala Arg Arg Glu Leu Arg Ser Leu
        10                  15                  20 atc gcg aac aag aac tgt gct cct atc atg ctc cga ttg gcg              143
Ile Ala Asn Lys Asn Cys Ala Pro Ile Met Leu Arg Leu Ala
 25                  30                  35 taagttttcg atttccttgg ttttttcgtcg agttgactgt tacagatttc gtttattcat   203
gtggagatcg ttcgattgta gttaggctgt agaatcgatt tgtttgttt ttgaatgttg     263 aaatgtttgt atcatctggt ttttatgaag a tgg cac gat gct gga acc tat       315
                                  Trp His Asp Ala Gly Thr Tyr
                                      40                  45 gat gct caa tcg aag acc ggt gga cct aat ggc tct atc agg aac gaa      363
Asp Ala Gln Ser Lys Thr Gly Gly Pro Asn Gly Ser Ile Arg Asn Glu
         50                  55                  60 gaa gag cac act cat ggt gcc aac agt ggt ttg aag atc gct ctc gat      411
Glu Glu His Thr His Gly Ala Asn Ser Gly Leu Lys Ile Ala Leu Asp
         65                  70                  75 ctc tgt ggtaggattt tgatttagtt tttgtagatt cactttctgg ataatttcat       467
Leu Cys gcgatgtatc cgttttatgt tgtggtttaa gaacactgtt caaataatt acattatgct      527 tttggaaatg gactttgtat cgcttaatta tgagatccta tctttgatgt tca gag       584
                                                            Glu
                                                             80 ggc gtg aaa gct aag cat ccc aaa atc aca tac gca gac ctg tat cag      632
Gly Val Lys Ala Lys His Pro Lys Ile Thr Tyr Ala Asp Leu Tyr Gln
         85                  90                  95 gtgagttaag gctgtgagag aaatctttt gatgtccttg ttgctttttc tgcacatttg     692
tttttcaaag ttcgctggaa ctgtattcgg cttgtgtcat tacctcgtcc caggtttgag    752
cttgttgttt aggagactta gttgatagtt gagcagctgt gtaaatatgg tttcagttgt    812
```

-continued

```
aatttgtttc aggagatgtt actgattgtg atttggttta caaaaatcat agattgacta      872
tgttgttcaa ctagaacttt tatctcttgc agtaatagct aaattcaagt aaaatataca      932
ctgaatgaat tcaaacgacc aagaaggaaa ctgtaatgta atgtcaatct gtttccatcc      992
taagtcacat gtctgtcgtc tgtacctata acctgtctct acgactgttt gtattgccgt     1052
ttctccattt tatatttggt cttacaaggt cgaggcttta tttatgaatt cccaatagaa     1112
gtgtaccagt ttaatggcaa ttaagttttg ggtatgaatt atttacttt aagtgttttg      1172 tttcag ctt gct ggt gtg gta gca gtt gag gtt act ggt gga cct gac        1220
       Leu Ala Gly Val Val Ala Val Glu Val Thr Gly Gly Pro Asp
               100             105             110 atc gtg ttc gtt ccc ggg aga aag g tatactttct catctcttga                1265
Ile Val Phe Val Pro Gly Arg Lys
            115 gacattataa cagcttatca gtttaacact aaagcaaaca taattactgt atgtttcttc     1325 ttgatagg at tca aat gtc tgc ccc aag gaa gga aga ctt cct gat gcc        1374
           Ser Asn Val Cys Pro Lys Glu Gly Arg Leu Pro Asp Ala
                   120             125             130 aaa caa ggt acactaaatt cttgtatcaa ttataacaaa cttttcatgt                1423
Lys Gln Gly
135 tttctactga taatcttgtt ttggaattgg aagatttttt ctatgaattc acattgttta     1483 tatctctgta ggt ttc caa cat ctc aga gat gtc ttc tac cgc atg gga        1532
           Phe Gln His Leu Arg Asp Val Phe Tyr Arg Met Gly
                   140             145 cta tct gat aag gat att gtg gca ctc tca ggg ggt cat act ctg           1577
Leu Ser Asp Lys Asp Ile Val Ala Leu Ser Gly Gly His Thr Leu
    150             155             160 gtaaattcat tggtcactta cttaacttcc gttgttttg aacaaatatg cttgttgtgc      1637
ttatgaccac attgggtgtt tag gga agg gct cac ccg gag agg tca ggc ttt     1690
                        Gly Arg Ala His Pro Glu Arg Ser Gly Phe
                                165             170 gat gga cca tgg acc caa gag ccg ctg aat ttt gac aac tcc tac ttc       1738
Asp Gly Pro Trp Thr Gln Glu Pro Leu Asn Phe Asp Asn Ser Tyr Phe
175             180             185 gt gtaattttca tttctttatc ctcagagatt tctttgtgc atttttttaa               1790
Val tcttttctgt ttgtgtctcc aagaaataaa agcagcaaac agatacttt ttacatgatc      1850 ggttatccat gattatttac tgttttggta c c agg gaa ctg ctg aaa gga gaa      1903
                                    Arg Glu Leu Leu Lys Gly Glu
                                            190             195 tca gag ggc ttg ttg aaa ctt cca act gac aag acc tta ttg gaa gac       1951
Ser Glu Gly Leu Leu Lys Leu Pro Thr Asp Lys Thr Leu Leu Glu Asp
            200             205             210 ccg gag ttc cgt cgt ctt gtt gag ctt tat gca aggtataat atactggaga      2004
Pro Glu Phe Arg Arg Leu Val Glu Leu Tyr Ala
        215             220 tcttctctgc ctctttgcca tttgtttctt gcgttgctat aataaccatt ggaacataac     2064
tcgatttcct ttattggttt cacattttca ctgaatccac aagcacacac actgaatcac    2124
aaaccaaatt atctagggtt ttgttctaga aaccccacg gatccttatc gcctttatag     2184
ttgctgatgt tgcaaaatga taaaatgaac actcttacta ctatcagtga aactgtaat     2244 attagctttt tgttagaacc gtaaacagaa attcctatgg ttctttatga tttccttgct    2304
taattaagtt tcaataagat aagaaagtgt tgttatgtgt tgacaagttc agtttgtggt    2364
```

```
ggcag gat gaa gat gca ttc ttc aga gac tac gcg gaa tcg cac aag aaa    2414
      Asp Glu Asp Ala Phe Phe Arg Asp Tyr Ala Glu Ser His Lys Lys
          225                 230                 235 ctc tct gag ctt ggt ttc aac cca aac tcc tca gca ggc aaa gca gtt      2462
Leu Ser Glu Leu Gly Phe Asn Pro Asn Ser Ser Ala Gly Lys Ala Val
240                 245                 250 gca gac agc acg att ctg gca cag agt gcg ttc ggg gtt gca gtt gct      2510
Ala Asp Ser Thr Ile Leu Ala Gln Ser Ala Phe Gly Val Ala Val Ala
255                 260                 265                 270 gct gcg gtt gtg gca ttt ggt tac ttt tac gag atc cgg aag agg atg      2558
Ala Ala Val Val Ala Phe Gly Tyr Phe Tyr Glu Ile Arg Lys Arg Met
                275                 280                 285 aag taa acgaaatagg aagtaa                                            2580
Lys *
```

<210> SEQ ID NO 18
<211> LENGTH: 287
<212> TYPE: PRT
<213> ORGANISM: Arabidopsis thaliana

<400> SEQUENCE: 18

```
Met Ala Ala Pro Ile Val Asp Ala Glu Tyr Leu Lys Glu Ile Thr Lys
 1               5                  10                  15

Ala Arg Arg Glu Leu Arg Ser Leu Ile Ala Asn Lys Asn Cys Ala Pro
            20                  25                  30

Ile Met Leu Arg Leu Ala Trp His Asp Ala Gly Thr Tyr Asp Ala Gln
        35                  40                  45

Ser Lys Thr Gly Gly Pro Asn Gly Ser Ile Arg Asn Glu Glu Glu His
    50                  55                  60

Thr His Gly Ala Asn Ser Gly Leu Lys Ile Ala Leu Asp Leu Cys Glu
65                  70                  75                  80

Gly Val Lys Ala Lys His Pro Lys Ile Thr Tyr Ala Asp Leu Tyr Gln
                85                  90                  95

Leu Ala Gly Val Val Ala Val Glu Val Thr Gly Gly Pro Asp Ile Val
            100                 105                 110

Phe Val Pro Gly Arg Lys Asp Ser Asn Val Cys Pro Lys Glu Gly Arg
        115                 120                 125

Leu Pro Asp Ala Lys Gln Gly Phe Gln His Leu Arg Asp Val Phe Tyr
    130                 135                 140

Arg Met Gly Leu Ser Asp Lys Asp Ile Val Ala Leu Ser Gly Gly His
145                 150                 155                 160

Thr Leu Gly Arg Ala His Pro Glu Arg Ser Gly Phe Asp Gly Pro Trp
                165                 170                 175

Thr Gln Glu Pro Leu Asn Phe Asp Asn Ser Tyr Phe Val Arg Glu Leu
            180                 185                 190

Leu Lys Gly Glu Ser Glu Gly Leu Leu Lys Leu Pro Thr Asp Lys Thr
        195                 200                 205

Leu Leu Glu Asp Pro Glu Phe Arg Arg Leu Val Glu Leu Tyr Ala Asp
    210                 215                 220

Glu Asp Ala Phe Phe Arg Asp Tyr Ala Glu Ser His Lys Lys Leu Ser
225                 230                 235                 240

Glu Leu Gly Phe Asn Pro Asn Ser Ser Ala Gly Lys Ala Val Ala Asp
                245                 250                 255

Ser Thr Ile Leu Ala Gln Ser Ala Phe Gly Val Ala Val Ala Ala Ala
            260                 265                 270
```

```
                Val Val Ala Phe Gly Tyr Phe Tyr Glu Ile Arg Lys Arg Met Lys
                        275                 280                 285

<210> SEQ ID NO 19
<211> LENGTH: 1861
<212> TYPE: DNA
<213> ORGANISM: Arabidopsis thaliana
<220> FEATURE:
<221> NAME/KEY: CDS
<222> LOCATION: (26)...(284)
<220> FEATURE:
<221> NAME/KEY: CDS
<222> LOCATION: (541)...(917)
<220> FEATURE:
<221> NAME/KEY: CDS
<222> LOCATION: (1257)...(1493)
<220> FEATURE:
<221> NAME/KEY: CDS
<222> LOCATION: (1584)...(1853)

<400> SEQUENCE: 19
atagaaaaac cctaagtagg ttgtg atg ttg cga gct tta gca cgg cct ctc        52
                            Met Leu Arg Ala Leu Ala Arg Pro Leu
                              1               5 gaa cgg tgt ttg gga agc aga gct agt ggt gat ggt tta ctc tgg caa       100
Glu Arg Cys Leu Gly Ser Arg Ala Ser Gly Asp Gly Leu Leu Trp Gln
 10                  15                  20                  25 tcg gaa ttg aga cct cac gct ggc ggt gat tat tcg atc gcg gtg gtt       148
Ser Glu Leu Arg Pro His Ala Gly Gly Asp Tyr Ser Ile Ala Val Val
                 30                  35                  40 caa gcc aat tcc agg ctt gaa gat cag agt cag gtt ttc aca tct tct       196
Gln Ala Asn Ser Arg Leu Glu Asp Gln Ser Gln Val Phe Thr Ser Ser
             45                  50                  55 tct gct act tac gtc ggt gta tac gat ggt cat ggt gga cct gaa gct       244
Ser Ala Thr Tyr Val Gly Val Tyr Asp Gly His Gly Gly Pro Glu Ala
         60                  65                  70 tct aga ttc gtt aac aga cat ctc ttt cct tat atg cac a gtaagttata      294
Ser Arg Phe Val Asn Arg His Leu Phe Pro Tyr Met His
     75                  80                  85 atcccactct tccttcccta aacttgtttt aggattcttt cttcttttga ctctttgact     354 acgttttga tggtcaaaac ttatgagatc tctattaccc tgatcatttc aatattaaaa      414
gattcgaatt ttgctatgaa gttttggtct ttgtgaacat gttcaggttt gtaaattgcc     474
tcttgaattg attttgtagt catgttcttg ttagtgaaat ttacaggatt ggttttatga     534 ttgcag aa ttt gca aga gaa cat ggg gga tta tct gta gat gtt atc aaa     584
       Lys Phe Ala Arg Glu His Gly Gly Leu Ser Val Asp Val Ile Lys
            90                  95                 100 aag gca ttc aaa gaa aca gaa gaa gag ttt tgt ggt atg gtt aaa cga       632
Lys Ala Phe Lys Glu Thr Glu Glu Glu Phe Cys Gly Met Val Lys Arg
             105                 110                 115 tcc ctt ccc atg aaa ccg caa atg gct act gta gga tct tgc tgt ctt       680
Ser Leu Pro Met Lys Pro Gln Met Ala Thr Val Gly Ser Cys Cys Leu
        120                 125                 130 gtt ggt gca atc tct aat gac aca ctg tat gtt gct aat ctt ggg gac       728
Val Gly Ala Ile Ser Asn Asp Thr Leu Tyr Val Ala Asn Leu Gly Asp
    135                 140                 145 tcg aga gcc gtt ctt gga agc gtt gtt tca ggg gtt gat agt aat aaa       776
Ser Arg Ala Val Leu Gly Ser Val Val Ser Gly Val Asp Ser Asn Lys
150                 155                 160                 165 ggt gcc gta gct gaa cgg tta tct act gat cat aat gtt gct gtt gaa       824
Gly Ala Val Ala Glu Arg Leu Ser Thr Asp His Asn Val Ala Val Glu
                170                 175                 180
```

| | | | | | | | | | | | | | | |
|---|---|---|---|---|---|---|---|---|---|---|---|---|---|---|
| gaa | gtg | aga | aag | gag | gtt | aag | gca | ctt | aac | cct | gat | gac | tca | caa atc |
| Glu | Val | Arg | Lys | Glu | Val | Lys | Ala | Leu | Asn | Pro | Asp | Asp | Ser | Gln Ile |
| | | 185 | | | | | 190 | | | | | 195 | | |

872

| | | | | | | | | | | | | | | |
|---|---|---|---|---|---|---|---|---|---|---|---|---|---|---|
| gtc | tta | tac | aca | cgt | gga | gtt | tgg | cgg | att | aaa | ggc | att | att | cag |
| Val | Leu | Tyr | Thr | Arg | Gly | Val | Trp | Arg | Ile | Lys | Gly | Ile | Ile | Gln |
| | 200 | | | | | 205 | | | | | 210 | | | |

917 gtataactta gttttgcttg cctgcttgtt aaattgcgtg tgattacata gcatctgtga    977
tgaagttata atatttaaaa ggtgtaatct gatgttgttt tttctttct cttttcattt    1037
atataaatgg gggcttgcaa tgttccagga atccgtcaca cgggctcctg caacgtttct    1097
tccccagtgg attttgtgct tttctaagaa ttcccggtag tcagagctat acataataat    1157
gaagatacat gctttttagt tgcttgtgac ctttccgtga atgtttgagc tcgttgtata    1217

| | | | | | | | | | | | | |
|---|---|---|---|---|---|---|---|---|---|---|---|---|
| ttagttagct | aaatcgtttt | catatacgct | tctttatag | gta | tcg | aga | tca | att | | | | |
| | | | | Val | Ser | Arg | Ser | Ile | | | | |
| | | | | | | | | 215 | | | | |

1271

| | | | | | | | | | | | | |
|---|---|---|---|---|---|---|---|---|---|---|---|---|
| ggg | gat | gta | tac | ttg | aaa | aaa | ccg | gag | tat | tac | agg | gac ccg att ttc |
| Gly | Asp | Val | Tyr | Leu | Lys | Lys | Pro | Glu | Tyr | Tyr | Arg | Asp Pro Ile Phe |
| | 220 | | | | | 225 | | | | | 230 | |

1319

| | | | | | | | | | | | | |
|---|---|---|---|---|---|---|---|---|---|---|---|---|
| cag | cga | cat | gga | aat | ccc | att | cct | ttg | agg | aga | ccc | gcg atg aca gcc |
| Gln | Arg | His | Gly | Asn | Pro | Ile | Pro | Leu | Arg | Arg | Pro | Ala Met Thr Ala |
| | 235 | | | | | 240 | | | | | 245 | |

1367

| | | | | | | | | | | | | | | |
|---|---|---|---|---|---|---|---|---|---|---|---|---|---|---|
| gaa | ccc | tcc | att | ata | gta | agg | aag | ctt | aag | cca | cag | gac | ttg | ttt ctg |
| Glu | Pro | Ser | Ile | Ile | Val | Arg | Lys | Leu | Lys | Pro | Gln | Asp | Leu | Phe Leu |
| 250 | | | | | 255 | | | | | 260 | | | | 265 |

1415

| | | | | | | | | | | | | | | |
|---|---|---|---|---|---|---|---|---|---|---|---|---|---|---|
| ata | ttt | gca | tca | gat | ggt | ctc | tgg | gaa | cat | ctt | agt | gat | gaa | aca gcc |
| Ile | Phe | Ala | Ser | Asp | Gly | Leu | Trp | Glu | His | Leu | Ser | Asp | Glu | Thr Ala |
| | | | 270 | | | | | 275 | | | | | 280 | |

1463

| | | | | | | | | | | |
|---|---|---|---|---|---|---|---|---|---|---|
| gta | gaa | atc | gtc | ctc | aaa | cac | cca | aga | act | gtaagttttc ctaaactca |
| Val | Glu | Ile | Val | Leu | Lys | His | Pro | Arg | Thr | |
| | | 285 | | | | | 290 | | | |

1513 agtttgcttt gtatcttcac atttatgtta gctacttagt ttatttattt attaactctg    1573

| | | | | | | | | | | | |
|---|---|---|---|---|---|---|---|---|---|---|---|
| tgttctacag | ggt | att | gcc | cga | aga | ctt | gta | aga | gct | gct | ctg gaa gaa |
| | Gly | Ile | Ala | Arg | Arg | Leu | Val | Arg | Ala | Ala | Leu Glu Glu |
| | | | 295 | | | | | 300 | | | |

1622

| | | | | | | | | | | | | | | |
|---|---|---|---|---|---|---|---|---|---|---|---|---|---|---|
| gcg | gca | aag | aag | aga | gaa | atg | aga | tat | gga | gat | ata | aag | aaa | ata gcc |
| Ala | Ala | Lys | Lys | Arg | Glu | Met | Arg | Tyr | Gly | Asp | Ile | Lys | Lys | Ile Ala |
| 305 | | | | | 310 | | | | | 315 | | | | 320 |

1670

| | | | | | | | | | | | | | | |
|---|---|---|---|---|---|---|---|---|---|---|---|---|---|---|
| aaa | gga | att | cga | cga | cat | ttc | cat | gac | gac | ata | agc | gtt | att | gta gtt |
| Lys | Gly | Ile | Arg | Arg | His | Phe | His | Asp | Asp | Ile | Ser | Val | Ile | Val Val |
| | | | 325 | | | | | 330 | | | | | 335 | |

1718

| | | | | | | | | | | | | | | |
|---|---|---|---|---|---|---|---|---|---|---|---|---|---|---|
| tat | cta | gat | caa | aac | aaa | acc | agt | tca | tcg | aat | agt | aaa | ttg | gtg aag |
| Tyr | Leu | Asp | Gln | Asn | Lys | Thr | Ser | Ser | Ser | Asn | Ser | Lys | Leu | Val Lys |
| | | | 340 | | | | | 345 | | | | | 350 | |

1766

| | | | | | | | | | | | | | | |
|---|---|---|---|---|---|---|---|---|---|---|---|---|---|---|
| caa | gga | ggt | atc | acc | gct | cca | ccg | gat | atc | tac | tca | tta | cac | tct gat |
| Gln | Gly | Gly | Ile | Thr | Ala | Pro | Pro | Asp | Ile | Tyr | Ser | Leu | His | Ser Asp |
| | | 355 | | | | | 360 | | | | | 365 | | |

1814

| | | | | | | | | | | | | |
|---|---|---|---|---|---|---|---|---|---|---|---|---|
| gaa | gca | gag | caa | cga | cgg | tta | ctc | aat | gtg | tta | tac | tga ctgtttga |
| Glu | Ala | Glu | Gln | Arg | Arg | Leu | Leu | Asn | Val | Leu | Tyr | * |
| | 370 | | | | | 375 | | | | | 380 | |

1861

<210> SEQ ID NO 20
<211> LENGTH: 380
<212> TYPE: PRT
<213> ORGANISM: Arabidopsis thaliana

<400> SEQUENCE: 20

| | | | | | | | | | | | | | | |
|---|---|---|---|---|---|---|---|---|---|---|---|---|---|---|
| Met | Leu | Arg | Ala | Leu | Ala | Arg | Pro | Leu | Glu | Arg | Cys | Leu | Gly | Ser Arg |
| 1 | | | | 5 | | | | | 10 | | | | | 15 |

```
Ala Ser Gly Asp Gly Leu Leu Trp Gln Ser Glu Leu Arg Pro His Ala
         20                  25                  30

Gly Gly Asp Tyr Ser Ile Ala Val Val Gln Ala Asn Ser Arg Leu Glu
             35                  40                  45

Asp Gln Ser Gln Val Phe Thr Ser Ser Ala Thr Tyr Val Gly Val
 50                      55                  60

Tyr Asp Gly His Gly Gly Pro Glu Ala Ser Arg Phe Val Asn Arg His
 65                  70                  75                  80

Leu Phe Pro Tyr Met His Lys Phe Ala Arg Glu His Gly Gly Leu Ser
                 85                  90                  95

Val Asp Val Ile Lys Lys Ala Phe Lys Glu Thr Glu Glu Phe Cys
             100                 105                 110

Gly Met Val Lys Arg Ser Leu Pro Met Lys Pro Gln Met Ala Thr Val
         115                 120                 125

Gly Ser Cys Cys Leu Val Gly Ala Ile Ser Asn Asp Thr Leu Tyr Val
 130                     135                 140

Ala Asn Leu Gly Asp Ser Arg Ala Val Leu Gly Ser Val Val Ser Gly
145                 150                 155                 160

Val Asp Ser Asn Lys Gly Ala Val Ala Glu Arg Leu Ser Thr Asp His
             165                 170                 175

Asn Val Ala Val Glu Glu Val Arg Lys Glu Val Lys Ala Leu Asn Pro
         180                 185                 190

Asp Asp Ser Gln Ile Val Leu Tyr Thr Arg Gly Val Trp Arg Ile Lys
         195                 200                 205

Gly Ile Ile Gln Val Ser Arg Ser Ile Gly Asp Val Tyr Leu Lys Lys
         210                 215                 220

Pro Glu Tyr Tyr Arg Asp Pro Ile Phe Gln Arg His Gly Asn Pro Ile
225                 230                 235                 240

Pro Leu Arg Arg Pro Ala Met Thr Ala Glu Pro Ser Ile Ile Val Arg
             245                 250                 255

Lys Leu Lys Pro Gln Asp Leu Phe Leu Ile Phe Ala Ser Asp Gly Leu
         260                 265                 270

Trp Glu His Leu Ser Asp Glu Thr Ala Val Glu Ile Val Leu Lys His
         275                 280                 285

Pro Arg Thr Gly Ile Ala Arg Arg Leu Val Arg Ala Ala Leu Glu Glu
290                 295                 300

Ala Ala Lys Lys Arg Glu Met Arg Tyr Gly Asp Ile Lys Lys Ile Ala
305                 310                 315                 320

Lys Gly Ile Arg Arg His Phe His Asp Asp Ile Ser Val Ile Val Val
                 325                 330                 335

Tyr Leu Asp Gln Asn Lys Thr Ser Ser Ser Asn Ser Lys Leu Val Lys
             340                 345                 350

Gln Gly Gly Ile Thr Ala Pro Pro Asp Ile Tyr Ser Leu His Ser Asp
         355                 360                 365

Glu Ala Glu Gln Arg Arg Leu Leu Asn Val Leu Tyr
370                 375                 380

<210> SEQ ID NO 21
<211> LENGTH: 3633
<212> TYPE: DNA
<213> ORGANISM: Arabidopsis thaliana
<220> FEATURE:
<221> NAME/KEY: CDS
<222> LOCATION: (41)...(356)
<220> FEATURE:
<221> NAME/KEY: CDS
```

```
<222> LOCATION: (811)...(956)
<220> FEATURE:
<221> NAME/KEY: CDS
<222> LOCATION: (1076)...(1389)
<220> FEATURE:
<221> NAME/KEY: CDS
<222> LOCATION: (1544)...(1592)
<220> FEATURE:
<221> NAME/KEY: CDS
<222> LOCATION: (1925)...(2010)
<220> FEATURE:
<221> NAME/KEY: CDS
<222> LOCATION: (2037)...(2120)
<220> FEATURE:
<221> NAME/KEY: CDS
<222> LOCATION: (2399)...(2501)
<220> FEATURE:
<221> NAME/KEY: CDS
<222> LOCATION: (2621)...(2718)
<220> FEATURE:
<221> NAME/KEY: CDS
<222> LOCATION: (2802)...(2924)
<220> FEATURE:
<221> NAME/KEY: CDS
<222> LOCATION: (3071)...(3185)
<220> FEATURE:
<221> NAME/KEY: CDS
<222> LOCATION: (3324)...(3431)
<220> FEATURE:
<221> NAME/KEY: CDS
<222> LOCATION: (3518)...(3619)

<400> SEQUENCE: 21
```

| | | |
|---|---|---|
| ggcgattgag cgaagaagaa accttcgttc tctctcggaa atg acg aag agg aag<br>                                                             Met Thr Lys Arg Lys<br>                                                              1               5 | | 55 |

```
aag gaa gta ata gat gtc gat tgc tcc gag aag aaa gat ttt gtg att        103
Lys Glu Val Ile Asp Val Asp Cys Ser Glu Lys Lys Asp Phe Val Ile
         10                  15                  20 gat tgg tct tcc gct atg gat aag gaa gac gaa gtt ccc gag ctc gag        151
Asp Trp Ser Ser Ala Met Asp Lys Glu Asp Glu Val Pro Glu Leu Glu
     25                  30                  35 att gtt aat acc acc aaa cct act cct ccg cca ccg cca acg ttt ttc        199
Ile Val Asn Thr Thr Lys Pro Thr Pro Pro Pro Pro Pro Thr Phe Phe
 40                  45                  50 tcc gac gat caa acc gat tct ccg aaa ctc cta acc gat cgt gac ctc        247
Ser Asp Asp Gln Thr Asp Ser Pro Lys Leu Leu Thr Asp Arg Asp Leu
55                  60                  65 gac gag cag cta gag cgt aaa aaa gcg atc ctg aca tta ggt ccg ggc        295
Asp Glu Gln Leu Glu Arg Lys Lys Ala Ile Leu Thr Leu Gly Pro Gly
 70                  75                  80                  85 tta ccc gac aag ggt gag aaa att cga ctc aaa atc gct gat ctc gaa        343
Leu Pro Asp Lys Gly Glu Lys Ile Arg Leu Lys Ile Ala Asp Leu Glu
                 90                  95                 100 gag gag aag cag c gtagagtttt agaaggctcg aaaatggttc gcattctgat          396
Glu Glu Lys Gln
            105 tcaattgcat gcttagttcg tttgattttc ttagatatgt tactgtttta ggttggggtt      456 ttcaagttta tgctaaagtt tggctttttt tgagtacatt tatgtgtatc tttactggtc      516 ttacctcata gtccaagcta gattcgagct catttatgtg tatgatctat agtcacagaa      576 catctatgtg ttcgagctca tttatgtgtt tgaatatgaa tatgatgcta caaaagactt      636 ttttggcagg aggtggacag aagttctaag gtcgtgtctt cgactagctc aggtattctt      696 ggtggataat gttaaagttg tttgcttcta acatagtggt tcattttcct gtatggtttt     756 tcgatttatc tttcattttt tggacttaag tttgatgagc catgtttcat gtag gt         812
```

-continued

```
                                                          Arg
tca gat gtt tta ccg caa gga aat gca gtt tca aaa gat acc tct aga       860
Ser Asp Val Leu Pro Gln Gly Asn Ala Val Ser Lys Asp Thr Ser Arg
            110                 115                 120 ggg aat gca gac tca aaa gac acc tct aga caa ggg aat gca gat tca       908
Gly Asn Ala Asp Ser Lys Asp Thr Ser Arg Gln Gly Asn Ala Asp Ser
        125                 130                 135 aaa gaa gtc tca cgg tca aca ttt tct gcg gtt ttc agt aaa cca aaa       956
Lys Glu Val Ser Arg Ser Thr Phe Ser Ala Val Phe Ser Lys Pro Lys
    140                 145                 150 gtatggagca tcgttttttt ttttttgttc aacgtatgga gcctctatat tttgcaattt    1016
taaaactgtt ttggatgggt acttcttcat gatacgattt tgtaatctgt gttcaacag    1075 acg gat tct cag tca aag aaa gcc ttt ggt aaa gaa cta gaa gat ctg      1123
Thr Asp Ser Gln Ser Lys Lys Ala Phe Gly Lys Glu Leu Glu Asp Leu
155                 160                 165                 170 gga tgt gaa agg agg aaa cac aag gct ggt aga aag cct gta aca agg      1171
Gly Cys Glu Arg Arg Lys His Lys Ala Gly Arg Lys Pro Val Thr Arg
                175                 180                 185 ctg agc aac ggg tgg cgg ttg ttg cca gat gta ggg aaa gct gag cac      1219
Leu Ser Asn Gly Trp Arg Leu Leu Pro Asp Val Gly Lys Ala Glu His
            190                 195                 200 agt gca aag cag ttt gat tct gga ctt aaa gaa tca aaa ggg aat aag      1267
Ser Ala Lys Gln Phe Asp Ser Gly Leu Lys Glu Ser Lys Gly Asn Lys
        205                 210                 215 aaa tcc aag gaa cct tat gga aag aaa agg ccc atg gaa tct tcg act      1315
Lys Ser Lys Glu Pro Tyr Gly Lys Lys Arg Pro Met Glu Ser Ser Thr
    220                 225                 230 tat tct ctg att gat gat gat gat gat gat gat gat gat gac aac          1363
Tyr Ser Leu Ile Asp Asp Asp Asp Asp Asp Asp Asp Asp Asp Asn
235                 240                 245                 250 gac acc agt ggc cat gaa act cct ag gttcgtttcc aactgtttct             1409
Asp Thr Ser Gly His Glu Thr Pro Arg
                255 gctactagtt tgttgttttc tctaagggtt ctcaagttta ccactgctgg ttactgcaat    1469 tttgttgtga catgacaatc tggtacataa tagaatgaga tgtattgtaa ttgctcaact    1529 tctttctctc atag g gag tgg tct tgg gaa aaa tct cca tca caa agt tca    1580
              Glu Trp Ser Trp Glu Lys Ser Pro Ser Gln Ser Ser
                  260                 265                 270 agg cgc cgt aag gtattcttgc ttactcccgc tactgtatat cttgcaattg          1632
Arg Arg Arg Lys
            275 cagttttttac gtagtcatta tagtccttaa gaaatttaca ccagcagaag catgactcat   1692
tttctaaacc ttcttgttat ctcccaacag aaaattttat gaattcctta aaaagacttc    1752
agttttcgaa cgtttgattc ctctctagat gaactgcagg atttatactt gccaggaaaa    1812
cttcctactt gactatatca tttatttggc ttctttaata ttgtctttac tccaactcat    1872
ttgttatgtt gttttctta cttattgatg atattcccta aaaaaactat ag aaa tca    1930
                                                         Lys Ser gag gac aca gtg ata aat gtg gat gaa gaa gaa gct cag cct tca aca      1978
Glu Asp Thr Val Ile Asn Val Asp Glu Glu Glu Ala Gln Pro Ser Thr
                280                 285                 290 gtg gcg gag caa gcg gct gaa ctg cct gaa gg gtaaatgtga cctatttttct    2030
Val Ala Glu Gln Ala Ala Glu Leu Pro Glu Gly
295                 300 ctttag c ctc att aag tta caa ctg gct ata tat aaa cta ata gtt gat     2079
        Leu Ile Lys Leu Gln Leu Ala Ile Tyr Lys Leu Ile Val Asp
```

-continued

```
                305                 310                 315
aaa aca tgc agc tta cag gaa gat ata tgc tac cca aca ag gtaaatctat   2130
Lys Thr Cys Ser Leu Gln Glu Asp Ile Cys Tyr Pro Thr Arg
        320                 325                 330 ctcaagactg atctaggcta acttcctgta aatttgtaac cctcaaaaga tttaatgctt   2190
ggtgattcag ggatgatcct cactttgttc aagtttgtct taaagatctt gaatgccttg   2250
cacctcgaga atatctgaca tcgccggtta tgaatttcta catgaggtat tttttggagt   2310
gatagacttg ccatatatgt catcttatat tatgctagcg ctatttgcat gttatttata   2370
taactattgt cctgttttct tttggtag g ttc ttg cag cag cag ata tca tca   2423
                                 Phe Leu Gln Gln Gln Ile Ser Ser
                                                 335                 340 tcg aat caa atc tct gct gat tgt cac ttc ttt aat acc tat ttc tac    2471
Ser Asn Gln Ile Ser Ala Asp Cys His Phe Phe Asn Thr Tyr Phe Tyr
                345                 350                 355 aag aag ctc agt gac gct gtt acg tac aag gtgattagaa aatgtgatc       2521
Lys Lys Leu Ser Asp Ala Val Thr Tyr Lys
        360                 365 ctttaaaaat aattatctgt tggcattctt gcgattcaaa ttttatcat tgttatttat    2581 gttaactggt ctatttatct tgtcctttca atgaaatag ggg aat gac aag gat     2635
                                              Gly Asn Asp Lys Asp
                                                              370 gcc ttc ttt gtg agg ttc agg cgg tgg tgg aag ggt att gat cta ttt   2683
Ala Phe Phe Val Arg Phe Arg Arg Trp Trp Lys Gly Ile Asp Leu Phe
            375                 380                 385 cgt aag gct tat att ttc ata cca ata cat gaa ga gtaagtatct          2728
Arg Lys Ala Tyr Ile Phe Ile Pro Ile His Glu Asp
        390                 395 ttccttttag cactctactt tcgattttttt cgcaagagtt ctcaagaatt cagattcttg  2788
taccatgttt cag t ctc cac tgg agc ctt gtg ata gtt tgc atc cct gat   2838
                  Leu His Trp Ser Leu Val Ile Val Cys Ile Pro Asp
                              400                 405                 410 aag aaa gat gaa tcg ggg ttg act ata ctt cac ctt gat tct cta gga   2886
Lys Lys Asp Glu Ser Gly Leu Thr Ile Leu His Leu Asp Ser Leu Gly
            415                 420                 425 ctt cac tcg aga aaa tca att gtt gaa aat gta aaa ag gtgagatgct      2934
Leu His Ser Arg Lys Ser Ile Val Glu Asn Val Lys Arg
        430                 435                 440 aggggcttta cccgtgactt tatgttctca catgcttgac gttgtatgca tatggtttca   2994
gttcataaaa ggaaaaatta ttacactggc ttgaaaatgt acgacattta ctagtttcta   3054
tgtcaatttg ttgtag g ttt cta aaa gac gaa tgg aat tat ttg aat caa   3104
                    Phe Leu Lys Asp Glu Trp Asn Tyr Leu Asn Gln
                                    445                 450 gat gac tat tcc ttg gat ctg cct atc tca gaa aaa gta tgg aaa aac   3152
Asp Asp Tyr Ser Leu Asp Leu Pro Ile Ser Glu Lys Val Trp Lys Asn
            455                 460                 465 ctc cct cgt agg atc agc gaa gct gtt gtt cag gtcagtcttt taccttctta  3205
Leu Pro Arg Arg Ile Ser Glu Ala Val Val Gln
        470                 475 atcccatgat tcaaggaact ttgtttatac ggtttcttcg gaaatatgat tatattcaga   3265
cactagaacc acaggaagtt caattcgtct tatgatatta ttctctttgt gcaaccag    3323 gtt ccg cag cag aaa aac gat ttt gat tgt ggt ccg ttt gtg ctc ttc    3371
Val Pro Gln Gln Lys Asn Asp Phe Asp Cys Gly Pro Phe Val Leu Phe
        480                 485                 490 ttc att aaa cgg ttc att gaa gag gcg cct caa agg ctg aaa agg aaa    3419
```

```
Phe Ile Lys Arg Phe Ile Glu Glu Ala Pro Gln Arg Leu Lys Arg Lys
495                 500                 505                 510 gac ctg gga atg gtgagtaatc tcaaactctt ttcctgatac cgaatcacat         3471
Asp Leu Gly Met atcttcttct tactcttgtc taaacttgtg tcctcaatgt atccag ttc gac aag      3526
                                                   Phe Asp Lys
                                                       515 aag tgg ttt aga ccc gat gaa gcc tct gct ctg aga atc aaa atc cga    3574
Lys Trp Phe Arg Pro Asp Glu Ala Ser Ala Leu Arg Ile Lys Ile Arg
        520                 525                 530 aac acg ctc atc gag cta ttc cgt gtc agt gac cag aca gag taa        3619
Asn Thr Leu Ile Glu Leu Phe Arg Val Ser Asp Gln Thr Glu  *
535                 540                 545 accagtacag atta                                                     3633

<210> SEQ ID NO 22
<211> LENGTH: 548
<212> TYPE: PRT
<213> ORGANISM: Arabidopsis thaliana

<400> SEQUENCE: 22

Met Thr Lys Arg Lys Lys Glu Val Ile Asp Val Asp Cys Ser Glu Lys
 1               5                  10                  15

Lys Asp Phe Val Ile Asp Trp Ser Ser Ala Met Asp Lys Glu Asp Glu
                20                  25                  30

Val Pro Glu Leu Glu Ile Val Asn Thr Thr Lys Pro Thr Pro Pro
            35                  40                  45

Pro Pro Thr Phe Phe Ser Asp Asp Gln Thr Asp Ser Pro Lys Leu Leu
        50                  55                  60

Thr Asp Arg Asp Leu Asp Glu Gln Leu Glu Arg Lys Lys Ala Ile Leu
65                  70                  75                  80

Thr Leu Gly Pro Gly Leu Pro Asp Lys Gly Glu Lys Ile Arg Leu Lys
                85                  90                  95

Ile Ala Asp Leu Glu Glu Glu Lys Gln Arg Ser Asp Val Leu Pro Gln
            100                 105                 110

Gly Asn Ala Val Ser Lys Asp Thr Ser Arg Gly Asn Ala Asp Ser Lys
        115                 120                 125

Asp Thr Ser Arg Gln Gly Asn Ala Asp Ser Lys Glu Val Ser Arg Ser
    130                 135                 140

Thr Phe Ser Ala Val Phe Ser Lys Pro Lys Thr Asp Ser Gln Ser Lys
145                 150                 155                 160

Lys Ala Phe Gly Lys Glu Leu Glu Asp Leu Gly Cys Glu Arg Arg Lys
                165                 170                 175

His Lys Ala Gly Arg Lys Pro Val Thr Arg Leu Ser Asn Gly Trp Arg
            180                 185                 190

Leu Leu Pro Asp Val Gly Lys Ala Glu His Ser Ala Lys Gln Phe Asp
        195                 200                 205

Ser Gly Leu Lys Glu Ser Lys Gly Asn Lys Lys Ser Lys Glu Pro Tyr
    210                 215                 220

Gly Lys Lys Arg Pro Met Glu Ser Ser Thr Tyr Ser Leu Ile Asp Asp
225                 230                 235                 240

Asp Asp Asp Asp Asp Asp Asp Asn Asp Thr Ser Gly His Glu
                245                 250                 255

Thr Pro Arg Glu Trp Ser Trp Glu Lys Ser Pro Ser Gln Ser Ser Arg
            260                 265                 270
```

```
Arg Arg Lys Lys Ser Glu Asp Thr Val Ile Asn Val Asp Glu Glu Glu
        275                 280                 285

Ala Gln Pro Ser Thr Val Ala Glu Gln Ala Ala Glu Leu Pro Glu Gly
    290                 295                 300

Leu Ile Lys Leu Gln Leu Ala Ile Tyr Lys Leu Ile Val Asp Lys Thr
305                 310                 315                 320

Cys Ser Leu Gln Glu Asp Ile Cys Tyr Pro Thr Arg Ser Phe Leu Gln
                325                 330                 335

Gln Gln Ile Ser Ser Asn Gln Ile Ser Ala Asp Cys His Phe Phe
            340                 345                 350

Asn Thr Tyr Phe Tyr Lys Lys Leu Ser Asp Ala Val Thr Tyr Lys Gly
            355                 360                 365

Asn Asp Lys Asp Ala Phe Phe Val Arg Phe Arg Arg Trp Trp Lys Gly
    370                 375                 380

Ile Asp Leu Phe Arg Lys Ala Tyr Ile Phe Ile Pro Ile His Glu Asp
385                 390                 395                 400

Leu His Trp Ser Leu Val Ile Val Cys Ile Pro Asp Lys Lys Asp Glu
                405                 410                 415

Ser Gly Leu Thr Ile Leu His Leu Asp Ser Leu Gly Leu His Ser Arg
            420                 425                 430

Lys Ser Ile Val Glu Asn Val Lys Arg Phe Leu Lys Asp Glu Trp Asn
            435                 440                 445

Tyr Leu Asn Gln Asp Asp Tyr Ser Leu Asp Leu Pro Ile Ser Glu Lys
    450                 455                 460

Val Trp Lys Asn Leu Pro Arg Arg Ile Ser Glu Ala Val Val Gln Val
465                 470                 475                 480

Pro Gln Gln Lys Asn Asp Phe Asp Cys Gly Pro Phe Val Leu Phe Phe
                485                 490                 495

Ile Lys Arg Phe Ile Glu Glu Ala Pro Gln Arg Leu Lys Arg Lys Asp
            500                 505                 510

Leu Gly Met Phe Asp Lys Lys Trp Phe Arg Pro Asp Glu Ala Ser Ala
            515                 520                 525

Leu Arg Ile Lys Ile Arg Asn Thr Leu Ile Glu Leu Phe Arg Val Ser
    530                 535                 540

Asp Gln Thr Glu
545

<210> SEQ ID NO 23
<211> LENGTH: 1109
<212> TYPE: DNA
<213> ORGANISM: Arabidopsis thaliana
<220> FEATURE:
<221> NAME/KEY: CDS
<222> LOCATION: (22)...(1107)

<400> SEQUENCE: 23
aggagttaga gcatcatcaa g atg aag gca ctc att ctt gtt gga ggc ttc         51
                        Met Lys Ala Leu Ile Leu Val Gly Gly Phe
                          1               5                  10 ggc act cgc ttg aga cca ttg act ctc agt ttc cca aag ccc ctt gtt         99
Gly Thr Arg Leu Arg Pro Leu Thr Leu Ser Phe Pro Lys Pro Leu Val
             15                  20                  25 gat ttt gct aat aaa ccc atg atc ctt cat cag ata gag gct ctt aag       147
Asp Phe Ala Asn Lys Pro Met Ile Leu His Gln Ile Glu Ala Leu Lys
         30                  35                  40 gca gtt gga gtt gat gaa gtg gtt ttg gcc atc aat tat cag cca gag       195
Ala Val Gly Val Asp Glu Val Val Leu Ala Ile Asn Tyr Gln Pro Glu
```

-continued

```
                45                      50                      55
gtg atg ctg aac ttc ttg aag gac ttt gag acc aag ctg gaa atc aaa      243
Val Met Leu Asn Phe Leu Lys Asp Phe Glu Thr Lys Leu Glu Ile Lys
     60                      65                      70 atc act tgc tca caa gag acc gag cca cta ggt acc gct ggt cct ctg      291
Ile Thr Cys Ser Gln Glu Thr Glu Pro Leu Gly Thr Ala Gly Pro Leu
 75                      80                      85                  90 gct cta gcg aga gac aaa ttg ctt gat gga tct gga gag ccc ttc ttt      339
Ala Leu Ala Arg Asp Lys Leu Leu Asp Gly Ser Gly Glu Pro Phe Phe
                     95                     100                     105 gtt ctt aac agt gat gtg att agt gag tac cct ctt aaa gaa atg ctt      387
Val Leu Asn Ser Asp Val Ile Ser Glu Tyr Pro Leu Lys Glu Met Leu
                110                     115                     120 gag ttt cac aaa tct cac ggt ggg gaa gcc tcc ata atg gta aca aag      435
Glu Phe His Lys Ser His Gly Gly Glu Ala Ser Ile Met Val Thr Lys
            125                     130                     135 gtg gat gaa ccg tcg aaa tat gga gtg gtt gtt atg gaa gaa agc act      483
Val Asp Glu Pro Ser Lys Tyr Gly Val Val Val Met Glu Glu Ser Thr
    140                     145                     150 gga aga gtg gag aag ttt gtg gaa aag cca aaa ctg tat gta ggt aac      531
Gly Arg Val Glu Lys Phe Val Glu Lys Pro Lys Leu Tyr Val Gly Asn
155                     160                     165                     170 aag atc aac gct ggg att tat ctt ctg aac cca tct gtt ctt gat aag      579
Lys Ile Asn Ala Gly Ile Tyr Leu Leu Asn Pro Ser Val Leu Asp Lys
                175                     180                     185 att gag cta aga ccg act tca atc gaa aaa gag act ttc cct aag att      627
Ile Glu Leu Arg Pro Thr Ser Ile Glu Lys Glu Thr Phe Pro Lys Ile
            190                     195                     200 gca gca gcg caa ggg ctc tat gct atg gtg cta cca ggg ttt tgg atg      675
Ala Ala Ala Gln Gly Leu Tyr Ala Met Val Leu Pro Gly Phe Trp Met
        205                     210                     215 gac att ggg caa ccc cgt gac tac ata acg ggt ttg aga ctc tac tta      723
Asp Ile Gly Gln Pro Arg Asp Tyr Ile Thr Gly Leu Arg Leu Tyr Leu
    220                     225                     230 gac tcc ctt agg aag aaa tct cct gcc aaa tta acc agt ggg cca cac      771
Asp Ser Leu Arg Lys Lys Ser Pro Ala Lys Leu Thr Ser Gly Pro His
235                     240                     245                     250 ata gtt ggg aat gtt ctt gtt gac gaa acc gct aca att ggg gaa gga      819
Ile Val Gly Asn Val Leu Val Asp Glu Thr Ala Thr Ile Gly Glu Gly
                255                     260                     265 tgt ttg att gga cca gac gtt gcc att ggt cca ggc tgc att gtt gag      867
Cys Leu Ile Gly Pro Asp Val Ala Ile Gly Pro Gly Cys Ile Val Glu
            270                     275                     280 tca gga gtc aga ctc tcc cga tgc acg gtc atg cgt gga gtc cgc atc      915
Ser Gly Val Arg Leu Ser Arg Cys Thr Val Met Arg Gly Val Arg Ile
        285                     290                     295 aag aag cat gcg tgt atc tcg agc agt atc atc ggg tgg cac tca acg      963
Lys Lys His Ala Cys Ile Ser Ser Ser Ile Ile Gly Trp His Ser Thr
300                     305                     310 gtt ggt caa tgg gcc agg atc gag aac atg acg atc ctc ggt gag gat     1011
Val Gly Gln Trp Ala Arg Ile Glu Asn Met Thr Ile Leu Gly Glu Asp
                315                     320                     325                     330 gtt cat gtg agc gat gag atc tat agc aat gga gga gtt gtt ttg cca     1059
Val His Val Ser Asp Glu Ile Tyr Ser Asn Gly Gly Val Val Leu Pro
            335                     340                     345 cac aag gag atc aaa tca aac atc ttg aag cca gag ata gtg atg tga     1107
His Lys Glu Ile Lys Ser Asn Ile Leu Lys Pro Glu Ile Val Met  *
        350                     355                     360 aa                                                                  1109
```

<210> SEQ ID NO 24
<211> LENGTH: 361
<212> TYPE: PRT
<213> ORGANISM: Arabidopsis thaliana

<400> SEQUENCE: 24

Met Lys Ala Leu Ile Leu Val Gly Gly Phe Gly Thr Arg Leu Arg Pro
 1               5                  10                  15

Leu Thr Leu Ser Phe Pro Lys Pro Leu Val Asp Phe Ala Asn Lys Pro
                20                  25                  30

Met Ile Leu His Gln Ile Glu Ala Leu Lys Ala Val Gly Val Asp Glu
            35                  40                  45

Val Val Leu Ala Ile Asn Tyr Gln Pro Glu Val Met Leu Asn Phe Leu
50                  55                  60

Lys Asp Phe Glu Thr Lys Leu Glu Ile Lys Ile Thr Cys Ser Gln Glu
65                  70                  75                  80

Thr Glu Pro Leu Gly Thr Ala Gly Pro Leu Ala Leu Ala Arg Asp Lys
                85                  90                  95

Leu Leu Asp Gly Ser Gly Glu Pro Phe Phe Val Leu Asn Ser Asp Val
            100                 105                 110

Ile Ser Glu Tyr Pro Leu Lys Glu Met Leu Glu Phe His Lys Ser His
        115                 120                 125

Gly Gly Glu Ala Ser Ile Met Val Thr Lys Val Asp Glu Pro Ser Lys
130                 135                 140

Tyr Gly Val Val Val Met Glu Glu Ser Thr Gly Arg Val Glu Lys Phe
145                 150                 155                 160

Val Glu Lys Pro Lys Leu Tyr Val Gly Asn Lys Ile Asn Ala Gly Ile
                165                 170                 175

Tyr Leu Leu Asn Pro Ser Val Leu Asp Lys Ile Glu Leu Arg Pro Thr
            180                 185                 190

Ser Ile Glu Lys Glu Thr Phe Pro Lys Ile Ala Ala Gln Gly Leu
        195                 200                 205

Tyr Ala Met Val Leu Pro Gly Phe Trp Met Asp Ile Gly Gln Pro Arg
210                 215                 220

Asp Tyr Ile Thr Gly Leu Arg Leu Tyr Leu Asp Ser Leu Arg Lys Lys
225                 230                 235                 240

Ser Pro Ala Lys Leu Thr Ser Gly Pro His Ile Val Gly Asn Val Leu
                245                 250                 255

Val Asp Glu Thr Ala Thr Ile Gly Glu Gly Cys Leu Ile Gly Pro Asp
            260                 265                 270

Val Ala Ile Gly Pro Gly Cys Ile Val Glu Ser Gly Val Arg Leu Ser
        275                 280                 285

Arg Cys Thr Val Met Arg Gly Val Arg Ile Lys Lys His Ala Cys Ile
290                 295                 300

Ser Ser Ser Ile Ile Gly Trp His Ser Thr Val Gly Gln Trp Ala Arg
305                 310                 315                 320

Ile Glu Asn Met Thr Ile Leu Gly Glu Asp Val His Val Ser Asp Glu
                325                 330                 335

Ile Tyr Ser Asn Gly Gly Val Val Leu Pro His Lys Glu Ile Lys Ser
            340                 345                 350

Asn Ile Leu Lys Pro Glu Ile Val Met
        355                 360

```
<210> SEQ ID NO 25
<211> LENGTH: 1071
<212> TYPE: DNA
<213> ORGANISM: Arabidopsis thaliana
<220> FEATURE:
<221> NAME/KEY: CDS
<222> LOCATION: (9)...(1055)

<400> SEQUENCE: 25 tccaataa atg aaa gca act cta gca gca ccc tct tct ctc aca agc ctc        50
         Met Lys Ala Thr Leu Ala Ala Pro Ser Ser Leu Thr Ser Leu
         1               5                   10 cct tat cga acc aac tct tct ttc ggc tca aag tca tcg ctt ctc ttt         98
Pro Tyr Arg Thr Asn Ser Ser Phe Gly Ser Lys Ser Ser Leu Leu Phe
15                  20                  25                  30 cgg tct cca tcc tcc tcc tcc tca gtc tct atg acg aca acg cgt gga        146
Arg Ser Pro Ser Ser Ser Ser Ser Val Ser Met Thr Thr Thr Arg Gly
                35                  40                  45 aac gtg gct gtg gcg gct gct gct aca tcc act gag gcg cta aga aaa        194
Asn Val Ala Val Ala Ala Ala Ala Thr Ser Thr Glu Ala Leu Arg Lys
        50                  55                  60 gga ata gcg gag ttc tac aat gaa act tcg ggt ttg tgg gaa gag att        242
Gly Ile Ala Glu Phe Tyr Asn Glu Thr Ser Gly Leu Trp Glu Glu Ile
65                  70                  75 tgg gga gat cat atg cat cat ggc ttt tat gac cct gat tct tct gtt        290
Trp Gly Asp His Met His His Gly Phe Tyr Asp Pro Asp Ser Ser Val
80                  85                  90 caa ctt tct gat tct ggt cac aag gaa gct cag atc cgt atg att gaa        338
Gln Leu Ser Asp Ser Gly His Lys Glu Ala Gln Ile Arg Met Ile Glu
95                  100                 105                 110 gag tct ctc cgt ttc gcc ggt gtt act gat gaa gag gag gag aaa aag        386
Glu Ser Leu Arg Phe Ala Gly Val Thr Asp Glu Glu Glu Glu Lys Lys
                115                 120                 125 ata aag aaa gta gtg gat gtt ggg tgt ggg att gga gga agc tca aga        434
Ile Lys Lys Val Val Asp Val Gly Cys Gly Ile Gly Gly Ser Ser Arg
        130                 135                 140 tat ctt gcc tct aaa ttt gga gct gaa tgc att ggc att act ctc agc        482
Tyr Leu Ala Ser Lys Phe Gly Ala Glu Cys Ile Gly Ile Thr Leu Ser
145                 150                 155 cct gtt cag gcc aag aga gcc aat gat ctc gcg gct gct caa tca ctc        530
Pro Val Gln Ala Lys Arg Ala Asn Asp Leu Ala Ala Ala Gln Ser Leu
160                 165                 170 tct cat aag gct tcc ttc caa gtt gcg gat gcg ttg gat cag cca ttc        578
Ser His Lys Ala Ser Phe Gln Val Ala Asp Ala Leu Asp Gln Pro Phe
175                 180                 185                 190 gaa gat gga aaa ttc gat cta gtg tgg tcg atg gag agt ggt gag cat        626
Glu Asp Gly Lys Phe Asp Leu Val Trp Ser Met Glu Ser Gly Glu His
                195                 200                 205 atg cct gac aag gcc aag ttt gta aaa gag ttg gta cgt gtg gcg gct        674
Met Pro Asp Lys Ala Lys Phe Val Lys Glu Leu Val Arg Val Ala Ala
        210                 215                 220 cca gga ggt agg ata ata ata gtg aca tgg tgc cat aga aat cta tct        722
Pro Gly Gly Arg Ile Ile Ile Val Thr Trp Cys His Arg Asn Leu Ser
225                 230                 235 gcg ggg gag gaa gct ttg cag ccg tgg gag caa aac atc ttg gac aaa        770
Ala Gly Glu Glu Ala Leu Gln Pro Trp Glu Gln Asn Ile Leu Asp Lys
240                 245                 250 atc tgt aag acg ttc tat ctc ccg gct tgg tgc tcc acc gat gat tat        818
Ile Cys Lys Thr Phe Tyr Leu Pro Ala Trp Cys Ser Thr Asp Asp Tyr
255                 260                 265                 270 gtc aac ttg ctt caa tcc cat tct ctc cag gat att aag tgt gcg gat        866
```

```
Val Asn Leu Leu Gln Ser His Ser Leu Gln Asp Ile Lys Cys Ala Asp
                275                 280                 285 tgg tca gag aac gta gct cct ttc tgg cct gcg gtt ata cgg act gca    914
Trp Ser Glu Asn Val Ala Pro Phe Trp Pro Ala Val Ile Arg Thr Ala
        290                 295                 300 tta aca tgg aag ggc ctt gtg tct ctg ctt cgt agt ggt atg aaa agt    962
Leu Thr Trp Lys Gly Leu Val Ser Leu Leu Arg Ser Gly Met Lys Ser
            305                 310                 315 att aaa gga gca ttg aca atg cca ttg atg att gaa ggt tac aag aaa   1010
Ile Lys Gly Ala Leu Thr Met Pro Leu Met Ile Glu Gly Tyr Lys Lys
320                 325                 330 ggt gtc att aag ttt ggt atc atc act tgc cag aag cca ctc taa       1055
Gly Val Ile Lys Phe Gly Ile Ile Thr Cys Gln Lys Pro Leu *
335                 340                 345 gtctaaagct atacta                                                  1071

<210> SEQ ID NO 26
<211> LENGTH: 348
<212> TYPE: PRT
<213> ORGANISM: Arabidopsis thaliana

<400> SEQUENCE: 26

Met Lys Ala Thr Leu Ala Ala Pro Ser Ser Leu Thr Ser Leu Pro Tyr
 1               5                  10                  15

Arg Thr Asn Ser Ser Phe Gly Ser Lys Ser Ser Leu Leu Phe Arg Ser
            20                  25                  30

Pro Ser Ser Ser Ser Val Ser Met Thr Thr Thr Arg Gly Asn Val
        35                  40                  45

Ala Val Ala Ala Ala Ala Thr Ser Thr Glu Ala Leu Arg Lys Gly Ile
 50                  55                  60

Ala Glu Phe Tyr Asn Glu Thr Ser Gly Leu Trp Glu Ile Trp Gly
 65                  70                  75                  80

Asp His Met His His Gly Phe Tyr Asp Pro Asp Ser Ser Val Gln Leu
                 85                  90                  95

Ser Asp Ser Gly His Lys Glu Ala Gln Ile Arg Met Ile Glu Glu Ser
            100                 105                 110

Leu Arg Phe Ala Gly Val Thr Asp Glu Glu Glu Lys Lys Ile Lys
        115                 120                 125

Lys Val Val Asp Val Gly Cys Gly Ile Gly Gly Ser Ser Arg Tyr Leu
130                 135                 140

Ala Ser Lys Phe Gly Ala Glu Cys Ile Gly Ile Thr Leu Ser Pro Val
145                 150                 155                 160

Gln Ala Lys Arg Ala Asn Asp Leu Ala Ala Gln Ser Leu Ser His
                165                 170                 175

Lys Ala Ser Phe Gln Val Ala Asp Ala Leu Asp Gln Pro Phe Glu Asp
                180                 185                 190

Gly Lys Phe Asp Leu Val Trp Ser Met Glu Ser Gly Glu His Met Pro
            195                 200                 205

Asp Lys Ala Lys Phe Val Lys Glu Leu Val Arg Val Ala Ala Pro Gly
210                 215                 220

Gly Arg Ile Ile Ile Val Thr Trp Cys His Arg Asn Leu Ser Ala Gly
225                 230                 235                 240

Glu Glu Ala Leu Gln Pro Trp Glu Gln Asn Ile Leu Asp Lys Ile Cys
                245                 250                 255

Lys Thr Phe Tyr Leu Pro Ala Trp Cys Ser Thr Asp Asp Tyr Val Asn
                260                 265                 270
```

```
Leu Leu Gln Ser His Ser Leu Gln Asp Ile Lys Cys Ala Asp Trp Ser
        275                 280                 285

Glu Asn Val Ala Pro Phe Trp Pro Ala Val Ile Arg Thr Ala Leu Thr
        290                 295                 300

Trp Lys Gly Leu Val Ser Leu Leu Arg Ser Gly Met Lys Ser Ile Lys
305                 310                 315                 320

Gly Ala Leu Thr Met Pro Leu Met Ile Glu Gly Tyr Lys Lys Gly Val
                325                 330                 335

Ile Lys Phe Gly Ile Ile Thr Cys Gln Lys Pro Leu
            340                 345

<210> SEQ ID NO 27
<211> LENGTH: 768
<212> TYPE: DNA
<213> ORGANISM: Arabidopsis thaliana
<220> FEATURE:
<221> NAME/KEY: CDS
<222> LOCATION: (3)...(752)

<400> SEQUENCE: 27 ag atg aag ttc aac gtt gcg aat cca act act gga tgc cag aag aag         47
   Met Lys Phe Asn Val Ala Asn Pro Thr Thr Gly Cys Gln Lys Lys
    1               5                  10                  15 ctc gag atc gac gat gac cag aaa cta cgt gcg ttt tac gac aag aga        95
Leu Glu Ile Asp Asp Asp Gln Lys Leu Arg Ala Phe Tyr Asp Lys Arg
                 20                  25                  30 atc tct caa gaa gtc agt gga gat gct ttg ggc gag gag ttc aaa gga       143
Ile Ser Gln Glu Val Ser Gly Asp Ala Leu Gly Glu Glu Phe Lys Gly
             35                  40                  45 tac gtt ttc aag atc aag ggt ggt tgc gat aag caa ggt ttc cca atg       191
Tyr Val Phe Lys Ile Lys Gly Gly Cys Asp Lys Gln Gly Phe Pro Met
         50                  55                  60 aag cag gga gtt ttg act cca ggc cgt gtt cgc ctt ttg ctt cac cga       239
Lys Gln Gly Val Leu Thr Pro Gly Arg Val Arg Leu Leu Leu His Arg
 65                  70                  75 gga act cct tgc ttc aga gga cat gga agg aga act ggt gag agg aga       287
Gly Thr Pro Cys Phe Arg Gly His Gly Arg Arg Thr Gly Glu Arg Arg
 80                  85                  90                  95 aga aag tct gtt cgt ggt tgc att gtg agc cct gat ctc tct gtt ctg       335
Arg Lys Ser Val Arg Gly Cys Ile Val Ser Pro Asp Leu Ser Val Leu
                100                 105                 110 aac ctt gtc att gtg aag aag ggt gag aac gat ctt cct ggg ctt acc       383
Asn Leu Val Ile Val Lys Lys Gly Glu Asn Asp Leu Pro Gly Leu Thr
            115                 120                 125 gat cat gag agc aag atg aga gga cca aag aga gcc tcc aag atc cgt       431
Asp His Glu Ser Lys Met Arg Gly Pro Lys Arg Ala Ser Lys Ile Arg
        130                 135                 140 aaa ctg ttt aac ctc aag aag gaa gat gat gtc agg acc tat gtc aac       479
Lys Leu Phe Asn Leu Lys Lys Glu Asp Asp Val Arg Thr Tyr Val Asn
145                 150                 155 act tac cgc cgc aag ttc aca aac aag aag ggc aag gaa gtt agc aaa       527
Thr Tyr Arg Arg Lys Phe Thr Asn Lys Lys Gly Lys Glu Val Ser Lys
160                 165                 170                 175 gcc cct aag atc cag agg ctt gtg acc cca ttg act ctt cag agg aag       575
Ala Pro Lys Ile Gln Arg Leu Val Thr Pro Leu Thr Leu Gln Arg Lys
                180                 185                 190 aga gct aga att gct gac aag aag aag aaa att gct aag gct aat tct       623
Arg Ala Arg Ile Ala Asp Lys Lys Lys Lys Ile Ala Lys Ala Asn Ser
            195                 200                 205
```

```
gat gct gct gat tac cag aag ctt ctc gcc tcg agg ttg aag gaa cag    671
Asp Ala Ala Asp Tyr Gln Lys Leu Leu Ala Ser Arg Leu Lys Glu Gln
        210                 215                 220 cgt gac agg agg agt gag agt ttg gca aaa gag agg tcg aga ctc tct    719
Arg Asp Arg Arg Ser Glu Ser Leu Ala Lys Glu Arg Ser Arg Leu Ser
    225                 230                 235 tct gct gct gcc aag ccc tct gtc aca gct taa aaaagcttga gattca      768
Ser Ala Ala Ala Lys Pro Ser Val Thr Ala *
240                 245
```

<210> SEQ ID NO 28
<211> LENGTH: 249
<212> TYPE: PRT
<213> ORGANISM: Arabidopsis thaliana

<400> SEQUENCE: 28

```
Met Lys Phe Asn Val Ala Asn Pro Thr Thr Gly Cys Gln Lys Lys Leu
 1               5                  10                  15

Glu Ile Asp Asp Gln Lys Leu Arg Ala Phe Tyr Asp Lys Arg Ile
                20                  25                  30

Ser Gln Glu Val Ser Gly Asp Ala Leu Gly Glu Glu Phe Lys Gly Tyr
            35                  40                  45

Val Phe Lys Ile Lys Gly Gly Cys Asp Lys Gln Gly Phe Pro Met Lys
         50                  55                  60

Gln Gly Val Leu Thr Pro Gly Arg Val Arg Leu Leu His Arg Gly
65                   70                  75                  80

Thr Pro Cys Phe Arg Gly His Gly Arg Arg Thr Gly Glu Arg Arg
                    85                  90                  95

Lys Ser Val Arg Gly Cys Ile Val Ser Pro Asp Leu Ser Val Leu Asn
                100                 105                 110

Leu Val Ile Val Lys Lys Gly Glu Asn Asp Leu Pro Gly Leu Thr Asp
            115                 120                 125

His Glu Ser Lys Met Arg Gly Pro Lys Arg Ala Ser Lys Ile Arg Lys
        130                 135                 140

Leu Phe Asn Leu Lys Lys Glu Asp Asp Val Arg Thr Tyr Val Asn Thr
145                 150                 155                 160

Tyr Arg Arg Lys Phe Thr Asn Lys Lys Gly Lys Glu Val Ser Lys Ala
                    165                 170                 175

Pro Lys Ile Gln Arg Leu Val Thr Pro Leu Thr Leu Gln Arg Lys Arg
                180                 185                 190

Ala Arg Ile Ala Asp Lys Lys Lys Ile Ala Lys Ala Asn Ser Asp
            195                 200                 205

Ala Ala Asp Tyr Gln Lys Leu Leu Ala Ser Arg Leu Lys Glu Gln Arg
        210                 215                 220

Asp Arg Arg Ser Glu Ser Leu Ala Lys Glu Arg Ser Arg Leu Ser Ser
225                 230                 235                 240

Ala Ala Ala Lys Pro Ser Val Thr Ala
                245
```

<210> SEQ ID NO 29
<211> LENGTH: 1201
<212> TYPE: DNA
<213> ORGANISM: Arabidopsis thaliana
<220> FEATURE:
<221> NAME/KEY: CDS
<222> LOCATION: (24)...(35)
<220> FEATURE:
<221> NAME/KEY: CDS
<222> LOCATION: (147)...(187)

```
<220> FEATURE:
<221> NAME/KEY: CDS
<222> LOCATION: (283)...(383)
<220> FEATURE:
<221> NAME/KEY: CDS
<222> LOCATION: (689)...(833)
<220> FEATURE:
<221> NAME/KEY: CDS
<222> LOCATION: (916)...(1005)
<220> FEATURE:
<221> NAME/KEY: CDS
<222> LOCATION: (1103)...(1196)

<400> SEQUENCE: 29
cacgcgggag ctcaacatca gcc atg gcg gaa cag gttactcgat ctgttctctc      55
                          Met Ala Glu Gln
                            1 ctctaagctt atcctcgttt tatgatctat tgatccttat tcactcaaat gattctaata    115 yctcttctct ttctctgtca ctaattttca g act gag aaa gct ttt ctt aag       167
                                   Thr Glu Lys Ala Phe Leu Lys
                                     5                  10 cag cct aag gtc ttc ctt ag gtaattttgc gattcgattt ctctctgttc          217
Gln Pro Lys Val Phe Leu Ser
            15 tctattgttt cattgtattt aagttccaag ttgtttatat tgttcattgt ttctgattta    277 tcaag c tcg aag aaa tct gga aag gga aag aga cct gga aaa ggt gga      325
        Ser Lys Lys Ser Gly Lys Gly Lys Arg Pro Gly Lys Gly Gly
          20                  25                  30 aac cgt ttc tgg aag aac att ggt ttg ggc ttc aag act cct cgt gaa      373
Asn Arg Phe Trp Lys Asn Ile Gly Leu Gly Phe Lys Thr Pro Arg Glu
            35                  40                  45 gcc att gat g gtatgtttaa gcttttaact cgttataata gataaggaac            423
Ala Ile Asp
       50 tcttggattg tgttgttcat atagtcgata gatttcaaat gctattttgt cttgtagaat    483 cttaagcttt ggtttagtga gttctgattc ttcagcttta tctggatcta cattactgtt    543 tcagtgatgc aaatgttatc agtagatttt gaattagtag gatgtcactg atttgaatat    603 gtgatcaagc ttcatagaaa cctgcatcat tctctatata cctttaagtc agattctcag    663 gttattgtgt atttgtgtgg aacag ga gct tac gtt gac aag aaa tgc ccc       714
                             Gly Ala Tyr Val Asp Lys Lys Cys Pro
                                    55                  60 ttc act gga act gtt tcc att aga ggt cgt atc tta gct ggt act tgc      762
Phe Thr Gly Thr Val Ser Ile Arg Gly Arg Ile Leu Ala Gly Thr Cys
            65                  70                  75 cac agt gcg aaa atg cag agg acc att atc gtg cga agg gat tac ctt      810
His Ser Ala Lys Met Gln Arg Thr Ile Ile Val Arg Arg Asp Tyr Leu
        80                  85                  90 cac ttt gtg aag aag tat cag ag gtaaattcat acattctcat acttctttcc      863
His Phe Val Lys Lys Tyr Gln Arg
        95                  100 atagagtctt acacattgat gtttaagaaa gtaatatcct ttttgttctt ag g tat      919
                                                           Tyr gag aag agg cat tca aac att ccg gct cat gtc tca cca tgc ttc cgt      967
Glu Lys Arg His Ser Asn Ile Pro Ala His Val Ser Pro Cys Phe Arg
        105                 110                 115 gtt aag gaa gga gac cat atc atc att ggc caa tgc ag gttatgatct        1015
Val Lys Glu Gly Asp His Ile Ile Ile Gly Gln Cys Arg
        120                 125                 130 gattcaaacc tacaaattgt ctccattgat tctgattatc gtgaatttgt tttgatcttt    1075
```

| | |
|---|---|
| ttgtttgtta atgattgata atttcag g cca ttg tcg aag aca gtg agg ttc<br>                                                    Pro Leu Ser Lys Thr Val Arg Phe<br>                                                                 135 | 1127 |
| aat gtg ttg aag gtg ata cca gct ggg tct tct tct tca ttt gga aag<br>Asn Val Leu Lys Val Ile Pro Ala Gly Ser Ser Ser Ser Phe Gly Lys<br>   140                        145                        150 | 1175 |
| aag gca ttc act gga atg taa gctgc<br>Lys Ala Phe Thr Gly Met *<br>155                   160 | 1201 |

<210> SEQ ID NO 30
<211> LENGTH: 160
<212> TYPE: PRT
<213> ORGANISM: Arabidopsis thaliana

<400> SEQUENCE: 30

Met Ala Glu Gln Thr Glu Lys Ala Phe Leu Lys Gln Pro Lys Val Phe
1               5                   10                  15

Leu Ser Ser Lys Lys Ser Gly Lys Gly Lys Arg Pro Gly Lys Gly Gly
            20                  25                  30

Asn Arg Phe Trp Lys Asn Ile Gly Leu Gly Phe Lys Thr Pro Arg Glu
        35                  40                  45

Ala Ile Asp Gly Ala Tyr Val Asp Lys Lys Cys Pro Phe Thr Gly Thr
    50                  55                  60

Val Ser Ile Arg Gly Arg Ile Leu Ala Gly Thr Cys His Ser Ala Lys
65                  70                  75                  80

Met Gln Arg Thr Ile Ile Val Arg Arg Asp Tyr Leu His Phe Val Lys
                85                  90                  95

Lys Tyr Gln Arg Tyr Glu Lys Arg His Ser Asn Ile Pro Ala His Val
            100                 105                 110

Ser Pro Cys Phe Arg Val Lys Glu Gly Asp His Ile Ile Ile Gly Gln
        115                 120                 125

Cys Arg Pro Leu Ser Lys Thr Val Arg Phe Asn Val Leu Lys Val Ile
    130                 135                 140

Pro Ala Gly Ser Ser Ser Ser Phe Gly Lys Lys Ala Phe Thr Gly Met
145                 150                 155                 160

<210> SEQ ID NO 31
<211> LENGTH: 1791
<212> TYPE: DNA
<213> ORGANISM: Arabidopsis thaliana
<220> FEATURE:
<221> NAME/KEY: CDS
<222> LOCATION: (23)...(1780)

<400> SEQUENCE: 31

| | |
|---|---|
| tgtgagtaat ttagcgaaaa cg atg ggt tcc atc gaa gaa gaa gca aga cct<br>                                   Met Gly Ser Ile Glu Glu Glu Ala Arg Pro<br>                                    1              5                     10 | 52 |
| ctc atc gaa gaa ggt tta att tta cag gaa gtg aaa ttg tat gct gaa<br>Leu Ile Glu Glu Gly Leu Ile Leu Gln Glu Val Lys Leu Tyr Ala Glu<br>               15                     20                     25 | 100 |
| gat ggt tca gtg gac ttt aat gga aac cca cca ttg aag gag aaa aca<br>Asp Gly Ser Val Asp Phe Asn Gly Asn Pro Pro Leu Lys Glu Lys Thr<br>        30                     35                     40 | 148 |
| gga aac tgg aaa gct tgt cct ttt att ctt ggt aat gaa tgt tgt gag<br>Gly Asn Trp Lys Ala Cys Pro Phe Ile Leu Gly Asn Glu Cys Cys Glu<br>     45                     50                     55 | 196 |
| agg cta gct tac tat ggt att gct ggg aat tta atc act tac ctc acc<br>Arg Leu Ala Tyr Tyr Gly Ile Ala Gly Asn Leu Ile Thr Tyr Leu Thr | 244 |

|  |  |
|---|---:|
| ```
                 60                  65                  70
act aag ctt cac caa gga aat gtt tct gct gct aca aac gtt acc aca
Thr Lys Leu His Gln Gly Asn Val Ser Ala Ala Thr Asn Val Thr Thr
 75                  80                  85                  90
``` | 292 |
| ```
tgg caa ggg act tgt tat ctc act cct ctc att gga gct gtt ctg gct
Trp Gln Gly Thr Cys Tyr Leu Thr Pro Leu Ile Gly Ala Val Leu Ala
                 95                 100                 105
``` | 340 |
| ```
gat gct tac tgg gga cgt tac tgg acc atc gct tgt ttc tcc ggg att
Asp Ala Tyr Trp Gly Arg Tyr Trp Thr Ile Ala Cys Phe Ser Gly Ile
            110                 115                 120
``` | 388 |
| ```
tat ttc atc ggg atg tct gcg tta act ctt tca gct tca gtt ccg gca
Tyr Phe Ile Gly Met Ser Ala Leu Thr Leu Ser Ala Ser Val Pro Ala
        125                 130                 135
``` | 436 |
| ```
ttg aag cca gcg gaa tgt att ggt gac ttt tgt cca tct gca acg cca
Leu Lys Pro Ala Glu Cys Ile Gly Asp Phe Cys Pro Ser Ala Thr Pro
    140                 145                 150
``` | 484 |
| ```
gct cag tat gcg atg ttc ttt ggt ggg ctt tac ctg atc gct ctt gga
Ala Gln Tyr Ala Met Phe Phe Gly Gly Leu Tyr Leu Ile Ala Leu Gly
155                 160                 165                 170
``` | 532 |
| ```
act gga ggt atc aaa ccg tgt gtc tca tcc ttc ggt gcc gat cag ttt
Thr Gly Gly Ile Lys Pro Cys Val Ser Ser Phe Gly Ala Asp Gln Phe
                175                 180                 185
``` | 580 |
| ```
gat gac acg gac tct cgg gaa cga gtt aga aaa gct tcg ttc ttt aac
Asp Asp Thr Asp Ser Arg Glu Arg Val Arg Lys Ala Ser Phe Phe Asn
            190                 195                 200
``` | 628 |
| ```
tgg ttt tac ttc tcc atc aat att gga gca ctt gtg tca tct agt ctt
Trp Phe Tyr Phe Ser Ile Asn Ile Gly Ala Leu Val Ser Ser Ser Leu
        205                 210                 215
``` | 676 |
| ```
cta gtt tgg att caa gag aat cgg ggg tgg ggt tta ggg ttt ggg ata
Leu Val Trp Ile Gln Glu Asn Arg Gly Trp Gly Leu Gly Phe Gly Ile
    220                 225                 230
``` | 724 |
| ```
cca aca gtg ttc atg gga cta gcc att gca agt ttc ttc ttt ggc aca
Pro Thr Val Phe Met Gly Leu Ala Ile Ala Ser Phe Phe Phe Gly Thr
235                 240                 245                 250
``` | 772 |
| ```
cct ctt tat agg ttt cag aaa cct gga gga agc cct ata act cgg att
Pro Leu Tyr Arg Phe Gln Lys Pro Gly Gly Ser Pro Ile Thr Arg Ile
                255                 260                 265
``` | 820 |
| ```
tcc caa gtc gtg gtt gct tcg ttc cgg aaa tcg tct gtc aaa gtc cct
Ser Gln Val Val Val Ala Ser Phe Arg Lys Ser Ser Val Lys Val Pro
            270                 275                 280
``` | 868 |
| ```
gaa gac gcc aca ctt ctg tat gaa act caa gac aag aac tct gct att
Glu Asp Ala Thr Leu Leu Tyr Glu Thr Gln Asp Lys Asn Ser Ala Ile
        285                 290                 295
``` | 916 |
| ```
gct gga agt aga aaa atc gag cat acc gat gat tgc cag tat ctt gac
Ala Gly Ser Arg Lys Ile Glu His Thr Asp Asp Cys Gln Tyr Leu Asp
    300                 305                 310
``` | 964 |
| ```
aaa gcc gct gtt atc tca gaa gaa gaa tcg aaa tcc gga gat tat tcc
Lys Ala Ala Val Ile Ser Glu Glu Glu Ser Lys Ser Gly Asp Tyr Ser
315                 320                 325                 330
``` | 1012 |
| ```
aac tcg tgg aga cta tgc acg gtt acg caa gtc gaa gaa ctc aag att
Asn Ser Trp Arg Leu Cys Thr Val Thr Gln Val Glu Glu Leu Lys Ile
                335                 340                 345
``` | 1060 |
| ```
ctg atc cga atg ttc cca atc tgg gct tct ggt atc att ttc tca gct
Leu Ile Arg Met Phe Pro Ile Trp Ala Ser Gly Ile Ile Phe Ser Ala
            350                 355                 360
``` | 1108 |
| ```
gta tac gca caa atg tcc aca atg ttt gtt caa caa ggc cga gcc atg
Val Tyr Ala Gln Met Ser Thr Met Phe Val Gln Gln Gly Arg Ala Met
        365                 370                 375
``` | 1156 |
| ```
aac tgc aaa att gga tca ttc cag ctt cct cct gca gca ctc ggg aca
``` | 1204 |

```
Asn Cys Lys Ile Gly Ser Phe Gln Leu Pro Pro Ala Ala Leu Gly Thr
            380                 385                 390 ttc gac aca gca agc gtc atc atc tgg gtg ccg ctc tac gac cgg ttc      1252
Phe Asp Thr Ala Ser Val Ile Ile Trp Val Pro Leu Tyr Asp Arg Phe
395                 400                 405                 410 atc gtt ccc tta gca aga aag ttc aca gga gta gac aaa gga ttc act      1300
Ile Val Pro Leu Ala Arg Lys Phe Thr Gly Val Asp Lys Gly Phe Thr
            415                 420                 425 gag ata caa aga atg gga att ggt ctg ttt gtc tct gtt ctc tgt atg      1348
Glu Ile Gln Arg Met Gly Ile Gly Leu Phe Val Ser Val Leu Cys Met
                430                 435                 440 gca gct gca gct atc gtc gaa atc atc cgt ctc cat atg gcc aac gat      1396
Ala Ala Ala Ala Ile Val Glu Ile Ile Arg Leu His Met Ala Asn Asp
            445                 450                 455 ctt gga tta gtc gag tca gga gcc cca gtt ccc ata tcc gtc ttg tgg      1444
Leu Gly Leu Val Glu Ser Gly Ala Pro Val Pro Ile Ser Val Leu Trp
460                 465                 470 cag att cca cag tac ttc att ctc ggt gca gcc gaa gta ttc tac ttc      1492
Gln Ile Pro Gln Tyr Phe Ile Leu Gly Ala Ala Glu Val Phe Tyr Phe
475                 480                 485                 490 atc ggt cag ctc gag ttc ttc tac gac caa tct cca gat gca atg aga      1540
Ile Gly Gln Leu Glu Phe Phe Tyr Asp Gln Ser Pro Asp Ala Met Arg
                495                 500                 505 agc ttg tgc agt gcc tta gct ctt ttg acc aat gca ctt ggt aac tac      1588
Ser Leu Cys Ser Ala Leu Ala Leu Leu Thr Asn Ala Leu Gly Asn Tyr
            510                 515                 520 ttg agc tcg ttg atc ctc acg ctc gtg act tat ttt aca aca aga aat      1636
Leu Ser Ser Leu Ile Leu Thr Leu Val Thr Tyr Phe Thr Thr Arg Asn
525                 530                 535 ggg caa gaa ggt tgg att tcg gat aat ctc aat tca ggt cat ctc gat      1684
Gly Gln Glu Gly Trp Ile Ser Asp Asn Leu Asn Ser Gly His Leu Asp
540                 545                 550 tac ttc ttc tgg ctc ttg gct ggt ctt agc ctt gtg aac atg gcg gtt      1732
Tyr Phe Phe Trp Leu Leu Ala Gly Leu Ser Leu Val Asn Met Ala Val
555                 560                 565                 570 tac ttc ttc tct gct gct agg tat aag caa aag aaa gct tcg tcg tag      1780
Tyr Phe Phe Ser Ala Ala Arg Tyr Lys Gln Lys Lys Ala Ser Ser *
                575                 580                 585 taatgctgtt a                                                          1791

<210> SEQ ID NO 32
<211> LENGTH: 585
<212> TYPE: PRT
<213> ORGANISM: Arabidopsis thaliana

<400> SEQUENCE: 32

Met Gly Ser Ile Glu Glu Ala Arg Pro Leu Ile Glu Glu Gly Leu
1               5                   10                  15

Ile Leu Gln Glu Val Lys Leu Tyr Ala Glu Asp Gly Ser Val Asp Phe
            20                  25                  30

Asn Gly Asn Pro Pro Leu Lys Glu Lys Thr Gly Asn Trp Lys Ala Cys
        35                  40                  45

Pro Phe Ile Leu Gly Asn Glu Cys Cys Glu Arg Leu Ala Tyr Tyr Gly
    50                  55                  60

Ile Ala Gly Asn Leu Ile Thr Tyr Leu Thr Lys Leu His Gln Gly
65                  70                  75                  80

Asn Val Ser Ala Ala Thr Asn Val Thr Thr Trp Gln Gly Thr Cys Tyr
                85                  90                  95
```

```
Leu Thr Pro Leu Ile Gly Ala Val Leu Ala Asp Ala Tyr Trp Gly Arg
        100                 105                 110

Tyr Trp Thr Ile Ala Cys Phe Ser Gly Ile Tyr Phe Ile Gly Met Ser
        115                 120                 125

Ala Leu Thr Leu Ser Ala Ser Val Pro Ala Leu Lys Pro Ala Glu Cys
        130                 135                 140

Ile Gly Asp Phe Cys Pro Ser Ala Thr Pro Ala Gln Tyr Ala Met Phe
145                 150                 155                 160

Phe Gly Gly Leu Tyr Leu Ile Ala Leu Gly Thr Gly Ile Lys Pro
                    165                 170                 175

Cys Val Ser Ser Phe Gly Ala Asp Gln Phe Asp Thr Asp Ser Arg
                180                 185                 190

Glu Arg Val Arg Lys Ala Ser Phe Phe Asn Trp Phe Tyr Phe Ser Ile
        195                 200                 205

Asn Ile Gly Ala Leu Val Ser Ser Leu Leu Val Trp Ile Gln Glu
210                 215                 220

Asn Arg Gly Trp Gly Leu Gly Phe Gly Ile Pro Thr Val Phe Met Gly
225                 230                 235                 240

Leu Ala Ile Ala Ser Phe Phe Phe Gly Thr Pro Leu Tyr Arg Phe Gln
                    245                 250                 255

Lys Pro Gly Gly Ser Pro Ile Thr Arg Ile Ser Gln Val Val Ala
                260                 265                 270

Ser Phe Arg Lys Ser Ser Val Lys Val Pro Glu Asp Ala Thr Leu Leu
        275                 280                 285

Tyr Glu Thr Gln Asp Lys Asn Ser Ala Ile Ala Gly Ser Arg Lys Ile
        290                 295                 300

Glu His Thr Asp Asp Cys Gln Tyr Leu Asp Lys Ala Ala Val Ile Ser
305                 310                 315                 320

Glu Glu Glu Ser Lys Ser Gly Asp Tyr Ser Asn Ser Trp Arg Leu Cys
                325                 330                 335

Thr Val Thr Gln Val Glu Glu Leu Lys Ile Leu Ile Arg Met Phe Pro
        340                 345                 350

Ile Trp Ala Ser Gly Ile Ile Phe Ser Ala Val Tyr Ala Gln Met Ser
        355                 360                 365

Thr Met Phe Val Gln Gln Gly Arg Ala Met Asn Cys Lys Ile Gly Ser
        370                 375                 380

Phe Gln Leu Pro Pro Ala Ala Leu Gly Thr Phe Asp Thr Ala Ser Val
385                 390                 395                 400

Ile Ile Trp Val Pro Leu Tyr Asp Arg Phe Ile Val Pro Leu Ala Arg
                405                 410                 415

Lys Phe Thr Gly Val Asp Lys Gly Phe Thr Glu Ile Gln Arg Met Gly
                420                 425                 430

Ile Gly Leu Phe Val Ser Val Leu Cys Met Ala Ala Ala Ile Val
                435                 440                 445

Glu Ile Ile Arg Leu His Met Ala Asn Asp Leu Gly Leu Val Glu Ser
        450                 455                 460

Gly Ala Pro Val Pro Ile Ser Val Leu Trp Gln Ile Pro Gln Tyr Phe
465                 470                 475                 480

Ile Leu Gly Ala Ala Glu Val Phe Tyr Phe Ile Gly Gln Leu Glu Phe
                    485                 490                 495

Phe Tyr Asp Gln Ser Pro Asp Ala Met Arg Ser Leu Cys Ser Ala Leu
                500                 505                 510

Ala Leu Leu Thr Asn Ala Leu Gly Asn Tyr Leu Ser Ser Leu Ile Leu
```

```
                      515                 520                 525
Thr Leu Val Thr Tyr Phe Thr Thr Arg Asn Gly Gln Glu Gly Trp Ile
            530                 535                 540

Ser Asp Asn Leu Asn Ser Gly His Leu Asp Tyr Phe Trp Leu Leu
545                 550                 555                 560

Ala Gly Leu Ser Leu Val Asn Met Ala Val Tyr Phe Ser Ala Ala
                565                 570                 575

Arg Tyr Lys Gln Lys Lys Ala Ser Ser
            580                 585

<210> SEQ ID NO 33
<211> LENGTH: 1984
<212> TYPE: DNA
<213> ORGANISM: Arabidopsis thaliana
<220> FEATURE:
<221> NAME/KEY: CDS
<222> LOCATION: (20)...(1975)

<400> SEQUENCE: 33
ttcaccgtcg gcttctcaa atg cag gat att ctc gga tcg gtt cgc cga tcc         52
                    Met Gln Asp Ile Leu Gly Ser Val Arg Arg Ser
                     1               5                  10 ttg gtt ttc cgg tcg tct ttg gcc gga gac gat ggt act agc ggc gga        100
Leu Val Phe Arg Ser Ser Leu Ala Gly Asp Asp Gly Thr Ser Gly Gly
             15                  20                  25 ggt ctt agc gga ttc gtc ggg aag att aac tct agt atc cgt agc tct        148
Gly Leu Ser Gly Phe Val Gly Lys Ile Asn Ser Ser Ile Arg Ser Ser
         30                  35                  40 cga att ggg ctc ttt tct aag ccg cct cca ggg ctt cct gct cct aga        196
Arg Ile Gly Leu Phe Ser Lys Pro Pro Pro Gly Leu Pro Ala Pro Arg
     45                  50                  55 aaa gaa gaa gcg ccg tcg att cgg tgg agg aaa ggg gaa tta atc ggt        244
Lys Glu Glu Ala Pro Ser Ile Arg Trp Arg Lys Gly Glu Leu Ile Gly
 60                  65                  70                  75 tgc ggt gct ttt gga aga gtt tac atg gga atg aac ctc gat tcc ggc        292
Cys Gly Ala Phe Gly Arg Val Tyr Met Gly Met Asn Leu Asp Ser Gly
                 80                  85                  90 gag ctt ctt gca att aaa cag gtt tta atc gct cca agc agt gct tca        340
Glu Leu Leu Ala Ile Lys Gln Val Leu Ile Ala Pro Ser Ser Ala Ser
             95                 100                 105 aag gag aag act cag ggt cac atc cga gag ctt gag gaa gaa gta caa        388
Lys Glu Lys Thr Gln Gly His Ile Arg Glu Leu Glu Glu Glu Val Gln
        110                 115                 120 ctt ctt aag aat ctt tca cat ccg aac atc gtt aga tac ttg ggt act        436
Leu Leu Lys Asn Leu Ser His Pro Asn Ile Val Arg Tyr Leu Gly Thr
    125                 130                 135 gta aga gag agt gat tcg ttg aat att ttg atg gag ttt gtt cct ggt        484
Val Arg Glu Ser Asp Ser Leu Asn Ile Leu Met Glu Phe Val Pro Gly
140                 145                 150                 155 gga tca ata tca tct ttg ttg gag aag ttt gga tct ttt cct gag cct        532
Gly Ser Ile Ser Ser Leu Leu Glu Lys Phe Gly Ser Phe Pro Glu Pro
                160                 165                 170 gtg att att atg tac aca aag caa ctt ctg ctt ggg ctg gaa tat ctt        580
Val Ile Ile Met Tyr Thr Lys Gln Leu Leu Leu Gly Leu Glu Tyr Leu
            175                 180                 185 cac aac aat ggg atc atg cat cga gat att aag ggg gca aat att ttg        628
His Asn Asn Gly Ile Met His Arg Asp Ile Lys Gly Ala Asn Ile Leu
        190                 195                 200 gtc gat aac aaa ggt tgc atc aga ctc gca gat ttt ggt gct tcc aag        676
Val Asp Asn Lys Gly Cys Ile Arg Leu Ala Asp Phe Gly Ala Ser Lys
```

```
                 205                 210                 215
aaa gtt gta gag cta gct act gta aat ggt gcc aaa tct atg aag ggg      724
Lys Val Glu Leu Ala Thr Val Asn Gly Ala Lys Ser Met Lys Gly
220             225                 230                 235 acg cct tat tgg atg gct cct gaa gtc att ctc cag act ggt cat agc      772
Thr Pro Tyr Trp Met Ala Pro Glu Val Ile Leu Gln Thr Gly His Ser
        240                 245                 250 ttc tct gct gat ata tgg agt gtt ggg tgc act gtg att gag atg gct      820
Phe Ser Ala Asp Ile Trp Ser Val Gly Cys Thr Val Ile Glu Met Ala
            255                 260                 265 acg ggg aag cct ccc tgg agc gag cag tat cag cag ttt gct gct gtc      868
Thr Gly Lys Pro Pro Trp Ser Glu Gln Tyr Gln Gln Phe Ala Ala Val
                270                 275                 280 ctt cat att ggt aga aca aaa gct cat cct cca att cca gaa gac ctc      916
Leu His Ile Gly Arg Thr Lys Ala His Pro Pro Ile Pro Glu Asp Leu
    285                 290                 295 tca cca gag gct aaa gac ttt cta atg aaa tgc tta cac aaa gaa cca      964
Ser Pro Glu Ala Lys Asp Phe Leu Met Lys Cys Leu His Lys Glu Pro
300                 305                 310                 315 agc ttg aga ctc tct gca acc gaa ttg ctt cag cac ccg ttt gtc act     1012
Ser Leu Arg Leu Ser Ala Thr Glu Leu Leu Gln His Pro Phe Val Thr
        320                 325                 330 gga aag cgc cag gaa cct tat cca gct tac cgt aat tct ctt acg gaa     1060
Gly Lys Arg Gln Glu Pro Tyr Pro Ala Tyr Arg Asn Ser Leu Thr Glu
            335                 340                 345 tgt gga aac cca ata act act caa gga atg aat gtt cgg agt tca ata     1108
Cys Gly Asn Pro Ile Thr Thr Gln Gly Met Asn Val Arg Ser Ser Ile
                350                 355                 360 aat tcg ttg atc agg agg tcg aca tgt tca ggc ttg aag gat gtc tgt     1156
Asn Ser Leu Ile Arg Arg Ser Thr Cys Ser Gly Leu Lys Asp Val Cys
365                 370                 375 gaa ctg gga agc ttg agg agt tcc att ata tac cca cag aag tca aat     1204
Glu Leu Gly Ser Leu Arg Ser Ser Ile Ile Tyr Pro Gln Lys Ser Asn
380                 385                 390                 395 aac tca gga ttt ggt tgg cga gat gga gac tct gat gac ctt tgt cag     1252
Asn Ser Gly Phe Gly Trp Arg Asp Gly Asp Ser Asp Asp Leu Cys Gln
            400                 405                 410 acc gat atg gat gat ctc tgc aac att gaa tca gtc aga aac aat gtt     1300
Thr Asp Met Asp Asp Leu Cys Asn Ile Glu Ser Val Arg Asn Asn Val
                415                 420                 425 ttg tca cag tcc acc gat tta aac aag agt ttt aat ccc atg tgt gat     1348
Leu Ser Gln Ser Thr Asp Leu Asn Lys Ser Phe Asn Pro Met Cys Asp
        430                 435                 440 tcc acg gat aac tgg tct tgc aag ttt gat gaa agc cca aaa gtg atg     1396
Ser Thr Asp Asn Trp Ser Cys Lys Phe Asp Glu Ser Pro Lys Val Met
445                 450                 455 aaa agc aaa tct aac ctg ctt tct tac caa gct tct caa ctc caa act     1444
Lys Ser Lys Ser Asn Leu Leu Ser Tyr Gln Ala Ser Gln Leu Gln Thr
460                 465                 470                 475 gga gtt cca tgt gat gag gaa acc agc tta aca ttt gct ggt ggc tct     1492
Gly Val Pro Cys Asp Glu Glu Thr Ser Leu Thr Phe Ala Gly Gly Ser
            480                 485                 490 tcc gtt gca gag gat gat tat aaa ggc aca gag ttg aaa ata aaa tca     1540
Ser Val Ala Glu Asp Asp Tyr Lys Gly Thr Glu Leu Lys Ile Lys Ser
                495                 500                 505 ttt ttg gat gag aag gct cag gat ttg aaa agg ttg cag acc cct ctg     1588
Phe Leu Asp Glu Lys Ala Gln Asp Leu Lys Arg Leu Gln Thr Pro Leu
        510                 515                 520 ctt gaa gaa ttc cac aat gct atg aat cca gga ata ccc caa ggt gca     1636
```

```
Leu Glu Glu Phe His Asn Ala Met Asn Pro Gly Ile Pro Gln Gly Ala
    525                 530                 535 ctt gga gac acc aat atc tac aat tta cca aac tta cca agt ata agc   1684
Leu Gly Asp Thr Asn Ile Tyr Asn Leu Pro Asn Leu Pro Ser Ile Ser
540                 545                 550                 555 aag aca cct aaa cga ctt ccg agt aga cga ctc tca gca atc agt gat   1732
Lys Thr Pro Lys Arg Leu Pro Ser Arg Arg Leu Ser Ala Ile Ser Asp
                560                 565                 570 gct atg ccc agc cca ctc aaa agc tcc aaa cgt aca ctg aac aca agc   1780
Ala Met Pro Ser Pro Leu Lys Ser Ser Lys Arg Thr Leu Asn Thr Ser
            575                 580                 585 aga gtg atg cag tca gga act gaa cca act caa gtc aac gag tcg acc   1828
Arg Val Met Gln Ser Gly Thr Glu Pro Thr Gln Val Asn Glu Ser Thr
        590                 595                 600 aag aag gga gta aat aat agc cgt tgt ttc tca gag ata cgt cgg aag   1876
Lys Lys Gly Val Asn Asn Ser Arg Cys Phe Ser Glu Ile Arg Arg Lys
    605                 610                 615 tgg gaa gaa gaa ctc tat gaa gag ctt gag agg cat cga gag aat ctg   1924
Trp Glu Glu Glu Leu Tyr Glu Glu Leu Glu Arg His Arg Glu Asn Leu
620                 625                 630                 635 cga cac gct ggt gca gga ggg aag act cca tta tca ggc cac aaa gga   1972
Arg His Ala Gly Ala Gly Gly Lys Thr Pro Leu Ser Gly His Lys Gly
                640                 645                 650 tag tgaacggct                                                     1984
 *
```

<210> SEQ ID NO 34
<211> LENGTH: 651
<212> TYPE: PRT
<213> ORGANISM: Arabidopsis thaliana

<400> SEQUENCE: 34

```
Met Gln Asp Ile Leu Gly Ser Val Arg Arg Ser Leu Val Phe Arg Ser
1               5                   10                  15

Ser Leu Ala Gly Asp Asp Gly Thr Ser Gly Gly Leu Ser Gly Phe
            20                  25                  30

Val Gly Lys Ile Asn Ser Ser Ile Arg Ser Ser Arg Ile Gly Leu Phe
        35                  40                  45

Ser Lys Pro Pro Pro Gly Leu Pro Ala Pro Arg Lys Glu Glu Ala Pro
    50                  55                  60

Ser Ile Arg Trp Arg Lys Gly Glu Leu Ile Gly Cys Gly Ala Phe Gly
65                  70                  75                  80

Arg Val Tyr Met Gly Met Asn Leu Asp Ser Gly Glu Leu Leu Ala Ile
                85                  90                  95

Lys Gln Val Leu Ile Ala Pro Ser Ser Ala Ser Lys Glu Lys Thr Gln
            100                 105                 110

Gly His Ile Arg Glu Leu Glu Glu Val Gln Leu Leu Lys Asn Leu
        115                 120                 125

Ser His Pro Asn Ile Val Arg Tyr Leu Gly Thr Val Arg Glu Ser Asp
    130                 135                 140

Ser Leu Asn Ile Leu Met Glu Phe Val Pro Gly Gly Ser Ile Ser Ser
145                 150                 155                 160

Leu Leu Glu Lys Phe Gly Ser Phe Pro Glu Pro Val Ile Ile Met Tyr
                165                 170                 175

Thr Lys Gln Leu Leu Leu Gly Leu Glu Tyr Leu His Asn Asn Gly Ile
            180                 185                 190

Met His Arg Asp Ile Lys Gly Ala Asn Ile Leu Val Asp Asn Lys Gly
```

```
                195                 200                 205
Cys Ile Arg Leu Ala Asp Phe Gly Ala Ser Lys Lys Val Val Glu Leu
    210                 215                 220
Ala Thr Val Asn Gly Ala Lys Ser Met Lys Gly Thr Pro Tyr Trp Met
225                 230                 235                 240
Ala Pro Glu Val Ile Leu Gln Thr Gly His Ser Phe Ser Ala Asp Ile
                245                 250                 255
Trp Ser Val Gly Cys Thr Val Ile Glu Met Ala Thr Gly Lys Pro Pro
            260                 265                 270
Trp Ser Glu Gln Tyr Gln Gln Phe Ala Ala Val Leu His Ile Gly Arg
        275                 280                 285
Thr Lys Ala His Pro Pro Ile Pro Glu Asp Leu Ser Pro Glu Ala Lys
    290                 295                 300
Asp Phe Leu Met Lys Cys Leu His Lys Glu Pro Ser Leu Arg Leu Ser
305                 310                 315                 320
Ala Thr Glu Leu Leu Gln His Pro Phe Val Thr Gly Lys Arg Gln Glu
                325                 330                 335
Pro Tyr Pro Ala Tyr Arg Asn Ser Leu Thr Glu Cys Gly Asn Pro Ile
            340                 345                 350
Thr Thr Gln Gly Met Asn Val Arg Ser Ser Ile Asn Ser Leu Ile Arg
        355                 360                 365
Arg Ser Thr Cys Ser Gly Leu Lys Asp Val Cys Glu Leu Gly Ser Leu
    370                 375                 380
Arg Ser Ser Ile Ile Tyr Pro Gln Lys Ser Asn Asn Ser Gly Phe Gly
385                 390                 395                 400
Trp Arg Asp Gly Asp Ser Asp Asp Leu Cys Gln Thr Asp Met Asp Asp
                405                 410                 415
Leu Cys Asn Ile Glu Ser Val Arg Asn Asn Val Leu Ser Gln Ser Thr
            420                 425                 430
Asp Leu Asn Lys Ser Phe Asn Pro Met Cys Asp Ser Thr Asp Asn Trp
        435                 440                 445
Ser Cys Lys Phe Asp Glu Ser Pro Lys Val Met Lys Ser Lys Ser Asn
    450                 455                 460
Leu Leu Ser Tyr Gln Ala Ser Gln Leu Gln Thr Gly Val Pro Cys Asp
465                 470                 475                 480
Glu Glu Thr Ser Leu Thr Phe Ala Gly Gly Ser Ser Val Ala Glu Asp
                485                 490                 495
Asp Tyr Lys Gly Thr Glu Leu Lys Ile Lys Ser Phe Leu Asp Glu Lys
            500                 505                 510
Ala Gln Asp Leu Lys Arg Leu Gln Thr Pro Leu Leu Glu Glu Phe His
        515                 520                 525
Asn Ala Met Asn Pro Gly Ile Pro Gln Gly Ala Leu Gly Asp Thr Asn
    530                 535                 540
Ile Tyr Asn Leu Pro Asn Leu Pro Ser Ile Ser Lys Thr Pro Lys Arg
545                 550                 555                 560
Leu Pro Ser Arg Arg Leu Ser Ala Ile Ser Asp Ala Met Pro Ser Pro
                565                 570                 575
Leu Lys Ser Ser Lys Arg Thr Leu Asn Thr Ser Arg Val Met Gln Ser
            580                 585                 590
Gly Thr Glu Pro Thr Gln Val Asn Glu Ser Thr Lys Lys Gly Val Asn
        595                 600                 605
Asn Ser Arg Cys Phe Ser Glu Ile Arg Arg Lys Trp Glu Glu Glu Leu
    610                 615                 620
```

```
Tyr Glu Glu Leu Glu Arg His Arg Glu Asn Leu Arg His Ala Gly Ala
625                 630                 635                 640

Gly Gly Lys Thr Pro Leu Ser Gly His Lys Gly
            645                 650

<210> SEQ ID NO 35
<211> LENGTH: 1736
<212> TYPE: DNA
<213> ORGANISM: Arabidopsis thaliana
<220> FEATURE:
<221> NAME/KEY: CDS
<222> LOCATION: (1)...(1605)

<400> SEQUENCE: 35 atg ccc cct cct aag atg ctt cca cca acg gca agg gat tca gta gca    48
Met Pro Pro Pro Lys Met Leu Pro Pro Thr Ala Arg Asp Ser Val Ala
 1               5                  10                  15 ggg aca ggg ggt agt cca cca cct cca cct cca cca gct cgg tgg        96
Gly Thr Gly Gly Ser Pro Pro Pro Pro Pro Pro Pro Ala Arg Trp
             20                  25                  30 agg gta gcg ggg gag gga gga ttg gat aca aca cca ccg ccg ccc cct   144
Arg Val Ala Gly Glu Gly Gly Leu Asp Thr Thr Pro Pro Pro Pro Pro
         35                  40                  45 cca acg gca gat aca gtc gtg gcg gga agg acg agt tta ggt gag gcg   192
Pro Thr Ala Asp Thr Val Val Ala Gly Arg Thr Ser Leu Gly Glu Ala
 50                  55                  60 ccc cct cct cgt cag cct cca cgt cct cca aca gca cgg tgg tca gcg   240
Pro Pro Pro Arg Gln Pro Pro Arg Pro Pro Thr Ala Arg Trp Ser Ala
 65                  70                  75                  80 atg ggc aga gtg atg tgc agt ccg ccg ata cca cta tcg cgg agt aga   288
Met Gly Arg Val Met Cys Ser Pro Pro Ile Pro Leu Ser Arg Ser Arg
                 85                  90                  95 cta gcg ctt gac gac caa cgt tgg ccg gat tgg aca acg aac ggt tgg   336
Leu Ala Leu Asp Asp Gln Arg Trp Pro Asp Trp Thr Thr Asn Gly Trp
            100                 105                 110 cta agc atg aga ccg acg tcc tcg cca aca agg cga att gac cca caa   384
Leu Ser Met Arg Pro Thr Ser Ser Pro Thr Arg Arg Ile Asp Pro Gln
        115                 120                 125 ggg gcc cga cga tcc tca gtg tca cca gcg ccg gtg aca acg ggg atg   432
Gly Ala Arg Arg Ser Ser Val Ser Pro Ala Pro Val Thr Thr Gly Met
    130                 135                 140 gcc acc tct cgc act gac gat acg cta ata gag gca gag acc ggt cgc   480
Ala Thr Ser Arg Thr Asp Asp Thr Leu Ile Glu Ala Glu Thr Gly Arg
145                 150                 155                 160 gac tgg acg agg aaa cga atg gtc agg aaa ttg ctt aaa gca agg gcg   528
Asp Trp Thr Arg Lys Arg Met Val Arg Lys Leu Leu Lys Ala Arg Ala
                165                 170                 175 aaa gac tac aag gag ggg gga att gcg gca tac ttt ggt tta cga gtg   576
Lys Asp Tyr Lys Glu Gly Gly Ile Ala Ala Tyr Phe Gly Leu Arg Val
            180                 185                 190 ctg cga tgc tac tcg agg atc gta cga tcg atg aaa cgc cca ggc aac   624
Leu Arg Cys Tyr Ser Arg Ile Val Arg Ser Met Lys Arg Pro Gly Asn
        195                 200                 205 ttg aaa ttc acg tgc cgg agg gat gtg gca ata gcc acg ttc agc ggc   672
Leu Lys Phe Thr Cys Arg Arg Asp Val Ala Ile Ala Thr Phe Ser Gly
    210                 215                 220 aca ggc aga atg cag ctg agt atg aac agc cgt ttg cga gtc gag agc   720
Thr Gly Arg Met Gln Leu Ser Met Asn Ser Arg Leu Arg Val Glu Ser
225                 230                 235                 240 ctc gtg tcc gcg ggc cag agc gtg gcg tca ttc tgc ctt ttc ctg ata   768
```

-continued

```
                Leu Val Ser Ala Gly Gln Ser Val Ala Ser Phe Cys Leu Phe Leu Ile
                                245                 250                 255 tgc acg gcg ccc tcg gcg atg cgg ctg gtt agc ctt ctt aca ctg acc          816
Cys Thr Ala Pro Ser Ala Met Arg Leu Val Ser Leu Leu Thr Leu Thr
            260                 265                 270 cca agc atg acc tac cta aca tgc ggg ctg gga tgg atg acc gtc gtc          864
Pro Ser Met Thr Tyr Leu Thr Cys Gly Leu Gly Trp Met Thr Val Val
        275                 280                 285 gta ctg ccg gcg ata gtg gtc cac tgt tat atg cgc cga cat acg gaa          912
Val Leu Pro Ala Ile Val Val His Cys Tyr Met Arg Arg His Thr Glu
    290                 295                 300 ggg gga tgg cgg tat gcg gca ctc gag gag cat aag acg gag ccg gga          960
Gly Gly Trp Arg Tyr Ala Ala Leu Glu Glu His Lys Thr Glu Pro Gly
305                 310                 315                 320 cga aat gaa aag atc acc cgg agt aga cgc aac tcg gcg ttc ggc ggg         1008
Arg Asn Glu Lys Ile Thr Arg Ser Arg Arg Asn Ser Ala Phe Gly Gly
                325                 330                 335 ctg gtc ggt cga aat aaa aga cga aag aag tcc aag gtc tcc ggg gca         1056
Leu Val Gly Arg Asn Lys Arg Arg Lys Lys Ser Lys Val Ser Gly Ala
            340                 345                 350 ccg aca gcg gtt tac aca gcg atg ttt ttc atg ttc tcc acg gca atc         1104
Pro Thr Ala Val Tyr Thr Ala Met Phe Phe Met Phe Ser Thr Ala Ile
        355                 360                 365 aag ggg atg gtg gtg tgc aca atg aaa aaa aaa gtc aaa aaa agt gcg         1152
Lys Gly Met Val Val Cys Thr Met Lys Lys Lys Val Lys Lys Ser Ala
    370                 375                 380 aat cgc aga ctc cgc cag ttg ctc cga tgg gcg cga tac cac gcg aac         1200
Asn Arg Arg Leu Arg Gln Leu Leu Arg Trp Ala Arg Tyr His Ala Asn
385                 390                 395                 400 gcg ttc ttg ctc tgt tct ctt gca tgc gca cga ttc gcg gca tcg cga         1248
Ala Phe Leu Leu Cys Ser Leu Ala Cys Ala Arg Phe Ala Ala Ser Arg
                405                 410                 415 acg gtc atc cat tgc agt att tac cca cgt ttc ggc ccc tta gcc acg         1296
Thr Val Ile His Cys Ser Ile Tyr Pro Arg Phe Gly Pro Leu Ala Thr
            420                 425                 430 gtg acg gcc ata tgt ttg ata cta cac acg tgt acg tac cga cgt acg         1344
Val Thr Ala Ile Cys Leu Ile Leu His Thr Cys Thr Tyr Arg Arg Thr
        435                 440                 445 gag gca gac acg acg cga cac gaa aat gac gac gcc cgg aag gtg atg         1392
Glu Ala Asp Thr Thr Arg His Glu Asn Asp Asp Ala Arg Lys Val Met
    450                 455                 460 gaa gac atg gcc aaa cga atg gac gat agt agc agt ggg agc acg ttg         1440
Glu Asp Met Ala Lys Arg Met Asp Asp Ser Ser Ser Gly Ser Thr Leu
465                 470                 475                 480 agc acg ctc acg act gac gag acg tac cac acc acc acg gag gtg acc         1488
Ser Thr Leu Thr Thr Asp Glu Thr Tyr His Thr Thr Thr Glu Val Thr
                485                 490                 495 gat ttt gat tca tct cca tcg tgg gga cga tgc tca tcg cgg cgc ccg         1536
Asp Phe Asp Ser Ser Pro Ser Trp Gly Arg Cys Ser Ser Arg Arg Pro
            500                 505                 510 ccg gcg ctg ctg gaa tcg aca ttt cgg cga tcc ccg aga ggg tcg acg         1584
Pro Ala Leu Leu Glu Ser Thr Phe Arg Arg Ser Pro Arg Gly Ser Thr
        515                 520                 525 gga cga cga tgg cga gag tag attcggagtc aggaacgttg gaccgacagg            1635
Gly Arg Arg Trp Arg Glu  *
    530 tggaccggtt tagggcagtt gacggtaggg gttgcctgac cagccttgac gctcgacagc       1695 taaaaaaaac aacaaaaaaa aaaaaaaaac aaaaaaaaa a                            1736
```

```
<210> SEQ ID NO 36
<211> LENGTH: 534
<212> TYPE: PRT
<213> ORGANISM: Arabidopsis thaliana

<400> SEQUENCE: 36

Met Pro Pro Lys Met Leu Pro Pro Thr Ala Arg Asp Ser Val Ala
 1               5                  10                  15

Gly Thr Gly Gly Ser Pro Pro Pro Pro Pro Pro Ala Arg Trp
                20                  25                  30

Arg Val Ala Gly Glu Gly Gly Leu Asp Thr Thr Pro Pro Pro Pro
             35                  40                  45

Pro Thr Ala Asp Thr Val Val Ala Gly Arg Thr Ser Leu Gly Glu Ala
         50                  55                  60

Pro Pro Pro Arg Gln Pro Pro Arg Pro Pro Thr Ala Arg Trp Ser Ala
65                  70                  75                  80

Met Gly Arg Val Met Cys Ser Pro Pro Ile Pro Leu Ser Arg Ser Arg
                 85                  90                  95

Leu Ala Leu Asp Asp Gln Arg Trp Pro Asp Trp Thr Thr Asn Gly Trp
                100                 105                 110

Leu Ser Met Arg Pro Thr Ser Pro Thr Arg Arg Ile Asp Pro Gln
            115                 120                 125

Gly Ala Arg Arg Ser Ser Val Ser Pro Ala Pro Val Thr Thr Gly Met
        130                 135                 140

Ala Thr Ser Arg Thr Asp Asp Thr Leu Ile Glu Ala Glu Thr Gly Arg
145                 150                 155                 160

Asp Trp Thr Arg Lys Arg Met Val Arg Lys Leu Leu Lys Ala Arg Ala
                165                 170                 175

Lys Asp Tyr Lys Glu Gly Gly Ile Ala Ala Tyr Phe Gly Leu Arg Val
                180                 185                 190

Leu Arg Cys Tyr Ser Arg Ile Val Arg Ser Met Lys Arg Pro Gly Asn
            195                 200                 205

Leu Lys Phe Thr Cys Arg Arg Asp Val Ala Ile Ala Thr Phe Ser Gly
    210                 215                 220

Thr Gly Arg Met Gln Leu Ser Met Asn Ser Arg Leu Arg Val Glu Ser
225                 230                 235                 240

Leu Val Ser Ala Gly Gln Ser Val Ala Ser Phe Cys Leu Phe Leu Ile
                245                 250                 255

Cys Thr Ala Pro Ser Ala Met Arg Leu Val Ser Leu Leu Thr Leu Thr
                260                 265                 270

Pro Ser Met Thr Tyr Leu Thr Cys Gly Leu Gly Trp Met Thr Val Val
            275                 280                 285

Val Leu Pro Ala Ile Val Val His Cys Tyr Met Arg Arg His Thr Glu
    290                 295                 300

Gly Gly Trp Arg Tyr Ala Ala Leu Glu Glu His Lys Thr Glu Pro Gly
305                 310                 315                 320

Arg Asn Glu Lys Ile Thr Arg Ser Arg Asn Ser Ala Phe Gly Gly
                325                 330                 335

Leu Val Gly Arg Asn Lys Arg Lys Lys Ser Lys Val Ser Gly Ala
            340                 345                 350

Pro Thr Ala Val Tyr Thr Ala Met Phe Phe Met Phe Ser Thr Ala Ile
            355                 360                 365

Lys Gly Met Val Val Cys Thr Met Lys Lys Val Lys Lys Ser Ala
370                 375                 380
```

```
Asn Arg Arg Leu Arg Gln Leu Leu Arg Trp Ala Arg Tyr His Ala Asn
385                 390                 395                 400

Ala Phe Leu Leu Cys Ser Leu Ala Cys Ala Arg Phe Ala Ala Ser Arg
            405                 410                 415

Thr Val Ile His Cys Ser Ile Tyr Pro Arg Phe Gly Pro Leu Ala Thr
        420                 425                 430

Val Thr Ala Ile Cys Leu Ile Leu His Thr Cys Thr Tyr Arg Arg Thr
            435                 440                 445

Glu Ala Asp Thr Thr Arg His Glu Asn Asp Ala Arg Lys Val Met
450                 455                 460

Glu Asp Met Ala Lys Arg Met Asp Asp Ser Ser Gly Ser Thr Leu
465                 470                 475                 480

Ser Thr Leu Thr Thr Asp Glu Thr Tyr His Thr Thr Thr Glu Val Thr
                485                 490                 495

Asp Phe Asp Ser Ser Pro Ser Trp Gly Arg Cys Ser Ser Arg Arg Pro
            500                 505                 510

Pro Ala Leu Leu Glu Ser Thr Phe Arg Arg Ser Pro Arg Gly Ser Thr
            515                 520                 525

Gly Arg Arg Trp Arg Glu
    530

<210> SEQ ID NO 37
<211> LENGTH: 508
<212> TYPE: DNA
<213> ORGANISM: Arabidopsis thaliana
<220> FEATURE:
<221> NAME/KEY: CDS
<222> LOCATION: (18)...(77)
<220> FEATURE:
<221> NAME/KEY: CDS
<222> LOCATION: (156)...(314)
<220> FEATURE:
<221> NAME/KEY: CDS
<222> LOCATION: (374)...(493)

<400> SEQUENCE: 37
gaagaaaatc tatcatc atg caa gtg gct gac ata tcc tta cag ggc gat       50
                   Met Gln Val Ala Asp Ile Ser Leu Gln Gly Asp
                    1               5                  10 gct aag aag ggt gcc aac ctc ttc aag gtacgaacag agcaaagatg            97
Ala Lys Lys Gly Ala Asn Leu Phe Lys
            15                  20 ccgctgaaaa ttctcacggc gcattctatc ccgcagaact tttctgacca ctttgtag    155 acc cgc tgc gct cag tgc cac acc ctg aag gcc ggc gag ggc aac aag   203
Thr Arg Cys Ala Gln Cys His Thr Leu Lys Ala Gly Glu Gly Asn Lys
                25                  30                  35 att ggc cct gag ctc cac ggt ctc ttc ggc cgc aag act ggt tcc gtc   251
Ile Gly Pro Glu Leu His Gly Leu Phe Gly Arg Lys Thr Gly Ser Val
        40                  45                  50 gct ggc tac tca tac acc gac gcc aac aag cag aag ggt atc gag tgg   299
Ala Gly Tyr Ser Tyr Thr Asp Ala Asn Lys Gln Lys Gly Ile Glu Trp
    55                  60                  65 aag gac gac act ctc gtacgtcacg ccaccggaag attgaaatgt ccccgagacc   354
Lys Asp Asp Thr Leu
            70 ctccgctaac acgacacag ttc gag tac ctc gag aac ccc aag aag tac att   406
                    Phe Glu Tyr Leu Glu Asn Pro Lys Lys Tyr Ile
                              75                  80 ccc ggt acc aag atg gcc ttc ggt ggt ctc aag aag ccc aag gac cgc   454
```

```
Pro Gly Thr Lys Met Ala Phe Gly Gly Leu Lys Lys Pro Lys Asp Arg
 85                  90                  95                 100 aac gac ctc atc acc ttc ctt gag gag gag acc aaa taa gcgtcttgct        503
Asn Asp Leu Ile Thr Phe Leu Glu Glu Glu Thr Lys  *
                105                 110 acccc                                                                 508
```

<210> SEQ ID NO 38
<211> LENGTH: 112
<212> TYPE: PRT
<213> ORGANISM: Arabidopsis thaliana

<400> SEQUENCE: 38

```
Met Gln Val Ala Asp Ile Ser Leu Gln Gly Asp Ala Lys Lys Gly Ala
 1               5                  10                  15

Asn Leu Phe Lys Thr Arg Cys Ala Gln Cys His Thr Leu Lys Ala Gly
                20                  25                  30

Glu Gly Asn Lys Ile Gly Pro Glu Leu His Gly Leu Phe Gly Arg Lys
             35                  40                  45

Thr Gly Ser Val Ala Gly Tyr Ser Tyr Thr Asp Ala Asn Lys Gln Lys
         50                  55                  60

Gly Ile Glu Trp Lys Asp Asp Thr Leu Phe Glu Tyr Leu Glu Asn Pro
 65                  70                  75                  80

Lys Lys Tyr Ile Pro Gly Thr Lys Met Ala Phe Gly Gly Leu Lys Lys
                 85                  90                  95

Pro Lys Asp Arg Asn Asp Leu Ile Thr Phe Leu Glu Glu Thr Lys
                100                 105                 110
```

<210> SEQ ID NO 39
<211> LENGTH: 5156
<212> TYPE: DNA
<213> ORGANISM: Arabidopsis thaliana
<220> FEATURE:
<221> NAME/KEY: CDS
<222> LOCATION: (1)...(609)
<220> FEATURE:
<221> NAME/KEY: CDS
<222> LOCATION: (686)...(841)
<220> FEATURE:
<221> NAME/KEY: CDS
<222> LOCATION: (933)...(1040)
<220> FEATURE:
<221> NAME/KEY: CDS
<222> LOCATION: (1130)...(1240)
<220> FEATURE:
<221> NAME/KEY: CDS
<222> LOCATION: (1341)...(2729)
<220> FEATURE:
<221> NAME/KEY: CDS
<222> LOCATION: (2772)...(2984)
<220> FEATURE:
<221> NAME/KEY: CDS
<222> LOCATION: (4112)...(4200)
<220> FEATURE:
<221> NAME/KEY: CDS
<222> LOCATION: (4241)...(4332)
<220> FEATURE:
<221> NAME/KEY: CDS
<222> LOCATION: (4478)...(4521)
<220> FEATURE:
<221> NAME/KEY: CDS
<222> LOCATION: (5088)...(5156)

<400> SEQUENCE: 39

```
atg gca ccg aca cca tct tct tca aga tca aat caa act caa tac acc      48
Met Ala Pro Thr Pro Ser Ser Ser Arg Ser Asn Gln Thr Gln Tyr Thr
 1               5                  10                  15
```

```
tta atc aga act cca caa aca aaa caa cgt ctc aat ttc cac tca aaa         96
Leu Ile Arg Thr Pro Gln Thr Lys Gln Arg Leu Asn Phe His Ser Lys
            20                  25                  30 acc cca aac cca gac gga tct aaa gat cca tct cca ccg gag cat cca        144
Thr Pro Asn Pro Asp Gly Ser Lys Asp Pro Ser Pro Pro Glu His Pro
        35                  40                  45 gtt gaa gta atc ggc cgg atc cga gat tac cct gac cgg aaa gag aaa        192
Val Glu Val Ile Gly Arg Ile Arg Asp Tyr Pro Asp Arg Lys Glu Lys
     50                  55                  60 tca cct tcg atc tta caa gtc aac aca gat aat caa acg gta cga gtc        240
Ser Pro Ser Ile Leu Gln Val Asn Thr Asp Asn Gln Thr Val Arg Val
 65                  70                  75                  80 aga gct gat gtt ggg tac aga gac ttc aca ctc gac ggt gtt tct ttc        288
Arg Ala Asp Val Gly Tyr Arg Asp Phe Thr Leu Asp Gly Val Ser Phe
                 85                  90                  95 tcg gag caa gaa ggt ctt gaa gag ttc tac aag aag ttt ata gaa gag        336
Ser Glu Gln Glu Gly Leu Glu Glu Phe Tyr Lys Lys Phe Ile Glu Glu
            100                 105                 110 agg att aaa gga gtg aaa gtt ggg aat aaa tgc acg att atg atg tat        384
Arg Ile Lys Gly Val Lys Val Gly Asn Lys Cys Thr Ile Met Met Tyr
        115                 120                 125 gga cct act ggt gct gga aag agt cat act atg ttt ggt tgt ggg aaa        432
Gly Pro Thr Gly Ala Gly Lys Ser His Thr Met Phe Gly Cys Gly Lys
130                 135                 140 gag cct ggg att gtg tat cgt tct ttg aga gat ata ttg gga gat tct        480
Glu Pro Gly Ile Val Tyr Arg Ser Leu Arg Asp Ile Leu Gly Asp Ser
145                 150                 155                 160 gat caa gat ggt gtt act ttt gtt caa gtt act gtt ctt gag gtt tat        528
Asp Gln Asp Gly Val Thr Phe Val Gln Val Thr Val Leu Glu Val Tyr
                165                 170                 175 aat gag gag att tat gat ctt ctt tcg act aat agt agt aac aat tta        576
Asn Glu Glu Ile Tyr Asp Leu Leu Ser Thr Asn Ser Ser Asn Asn Leu
            180                 185                 190 ggt att ggt tgg cct aaa gga gca agc act aag gtaaagtttc ttgattgata      629
Gly Ile Gly Trp Pro Lys Gly Ala Ser Thr Lys
        195                 200 actttagtat acattgaatt ggctttaaag gtgtgtactt tgttgttttg ttacag gtg      688
                                                              Val agg ctt gaa gta atg ggg aaa aag gcg aaa aac gca agt ttt att tct        736
Arg Leu Glu Val Met Gly Lys Lys Ala Lys Asn Ala Ser Phe Ile Ser
205                 210                 215                 220 ggg aca gag gct ggg aag att tct aaa gaa att gtc aaa gtg gag aaa        784
Gly Thr Glu Ala Gly Lys Ile Ser Lys Glu Ile Val Lys Val Glu Lys
                225                 230                 235 cgg aga att gtg aag agt aca ctt tgt aac gaa aga agt tct cgg agt        832
Arg Arg Ile Val Lys Ser Thr Leu Cys Asn Glu Arg Ser Ser Arg Ser
            240                 245                 250 cac tgc att gtaagaacga tcttcttgat tgatgtgtat gcatagcttt                881
His Cys Ile
        255 atgcagctta tctctgtttt aacttactag tgtggttgtt tcttttttgta g atc ata      938
                                                          Ile Ile ctt gat gtg cca act gtt ggg gga aga ttg atg ctt gtt gac atg gct        986
Leu Asp Val Pro Thr Val Gly Gly Arg Leu Met Leu Val Asp Met Ala
        260                 265                 270 ggt tct gaa aat ata gac caa gct ggg cag act gga ttt gaa gct aag       1034
Gly Ser Glu Asn Ile Asp Gln Ala Gly Gln Thr Gly Phe Glu Ala Lys
275                 280                 285
```

-continued

```
atg caa gtaatgtttc ctctctcaat ttgtttgatt ctactaaagt tattgtagtt       1090
Met Gln
290 atggatatca actgacttat atctctcatt attcaacag act gct aag atc aac       1144
                                           Thr Ala Lys Ile Asn
                                                           295 cag gga aat att gca ctg aag cga gtt gtg gaa tct ata gca aat gga      1192
Gln Gly Asn Ile Ala Leu Lys Arg Val Val Glu Ser Ile Ala Asn Gly
            300                 305                 310 gat tct cat gta ccc ttt aga gac agc aag ctg acc atg ctt ctc cag      1240
Asp Ser His Val Pro Phe Arg Asp Ser Lys Leu Thr Met Leu Leu Gln
        315                 320                 325 gtgaaattct tgttccattg ttttatcttc tggaaaatgt tttacgtgtt gcttggtttt    1300
cttgaagata tttagtgttg tttctattct ctgaatgcag gac tct ttt gaa gat      1355
                                             Asp Ser Phe Glu Asp
                                                         330 gac aag tca aag att cta atg atc ctg tgt gcg agc ccg gat cca aag      1403
Asp Lys Ser Lys Ile Leu Met Ile Leu Cys Ala Ser Pro Asp Pro Lys
        335                 340                 345 gaa atg cac aag act ctc tgt act cta gag tat ggg gca aaa gca aag      1451
Glu Met His Lys Thr Leu Cys Thr Leu Glu Tyr Gly Ala Lys Ala Lys
350                 355                 360                 365 tgc ata gtt cgt ggg tct cat act cca aac aaa gat aag tat ggg ggt      1499
Cys Ile Val Arg Gly Ser His Thr Pro Asn Lys Asp Lys Tyr Gly Gly
                370                 375                 380 gat gag tct gct tct gct gtg att ttg gga tca aga ata gct gcc atg      1547
Asp Glu Ser Ala Ser Ala Val Ile Leu Gly Ser Arg Ile Ala Ala Met
            385                 390                 395 gat gag ttc att atc aaa ctc cag tct gag aag aag caa aaa gaa aaa      1595
Asp Glu Phe Ile Ile Lys Leu Gln Ser Glu Lys Lys Gln Lys Glu Lys
        400                 405                 410 gaa agg aat gag gca caa aag cag ctg aag aag aag gaa gag gaa gtt      1643
Glu Arg Asn Glu Ala Gln Lys Gln Leu Lys Lys Lys Glu Glu Glu Val
    415                 420                 425 gct gct tta aga tct ctt tta aca cag agg gaa gct tgt gct acc aat      1691
Ala Ala Leu Arg Ser Leu Leu Thr Gln Arg Glu Ala Cys Ala Thr Asn
430                 435                 440                 445 gaa gag gag ata aaa gag aaa gta aac gag aga acc cag ctt ttg aag      1739
Glu Glu Glu Ile Lys Glu Lys Val Asn Glu Arg Thr Gln Leu Leu Lys
                450                 455                 460 tcg gaa cta gat aag aaa ctt gaa gaa tgc cga aga atg gct gag gaa      1787
Ser Glu Leu Asp Lys Lys Leu Glu Glu Cys Arg Arg Met Ala Glu Glu
            465                 470                 475 ttt gtt gag atg gag aga agg aga atg gag gaa agg ata gtt cag cag      1835
Phe Val Glu Met Glu Arg Arg Arg Met Glu Glu Arg Ile Val Gln Gln
        480                 485                 490 caa gag gaa ctg gag atg atg agg aga cgg tta gag gaa atc gag gtt      1883
Gln Glu Glu Leu Glu Met Met Arg Arg Arg Leu Glu Glu Ile Glu Val
    495                 500                 505 gag ttc cgc cgc tca aat gga gga agt gtt gat gaa act agt ggg ttt      1931
Glu Phe Arg Arg Ser Asn Gly Gly Ser Val Asp Glu Thr Ser Gly Phe
510                 515                 520                 525 gcc aaa aga ctc agg agt ctt tac tct gat gat gat cct ggt atg gtg      1979
Ala Lys Arg Leu Arg Ser Leu Tyr Ser Asp Asp Asp Pro Gly Met Val
                530                 535                 540 aag tca atg gac ctt gac atg ggt gat cca gaa cct gtc aag caa gtg      2027
Lys Ser Met Asp Leu Asp Met Gly Asp Pro Glu Pro Val Lys Gln Val
            545                 550                 555 tgg gga gct gtt tca cac caa tca agc aac act att agt agc aac ttc      2075
```

| | |
|---|---|
| Trp Gly Ala Val Ser His Gln Ser Ser Asn Thr Ile Ser Ser Asn Phe<br>     560                   565                   570 | |
| act aac ctt ttg caa ccg aag cct tca gag aat atg ctt aca cag atg<br>Thr Asn Leu Leu Gln Pro Lys Pro Ser Glu Asn Met Leu Thr Gln Met<br>575                  580                   585 | 2123 |
| tat cct gac cgg gta tgc ttg agc act gtc ttt gaa gaa gaa gaa gtt<br>Tyr Pro Asp Arg Val Cys Leu Ser Thr Val Phe Glu Glu Glu Glu Val<br>590                  595                   600                   605 | 2171 |
| gaa gaa gag gaa gaa aaa gtg ata gtc gag gat aaa agc atc tgc ttg<br>Glu Glu Glu Glu Glu Lys Val Ile Val Glu Asp Lys Ser Ile Cys Leu<br>                   610                   615                   620 | 2219 |
| ata aca aca cca atg cct agt ttg aac tct gaa ggt ttg ggt aaa gag<br>Ile Thr Thr Pro Met Pro Ser Leu Asn Ser Glu Gly Leu Gly Lys Glu<br>                   625                   630                   635 | 2267 |
| aac tgc ttc aac ggt gca gat gac aag gaa tca gcc tcg tct aga agg<br>Asn Cys Phe Asn Gly Ala Asp Asp Lys Glu Ser Ala Ser Ser Arg Arg<br>            640                   645                   650 | 2315 |
| ttg aga att caa aac att ttc acc ctt tgt ggc aat cag aga gag ctg<br>Leu Arg Ile Gln Asn Ile Phe Thr Leu Cys Gly Asn Gln Arg Glu Leu<br>            655                   660                   665 | 2363 |
| tct caa cac agt gga cag gag gag gat caa gcc aat att gca tca cct<br>Ser Gln His Ser Gly Gln Glu Glu Asp Gln Ala Asn Ile Ala Ser Pro<br>670                  675                   680                   685 | 2411 |
| gat aag aaa gac aat cag ttc ttt tct att acg aat aag gcc gaa gca<br>Asp Lys Lys Asp Asn Gln Phe Phe Ser Ile Thr Asn Lys Ala Glu Ala<br>                   690                   695                   700 | 2459 |
| cta gca gta gaa gaa gca aag gaa aac aat atc tca gtc gat caa agg<br>Leu Ala Val Glu Glu Ala Lys Glu Asn Asn Ile Ser Val Asp Gln Arg<br>            705                   710                   715 | 2507 |
| gaa aac ggt cag cta gat atc tat gtt aaa tgg gaa aca gct gct gat<br>Glu Asn Gly Gln Leu Asp Ile Tyr Val Lys Trp Glu Thr Ala Ala Asp<br>                720                   725                   730 | 2555 |
| aac cct cga aag ctc ata aca aca ctg aga gtt aca aag gat gca aca<br>Asn Pro Arg Lys Leu Ile Thr Thr Leu Arg Val Thr Lys Asp Ala Thr<br>735                  740                   745 | 2603 |
| cta gct gac ttg agg aag ctt att gag atc tac ctt gga tct gat aat<br>Leu Ala Asp Leu Arg Lys Leu Ile Glu Ile Tyr Leu Gly Ser Asp Asn<br>750                  755                   760                   765 | 2651 |
| cag gct ttt acc ttt ctc aag ctc ggg gta ata aac ttg aac caa caa<br>Gln Ala Phe Thr Phe Leu Lys Leu Gly Val Ile Asn Leu Asn Gln Gln<br>                   770                   775                   780 | 2699 |
| gca caa aaa gct ttt cat ttt tat ctg ttt gttatgctct gatcctaaat<br>Ala Gln Lys Ala Phe His Phe Tyr Leu Phe<br>            785                   790 | 2749 |
| gcagttattt caatgtatga ag gaa cca tgt gga gct caa gtg gca aag gag<br>                                 Glu Pro Cys Gly Ala Gln Val Ala Lys Glu<br>                                          795                   800 | 2801 |
| aaa gaa tca aca gtt caa gct acg agc cta cct ctc tgc aac gga cac<br>Lys Glu Ser Thr Val Gln Ala Thr Ser Leu Pro Leu Cys Asn Gly His<br>805                  810                   815 | 2849 |
| gca tac ctc gcc act ttg aga cca gga aag agc tca caa cat aaa agt<br>Ala Tyr Leu Ala Thr Leu Arg Pro Gly Lys Ser Ser Gln His Lys Ser<br>            820                   825                   830 | 2897 |
| ctt caa cct gca agc cca ctt cca ctt aat ccc ata gaa aac atg atg<br>Leu Gln Pro Ala Ser Pro Leu Pro Leu Asn Pro Ile Glu Asn Met Met<br>835                  840                   845 | 2945 |
| gaa gtt acc ccc atc tca aaa gtg aca ccg aac cat caa gttgatgaat<br>Glu Val Thr Pro Ile Ser Lys Val Thr Pro Asn His Gln<br>850                  855                   860 | 2994 |

```
                                                        -continued
tttcatcacc caatctcgta gctcatctca gctccactcc attcatcact ctcagaagac       3054
attagtcgct atgtcttgtt ttctctattc ttcttttgtc tgtccaaagg tagcttttga       3114
aagatgtagc agcctttgtc tatttctctg tgttgagaaa aaaaaaactc ttatgtacga       3174
ccacttttgt agctatatat atgttctacg atgtttcagc agagtggtgt ttatcagaac       3234
gtataactgg tgtttcccaa aggatgctta gttctactta aacatatac ataagtagag        3294 agaatgctgc agccacatag agctacttct tacctctctc tgtcattgta acatatggac       3354
aaattccaaa agccctattc aattccaacc ccaatatctt tatgatcatc atcataacgt       3414
gaacaccaaa aacaagggca aaatttcaa aggctcttaa aaataacaat atcccggaag        3474
caaagattac ctgcaactgc aagggaaagc caagccctat tatagaaaag caacttcatt       3534
agttaagccc tatctctcaa tatgctcaca tgcatgcatt gaccaaatgt cttcttttat       3594
ctacaggtac tcagtcactt tcttagttac acactagatt aactcaattc ttctgcaacc      3654
tcattatctc caaagtaaaa gaccactgtt attgatgttt tatggataa tatatgatga       3714 ttcatcttta ttacattagc tgaatacaga acaacaacca attaactcaa ttattttgaa      3774
agatgtatgt agcctgtcta tttctcggtg ttgagaaaaa aaacgctatg tacgaccact      3834
ttcagcagtc aaagtgagtg actagagcca tcagcatgga gtgttttca agttgtacaa       3894 caagatttgt caacaaagtc taaaacttc ttttattcga ccataatatg actgactagg       3954
cacgttggtt ttcgatatac agtttaaaag gttggagaag atgactagat gagataggtt      4014
ttcatatttt acttccacat cgaagtttta gagaacagaa agaggagaaa attgaagtac      4074
acatgagaca agttacactt taaagcttta ttaacag att ctt tta aaa aca gag       4129
                                            Ile Leu Leu Lys Thr Glu
                                                                865 act gag aga ttg gga gag gca gat tac att aac tct ctt tct ctc tct        4177
Thr Glu Arg Leu Gly Glu Ala Asp Tyr Ile Asn Ser Leu Ser Leu Ser
    870             875                 880 cac ttt ctc atc ttg ttc cca ag gttaaaaaac aattcgagga catgtctttc        4230
His Phe Leu Ile Leu Phe Pro Arg
885                 890 ctattttcag a gga gag agc cat cag cac cga atg ttg tct ttt cac tct      4280
            Gly Glu Ser His Gln His Arg Met Leu Ser Phe His Ser
                895                 900                 905 cat caa act tct cct tcc cta tct tca ttt cct ctt ctt tcc aga gcc        4328
His Gln Thr Ser Pro Ser Leu Ser Ser Phe Pro Leu Leu Ser Arg Ala
        910                 915                 920 gat g gtaaggagct cgaagtttct aatggcatcc tcatgcccag gccttgctgc           4382
Asp agctgcagat tcatagctct gtggaacccg ttgggttgtg gcatgacgtg aaccacttga      4442
aaatagtcgg cttgagtggt tctcgcttgg ttcag ct gat gag cca ggt ctg gtg      4497
                                        Ala Asp Glu Pro Gly Leu Val
                                                                925 ctt gat atc aca cct ctc ttt gag gtacttccat ttcgagactc gtgctgcaaa       4551
Leu Asp Ile Thr Pro Leu Phe Glu
930                 935 tgaagccagc aaatcaaaac acacaaactt tctcatgttc tgattcccta cttattctga      4611
gaattacttt ggatcattac aacaagagaa ataacaacac aaactaacca cttccttggc      4671
agaagagggt atatcatcag aagatctgtg tctagagcga tcaccaagag cgccttggct      4731
tgaaacattt cgtctggtga atgcctcaat tgcacctgta atcttcctc gcaggtcctg       4791 tccgactaaa cagaataggg aaagaagttc tcagtttgag atcttccact attcaacaat      4851
```

```
ttaattaaat ctctggacac aaattcaaaa tcttctaagg gaaacaacat atgaatgtta      4911
atatctgaag ggtcaagtga gatagtgcac gtttttcagc acccaaaatt gtcaacactg      4971
tctcataaat ttacaactta aaataaactt tttgatatat ctctttgtat tcgtccctcc      5031
aatataagag acagagaaca tcaatgtacc tgtaggcttt tcagctcttt ctgcag gtg      5090
                                                               Val gtc ctg gag ggt cca acg ctg gtc ttg gag ttg gct gtt gta aat gat       5138
Val Leu Glu Gly Pro Thr Leu Val Leu Glu Leu Ala Val Val Asn Asp
    940             945                 950 aga cac ata gca gga taa                                               5156
Arg His Ile Ala Gly *
955
```

<210> SEQ ID NO 40
<211> LENGTH: 959
<212> TYPE: PRT
<213> ORGANISM: Arabidopsis thaliana

<400> SEQUENCE: 40

```
Met Ala Pro Thr Pro Ser Ser Arg Ser Asn Gln Thr Gln Tyr Thr
1               5                   10                  15

Leu Ile Arg Thr Pro Gln Thr Lys Gln Arg Leu Asn Phe His Ser Lys
                20                  25                  30

Thr Pro Asn Pro Asp Gly Ser Lys Asp Pro Ser Pro Glu His Pro
            35                  40                  45

Val Glu Val Ile Gly Arg Ile Arg Asp Tyr Pro Asp Arg Lys Glu Lys
50                  55                  60

Ser Pro Ser Ile Leu Gln Val Asn Thr Asp Asn Gln Thr Val Arg Val
65                  70                  75                  80

Arg Ala Asp Val Gly Tyr Arg Asp Phe Thr Leu Asp Gly Val Ser Phe
                85                  90                  95

Ser Glu Gln Glu Gly Leu Glu Glu Phe Tyr Lys Lys Phe Ile Glu Glu
                100                 105                 110

Arg Ile Lys Gly Val Lys Val Gly Asn Lys Cys Thr Ile Met Met Tyr
            115                 120                 125

Gly Pro Thr Gly Ala Gly Lys Ser His Thr Met Phe Gly Cys Gly Lys
    130                 135                 140

Glu Pro Gly Ile Val Tyr Arg Ser Leu Arg Asp Ile Leu Gly Asp Ser
145                 150                 155                 160

Asp Gln Asp Gly Val Thr Phe Val Gln Val Thr Val Leu Glu Val Tyr
                165                 170                 175

Asn Glu Glu Ile Tyr Asp Leu Leu Ser Thr Asn Ser Ser Asn Asn Leu
            180                 185                 190

Gly Ile Gly Trp Pro Lys Gly Ala Ser Thr Lys Val Arg Leu Glu Val
        195                 200                 205

Met Gly Lys Lys Ala Lys Asn Ala Ser Phe Ile Ser Gly Thr Glu Ala
    210                 215                 220

Gly Lys Ile Ser Lys Glu Ile Lys Val Glu Lys Arg Arg Ile Val
225                 230                 235                 240

Lys Ser Thr Leu Cys Asn Glu Arg Ser Arg Ser His Cys Ile Ile
                245                 250                 255

Ile Leu Asp Val Pro Thr Val Gly Gly Arg Leu Met Leu Val Asp Met
            260                 265                 270

Ala Gly Ser Glu Asn Ile Asp Gln Ala Gly Gln Thr Gly Phe Glu Ala
        275                 280                 285
```

```
-continued

Lys Met Gln Thr Ala Lys Ile Asn Gln Gly Asn Ile Ala Leu Lys Arg
    290                 295                 300
Val Val Glu Ser Ile Ala Asn Gly Asp Ser His Val Pro Phe Arg Asp
305                 310                 315                 320
Ser Lys Leu Thr Met Leu Leu Gln Asp Ser Phe Glu Asp Lys Ser
                    325                 330                 335
Lys Ile Leu Met Ile Leu Cys Ala Ser Pro Asp Pro Lys Glu Met His
                340                 345                 350
Lys Thr Leu Cys Thr Leu Glu Tyr Gly Ala Lys Ala Lys Cys Ile Val
                355                 360                 365
Arg Gly Ser His Thr Pro Asn Lys Asp Lys Tyr Gly Asp Glu Ser
    370                 375                 380
Ala Ser Ala Val Ile Leu Gly Ser Arg Ile Ala Ala Met Asp Glu Phe
385                 390                 395                 400
Ile Ile Lys Leu Gln Ser Glu Lys Lys Gln Lys Glu Lys Glu Arg Asn
                405                 410                 415
Glu Ala Gln Lys Gln Leu Lys Lys Lys Glu Glu Val Ala Ala Leu
                420                 425                 430
Arg Ser Leu Leu Thr Gln Arg Glu Ala Cys Ala Thr Asn Glu Glu
    435                 440                 445
Ile Lys Glu Lys Val Asn Glu Arg Thr Gln Leu Leu Lys Ser Glu Leu
    450                 455                 460
Asp Lys Lys Leu Glu Glu Cys Arg Arg Met Ala Glu Glu Phe Val Glu
465                 470                 475                 480
Met Glu Arg Arg Arg Met Glu Glu Arg Ile Val Gln Gln Glu Glu
                485                 490                 495
Leu Glu Met Met Arg Arg Arg Leu Glu Glu Ile Glu Val Glu Phe Arg
                500                 505                 510
Arg Ser Asn Gly Gly Ser Val Asp Glu Thr Ser Gly Phe Ala Lys Arg
    515                 520                 525
Leu Arg Ser Leu Tyr Ser Asp Asp Pro Gly Met Val Lys Ser Met
    530                 535                 540
Asp Leu Asp Met Gly Asp Pro Glu Pro Val Lys Gln Val Trp Gly Ala
545                 550                 555                 560
Val Ser His Gln Ser Ser Asn Thr Ile Ser Ser Asn Phe Thr Asn Leu
                565                 570                 575
Leu Gln Pro Lys Pro Ser Glu Asn Met Leu Thr Gln Met Tyr Pro Asp
                580                 585                 590
Arg Val Cys Leu Ser Thr Val Phe Glu Glu Glu Val Glu Glu Glu
    595                 600                 605
Glu Glu Lys Val Ile Val Glu Asp Lys Ser Ile Cys Leu Ile Thr Thr
    610                 615                 620
Pro Met Pro Ser Leu Asn Ser Glu Gly Leu Gly Lys Glu Asn Cys Phe
625                 630                 635                 640
Asn Gly Ala Asp Asp Lys Glu Ser Ala Ser Ser Arg Arg Leu Arg Ile
                645                 650                 655
Gln Asn Ile Phe Thr Leu Cys Gly Asn Gln Arg Glu Leu Ser Gln His
                660                 665                 670
Ser Gly Gln Glu Glu Asp Gln Ala Asn Ile Ala Ser Pro Asp Lys Lys
    675                 680                 685
Asp Asn Gln Phe Phe Ser Ile Thr Asn Lys Ala Glu Ala Leu Ala Val
    690                 695                 700
Glu Glu Ala Lys Glu Asn Asn Ile Ser Val Asp Gln Arg Glu Asn Gly
```

```
                    705                 710                 715                 720
Gln Leu Asp Ile Tyr Val Lys Trp Glu Thr Ala Ala Asp Asn Pro Arg
                725                 730                 735
Lys Leu Ile Thr Thr Leu Arg Val Thr Lys Asp Ala Thr Leu Ala Asp
            740                 745                 750
Leu Arg Lys Leu Ile Glu Ile Tyr Leu Gly Ser Asp Asn Gln Ala Phe
        755                 760                 765
Thr Phe Leu Lys Leu Gly Val Ile Asn Leu Asn Gln Gln Ala Gln Lys
    770                 775                 780
Ala Phe His Phe Tyr Leu Phe Glu Pro Cys Gly Ala Gln Val Ala Lys
785                 790                 795                 800
Glu Lys Glu Ser Thr Val Gln Ala Thr Ser Leu Pro Leu Cys Asn Gly
                805                 810                 815
His Ala Tyr Leu Ala Thr Leu Arg Pro Gly Lys Ser Ser Gln His Lys
            820                 825                 830
Ser Leu Gln Pro Ala Ser Pro Leu Pro Leu Asn Pro Ile Glu Asn Met
        835                 840                 845
Met Glu Val Thr Pro Ile Ser Lys Val Thr Pro Asn His Gln Ile Leu
    850                 855                 860
Leu Lys Thr Glu Thr Glu Arg Leu Gly Glu Ala Asp Tyr Ile Asn Ser
865                 870                 875                 880
Leu Ser Leu Ser His Phe Leu Ile Leu Phe Pro Arg Gly Glu Ser His
                885                 890                 895
Gln His Arg Met Leu Ser Phe Ser His Gln Thr Ser Pro Ser Leu
            900                 905                 910
Ser Ser Phe Pro Leu Leu Ser Arg Ala Asp Ala Asp Glu Pro Gly Leu
        915                 920                 925
Val Leu Asp Ile Thr Pro Leu Phe Glu Val Val Leu Glu Gly Pro Thr
    930                 935                 940
Leu Val Leu Glu Leu Ala Val Val Asn Asp Arg His Ile Ala Gly
945                 950                 955

<210> SEQ ID NO 41
<211> LENGTH: 6960
<212> TYPE: DNA
<213> ORGANISM: Arabidopsis thaliana
<220> FEATURE:
<221> NAME/KEY: CDS
<222> LOCATION: (147)...(327)
<220> FEATURE:
<221> NAME/KEY: CDS
<222> LOCATION: (405)...(796)
<220> FEATURE:
<221> NAME/KEY: CDS
<222> LOCATION: (1426)...(1500)
<220> FEATURE:
<221> NAME/KEY: CDS
<222> LOCATION: (3486)...(3638)
<220> FEATURE:
<221> NAME/KEY: CDS
<222> LOCATION: (3754)...(3864)
<220> FEATURE:
<221> NAME/KEY: CDS
<222> LOCATION: (4030)...(4096)
<220> FEATURE:
<221> NAME/KEY: CDS
<222> LOCATION: (4252)...(4523)
<220> FEATURE:
<221> NAME/KEY: CDS
<222> LOCATION: (4732)...(4834)
<220> FEATURE:
<221> NAME/KEY: CDS
<222> LOCATION: (6735)...(6907)
```

<400> SEQUENCE: 41

```
cccaaaaagc ttgacctaac ggctatgttt tctttacttt caccataaat aagcacctct      60
tgaggttgca acacacaca cacacacaca ctcacttcaa aagagttagt aagaagttgg     120
ggtttgatta acgttttgca tcggag atg ggt ttg gtc atg agg ttt gat ctt     173
                              Met Gly Leu Val Met Arg Phe Asp Leu
                                1               5 tac ctt atg ttt gtg atg ttg atg ggt tta ggg ttt acg ata tca aat     221
Tyr Leu Met Phe Val Met Leu Met Gly Leu Gly Phe Thr Ile Ser Asn
 10              15                  20                  25 gga tac aag ttc tat gtt ggt ggg aaa gat ggt tgg gtc ccg act cct     269
Gly Tyr Lys Phe Tyr Val Gly Gly Lys Asp Gly Trp Val Pro Thr Pro
                 30                  35                  40 tcc gaa gat tat tct cat tgg tct cac cga aac cgg ttt caa gtc aac     317
Ser Glu Asp Tyr Ser His Trp Ser His Arg Asn Arg Phe Gln Val Asn
                     45                  50                  55 gac act ctt c gtaagtctat ttcctcttct ctactatata tacacaatgt           367
Asp Thr Leu
        60 gtcaatatta atgcatagta attttgattt ttacaag at ttt aag tac gcc aag     421
                                          His Phe Lys Tyr Ala Lys
                                                              65 gga aaa gat tca gtg ttg gag gtg act gaa caa gag tac aac aca tgc     469
Gly Lys Asp Ser Val Leu Glu Val Thr Glu Gln Glu Tyr Asn Thr Cys
             70                  75                  80 aac acg aca cac ccc ctg act tcc ctc tca gac gga gac tct ctc ttc     517
Asn Thr Thr His Pro Leu Thr Ser Leu Ser Asp Gly Asp Ser Leu Phe
                 85                  90                  95 cta ctt agc cac tca ggt tcc tac ttt ttc att agt ggc aac tct caa     565
Leu Leu Ser His Ser Gly Ser Tyr Phe Phe Ile Ser Gly Asn Ser Gln
100                 105                 110 aac tgt ctt aaa ggt cag aag cta gcc gtc aag gtc ttg tcc acc gtc     613
Asn Cys Leu Lys Gly Gln Lys Leu Ala Val Lys Val Leu Ser Thr Val
115                 120                 125                 130 cac cac agc cac tct cct cgt cat acc tct ccc tcc ccg tct ccg gtc     661
His His Ser His Ser Pro Arg His Thr Ser Pro Ser Pro Ser Pro Val
                135                 140                 145 cat cag gag ttg tct tcg ccg ggg cct tct cca gga gtg gaa cca tca     709
His Gln Glu Leu Ser Ser Pro Gly Pro Ser Pro Gly Val Glu Pro Ser
                150                 155                 160 tct gat tca aac tct cgt gtt cca gct cca gga ccg gct aca gct ccc     757
Ser Asp Ser Asn Ser Arg Val Pro Ala Pro Gly Pro Ala Thr Ala Pro
165                 170                 175 aat tcg gcc ggt ttg gtt ggt ccg ggg atg gtg gtt ctt gtgattatga     806
Asn Ser Ala Gly Leu Val Gly Pro Gly Met Val Val Leu
180                 185                 190 taagttctct gttttgaggg gtttatatat tgtcgctagt cattaaattt gtgagggtat     866
taattactct accattgagt ttcatattta tgtgcctttt tatttgtatg tttgaagcat     926
cttgtaaccc atttttaatg tttccgctgt ctcgtttttg ttcttactaa agaaaatatt     986
taagatgttt ttttgtattg attagatgcg aatgttttta ttttgtgttt taattatgat    1046
cacactaata tgaatatata cgacgaatat gtagagttca catagctcat gcaataaaac    1106
ttctccacac aaactaaaat cttgttgaaa catataaata gatcttatac acttttttgta   1166 catataagaa tggtttgaac aatttaactt taatcaatat attaaaccgg tacaccgaaa    1226
tccaatagag agaatatgtc aaggagttaa caaaaaaaat atactaccgc cgtctgtggg    1286
```

-continued

```
gatcgaaccc acggcctcgt gggtaaaagc cacgcgctct accactgagc taagacggct   1346
atatgacaaa aaatttaaat tatgttaatt attgtatgtt tttgcagatc aaattaccaa   1406
tgaaatagtt ggtatttag gtt gtt aac tca atc ata aag ccg att gac tct    1458
                     Val Val Asn Ser Ile Ile Lys Pro Ile Asp Ser
                                 195                 200 ttt ttg ttg aag agc ttg cct ctt gtt gtg gat gtg gct gtt              1500
Phe Leu Leu Lys Ser Leu Pro Leu Val Val Asp Val Ala Val
            205                 210                 215 gtaagactaa taccagccct tgggtcgaaa gttgaaagtt tgattctgga tctctaatgt   1560
ctctagtatg gacgctcctg tttggaagtc ttttgtttgg aatatgatat agattcataa   1620
aaatgcgggt atctactacc atttgctatt gaccatcaaa aaacaacaa agtctcttaa    1680 ctatcttaaa attttattag gagattttca tgcgactaga acaagatttt caagcagtgg   1740
atgataagac aaaactgata ggccaacaac ttgatgaaat gggcaatatt atgaaataat   1800
acacaagtat agcttccacc tccaaccacc taaggacctc taataaattt acccaccaaa   1860
ggtggtggga ctccgtcaca gagccgtgcc tcaaggcaaa agaaagaaac attcgcctac   1920
gtcctcaaat ttttgaaaaa aacttaggag catatatttt tacaagataa ctttagtttc   1980
ataggtttaa tattgacaaa tcacttacat ttacctaaat aataaaata tagaattaaa    2040 aatagaaaaa tattcacaga ataaataaat aaaacagaac aaagcattat aaatttaggt   2100
taaagcattc gatatagaat tggttaaaaa aattaacttt gaatcttttg tcatatgaca   2160
atttattttt gtaaacactt ttacttctat tattataagc atctttgctt gtgaattggg   2220
gcaaatttca tttggccgcc tccggcaacc attgaccttg gcacggctct gctccgtcac   2280
ctcttatatt tgctgcaatg gcacagagaa gagaaattag ttgctggtgt tgatccctaa   2340
tatgtgctag ttcatcatct acatgtccaa atctaaatct catcccttct cctatcgcac   2400
ggacctgcaa gtgtagaaag caaaaacatc aacatatttt aataataatt acaaaacaca   2460
ttaggttctt aaacttatca aaactaatta cttcaaaaaa tatctttcta aaagttaata   2520
taccggaatt taatgcattt aaactagaat ttttttttcta taaattaaat gtataataaa   2580
atccataaaa taaatttttaa taagctctta ctaattaaac ataagataaa acaatattat   2640
taatttctca acaatcaaat gtggatagaa accaaaaaga taaaataaac tcggatgtca   2700
taggcccata atccagcctt ttctcaaagc ttaaacgtaa cgggctcggc ccaaatttgg   2760
tgtgttcatc atcttcccca caaaacctaa ttttgtttct tcagtagtac tgtagcttca   2820
gatgcaactc ctcgaaaacc cgtagaaccg gcattgagcc aatcgtttac attctctgat   2880
tcatatcctt agcgttttca gaaacaaaat ggtgggttgg aagaggaatt tgcagactgt   2940
tattcgtcaa gttggtagaa gagtgaagaa cagtcacatt tctacagcaa attactcttc   3000
ttctactcgg aatttagaat cccctttctc acaaggttga cttttgatc atttccgaaa    3060 tctagtgtgt ttcttagtgg gtctttcaaa gggcatgtgt tatctggtct tcgtgttttgt   3120 gaattgtgtg tttgagttga gttttttttgc tggtgattat aggttacttg cagagtctcc   3180
tgagaccatc ctactcctcc agaccactgt atcatcatct acaacaactg gtaatgcatt    3240
tgaatcgaca tttctttttgt gttttactga gattggagtt tcttgtttcc tgatatagca   3300
aatttgttgc tgcattgaaa aatcgaattt caaatttgg gaagtgagaa tgttgctagt    3360
gggagactat atctgttatc catgtgaatt aggcgaagag actcatcttt tggaactatg   3420
cgtctctagt caacttaggg acctgtactt tagggtatga aatttcaatt tgggtatgtt   3480 ttcag ggg atc tct acc tcg aga caa ttg cag gcg agt gaa gag cct gta   3530
```

-continued

|  |  |
|---|---|
| Gly Ile Ser Thr Ser Arg Gln Leu Gln Ala Ser Glu Glu Pro Val<br>         220                225                230 | |
| tca tca cct ttg tca tct cca gct ctg ttg ggt agt gga aaa gaa gaa<br>Ser Ser Pro Leu Ser Ser Pro Ala Leu Leu Gly Ser Gly Lys Glu Glu<br>        235                240                245 | 3578 |
| gag cag aag att atc cca aag cgt cag aaa gtt cag gct gtc ctc aag<br>Glu Gln Lys Ile Ile Pro Lys Arg Gln Lys Val Gln Ala Val Leu Lys<br>        250                255                260 | 3626 |
| tct ata aag cag gtgtcttctt taactcctag aacagtttta cttttcagat<br>Ser Ile Lys Gln<br>    265 | 3678 |
| gatctgctcc atttcgttta atatttttcc atctcaatct agttatataa tgtgcccaac | 3738 |
| cttgcttgtt ttcag agt cct aag aag gtc aac ctg gtt gca gca cta gtc<br>                 Ser Pro Lys Lys Val Asn Leu Val Ala Ala Leu Val<br>                            270                275 | 3789 |
| cgt ggc atg cgt gtt gaa gat gct ttg atc caa ttg cag gtc aca gtc<br>Arg Gly Met Arg Val Glu Asp Ala Leu Ile Gln Leu Gln Val Thr Val<br>280                285                290                295 | 3837 |
| aaa cga gct gca caa act gtg tac cgg gtaatctctg agatccgagt<br>Lys Arg Ala Ala Gln Thr Val Tyr Arg<br>        300 | 3884 |
| ttacaaacaa atcactgttg gatttcgagt gtctagtcta atctcctctc caggcatttg | 3944 |
| ataactttcc tcatctaatg atacttagca tacaacttgt tttgttaata caatgcttaa | 4004 |
| aggagttaaa tacattatac tgcag gtt atc cac gct gcc cgg gca aat gct<br>                                 Val Ile His Ala Ala Arg Ala Asn Ala<br>                                      305                310 | 4056 |
| act cat aac cat gga cta gat cct gac cgt ctc ctt gtt g gtatgtaaaa<br>Thr His Asn His Gly Leu Asp Pro Asp Arg Leu Leu Val<br>        315                320                325 | 4106 |
| ctgattctgg atccctgatt tccttgtttt acatttaaaa agagaacgtg atattttaga | 4166 |
| gagttcgccg attggtactt taaggaagca aacatgatat gccagaacga tgtatttcat | 4226 |
| ctaagcttgt gatatgtgat tgcag cg gaa gca ttt gtt ggg aag gga ctg<br>                                Ala Glu Ala Phe Val Gly Lys Gly Leu<br>                                     330                335 | 4277 |
| ttt ggg aag aag gta gct tac cat gca aaa gga aga agc ggg att ata<br>Phe Gly Lys Lys Val Ala Tyr His Ala Lys Gly Arg Ser Gly Ile Ile<br>        340                345                350 | 4325 |
| tca ata ccc cgg tgt cgc cta aca gtc ata gtt aga gag acg act cca<br>Ser Ile Pro Arg Cys Arg Leu Thr Val Ile Val Arg Glu Thr Thr Pro<br>        355                360                365 | 4373 |
| gag gaa gaa gct gag att gca agg ctc aaa gtt cac aat ttt aag aag<br>Glu Glu Glu Ala Glu Ile Ala Arg Leu Lys Val His Asn Phe Lys Lys<br>        370                375                380 | 4421 |
| aaa agc aaa cgg gag aga cag ctt gta cca cac aag ctc atc gag aca<br>Lys Ser Lys Arg Glu Arg Gln Leu Val Pro His Lys Leu Ile Glu Thr<br>385                390                395 | 4469 |
| agt cca ata tgg aac cgc aga ggt acc aaa gcc aat cat cgg tcc tca<br>Ser Pro Ile Trp Asn Arg Arg Gly Thr Lys Ala Asn His Arg Ser Ser<br>400                405                410                415 | 4517 |
| gag ttg gtacggtcgt ctcactagta tctttgttcc cgcaattgca acaagagctt<br>Glu Leu | 4573 |
| ctctgttatg gtaaattgct ttttttttg gttttggttt gatattgtat tggaactcta | 4633 |
| taggacctgt ttgcttcttg tattcaataa acatgttccc agagaggaaa cttcacttaa | 4693 |
| caaaagcgtc tctgttttc tccattctgt ttctggag gtg tta aca atc att ttg<br>                                       Val Leu Thr Ile Ile Leu<br>                                                420 | 4749 |

-continued

```
gat gta act tgt gtt gga aac atg gaa aaa aat cgt ctg gat aat ttg      4797
Asp Val Thr Cys Val Gly Asn Met Glu Lys Asn Arg Leu Asp Asn Leu
    425                 430                 435 acg aat caa aac aac att tat cat cat aat ccc gaa g gtccataatt         4844
Thr Asn Gln Asn Asn Ile Tyr His His Asn Pro Glu
440                 445                 450 tttatcagtt tgttccactt cttaatgcaa ttttttggata ttaaaagaat aaatgaatga   4904
atatacatat gcattttgtt tgttgagaat atttatttag tcatttattt aagaaattta   4964
tattttaatt ttttattatt aatatgatat ttgttttgtc actatgttac aacataattc   5024
aattttaata tcattataat tgatagtaat aataataaat aacagtcaca ggcccctacc   5084
atcatcccaa aatgattcat gcaatttagt catcaaatac atacaatctt atatacaaaa   5144
gaatcacaca gcatgtataa actaatagta tagaaattcg attaaaaaat actcccaggc   5204
tagttttttc accttccatg aagaatagaa tcataagttt ggaaggaatt agaataagaa   5264
gacgaattcc atacatcttg aacgtggga tgttgttgtc tgcttccctc accagtttcc    5324
aacaagtaag agctcttcac tctctccaac aagcttattt ccctttcacc accatcctcc   5384
actaatctcc cttgttccaa tatctgcacc acttgtctca tcttcggacg cactctcgga   5444
tcaggatgca cacacaacag tcctattctc agagccatct ccacttcctc gaccacgaac   5504
actccattcg cctttattct ctcgtctaaa ccatcaacca ctttgtcttt ctccattagt   5564
ccccatatcc attccactat cccttctctt ccttcctcta ttggcctcct tccacacact   5624
acctccaaca caaacactcc aaagctatac acatcggttt gcgctgatgc tctccctgtc   5684
ttaaccaact caggcgccat ataacccgct gttccaacaa catgtgtcgt gctaaccatc   5744
tctttactag tgttctgcaa cttagccaac ccaaaatcac ctaccctcgc gttcatatcc   5804
ttgtcaagca acacattgct tgactttata tctctatgta acacctttgt ctcccaccct   5864
tcgtgtagat acaacatccc tgaggctagg tctcttatca ctctcattct ttcctcccaa   5924
ttcaacatct cgttacaatc aaatatccgc ttatcgacac ttccattctc catatactcg   5984
taaatcaata tcagactctc tcctcctttc ttagaccaac cttttagtcc aactatattc   6044
ttgtgtctca acctccctaa gctcgagacc tcagctaaga actcactcgt cgcgccaacg   6104
ctctctcgag gactcatcat tattctctta accgcaactt cttttaccttc caacactccc   6164
ctgtacactt tagaattccc tccgtatccg atcatgttct catcggaaaa ccttttgtt    6224
gcttccaaaa catctttgta ttgcactctg tgaggccaat actctgtttc ccaatcttcc   6284
acgtctcctt ctagtctctg ccttcgacgc cttacaacgt agaaacagag gagcccaata   6344
acagagacta caacacaac accactagag accccagcaa tgaagccttt agacttcaaa   6404
acagagtcac ctgacaattt aaacgaaggt agattcctag tgatcaaagc atcaccaatg   6464
gagaaattgg agttactaaa actccatgag agaatcctat ggctctgcac tagttgtcct   6524
gtggaggcag tgaatccaac gaacatatca tcaagtaaga ctccagtgag atttaatgga   6584
atgcttatga gtggtcttat gggctttcta gagctagctc tagccatcgt gacattgatc   6644
gctgacccat taaactcgat ccacgcctga taattctcgc cactgttaag cttcagctcc   6704
gtgaatctct ggccgtctct gcctccatag aa acc tgc agt ttc aga tgc aac   6757
                                  Glu Thr Cys Ser Phe Arg Cys Asn
                                                 455 gga agt gag aga att gac gtc gac gcc gac gtg gtt gtc gtt gat gtc    6805
Gly Ser Glu Arg Ile Asp Val Asp Ala Asp Val Val Val Asp Val
460                 465                 470                 475
```

```
gtt gaa ctc ttg gtt agc gaa aac atc gaa ttc aac ggc gaa gat tcg      6853
Val Glu Leu Leu Val Ser Glu Asn Ile Glu Phe Asn Gly Glu Asp Ser
                480                 485                 490 gct att ggg gtc acc gtt att ggt gaa gtt gaa gag gcc gag atg ctg      6901
Ala Ile Gly Val Thr Val Ile Gly Glu Val Glu Glu Ala Glu Met Leu
            495                 500                 505 aga tga gcttgcggcg gaggtttcgg agaaaggaag gaagacgaag gcgaagccgt       6957
Arg  * ggc                                                                   6960
```

<210> SEQ ID NO 42
<211> LENGTH: 508
<212> TYPE: PRT
<213> ORGANISM: Arabidopsis thaliana

<400> SEQUENCE: 42

```
Met Gly Leu Val Met Arg Phe Asp Leu Tyr Leu Met Phe Val Met Leu
 1               5                  10                  15

Met Gly Leu Gly Phe Thr Ile Ser Asn Gly Tyr Lys Phe Tyr Val Gly
             20                  25                  30

Gly Lys Asp Gly Trp Val Pro Thr Pro Ser Glu Asp Tyr Ser His Trp
         35                  40                  45

Ser His Arg Asn Arg Phe Gln Val Asn Asp Thr Leu His Phe Lys Tyr
     50                  55                  60

Ala Lys Gly Lys Asp Ser Val Leu Glu Val Thr Glu Gln Glu Tyr Asn
 65                  70                  75                  80

Thr Cys Asn Thr Thr His Pro Leu Thr Ser Leu Ser Asp Gly Asp Ser
                 85                  90                  95

Leu Phe Leu Leu Ser His Ser Gly Ser Tyr Phe Phe Ile Ser Gly Asn
            100                 105                 110

Ser Gln Asn Cys Leu Lys Gly Gln Lys Leu Ala Val Lys Val Leu Ser
        115                 120                 125

Thr Val His His Ser His Ser Pro Arg His Thr Ser Pro Ser Pro Ser
130                 135                 140

Pro Val His Gln Glu Leu Ser Ser Pro Gly Pro Ser Pro Gly Val Glu
145                 150                 155                 160

Pro Ser Ser Asp Ser Asn Ser Arg Val Pro Ala Pro Gly Pro Ala Thr
                165                 170                 175

Ala Pro Asn Ser Ala Gly Leu Val Gly Pro Gly Met Val Val Leu Val
            180                 185                 190

Val Asn Ser Ile Ile Lys Pro Ile Asp Ser Phe Leu Leu Lys Ser Leu
        195                 200                 205

Pro Leu Val Val Asp Val Ala Val Gly Ile Ser Thr Ser Arg Gln Leu
    210                 215                 220

Gln Ala Ser Glu Glu Pro Val Ser Ser Pro Leu Ser Ser Pro Ala Leu
225                 230                 235                 240

Leu Gly Ser Gly Lys Glu Glu Gln Lys Ile Ile Pro Lys Arg Gln
                245                 250                 255

Lys Val Gln Ala Val Leu Lys Ser Ile Lys Gln Ser Pro Lys Lys Val
            260                 265                 270

Asn Leu Val Ala Ala Leu Val Arg Gly Met Arg Val Glu Asp Ala Leu
        275                 280                 285

Ile Gln Leu Gln Val Thr Val Lys Arg Ala Ala Gln Thr Val Tyr Arg
    290                 295                 300

Val Ile His Ala Ala Arg Ala Asn Ala Thr His Asn His Gly Leu Asp
```

```
                305                 310                 315                 320
Pro Asp Arg Leu Leu Val Ala Glu Ala Phe Val Gly Lys Gly Leu Phe
                325                 330                 335

Gly Lys Lys Val Ala Tyr His Ala Lys Gly Arg Ser Gly Ile Ile Ser
                340                 345                 350

Ile Pro Arg Cys Arg Leu Thr Val Ile Val Arg Glu Thr Thr Pro Glu
                355                 360                 365

Glu Glu Ala Glu Ile Ala Arg Leu Lys Val His Asn Phe Lys Lys Lys
        370                 375                 380

Ser Lys Arg Glu Arg Gln Leu Val Pro His Lys Leu Ile Glu Thr Ser
385                 390                 395                 400

Pro Ile Trp Asn Arg Arg Gly Thr Lys Ala Asn His Arg Ser Ser Glu
                405                 410                 415

Leu Val Leu Thr Ile Ile Leu Asp Val Thr Cys Val Gly Asn Met Glu
                420                 425                 430

Lys Asn Arg Leu Asp Asn Leu Thr Asn Gln Asn Asn Ile Tyr His His
                435                 440                 445

Asn Pro Glu Thr Cys Ser Phe Arg Cys Asn Gly Ser Glu Arg Ile
        450                 455                 460

Asp Val Asp Ala Asp Val Val Val Asp Val Val Glu Leu Leu Val
465                 470                 475                 480

Ser Glu Asn Ile Glu Phe Asn Gly Glu Asp Ser Ala Ile Gly Val Thr
                485                 490                 495

Val Ile Gly Glu Val Glu Glu Ala Glu Met Leu Arg
                500                 505

<210> SEQ ID NO 43
<211> LENGTH: 729
<212> TYPE: DNA
<213> ORGANISM: Arabidopsis thaliana
<220> FEATURE:
<221> NAME/KEY: CDS
<222> LOCATION: (26)...(718)

<400> SEQUENCE: 43
ctgcggcacc ggcgtcggag ttgcg atg ttc gcc aac aag ttc ccg ggc gtc        52
                           Met Phe Ala Asn Lys Phe Pro Gly Val
                             1               5 tac gca gcc act tgt ctc tcc gtc gaa gac gcc gtc aac gct cga tca       100
Tyr Ala Ala Thr Cys Leu Ser Val Glu Asp Ala Val Asn Ala Arg Ser
 10                  15                  20                  25 ata agc aat tgc aat gtc ctc gca ttc tcc ggc atc aaa aca tcc ccg       148
Ile Ser Asn Cys Asn Val Leu Ala Phe Ser Gly Ile Lys Thr Ser Pro
                 30                  35                  40 gaa acc gcc ttg gaa atc ttc gac gct tgg atc aaa act cct ttc aaa       196
Glu Thr Ala Leu Glu Ile Phe Asp Ala Trp Ile Lys Thr Pro Phe Lys
             45                  50                  55 tct cct tgt cct gcg tcc gga tcc gaa cca tgg agc tca gtt atc tct       244
Ser Pro Cys Pro Ala Ser Gly Ser Glu Pro Trp Ser Ser Val Ile Ser
         60                  65                  70 tcc ttc ctc gac aat tct ctc tcc gag atg tct cag att gga aag tca       292
Ser Phe Leu Asp Asn Ser Leu Ser Glu Met Ser Gln Ile Gly Lys Ser
     75                  80                  85 acc gcc ggc gat tca aca acc aag aag atc gat gaa aca acc gcg tct       340
Thr Ala Gly Asp Ser Thr Thr Lys Lys Ile Asp Glu Thr Thr Ala Ser
 90                  95                 100                 105 tgc gta att tgc tgc ttg gcg aag aac aga gag ttc act cca gtg gac       388
Cys Val Ile Cys Cys Leu Ala Lys Asn Arg Glu Phe Thr Pro Val Asp
```

```
                  110                 115                 120
atc atg ccg gga ggc tcg atg aag atc gtt aga gag acg ccg acg tcg      436
Ile Met Pro Gly Gly Ser Met Lys Ile Val Arg Glu Thr Pro Thr Ser
        125                 130                 135 gcg att gta aga ttc aaa gcg gga agt gtg gaa ccg gcg cat cac cac      484
Ala Ile Val Arg Phe Lys Ala Gly Ser Val Glu Pro Ala His His His
            140                 145                 150 aca ttc ggc cat gac ctt gta gtc ata aag gga aag aaa agt gtg tgg      532
Thr Phe Gly His Asp Leu Val Val Ile Lys Gly Lys Lys Ser Val Trp
155                 160                 165 aat ctg agc aag aag gag aga gct gat ctc gtt gac ggc gat tac cta      580
Asn Leu Ser Lys Lys Glu Arg Ala Asp Leu Val Asp Gly Asp Tyr Leu
170                 175                 180                 185 ttc act ccc gcc ggt gat gtt cac cga gtc aaa tat cac gaa gac act      628
Phe Thr Pro Ala Gly Asp Val His Arg Val Lys Tyr His Glu Asp Thr
                190                 195                 200 gag ttc ttc atc act tgg gat ggc cat tgg gac ata ttc ctt gac gaa      676
Glu Phe Phe Ile Thr Trp Asp Gly His Trp Asp Ile Phe Leu Asp Glu
        205                 210                 215 gac ctc gaa act gca aag aaa gcc atc gaa gaa gaa gct tga              718
Asp Leu Glu Thr Ala Lys Lys Ala Ile Glu Glu Glu Ala *
            220                 225                 230 aggtgtaaac t                                                         729

<210> SEQ ID NO 44
<211> LENGTH: 230
<212> TYPE: PRT
<213> ORGANISM: Arabidopsis thaliana

<400> SEQUENCE: 44

Met Phe Ala Asn Lys Phe Pro Gly Val Tyr Ala Ala Thr Cys Leu Ser
1               5                   10                  15

Val Glu Asp Ala Val Asn Ala Arg Ser Ile Ser Asn Cys Asn Val Leu
            20                  25                  30

Ala Phe Ser Gly Ile Lys Thr Ser Pro Glu Thr Ala Leu Glu Ile Phe
        35                  40                  45

Asp Ala Trp Ile Lys Thr Pro Phe Lys Ser Pro Cys Pro Ala Ser Gly
    50                  55                  60

Ser Glu Pro Trp Ser Ser Val Ile Ser Ser Phe Leu Asp Asn Ser Leu
65                  70                  75                  80

Ser Glu Met Ser Gln Ile Gly Lys Ser Thr Ala Gly Asp Ser Thr Thr
                85                  90                  95

Lys Lys Ile Asp Glu Thr Thr Ala Ser Cys Val Ile Cys Cys Leu Ala
            100                 105                 110

Lys Asn Arg Glu Phe Thr Pro Val Asp Ile Met Pro Gly Gly Ser Met
        115                 120                 125

Lys Ile Val Arg Glu Thr Pro Thr Ser Ala Ile Val Arg Phe Lys Ala
    130                 135                 140

Gly Ser Val Glu Pro Ala His His His Thr Phe Gly His Asp Leu Val
145                 150                 155                 160

Val Ile Lys Gly Lys Lys Ser Val Trp Asn Leu Ser Lys Lys Glu Arg
                165                 170                 175

Ala Asp Leu Val Asp Gly Asp Tyr Leu Phe Thr Pro Ala Gly Asp Val
            180                 185                 190

His Arg Val Lys Tyr His Glu Asp Thr Glu Phe Phe Ile Thr Trp Asp
        195                 200                 205
```

-continued

| | |
|---|---|
| Gly His Trp Asp Ile Phe Leu Asp Glu Asp Leu Glu Thr Ala Lys Lys<br>     210                   215                  220 | |
| Ala Ile Glu Glu Glu Ala<br>225                230 | |

<210> SEQ ID NO 45
<211> LENGTH: 1203
<212> TYPE: DNA
<213> ORGANISM: Arabidopsis thaliana
<220> FEATURE:
<221> NAME/KEY: CDS
<222> LOCATION: (12)...(1193)

<400> SEQUENCE: 45

| | |
|---|---:|
| aggaaagaga a atg act ata agg aac caa cga ttc tct ctt ctt aaa caa<br>            Met Thr Ile Arg Asn Gln Arg Phe Ser Leu Leu Lys Gln<br>             1               5                     10 | 50 |
| cct ata tcc tcc aca ctt aat cag cat tta gta gat tat cca acc ccg<br>Pro Ile Ser Ser Thr Leu Asn Gln His Leu Val Asp Tyr Pro Thr Pro<br>     15                   20                   25 | 98 |
| agc aat ctt agt tat tgg tgg ggg ttc ggt ccg tta gct gga att tgt<br>Ser Asn Leu Ser Tyr Trp Trp Gly Phe Gly Pro Leu Ala Gly Ile Cys<br>30               35                   40                  45 | 146 |
| tta gtc att cag ata gtg act ggc gtt ttt tta gct atg cat tac aca<br>Leu Val Ile Gln Ile Val Thr Gly Val Phe Leu Ala Met His Tyr Thr<br>               50                  55                  60 | 194 |
| cct cat gtg gat tta gct ttc aac agc gta gaa cac att atg aga gat<br>Pro His Val Asp Leu Ala Phe Asn Ser Val Glu His Ile Met Arg Asp<br>         65                   70                   75 | 242 |
| gtt gaa ggg ggc tgg ttg ctc cgt tat atg cat gct aat ggg gca agt<br>Val Glu Gly Gly Trp Leu Leu Arg Tyr Met His Ala Asn Gly Ala Ser<br>             80                  85                  90 | 290 |
| atg ttt ctt att gtg gtt tac ctt cat att ttt cgt ggt cta tat cat<br>Met Phe Leu Ile Val Val Tyr Leu His Ile Phe Arg Gly Leu Tyr His<br>               95                100              105 | 338 |
| gcg agt tat agc agt cct agg gaa ttt gtt tgg tgt ctt gga gtt gta<br>Ala Ser Tyr Ser Ser Pro Arg Glu Phe Val Trp Cys Leu Gly Val Val<br>110               115                120              125 | 386 |
| atc ttc cta tta atg att gtg aca gct ttt ata gga tat gta cta cct<br>Ile Phe Leu Leu Met Ile Val Thr Ala Phe Ile Gly Tyr Val Leu Pro<br>                  130                135              140 | 434 |
| tgg ggt cag atg agc ttt tgg gga gct aca gta att aca agc tta gct<br>Trp Gly Gln Met Ser Phe Trp Gly Ala Thr Val Ile Thr Ser Leu Ala<br>                 145                150              155 | 482 |
| agc gcc ata cct gta gta gga gat acc ata gtg act tgg ctt tgg ggt<br>Ser Ala Ile Pro Val Val Gly Asp Thr Ile Val Thr Trp Leu Trp Gly<br>              160                165              170 | 530 |
| ggt ttc tcc gtg gac aat gcc acc tta aat cgt ttt ttt agt ctt cat<br>Gly Phe Ser Val Asp Asn Ala Thr Leu Asn Arg Phe Phe Ser Leu His<br>175              180               185 | 578 |
| cat tta ctc ccc ttt att tta gta ggc gcc agt ctt ctt cat ctg gcc<br>His Leu Leu Pro Phe Ile Leu Val Gly Ala Ser Leu Leu His Leu Ala<br>190              195               200              205 | 626 |
| gca ttg cat caa tat gga tca aat aat cca ttg ggt gta cat tct gag<br>Ala Leu His Gln Tyr Gly Ser Asn Asn Pro Leu Gly Val His Ser Glu<br>                  210                215              220 | 674 |
| atg gat aaa ata gct ttt tac cct tat ttt tat gtc aag gat cta gtt<br>Met Asp Lys Ile Ala Phe Tyr Pro Tyr Phe Tyr Val Lys Asp Leu Val<br>                      225               230              235 | 722 |
| ggt tgg gta gct ttt gct atc ttt ttt tct att tgg att ttt tat gct<br>Gly Trp Val Ala Phe Ala Ile Phe Phe Ser Ile Trp Ile Phe Tyr Ala | 770 |

```
                 240                 245                 250
cct aat gtt ttg gga cat ccc gac aat tat ata cct gct aat ccg atg    818
Pro Asn Val Leu Gly His Pro Asp Asn Tyr Ile Pro Ala Asn Pro Met
    255                 260                 265 tcc acc ccg cct cat att gtg ccg gaa tgg tat ttc cta ccg atc cat    866
Ser Thr Pro Pro His Ile Val Pro Glu Trp Tyr Phe Leu Pro Ile His
270                 275                 280                 285 gcc att ctt cgt agt ata cct gac aaa gcg gga ggt gta gcc gca ata    914
Ala Ile Leu Arg Ser Ile Pro Asp Lys Ala Gly Gly Val Ala Ala Ile
                290                 295                 300 gca cca gtt ttt ata tgt ctc ttg gct tta cct ttt ttt aaa agt atg    962
Ala Pro Val Phe Ile Cys Leu Leu Ala Leu Pro Phe Phe Lys Ser Met
            305                 310                 315 tat gtg cgt agt tca agt ttt cga ccg att cac caa gga atg ttt tgg   1010
Tyr Val Arg Ser Ser Ser Phe Arg Pro Ile His Gln Gly Met Phe Trp
        320                 325                 330 ttg ctt ttg gcg gat tgc tta cta cta ggt tgg atc gga tgt caa cct   1058
Leu Leu Leu Ala Asp Cys Leu Leu Leu Gly Trp Ile Gly Cys Gln Pro
335                 340                 345 gtg gag gct cca ttt gtt act att gga caa att tct cct ttg gtt ttc   1106
Val Glu Ala Pro Phe Val Thr Ile Gly Gln Ile Ser Pro Leu Val Phe
350                 355                 360                 365 ttc ttg ttc ttt gcc ata acg ccc att ctg gga cga gtt gga aga gga   1154
Phe Leu Phe Phe Ala Ile Thr Pro Ile Leu Gly Arg Val Gly Arg Gly
                370                 375                 380 att cct aat tct tac acg gat gag act gat cac acc tga tcagtgaaaa   1203
Ile Pro Asn Ser Tyr Thr Asp Glu Thr Asp His Thr *
                385                 390

<210> SEQ ID NO 46
<211> LENGTH: 393
<212> TYPE: PRT
<213> ORGANISM: Arabidopsis thaliana

<400> SEQUENCE: 46

Met Thr Ile Arg Asn Gln Arg Phe Ser Leu Leu Lys Gln Pro Ile Ser
1               5                   10                  15

Ser Thr Leu Asn Gln His Leu Val Asp Tyr Pro Thr Pro Ser Asn Leu
            20                  25                  30

Ser Tyr Trp Trp Gly Phe Gly Pro Leu Ala Gly Ile Cys Leu Val Ile
        35                  40                  45

Gln Ile Val Thr Gly Val Phe Leu Ala Met His Tyr Thr Pro His Val
    50                  55                  60

Asp Leu Ala Phe Asn Ser Val Glu His Ile Met Arg Asp Val Glu Gly
65                  70                  75                  80

Gly Trp Leu Leu Arg Tyr Met His Ala Asn Gly Ala Ser Met Phe Leu
                85                  90                  95

Ile Val Val Tyr Leu His Ile Phe Arg Gly Leu Tyr His Ala Ser Tyr
            100                 105                 110

Ser Ser Pro Arg Glu Phe Val Trp Cys Leu Gly Val Val Ile Phe Leu
        115                 120                 125

Leu Met Ile Val Thr Ala Phe Ile Gly Tyr Val Leu Pro Trp Gly Gln
    130                 135                 140

Met Ser Phe Trp Gly Ala Thr Val Ile Thr Ser Leu Ala Ser Ala Ile
145                 150                 155                 160

Pro Val Val Gly Asp Thr Ile Val Thr Trp Leu Trp Gly Gly Phe Ser
                165                 170                 175
```

```
Val Asp Asn Ala Thr Leu Asn Arg Phe Phe Ser Leu His His Leu Leu
            180                 185                 190

Pro Phe Ile Leu Val Gly Ala Ser Leu Leu His Leu Ala Ala Leu His
        195                 200                 205

Gln Tyr Gly Ser Asn Asn Pro Leu Gly Val His Ser Glu Met Asp Lys
    210                 215                 220

Ile Ala Phe Tyr Pro Tyr Phe Tyr Val Lys Asp Leu Val Gly Trp Val
225                 230                 235                 240

Ala Phe Ala Ile Phe Phe Ser Ile Trp Ile Phe Tyr Ala Pro Asn Val
                245                 250                 255

Leu Gly His Pro Asp Asn Tyr Ile Pro Ala Asn Pro Met Ser Thr Pro
                260                 265                 270

Pro His Ile Val Pro Glu Trp Tyr Phe Leu Pro Ile His Ala Ile Leu
                275                 280                 285

Arg Ser Ile Pro Asp Lys Ala Gly Gly Val Ala Ala Ile Ala Pro Val
    290                 295                 300

Phe Ile Cys Leu Leu Ala Leu Pro Phe Phe Lys Ser Met Tyr Val Arg
305                 310                 315                 320

Ser Ser Ser Phe Arg Pro Ile His Gln Gly Met Phe Trp Leu Leu Leu
                325                 330                 335

Ala Asp Cys Leu Leu Leu Gly Trp Ile Gly Cys Gln Pro Val Glu Ala
                340                 345                 350

Pro Phe Val Thr Ile Gly Gln Ile Ser Pro Leu Val Phe Phe Leu Phe
                355                 360                 365

Phe Ala Ile Thr Pro Ile Leu Gly Arg Val Gly Arg Gly Ile Pro Asn
        370                 375                 380

Ser Tyr Thr Asp Glu Thr Asp His Thr
385                 390

<210> SEQ ID NO 47
<211> LENGTH: 1194
<212> TYPE: DNA
<213> ORGANISM: Arabidopsis thaliana
<220> FEATURE:
<221> NAME/KEY: CDS
<222> LOCATION: (1)...(1194)

<400> SEQUENCE: 47 atg aga aaa gtt tct tcc gta att tct gtc gtt gat ccc gtt att ttc      48
Met Arg Lys Val Ser Ser Val Ile Ser Val Val Asp Pro Val Ile Phe
1               5                   10                  15 cga gga aat tac gca gct aca ctc gat gtg tcg tat ccg gta ttc ccg      96
Arg Gly Asn Tyr Ala Ala Thr Leu Asp Val Ser Tyr Pro Val Phe Pro
                20                  25                  30 caa aat aaa gat ggc cgt gca ctt cag aaa gtt ctc gga acc att cgt     144
Gln Asn Lys Asp Gly Arg Ala Leu Gln Lys Val Leu Gly Thr Ile Arg
            35                  40                  45 aac gga gat ttg gct gtt tcg gct cct aaa aca agt ctt agg gca ggt     192
Asn Gly Asp Leu Ala Val Ser Ala Pro Lys Thr Ser Leu Arg Ala Gly
        50                  55                  60 att ttc ggt gaa ggt tcc agc ttg gtc gat cag atg ccc tgt aaa gtt     240
Ile Phe Gly Glu Gly Ser Ser Leu Val Asp Gln Met Pro Cys Lys Val
65                  70                  75                  80 tac gtg gcg ttc cac aaa gaa tca tac tgc tcg ctt acc ggg cta agc     288
Tyr Val Ala Phe His Lys Glu Ser Tyr Cys Ser Leu Thr Gly Leu Ser
                85                  90                  95 aaa cgc gga gtc gca ata aac gaa gca agt ctt tcc ctg gtc gga atc     336
Lys Arg Gly Val Ala Ile Asn Glu Ala Ser Leu Ser Leu Val Gly Ile
```

```
                100                 105                 110
act aaa gtt aga gcc ccc gtc gga aat acc gtt gga gcg gaa gca acc    384
Thr Lys Val Arg Ala Pro Val Gly Asn Thr Val Gly Ala Glu Ala Thr
            115                 120                 125 gta tac ata ggt agt cca aaa cct tat aca gag tgt agt act cca aat    432
Val Tyr Ile Gly Ser Pro Lys Pro Tyr Thr Glu Cys Ser Thr Pro Asn
    130                 135                 140 aaa atg tat gcg gtt gca gct ggt ttc aag gtg gca agt ttc gcc gct    480
Lys Met Tyr Ala Val Ala Ala Gly Phe Lys Val Ala Ser Phe Ala Ala
145                 150                 155                 160 agt acg tgc gta cgt ccg cct gca cgt gca cgt cgt acg ctg acc gtg    528
Ser Thr Cys Val Arg Pro Pro Ala Arg Ala Arg Arg Thr Leu Thr Val
                165                 170                 175 acg tcg acc gtg acg ctg tct atg gca act ggt aaa tgc gta aat aca    576
Thr Ser Thr Val Thr Leu Ser Met Ala Thr Gly Lys Cys Val Asn Thr
            180                 185                 190 gga aac gaa cca gta tct aaa cct aca gga gta cgt atg atg tta att    624
Gly Asn Glu Pro Val Ser Lys Pro Thr Gly Val Arg Met Met Leu Ile
        195                 200                 205 cct ctc gat gct act ctc att aaa gta tgg act ggg gaa gta aaa aaa    672
Pro Leu Asp Ala Thr Leu Ile Lys Val Trp Thr Gly Glu Val Lys Lys
    210                 215                 220 gcg ata gtt tcc cgg cct gca aaa att ttc aat agc gta gga aat tta    720
Ala Ile Val Ser Arg Pro Ala Lys Ile Phe Asn Ser Val Gly Asn Leu
225                 230                 235                 240 gaa cgt cct tca att tcg cat tct tgt gga caa ggt ttg gat gaa gct    768
Glu Arg Pro Ser Ile Ser His Ser Cys Gly Gln Gly Leu Asp Glu Ala
                245                 250                 255 gcc gct tat atc aag ggt aga ctt tct cca atc gtt aaa gca gaa aga    816
Ala Ala Tyr Ile Lys Gly Arg Leu Ser Pro Ile Val Lys Ala Glu Arg
            260                 265                 270 att aaa gtt ttg gtt aaa gac gag cac gaa gaa gta aaa gaa ctt ctt    864
Ile Lys Val Leu Val Lys Asp Glu His Glu Glu Val Lys Glu Leu Leu
        275                 280                 285 caa gaa ggt tac gaa gaa atc gtc ggt gag tct cca agt ttc aat tta    912
Gln Glu Gly Tyr Glu Glu Ile Val Gly Glu Ser Pro Ser Phe Asn Leu
    290                 295                 300 gca caa gaa gcg tgg gaa aaa gct gaa aga cga gca aaa ggt cag tcc    960
Ala Gln Glu Ala Trp Glu Lys Ala Glu Arg Arg Ala Lys Gly Gln Ser
305                 310                 315                 320 ccg tgc agt gcg gca aaa gca aac ctt gca acc tac tat ttt tca aca   1008
Pro Cys Ser Ala Ala Lys Ala Asn Leu Ala Thr Tyr Tyr Phe Ser Thr
                325                 330                 335 ggt gat ttc gaa aaa tca att aaa ctc tac gaa gaa cct atg ggt ttg   1056
Gly Asp Phe Glu Lys Ser Ile Lys Leu Tyr Glu Glu Pro Met Gly Leu
            340                 345                 350 aaa gat act gat aag agc tat ctg cga gaa cgt aga aaa aga gta gag   1104
Lys Asp Thr Asp Lys Ser Tyr Leu Arg Glu Arg Arg Lys Arg Val Glu
        355                 360                 365 gct act acg ttg cgt gca ccg ttc gtg gtc cag ctg acc gtg cgt agt   1152
Ala Thr Thr Leu Arg Ala Pro Phe Val Val Gln Leu Thr Val Arg Ser
    370                 375                 380 cgt acg acg atg atc gcc gtt ggt gaa agc aac gca aac tga            1194
Arg Thr Thr Met Ile Ala Val Gly Glu Ser Asn Ala Asn *
385                 390                 395
```

<210> SEQ ID NO 48
<211> LENGTH: 397
<212> TYPE: PRT
<213> ORGANISM: Arabidopsis thaliana

<400> SEQUENCE: 48

Met Arg Lys Val Ser Ser Val Ile Ser Val Asp Pro Val Ile Phe
1               5                   10                  15

Arg Gly Asn Tyr Ala Ala Thr Leu Asp Val Ser Tyr Pro Val Phe Pro
            20                  25                  30

Gln Asn Lys Asp Gly Arg Ala Leu Gln Lys Val Leu Gly Thr Ile Arg
        35                  40                  45

Asn Gly Asp Leu Ala Val Ser Ala Pro Lys Thr Ser Leu Arg Ala Gly
    50                  55                  60

Ile Phe Gly Glu Gly Ser Ser Leu Val Asp Gln Met Pro Cys Lys Val
65                  70                  75                  80

Tyr Val Ala Phe His Lys Glu Ser Tyr Cys Ser Leu Thr Gly Leu Ser
                85                  90                  95

Lys Arg Gly Val Ala Ile Asn Glu Ala Ser Leu Ser Leu Val Gly Ile
            100                 105                 110

Thr Lys Val Arg Ala Pro Val Gly Asn Thr Val Gly Ala Glu Ala Thr
        115                 120                 125

Val Tyr Ile Gly Ser Pro Lys Pro Tyr Thr Glu Cys Ser Thr Pro Asn
    130                 135                 140

Lys Met Tyr Ala Val Ala Ala Gly Phe Lys Val Ala Ser Phe Ala Ala
145                 150                 155                 160

Ser Thr Cys Val Arg Pro Pro Ala Arg Ala Arg Thr Leu Thr Val
                165                 170                 175

Thr Ser Thr Val Thr Leu Ser Met Ala Thr Gly Lys Cys Val Asn Thr
            180                 185                 190

Gly Asn Glu Pro Val Ser Lys Pro Thr Gly Val Arg Met Met Leu Ile
        195                 200                 205

Pro Leu Asp Ala Thr Leu Ile Lys Val Trp Thr Gly Glu Val Lys Lys
    210                 215                 220

Ala Ile Val Ser Arg Pro Ala Lys Ile Phe Asn Ser Val Gly Asn Leu
225                 230                 235                 240

Glu Arg Pro Ser Ile Ser His Ser Cys Gly Gln Gly Leu Asp Glu Ala
                245                 250                 255

Ala Ala Tyr Ile Lys Gly Arg Leu Ser Pro Ile Val Lys Ala Glu Arg
            260                 265                 270

Ile Lys Val Leu Val Lys Asp Glu His Glu Val Lys Glu Leu Leu
        275                 280                 285

Gln Glu Gly Tyr Glu Glu Ile Val Gly Glu Ser Pro Ser Phe Asn Leu
    290                 295                 300

Ala Gln Glu Ala Trp Glu Lys Ala Glu Arg Arg Ala Lys Gly Gln Ser
305                 310                 315                 320

Pro Cys Ser Ala Ala Lys Ala Asn Leu Ala Thr Tyr Tyr Phe Ser Thr
                325                 330                 335

Gly Asp Phe Glu Lys Ser Ile Lys Leu Tyr Glu Glu Pro Met Gly Leu
            340                 345                 350

Lys Asp Thr Asp Lys Ser Tyr Leu Arg Glu Arg Lys Arg Val Glu
        355                 360                 365

Ala Thr Thr Leu Arg Ala Pro Phe Val Val Gln Leu Thr Val Arg Ser
    370                 375                 380

Arg Thr Thr Met Ile Ala Val Gly Glu Ser Asn Ala Asn
385                 390                 395

<210> SEQ ID NO 49
<211> LENGTH: 611
<212> TYPE: DNA
<213> ORGANISM: Arabidopsis thaliana
<220> FEATURE:
<221> NAME/KEY: CDS
<222> LOCATION: (5)...(601)

<400> SEQUENCE: 49

```
gaaa atg atc gta ctt tct gtt ggt tcc gct tct tca tct ccg atc gtc      49
     Met Ile Val Leu Ser Val Gly Ser Ala Ser Ser Ser Pro Ile Val
       1               5                  10                  15 gtc gtc ttt tcc gtc gcg ctt ctt ctg ttc tac ttc tct gaa act tct      97
Val Val Phe Ser Val Ala Leu Leu Leu Phe Tyr Phe Ser Glu Thr Ser
                 20                  25                  30 cta gga gct cct tgt ccc atc aat ggc ttg cca atc gtg agg aat att     145
Leu Gly Ala Pro Cys Pro Ile Asn Gly Leu Pro Ile Val Arg Asn Ile
             35                  40                  45 agt gac ctt cct cag gat aac tat gga aga cca ggt ctt tcc cac atg     193
Ser Asp Leu Pro Gln Asp Asn Tyr Gly Arg Pro Gly Leu Ser His Met
         50                  55                  60 act gtt gct ggc tcc gta ttg cat gga atg aaa gag gtt gaa ata tgg     241
Thr Val Ala Gly Ser Val Leu His Gly Met Lys Glu Val Glu Ile Trp
     65                  70                  75 ctt cag aca ttt gct cca ggt tca gag aca cca att cac agg cac tcc     289
Leu Gln Thr Phe Ala Pro Gly Ser Glu Thr Pro Ile His Arg His Ser
 80                  85                  90                  95 tgt gaa gag gtt ttt gtt gtc cta aag ggc agt ggt act ctg tat ctc     337
Cys Glu Glu Val Phe Val Val Leu Lys Gly Ser Gly Thr Leu Tyr Leu
                100                 105                 110 gct gaa aca cat gga aat ttc cct ggg aaa cca atc gaa ttt cca atc     385
Ala Glu Thr His Gly Asn Phe Pro Gly Lys Pro Ile Glu Phe Pro Ile
            115                 120                 125 ttt gcc aac agt aca att cat att ccg atc aat gat gct cat cag gtc     433
Phe Ala Asn Ser Thr Ile His Ile Pro Ile Asn Asp Ala His Gln Val
        130                 135                 140 aaa aac acc ggt cat gag gac ctg cag gtg ttg gtt atc ata tct cgg     481
Lys Asn Thr Gly His Glu Asp Leu Gln Val Leu Val Ile Ile Ser Arg
    145                 150                 155 ccg cct att aaa atc ttc atc tac gaa gac tgg ttt atg cca cac act     529
Pro Pro Ile Lys Ile Phe Ile Tyr Glu Asp Trp Phe Met Pro His Thr
160                 165                 170                 175 gct gca agg ctg aag ttc cct tac tat tgg gat gag caa tgc att caa     577
Ala Ala Arg Leu Lys Phe Pro Tyr Tyr Trp Asp Glu Gln Cys Ile Gln
                180                 185                 190 gaa tca caa aaa gac gag ctt taa agcaaagtcc                          611
Glu Ser Gln Lys Asp Glu Leu *
            195
```

<210> SEQ ID NO 50
<211> LENGTH: 198
<212> TYPE: PRT
<213> ORGANISM: Arabidopsis thaliana

<400> SEQUENCE: 50

```
Met Ile Val Leu Ser Val Gly Ser Ala Ser Ser Ser Pro Ile Val Val
  1               5                  10                  15

Val Phe Ser Val Ala Leu Leu Leu Phe Tyr Phe Ser Glu Thr Ser Leu
                 20                  25                  30

Gly Ala Pro Cys Pro Ile Asn Gly Leu Pro Ile Val Arg Asn Ile Ser
             35                  40                  45
```

```
Asp Leu Pro Gln Asp Asn Tyr Gly Arg Pro Gly Leu Ser His Met Thr
 50                  55                  60

Val Ala Gly Ser Val Leu His Gly Met Lys Glu Val Glu Ile Trp Leu
 65                  70                  75                  80

Gln Thr Phe Ala Pro Gly Ser Glu Thr Pro Ile His Arg His Ser Cys
                 85                  90                  95

Glu Glu Val Phe Val Val Leu Lys Gly Ser Gly Thr Leu Tyr Leu Ala
                100                 105                 110

Glu Thr His Gly Asn Phe Pro Gly Lys Pro Ile Glu Phe Pro Ile Phe
            115                 120                 125

Ala Asn Ser Thr Ile His Ile Pro Ile Asn Asp Ala His Gln Val Lys
    130                 135                 140

Asn Thr Gly His Glu Asp Leu Gln Val Leu Val Ile Ile Ser Arg Pro
145                 150                 155                 160

Pro Ile Lys Ile Phe Ile Tyr Glu Asp Trp Phe Met Pro His Thr Ala
                165                 170                 175

Ala Arg Leu Lys Phe Pro Tyr Tyr Trp Asp Glu Gln Cys Ile Gln Glu
            180                 185                 190

Ser Gln Lys Asp Glu Leu
            195

<210> SEQ ID NO 51
<211> LENGTH: 1398
<212> TYPE: DNA
<213> ORGANISM: Arabidopsis thaliana
<220> FEATURE:
<221> NAME/KEY: CDS
<222> LOCATION: (1)...(1398)

<400> SEQUENCE: 51 atg cct cgt cgt cgt acg tgc tgt cgg cgt gaa ttc ggt ccg aca cag      48
Met Pro Arg Arg Arg Thr Cys Cys Arg Arg Glu Phe Gly Pro Thr Gln
  1               5                  10                  15 cca tgt aga ggc gcg tca atc act gga tct cta cgt gac cgt cga ccg      96
Pro Cys Arg Gly Ala Ser Ile Thr Gly Ser Leu Arg Asp Arg Arg Pro
             20                  25                  30 acc gct atc ctt atc gga acc ctc acc gct tta ggc ggt gga gtt aga     144
Thr Ala Ile Leu Ile Gly Thr Leu Thr Ala Leu Gly Gly Gly Val Arg
         35                  40                  45 tgt ggc tct tgc ccc agt gtc gac cgt tgc gga cac gca agt gcc gcc     192
Cys Gly Ser Cys Pro Ser Val Asp Arg Cys Gly His Ala Ser Ala Ala
     50                  55                  60 ata gcg cgt gat agc tgt gcc gtg ttc gca tgg aag cga ggt acg cga     240
Ile Ala Arg Asp Ser Cys Ala Val Phe Ala Trp Lys Arg Gly Thr Arg
 65                  70                  75                  80 caa gag tac tgg tgc tcg act gaa ccg acc ctt gac tgg ggc ccc ggt     288
Gln Glu Tyr Trp Cys Ser Thr Glu Pro Thr Leu Asp Trp Gly Pro Gly
                 85                  90                  95 ggt gga ccc gac ttc gat tgt gat gat ggt ggt gac gat ccg ctt ttg     336
Gly Gly Pro Asp Phe Asp Cys Asp Asp Gly Gly Asp Asp Pro Leu Leu
            100                 105                 110 att caa gat ggc gta aaa gct gcg gag gaa tat gct aaa tct gga aaa     384
Ile Gln Asp Gly Val Lys Ala Ala Glu Glu Tyr Ala Lys Ser Gly Lys
        115                 120                 125 gtt cca gat cca agc tgt act gat aat gct gag ttt caa gtt gtg ctt     432
Val Pro Asp Pro Ser Cys Thr Asp Asn Ala Glu Phe Gln Val Val Leu
    130                 135                 140 att att att agg gag ggg ttg aaa act gat cct tta aaa tac act aag     480
Ile Ile Ile Arg Glu Gly Leu Lys Thr Asp Pro Leu Lys Tyr Thr Lys
```

```
                    -continued
     145              150              155              160 cga ccc agt tgc ctt gtt ggt gtt tct gag gaa act act act ggt gtt    528
Arg Pro Ser Cys Leu Val Gly Val Ser Glu Glu Thr Thr Thr Gly Val
                165              170              175 aag aga agt tac caa atg cag ccg aaa tgt act ttg ctt ttg cat gct    576
Lys Arg Ser Tyr Gln Met Gln Pro Lys Cys Thr Leu Leu Leu His Ala
            180              185              190 act gat gtt tgt gac acc gtg atc aag agc aag att gat aac ttg tac    624
Thr Asp Val Cys Asp Thr Val Ile Lys Ser Lys Ile Asp Asn Leu Tyr
        195              200              205 gga tgc cgc cac tca ctt tcg gat ggt ctc atg agg gct act gat gtt    672
Gly Cys Arg His Ser Leu Ser Asp Gly Leu Met Arg Ala Thr Asp Val
    210              215              220 cgt cgc ccc tgc aag gta gcg ctt gta ggc ggt tac gga gat gtc ttt    720
Arg Arg Pro Cys Lys Val Ala Leu Val Gly Gly Tyr Gly Asp Val Phe
225              230              235              240 aag ggt tgg gtt gct gcc ttg aag caa gct ggt gca cgt gtc atc gtg    768
Lys Gly Trp Val Ala Ala Leu Lys Gln Ala Gly Ala Arg Val Ile Val
                245              250              255 act gag atc ccg caa atc tgt gcc gtc caa gct acc atg gaa ggt agt    816
Thr Glu Ile Pro Gln Ile Cys Ala Val Gln Ala Thr Met Glu Gly Ser
            260              265              270 tcg gtc ctt acc ctt gag gat gtc gtt tca gat gtt gat cgc ttc gtt    864
Ser Val Leu Thr Leu Glu Asp Val Val Ser Asp Val Asp Arg Phe Val
        275              280              285 acg aca acc ggt aac aag gac ctc atc atg gtt gac cac atg agg cga    912
Thr Thr Thr Gly Asn Lys Asp Leu Ile Met Val Asp His Met Arg Arg
    290              295              300 atg aag aac cag gcc ata gtt tgc aac att cga cgt ttc gac aat gaa    960
Met Lys Asn Gln Ala Ile Val Cys Asn Ile Arg Arg Phe Asp Asn Glu
305              310              315              320 atc gac atg cgc agt ctc gag acc ttc cct gga gtg aag cgg atc aca   1008
Ile Asp Met Arg Ser Leu Glu Thr Phe Pro Gly Val Lys Arg Ile Thr
                325              330              335 atc aag gcc cag act gac aga tgg gtc ttt cgc gac acc aac aga ggt   1056
Ile Lys Ala Gln Thr Asp Arg Trp Val Phe Arg Asp Thr Asn Arg Gly
            340              345              350 atc att gtc cca gcc gag ggg cgt ctc atg acg atg gga tgc gcc act   1104
Ile Ile Val Pro Ala Glu Gly Arg Leu Met Thr Met Gly Cys Ala Thr
        355              360              365 gga cac ccc agc ttc cgg acg tcc tgc tct ttc act aac caa gtc agt   1152
Gly His Pro Ser Phe Arg Thr Ser Cys Ser Phe Thr Asn Gln Val Ser
    370              375              380 tct cag ctc gag ttg tgg cgg gag aag agc acc ggc aag tat gag aag   1200
Ser Gln Leu Glu Leu Trp Arg Glu Lys Ser Thr Gly Lys Tyr Glu Lys
385              390              395              400 aaa gtg tac gtc ttc cca aag cac ctt gag aag aag gtt gcc gcc ctt   1248
Lys Val Tyr Val Phe Pro Lys His Leu Glu Lys Lys Val Ala Ala Leu
                405              410              415 cat ctc gta aag ctc gga gca agg ctc act aag ctt agt cgg tgc acg   1296
His Leu Val Lys Leu Gly Ala Arg Leu Thr Lys Leu Ser Arg Cys Thr
            420              425              430 ttg ttg tgc acg gac gac cca gtt gaa ggt cgt aaa gag cct cct cac   1344
Leu Leu Cys Thr Asp Asp Pro Val Glu Gly Arg Lys Glu Pro Pro His
        435              440              445 cgt gct ggc agc cct gaa ccg tgc cag ctg cag ctg acc gtg ttc agg   1392
Arg Ala Gly Ser Pro Glu Pro Cys Gln Leu Gln Leu Thr Val Phe Arg
    450              455              460 tag taa                                                           1398
```

<210> SEQ ID NO 52
<211> LENGTH: 464
<212> TYPE: PRT
<213> ORGANISM: Arabidopsis thaliana

<400> SEQUENCE: 52

Met Pro Arg Arg Thr Cys Cys Arg Arg Glu Phe Gly Pro Thr Gln
1               5                   10                  15

Pro Cys Arg Gly Ala Ser Ile Thr Gly Ser Leu Arg Asp Arg Pro
            20                  25                  30

Thr Ala Ile Leu Ile Gly Thr Leu Thr Ala Leu Gly Gly Val Arg
        35                  40                  45

Cys Gly Ser Cys Pro Ser Val Asp Arg Cys Gly His Ala Ser Ala Ala
    50                  55                  60

Ile Ala Arg Asp Ser Cys Ala Val Phe Ala Trp Lys Arg Gly Thr Arg
65                  70                  75                  80

Gln Glu Tyr Trp Cys Ser Thr Glu Pro Thr Leu Asp Trp Gly Pro Gly
                85                  90                  95

Gly Gly Pro Asp Phe Asp Cys Asp Asp Gly Gly Asp Asp Pro Leu Leu
            100                 105                 110

Ile Gln Asp Gly Val Lys Ala Ala Glu Glu Tyr Ala Lys Ser Gly Lys
        115                 120                 125

Val Pro Asp Pro Ser Cys Thr Asp Asn Ala Glu Phe Gln Val Val Leu
    130                 135                 140

Ile Ile Ile Arg Glu Gly Leu Lys Thr Asp Pro Leu Lys Tyr Thr Lys
145                 150                 155                 160

Arg Pro Ser Cys Leu Val Gly Val Ser Glu Glu Thr Thr Thr Gly Val
                165                 170                 175

Lys Arg Ser Tyr Gln Met Gln Pro Lys Cys Thr Leu Leu His Ala
            180                 185                 190

Thr Asp Val Cys Asp Thr Val Ile Lys Ser Lys Ile Asp Asn Leu Tyr
    195                 200                 205

Gly Cys Arg His Ser Leu Ser Asp Gly Leu Met Arg Ala Thr Asp Val
    210                 215                 220

Arg Arg Pro Cys Lys Val Ala Leu Val Gly Gly Tyr Gly Asp Val Phe
225                 230                 235                 240

Lys Gly Trp Val Ala Ala Leu Lys Gln Ala Gly Ala Arg Val Ile Val
                245                 250                 255

Thr Glu Ile Pro Gln Ile Cys Ala Val Gln Ala Thr Met Glu Gly Ser
            260                 265                 270

Ser Val Leu Thr Leu Glu Asp Val Val Ser Asp Val Asp Arg Phe Val
    275                 280                 285

Thr Thr Thr Gly Asn Lys Asp Leu Ile Met Val Asp His Met Arg Arg
    290                 295                 300

Met Lys Asn Gln Ala Ile Val Cys Asn Ile Arg Arg Phe Asp Asn Glu
305                 310                 315                 320

Ile Asp Met Arg Ser Leu Glu Thr Phe Pro Gly Val Lys Arg Ile Thr
                325                 330                 335

Ile Lys Ala Gln Thr Asp Arg Trp Val Phe Arg Asp Thr Asn Arg Gly
            340                 345                 350

Ile Ile Val Pro Ala Glu Gly Arg Leu Met Thr Met Gly Cys Ala Thr
    355                 360                 365

```
Gly His Pro Ser Phe Arg Thr Ser Cys Ser Phe Thr Asn Gln Val Ser
    370                 375                 380

Ser Gln Leu Glu Leu Trp Arg Glu Lys Ser Thr Gly Lys Tyr Glu Lys
385                 390                 395                 400

Lys Val Tyr Val Phe Pro Lys His Leu Glu Lys Val Ala Ala Leu
                405                 410                 415

His Leu Val Lys Leu Gly Ala Arg Leu Thr Lys Leu Ser Arg Cys Thr
                420                 425                 430

Leu Leu Cys Thr Asp Asp Pro Val Glu Gly Arg Lys Glu Pro Pro His
                435                 440                 445

Arg Ala Gly Ser Pro Glu Pro Cys Gln Leu Gln Leu Thr Val Phe Arg
    450                 455                 460

<210> SEQ ID NO 53
<211> LENGTH: 771
<212> TYPE: DNA
<213> ORGANISM: Arabidopsis thaliana
<220> FEATURE:
<221> NAME/KEY: CDS
<222> LOCATION: (1)...(537)

<400> SEQUENCE: 53 atg ccg cgt aac gtt gct ggt atg tgc gtt gcg tta gaa cga gtc ttc      48
Met Pro Arg Asn Val Ala Gly Met Cys Val Ala Leu Glu Arg Val Phe
  1               5                  10                  15 gac gtc gat gaa att gtc agg tta agg aag agg ttt ttc aag ttg gac      96
Asp Val Asp Glu Ile Val Arg Leu Arg Lys Arg Phe Phe Lys Leu Asp
                 20                  25                  30 aga gat tgt tca gga tca gaa ctt gga agt gag ttc atg agt ttg cct     144
Arg Asp Cys Ser Gly Ser Glu Leu Gly Ser Glu Phe Met Ser Leu Pro
             35                  40                  45 caa gtt agt tcg aac cct ctt cgg atg cgt gag atg cgt aat ttc gat     192
Gln Val Ser Ser Asn Pro Leu Arg Met Arg Glu Met Arg Asn Phe Asp
         50                  55                  60 aat gat tgc gta ggg agt gtg gat ttt atc gag ttc atc aat gga cgt     240
Asn Asp Cys Val Gly Ser Val Asp Phe Ile Glu Phe Ile Asn Gly Arg
 65                  70                  75                  80 tcc agt ttc agt act gtc ggg cag aag aat gct aaa ttg aga ttt gca     288
Ser Ser Phe Ser Thr Val Gly Gln Lys Asn Ala Lys Leu Arg Phe Ala
                 85                  90                  95 ccg att atc tat gat tgc gat aaa gat gga cct ata tca aac ggt gag     336
Pro Ile Ile Tyr Asp Cys Asp Lys Asp Gly Pro Ile Ser Asn Gly Glu
                100                 105                 110 tta ttt agg gtg ttg cgt att atg gtt cat gac aat ctg agt gat aat     384
Leu Phe Arg Val Leu Arg Ile Met Val His Asp Asn Leu Ser Asp Asn
            115                 120                 125 cag ctg cag cag cgt tgc gat tgc acg cgt agt ggc gga gat aat gac     432
Gln Leu Gln Gln Arg Cys Asp Cys Thr Arg Ser Gly Gly Asp Asn Asp
        130                 135                 140 ggg gat ggt cga ggt gcg aaa aac agc ttt gag gaa ttt tac ggt cgt     480
Gly Asp Gly Arg Gly Ala Lys Asn Ser Phe Glu Glu Phe Tyr Gly Arg
145                 150                 155                 160 ttg cca gct acc gta cgt cgg cgt ccg tac cgt acg ttg gta agc ggt     528
Leu Pro Ala Thr Val Arg Arg Arg Pro Tyr Arg Thr Leu Val Ser Gly
                165                 170                 175 gat gtg taa agttcagtgc accgtgaccg tgagcctgga agcctgaacg              577
Asp Val * ctgacaagcc ttaagccaa aaaattggct gaggcctgat gccctgagat gccaaaggct     637
ttttaggctt ttagagaaaa aggctaaaaa aaaggctaga aaaaaaggct cttaggcctg    697
```

```
cttgagcctg agcctgagcc tgatcgatca aaaaaaaagg agcctttttt ttttagctaa      757
aaaaaaaaag ctaa                                                        771

<210> SEQ ID NO 54
<211> LENGTH: 178
<212> TYPE: PRT
<213> ORGANISM: Arabidopsis thaliana

<400> SEQUENCE: 54

Met Pro Arg Asn Val Ala Gly Met Cys Val Ala Leu Glu Arg Val Phe
1               5                   10                  15

Asp Val Asp Glu Ile Val Arg Leu Arg Lys Arg Phe Phe Lys Leu Asp
            20                  25                  30

Arg Asp Cys Ser Gly Ser Glu Leu Gly Ser Glu Phe Met Ser Leu Pro
        35                  40                  45

Gln Val Ser Ser Asn Pro Leu Arg Met Arg Glu Met Arg Asn Phe Asp
    50                  55                  60

Asn Asp Cys Val Gly Ser Val Asp Phe Ile Glu Phe Ile Asn Gly Arg
65                  70                  75                  80

Ser Ser Phe Ser Thr Val Gly Gln Lys Asn Ala Lys Leu Arg Phe Ala
                85                  90                  95

Pro Ile Ile Tyr Asp Cys Asp Lys Asp Gly Pro Ile Ser Asn Gly Glu
            100                 105                 110

Leu Phe Arg Val Leu Arg Ile Met Val His Asp Asn Leu Ser Asp Asn
        115                 120                 125

Gln Leu Gln Gln Arg Cys Asp Cys Thr Arg Ser Gly Gly Asp Asn Asp
    130                 135                 140

Gly Asp Gly Arg Gly Ala Lys Asn Ser Phe Glu Glu Phe Tyr Gly Arg
145                 150                 155                 160

Leu Pro Ala Thr Val Arg Arg Pro Tyr Arg Thr Leu Val Ser Gly
                165                 170                 175

Asp Val

<210> SEQ ID NO 55
<211> LENGTH: 1617
<212> TYPE: DNA
<213> ORGANISM: Arabidopsis thaliana
<220> FEATURE:
<221> NAME/KEY: CDS
<222> LOCATION: (10)...(1557)

<400> SEQUENCE: 55 cgctacggt atg cgt acg tca aga aca gga ttt cgg atg cca ttg ggg ccc      51
          Met Arg Thr Ser Arg Thr Gly Phe Arg Met Pro Leu Gly Pro
          1               5                   10 tgt gcg gtg aac ccc tgc ttc att gct tcc tgt tcc tgt ctc ctc gtt       99
Trp Ala Val Asn Pro Cys Phe Ile Ala Ser Cys Ser Cys Leu Leu Val
15                  20                  25                  30 ggc ttc ggc gac gca atc ttc tac gag tcg ttc gcc ggg gat ttt gat      147
Gly Phe Gly Asp Ala Ile Phe Tyr Glu Ser Phe Ala Gly Asp Phe Asp
                35                  40                  45 gca cgc tgg att tta tcc ggc tca aag tgt ctc tcg gat tcg gcc aag      195
Ala Arg Trp Ile Leu Ser Gly Ser Lys Cys Leu Ser Asp Ser Ala Lys
            50                  55                  60 aat gct ggg ttt gat gat tat gga ctt ctt gtg ggt gaa caa gcc agg      243
Asn Ala Gly Phe Asp Asp Tyr Gly Leu Leu Val Gly Glu Gln Ala Arg
        65                  70                  75
```

```
aag cct cct ata gtc aag gaa ctt gcc gag tct ctc agt cta aag gac      291
Lys Pro Pro Ile Val Lys Glu Leu Ala Glu Ser Leu Ser Leu Lys Asp
    80              85                  90 gga aga gtt gtt ctt gag tgt gag act cgc ctt gac cat ggc atc gac      339
Gly Arg Val Val Leu Glu Cys Glu Thr Arg Leu Asp His Gly Ile Asp
 95              100                 105                 110 tgt gga ggt ccc tgt att aga tat ctt cga acc cag gag agc gga tgg      387
Cys Gly Gly Pro Cys Ile Arg Tyr Leu Arg Thr Gln Glu Ser Gly Trp
                115                 120                 125 aaa ttt gac agc tcc acc atg ttt ggt gct gct aag tat ggc gcg agg      435
Lys Phe Asp Ser Ser Thr Met Phe Gly Ala Ala Lys Tyr Gly Ala Arg
                130                 135                 140 agg acc cag ttc ttc ggg ggc cac ccc cag aac cca aac agt ggt gag      483
Arg Thr Gln Phe Phe Gly Gly His Pro Gln Asn Pro Asn Ser Gly Glu
        145                 150                 155 tgt gtt gac cat gat cac aac cag cgg gct tcc ctc aca tcg gac aaa      531
Cys Val Asp His Asp His Asn Gln Arg Ala Ser Leu Thr Ser Asp Lys
160                 165                 170 gta cct cgt ttg tac act gga att ctg tcg ccc gaa aat gaa ttc cag      579
Val Pro Arg Leu Tyr Thr Gly Ile Leu Ser Pro Glu Asn Glu Phe Gln
175                 180                 185                 190 atc ttg ata gat cgg ggg ttg gag acc aag gcc aaa atc ttc cct tgt      627
Ile Leu Ile Asp Arg Gly Leu Glu Thr Lys Ala Lys Ile Phe Pro Cys
                195                 200                 205 gag gac ttt gag cct cct gtt ata cca tcc aag aga agc cct gat aat      675
Glu Asp Phe Glu Pro Pro Val Ile Pro Ser Lys Arg Ser Pro Asp Asn
                210                 215                 220 ccg tcg aag cgg act gag gac tcg gac gaa aaa gcc aaa atc cca ggc      723
Pro Ser Lys Arg Thr Glu Asp Ser Asp Glu Lys Ala Lys Ile Pro Gly
            225                 230                 235 cca agt gcc ctg aag cga cag gaa agc gat gag gat ccg aac cgg gaa      771
Pro Ser Ala Leu Lys Arg Gln Glu Ser Asp Glu Asp Pro Asn Arg Glu
        240                 245                 250 atc tta cat gaa gaa gcc ggg aga cgt tcg tcc gat gtt ggg gcc cac      819
Ile Leu His Glu Glu Ala Gly Arg Arg Ser Ser Asp Val Gly Ala His
255                 260                 265                 270 gca aaa gac cag gca cac gaa cct gag cca aaa cac tgg ggt gct gaa      867
Ala Lys Asp Gln Ala His Glu Pro Glu Pro Lys His Trp Gly Ala Glu
                275                 280                 285 aag gat ggt gaa tgc gca ccc cca aag att gaa aac gca aag cgg ggg      915
Lys Asp Gly Glu Cys Ala Pro Pro Lys Ile Glu Asn Ala Lys Arg Gly
            290                 295                 300 gcc gcc cct agt tgt ggt gta tcg gag agg caa acc aag att agt cca      963
Ala Ala Pro Ser Cys Gly Val Ser Glu Arg Gln Thr Lys Ile Ser Pro
        305                 310                 315 aat tat aag gga aaa ccc tcc gtg ggt cca aac gtt tac caa ggg att     1011
Asn Tyr Lys Gly Lys Pro Ser Val Gly Pro Asn Val Tyr Gln Gly Ile
320                 325                 330 tgg aaa ccc cgc gag atg cta aac cct gga tcg ttc caa atc gca aaa     1059
Trp Lys Pro Arg Glu Met Leu Asn Pro Gly Ser Phe Gln Ile Ala Lys
335                 340                 345                 350 ccc gct tgt gag cct att gct ggt ata ggc atg gag att agg aag cag     1107
Pro Ala Cys Glu Pro Ile Ala Gly Ile Gly Met Glu Ile Arg Lys Gln
                355                 360                 365 ggc atc cta tta gac act gtg gtg ggg gtt agg ggg gat aca ggt gaa     1155
Gly Ile Leu Leu Asp Thr Val Val Gly Val Arg Gly Asp Thr Gly Glu
                370                 375                 380 gaa tat ggg gaa acc ccg ttg aag acc acg tgt acc gtc gag aag cac     1203
Glu Tyr Gly Glu Thr Pro Leu Lys Thr Thr Cys Thr Val Glu Lys His
                385                 390                 395
```

-continued

```
agt ttg cag gct caa gag gcg aga acc cgg tca gac gct ggt tca ccc        1251
Ser Leu Gln Ala Gln Glu Ala Arg Thr Arg Ser Asp Ala Gly Ser Pro
    400             405                 410 tac acc agg tac gta tct aaa atc ccc ggg aaa gcc gat aat ccc ttc        1299
Tyr Thr Arg Tyr Val Ser Lys Ile Pro Gly Lys Ala Asp Asn Pro Phe
415                 420                 425                 430 tcg agc gag cac aaa tgt aag aat ttc gat ctg att gag gct gag aaa        1347
Ser Ser Glu His Lys Cys Lys Asn Phe Asp Leu Ile Glu Ala Glu Lys
                435                 440                 445 cag tgt gcc aat gca gta atc ctg ggt gtt gtg gtt aac tcc ggt tca        1395
Gln Cys Ala Asn Ala Val Ile Leu Gly Val Val Val Asn Ser Gly Ser
            450                 455                 460 att aac tcc gtt gtg tct tgg ggc tac aaa cct ggc acg gtg aac aag        1443
Ile Asn Ser Val Val Ser Trp Gly Tyr Lys Pro Gly Thr Val Asn Lys
        465                 470                 475 aac caa gaa cgc aga gca ccc tcc cag cga cgt agc agc gag att gaa        1491
Asn Gln Glu Arg Arg Ala Pro Ser Gln Arg Arg Ser Ser Glu Ile Glu
    480                 485                 490 gga acc caa gac cga cga aaa cag gat gtt ggc cga cgc caa gct gcc        1539
Gly Thr Gln Asp Arg Arg Lys Gln Asp Val Gly Arg Arg Gln Ala Ala
495                 500                 505                 510 agc tcg ccc agg cgc tga taattaaatc cgatccgtcc tttaaccccc               1587
Ser Ser Pro Arg Arg *
                515 gttgttcaat accgtttttt ttttatttaa                                       1617
```

<210> SEQ ID NO 56
<211> LENGTH: 515
<212> TYPE: PRT
<213> ORGANISM: Arabidopsis thaliana

<400> SEQUENCE: 56

```
Met Arg Thr Ser Arg Thr Gly Phe Arg Met Pro Leu Gly Pro Trp Ala
  1               5                  10                  15

Val Asn Pro Cys Phe Ile Ala Ser Cys Ser Cys Leu Leu Val Gly Phe
             20                  25                  30

Gly Asp Ala Ile Phe Tyr Glu Ser Phe Ala Gly Asp Phe Asp Ala Arg
         35                  40                  45

Trp Ile Leu Ser Gly Ser Lys Cys Leu Ser Asp Ser Ala Lys Asn Ala
     50                  55                  60

Gly Phe Asp Asp Tyr Gly Leu Leu Val Gly Glu Gln Ala Arg Lys Pro
 65                  70                  75                  80

Pro Ile Val Lys Glu Leu Ala Glu Ser Leu Ser Leu Lys Asp Gly Arg
                 85                  90                  95

Val Val Leu Glu Cys Glu Thr Arg Leu Asp His Gly Ile Asp Cys Gly
            100                 105                 110

Gly Pro Cys Ile Arg Tyr Leu Arg Thr Gln Glu Ser Gly Trp Lys Phe
        115                 120                 125

Asp Ser Ser Thr Met Phe Gly Ala Ala Lys Tyr Gly Ala Arg Arg Thr
    130                 135                 140

Gln Phe Phe Gly Gly His Pro Gln Asn Pro Asn Ser Gly Glu Cys Val
145                 150                 155                 160

Asp His Asp His Asn Gln Arg Ala Ser Leu Thr Ser Asp Lys Val Pro
                165                 170                 175

Arg Leu Tyr Thr Gly Ile Leu Ser Pro Glu Asn Glu Phe Gln Ile Leu
            180                 185                 190
```

```
Ile Asp Arg Gly Leu Glu Thr Lys Ala Lys Ile Phe Pro Cys Glu Asp
        195                 200                 205

Phe Glu Pro Pro Val Ile Pro Ser Lys Arg Ser Pro Asp Asn Pro Ser
    210                 215                 220

Lys Arg Thr Glu Asp Ser Asp Glu Lys Ala Lys Ile Pro Gly Pro Ser
225                 230                 235                 240

Ala Leu Lys Arg Gln Glu Ser Asp Glu Asp Pro Asn Arg Glu Ile Leu
                245                 250                 255

His Glu Glu Ala Gly Arg Arg Ser Ser Asp Val Gly Ala His Ala Lys
            260                 265                 270

Asp Gln Ala His Glu Pro Glu Pro Lys His Trp Gly Ala Glu Lys Asp
        275                 280                 285

Gly Glu Cys Ala Pro Pro Lys Ile Glu Asn Ala Lys Arg Gly Ala Ala
    290                 295                 300

Pro Ser Cys Gly Val Ser Glu Arg Gln Thr Lys Ile Ser Pro Asn Tyr
305                 310                 315                 320

Lys Gly Lys Pro Ser Val Gly Pro Asn Val Tyr Gln Gly Ile Trp Lys
                325                 330                 335

Pro Arg Glu Met Leu Asn Pro Gly Ser Phe Gln Ile Ala Lys Pro Ala
            340                 345                 350

Cys Glu Pro Ile Ala Gly Ile Gly Met Glu Ile Arg Lys Gln Gly Ile
        355                 360                 365

Leu Leu Asp Thr Val Val Gly Val Arg Gly Asp Thr Gly Glu Glu Tyr
    370                 375                 380

Gly Glu Thr Pro Leu Lys Thr Thr Cys Thr Val Glu Lys His Ser Leu
385                 390                 395                 400

Gln Ala Gln Glu Ala Arg Thr Arg Ser Asp Ala Gly Ser Pro Tyr Thr
                405                 410                 415

Arg Tyr Val Ser Lys Ile Pro Gly Lys Ala Asp Asn Pro Phe Ser Ser
            420                 425                 430

Glu His Lys Cys Lys Asn Phe Asp Leu Ile Glu Ala Glu Lys Gln Cys
        435                 440                 445

Ala Asn Ala Val Ile Leu Gly Val Val Asn Ser Gly Ser Ile Asn
    450                 455                 460

Ser Val Val Ser Trp Gly Tyr Lys Pro Gly Thr Val Asn Lys Asn Gln
465                 470                 475                 480

Glu Arg Arg Ala Pro Ser Gln Arg Ser Ser Glu Ile Glu Gly Thr
                485                 490                 495

Gln Asp Arg Arg Lys Gln Asp Val Gly Arg Arg Gln Ala Ala Ser Ser
            500                 505                 510

Pro Arg Arg
        515

<210> SEQ ID NO 57
<211> LENGTH: 1281
<212> TYPE: DNA
<213> ORGANISM: Arabidopsis thaliana
<220> FEATURE:
<221> NAME/KEY: CDS
<222> LOCATION: (13)...(1266)

<400> SEQUENCE: 57
gctccgctcg ct atg agt tgg cga ccc cgg aag aac gtg ccg atg aaa aca      51
              Met Ser Trp Arg Pro Arg Lys Asn Val Pro Met Lys Thr
                1               5                  10 cgg gtg acc agg gac ggt tcg ggg ccc gga aaa acc ggt gtc aca cgc        99
```

```
                                                        -continued

Arg Val Thr Arg Asp Gly Ser Gly Pro Gly Lys Thr Gly Val Thr Arg
                     15                   20                  25 ggg tcg tca ccc atg cga tgg gca tgg aag cgg tgg caa gcc gtc ggg        147
Gly Ser Ser Pro Met Arg Trp Ala Trp Lys Arg Trp Gln Ala Val Gly
 30                  35                  40                  45 gca tcg acg gcc cgc acg tgg ttc ggg aca gag aac cag aaa gga ata        195
Ala Ser Thr Ala Arg Thr Trp Phe Gly Thr Glu Asn Gln Lys Gly Ile
                 50                  55                  60 acg aca agc acc cgc gcg cgg cgc tac gcg gtc tcg gcc aaa ttc ccg        243
Thr Thr Ser Thr Arg Ala Arg Arg Tyr Ala Val Ser Ala Lys Phe Pro
             65                  70                  75 aga tta agt aat aag ggc aaa gat tac atg cgt tgc gtc ctc caa tac        291
Arg Leu Ser Asn Lys Gly Lys Asp Tyr Met Arg Cys Val Leu Gln Tyr
         80                  85                  90 acc gtc aaa aat gaa caa aaa gtt gat tgt ggt ggc tca tat atc aag        339
Thr Val Lys Asn Glu Gln Lys Val Asp Cys Gly Gly Ser Tyr Ile Lys
     95                 100                 105 tta tta cct tcg aaa ttg cgc acg ggt gat ggt gat ggc gtg tca gaa        387
Leu Leu Pro Ser Lys Leu Arg Thr Gly Asp Gly Asp Gly Val Ser Glu
110                 115                 120                 125 tat tca att atg ttt ggt cca gat tcg aca ggt gca tca cgt act gtt        435
Tyr Ser Ile Met Phe Gly Pro Asp Ser Thr Gly Ala Ser Arg Thr Val
                130                 135                 140 cgt cga gct cgc aat tat aag ggt aaa cgg cat ttg cgg aaa aaa gaa        483
Arg Arg Ala Arg Asn Tyr Lys Gly Lys Arg His Leu Arg Lys Lys Glu
            145                 150                 155 cag aat aaa gtg gaa aca gat caa tta aca cat cag tat act acg agt        531
Gln Asn Lys Val Glu Thr Asp Gln Leu Thr His Gln Tyr Thr Thr Ser
        160                 165                 170 tgg tca cca gat tgg acc tac aac gtt cta gta gat aat aag gaa tcg        579
Trp Ser Pro Asp Trp Thr Tyr Asn Val Leu Val Asp Asn Lys Glu Ser
    175                 180                 185 caa gca ggg aac ctt gcc gac gac tgc gag tta ctt cca cag aag cga        627
Gln Ala Gly Asn Leu Ala Asp Asp Cys Glu Leu Leu Pro Gln Lys Arg
190                 195                 200                 205 atc ttc cga ccc agc tgc cga aaa caa tcc aaa cca gtc acc tgc gta        675
Ile Phe Arg Pro Ser Cys Arg Lys Gln Ser Lys Pro Val Thr Cys Val
                210                 215                 220 gac gtc aag cac cac gcc ccc cga cga aat gtg aaa ccc gcc ggg cac        723
Asp Val Lys His His Ala Pro Arg Arg Asn Val Lys Pro Ala Gly His
            225                 230                 235 gat gac att cca gcg cga cgg acg acg ccg gaa gcg gtc cgg aaa ggc        771
Asp Asp Ile Pro Ala Arg Arg Thr Thr Pro Glu Ala Val Arg Lys Gly
        240                 245                 250 cgc acg aac gag cga ccg gac cgg acg tgg gcg acc ggg acg acc cca        819
Arg Thr Asn Glu Arg Pro Asp Arg Thr Trp Ala Thr Gly Thr Thr Pro
    255                 260                 265 cgg cca cgg cgt tac aag gga gag acg aag gcc aaa aag cac cca cgg        867
Arg Pro Arg Arg Tyr Lys Gly Glu Thr Lys Ala Lys Lys His Pro Arg
270                 275                 280                 285 ccg gaa tac aaa ggg acc tgg gtc acg ccg tta cag gac aac ccc act        915
Pro Glu Tyr Lys Gly Thr Trp Val Thr Pro Leu Gln Asp Asn Pro Thr
                290                 295                 300 cca gcc ccc ccg aac gac cta tat cta ttc ttg gac ctg ggt gca gca        963
Pro Ala Pro Pro Asn Asp Leu Tyr Leu Phe Leu Asp Leu Gly Ala Ala
            305                 310                 315 ggg aca cgg acc tgg acc gtg aaa tcg ggc tca atc acg aac aac atg       1011
Gly Thr Arg Thr Trp Thr Val Lys Ser Gly Ser Ile Thr Asn Asn Met
        320                 325                 330
```

```
ata gtg aca acg tcc gtg gaa acc gcg acc gac ttc tca gag aaa acc    1059
Ile Val Thr Thr Ser Val Glu Thr Ala Thr Asp Phe Ser Glu Lys Thr
    335                 340                 345 aag gtg gca aac acc acg acc gag ctc aac gac gga cgc gac gcc gga    1107
Lys Val Ala Asn Thr Thr Thr Glu Leu Asn Asp Gly Arg Asp Ala Gly
350                 355                 360                 365 acg ggg atc ggt gcc gag cgc cac tgt gct gat gag aga tgg aaa gag    1155
Thr Gly Ile Gly Ala Glu Arg His Cys Ala Asp Glu Arg Trp Lys Glu
                370                 375                 380 aca acg gta gcc ccc gat tgc gcc gta tcg gca gcg aac gcc tcg cga    1203
Thr Thr Val Ala Pro Asp Cys Ala Val Ser Ala Ala Asn Ala Ser Arg
            385                 390                 395 cgc acc ggg gag ctg gcc acc ccg gtg acg atg ctg cct gat ccg ttg    1251
Arg Thr Gly Glu Leu Ala Thr Pro Val Thr Met Leu Pro Asp Pro Leu
        400                 405                 410 tac gga ccg gaa taa aatcgcctga tgcct                               1281
Tyr Gly Pro Glu *
    415
```

<210> SEQ ID NO 58
<211> LENGTH: 417
<212> TYPE: PRT
<213> ORGANISM: Arabidopsis thaliana

<400> SEQUENCE: 58

```
Met Ser Trp Arg Pro Arg Lys Asn Val Pro Met Lys Thr Arg Val Thr
1               5                   10                  15

Arg Asp Gly Ser Gly Pro Gly Lys Thr Gly Val Thr Arg Gly Ser Ser
            20                  25                  30

Pro Met Arg Trp Ala Trp Lys Arg Trp Gln Ala Val Gly Ala Ser Thr
        35                  40                  45

Ala Arg Thr Trp Phe Gly Thr Glu Asn Gln Lys Gly Ile Thr Thr Ser
    50                  55                  60

Thr Arg Ala Arg Arg Tyr Ala Val Ser Ala Lys Phe Pro Arg Leu Ser
65                  70                  75                  80

Asn Lys Gly Lys Asp Tyr Met Arg Cys Val Leu Gln Tyr Thr Val Lys
                85                  90                  95

Asn Glu Gln Lys Val Asp Cys Gly Gly Ser Tyr Ile Lys Leu Leu Pro
            100                 105                 110

Ser Lys Leu Arg Thr Gly Asp Gly Asp Gly Val Ser Glu Tyr Ser Ile
        115                 120                 125

Met Phe Gly Pro Asp Ser Thr Gly Ala Ser Arg Thr Val Arg Arg Ala
    130                 135                 140

Arg Asn Tyr Lys Gly Lys Arg His Leu Arg Lys Lys Glu Gln Asn Lys
145                 150                 155                 160

Val Glu Thr Asp Gln Leu Thr His Gln Tyr Thr Thr Ser Trp Ser Pro
                165                 170                 175

Asp Trp Thr Tyr Asn Val Leu Val Asp Asn Lys Glu Ser Gln Ala Gly
            180                 185                 190

Asn Leu Ala Asp Asp Cys Glu Leu Leu Pro Gln Lys Arg Ile Phe Arg
        195                 200                 205

Pro Ser Cys Arg Lys Gln Ser Lys Pro Val Thr Cys Val Asp Val Lys
    210                 215                 220

His His Ala Pro Arg Arg Asn Val Lys Pro Ala Gly His Asp Asp Ile
225                 230                 235                 240

Pro Ala Arg Arg Thr Thr Pro Glu Ala Val Arg Lys Gly Arg Thr Asn
                245                 250                 255
```

```
Glu Arg Pro Asp Arg Thr Trp Ala Thr Gly Thr Thr Pro Arg Pro Arg
            260                 265                 270

Arg Tyr Lys Gly Glu Thr Lys Ala Lys Lys His Pro Arg Pro Glu Tyr
        275                 280                 285

Lys Gly Thr Trp Val Thr Pro Leu Gln Asp Asn Pro Thr Pro Ala Pro
    290                 295                 300

Pro Asn Asp Leu Tyr Leu Phe Leu Asp Leu Gly Ala Ala Gly Thr Arg
305                 310                 315                 320

Thr Trp Thr Val Lys Ser Gly Ser Ile Thr Asn Asn Met Ile Val Thr
                325                 330                 335

Thr Ser Val Glu Thr Ala Thr Asp Phe Ser Glu Lys Thr Lys Val Ala
            340                 345                 350

Asn Thr Thr Thr Glu Leu Asn Asp Gly Arg Asp Ala Gly Thr Gly Ile
        355                 360                 365

Gly Ala Glu Arg His Cys Ala Asp Glu Arg Trp Lys Glu Thr Thr Val
    370                 375                 380

Ala Pro Asp Cys Ala Val Ser Ala Ala Asn Ala Ser Arg Arg Thr Gly
385                 390                 395                 400

Glu Leu Ala Thr Pro Val Thr Met Leu Pro Asp Pro Leu Tyr Gly Pro
                405                 410                 415

Glu

<210> SEQ ID NO 59
<211> LENGTH: 417
<212> TYPE: DNA
<213> ORGANISM: Arabidopsis thaliana
<220> FEATURE:
<221> NAME/KEY: CDS
<222> LOCATION: (1)...(411)

<400> SEQUENCE: 59 aag gaa gct ttt agc ctc ttc gac aaa gat ggc gat ggt tgc atc aca      48
Lys Glu Ala Phe Ser Leu Phe Asp Lys Asp Gly Asp Gly Cys Ile Thr
 1               5                  10                  15 aca aaa gag ctg gga aca gtt atg cgt tca cta gga caa aac cca aca      96
Thr Lys Glu Leu Gly Thr Val Met Arg Ser Leu Gly Gln Asn Pro Thr
            20                  25                  30 gag gct gag ctc caa gac atg atc aac gag gtt gat gca gat gga aac     144
Glu Ala Glu Leu Gln Asp Met Ile Asn Glu Val Asp Ala Asp Gly Asn
        35                  40                  45 ggc act atc gac ttc ccc gag ttc ctg aac ctg atg gct aag aag atg     192
Gly Thr Ile Asp Phe Pro Glu Phe Leu Asn Leu Met Ala Lys Lys Met
    50                  55                  60 aaa gac act gac tcc gag gaa gag cta aaa gaa gcc ttc agg gtt ttc     240
Lys Asp Thr Asp Ser Glu Glu Glu Leu Lys Glu Ala Phe Arg Val Phe
65                  70                  75                  80 gac aaa gac cag aac ggt ttc atc tcc gct gct gag cta cgc cat gtg     288
Asp Lys Asp Gln Asn Gly Phe Ile Ser Ala Ala Glu Leu Arg His Val
                85                  90                  95 atg acc aat ctt ggt gag aag cta act gat gaa gaa gtg gaa gag atg     336
Met Thr Asn Leu Gly Glu Lys Leu Thr Asp Glu Glu Val Glu Glu Met
            100                 105                 110 atc cgt gag gct gat gtt gat gga gat ggt cag att aac tat gaa gag     384
Ile Arg Glu Ala Asp Val Asp Gly Asp Gly Gln Ile Asn Tyr Glu Glu
        115                 120                 125 ttt gtc aag att atg atg gct aag tga tttgat                          417
Phe Val Lys Ile Met Met Ala Lys  *
    130                 135
```

<210> SEQ ID NO 60
<211> LENGTH: 136
<212> TYPE: PRT
<213> ORGANISM: Arabidopsis thaliana

<400> SEQUENCE: 60

Lys Glu Ala Phe Ser Leu Phe Asp Lys Asp Gly Asp Gly Cys Ile Thr
1               5                   10                  15

Thr Lys Glu Leu Gly Thr Val Met Arg Ser Leu Gly Gln Asn Pro Thr
            20                  25                  30

Glu Ala Glu Leu Gln Asp Met Ile Asn Glu Val Asp Ala Asp Gly Asn
        35                  40                  45

Gly Thr Ile Asp Phe Pro Glu Phe Leu Asn Leu Met Ala Lys Lys Met
    50                  55                  60

Lys Asp Thr Asp Ser Glu Glu Glu Leu Lys Glu Ala Phe Arg Val Phe
65                  70                  75                  80

Asp Lys Asp Gln Asn Gly Phe Ile Ser Ala Ala Glu Leu Arg His Val
                85                  90                  95

Met Thr Asn Leu Gly Glu Lys Leu Thr Asp Glu Val Glu Glu Met
            100                 105                 110

Ile Arg Glu Ala Asp Val Asp Gly Asp Gly Gln Ile Asn Tyr Glu Glu
        115                 120                 125

Phe Val Lys Ile Met Met Ala Lys
    130                 135

<210> SEQ ID NO 61
<211> LENGTH: 6070
<212> TYPE: DNA
<213> ORGANISM: Arabidopsis thaliana
<220> FEATURE:
<221> NAME/KEY: CDS
<222> LOCATION: (34)..(173)
<220> FEATURE:
<221> NAME/KEY: CDS
<222> LOCATION: (282)..(492)
<220> FEATURE:
<221> NAME/KEY: CDS
<222> LOCATION: (539)..(1135)
<220> FEATURE:
<221> NAME/KEY: CDS
<222> LOCATION: (1224)..(1320)
<220> FEATURE:
<221> NAME/KEY: CDS
<222> LOCATION: (1404)..(1585)
<220> FEATURE:
<221> NAME/KEY: CDS
<222> LOCATION: (1663)..(1778)
<220> FEATURE:
<221> NAME/KEY: CDS
<222> LOCATION: (1891)..(1993)
<220> FEATURE:
<221> NAME/KEY: CDS
<222> LOCATION: (2114)..(2266)
<220> FEATURE:
<221> NAME/KEY: CDS
<222> LOCATION: (2376)..(2522)
<220> FEATURE:
<221> NAME/KEY: CDS
<222> LOCATION: (2608)..(2808)
<220> FEATURE:
<221> NAME/KEY: CDS
<222> LOCATION: (3071)..(3235)
<220> FEATURE:
<221> NAME/KEY: CDS
<222> LOCATION: (3315)..(3419)
<220> FEATURE:
<221> NAME/KEY: CDS

```
<222> LOCATION: (3519)..(3656)
<220> FEATURE:
<221> NAME/KEY: CDS
<222> LOCATION: (3742)..(3936)
<220> FEATURE:
<221> NAME/KEY: CDS
<222> LOCATION: (4061)..(4187)
<220> FEATURE:
<221> NAME/KEY: CDS
<222> LOCATION: (4268)..(4470)
<220> FEATURE:
<221> NAME/KEY: CDS
<222> LOCATION: (4556)..(4738)
<220> FEATURE:
<221> NAME/KEY: CDS
<222> LOCATION: (4809)..(4904)
<220> FEATURE:
<221> NAME/KEY: CDS
<222> LOCATION: (4491)..(5188)
<220> FEATURE:
<221> NAME/KEY: CDS
<222> LOCATION: (5509)..(5780)
<220> FEATURE:
<221> NAME/KEY: CDS
<222> LOCATION: (5879)..(6059)

<400> SEQUENCE: 61
cagatctact acaatctctc tttttcttcg ggt atg gag ggc caa cga ggc agt        54
                                 Met Glu Gly Gln Arg Gly Ser
                                  1               5 aat tct tcg ttg agc tct ggc aat ggc acc gaa gtc gcc acc gac gtt       102
Asn Ser Ser Leu Ser Ser Gly Asn Gly Thr Glu Val Ala Thr Asp Val
         10                  15                  20 tct tct tgc ttc tat gtt ccc aat ccc tct gga acc gat ttc gat gcc       150
Ser Ser Cys Phe Tyr Val Pro Asn Pro Ser Gly Thr Asp Phe Asp Ala
 25                  30                  35 gag tcg tct tct ctt cct cct ctg taagtcttct ttgaattttt aaaaacattc       204
Glu Ser Ser Ser Leu Pro Pro Leu
 40                  45 actctcttgc tgctgtctct gttgatcctt cttctttgaa aatttgaaaa cattcttagt      264
ctctcgctct gtcacag ctc ccc agc tcc tca agt ggc att gtc aat tcc         314
                   Leu Pro Ser Ser Ser Ser Gly Ile Val Asn Ser
                                   50                  55 tgc gga gct tgc cgc cgc cat tcc cct cat cga tcg ctt cca ggt tga       362
Cys Gly Ala Cys Arg Arg His Ser Pro His Arg Ser Leu Pro Gly
 60                  65                  70 agc ttt tct gcg gct aat gca gaa aca aat cca gtc tgc tgg gaa gcg       410
Ser Phe Ser Ala Ala Asn Ala Glu Thr Asn Pro Val Cys Trp Glu Ala
 75                  80                  85                  90 tgg ctt ctt cta ttc caa aaa gtc ctc tgg ctc caa tgt ccg cga gcg       458
Trp Leu Leu Leu Phe Gln Lys Val Leu Trp Leu Gln Cys Pro Arg Ala
                 95                 100                 105 ctt cac att tga gga tat gct ttg ctt tca aaa ggt ttttctttcc            504
Leu His Ile     Gly Tyr Ala Leu Leu Ser Lys Gly
             110                 115 cccccttct tccccattga caatccattg actg aat atg tct ctc tcc cct tcc      559
                                     Asn Met Ser Leu Ser Pro Ser
                                                 120                 125 ttc ctt cag gat cca atc ccc aca tct ctc ctc aag att aac agc gat       607
Phe Leu Gln Asp Pro Ile Pro Thr Ser Leu Leu Lys Ile Asn Ser Asp
                 130                 135                 140 ctc gtc agc cgt gct acc aag ttg ttt cat ctc atc tta aaa tat atg       655
Leu Val Ser Arg Ala Thr Lys Leu Phe His Leu Ile Leu Lys Tyr Met
                 145                 150                 155 ggt gtt gat tca tct gat cga tct acg cct ccc agt tta gat gaa cgc       703
```

```
                                                                          -continued Gly Val Asp Ser Ser Asp Arg Ser Thr Pro Pro Ser Leu Asp Glu Arg
            160                 165                 170 att gac ctc gtt gga aag ctc ttc aaa aaa act ttg aag cgt gtt gaa      751
Ile Asp Leu Val Gly Lys Leu Phe Lys Lys Thr Leu Lys Arg Val Glu
175                 180                 185 ctc agg gac gaa ctt ttt gcc caa atc tcc aaa cag act aga cat aat      799
Leu Arg Asp Glu Leu Phe Ala Gln Ile Ser Lys Gln Thr Arg His Asn
190                 195                 200                 205 cct gac agg caa tac ttg atc aaa gct tgg gaa ttg atg tac tta tgt      847
Pro Asp Arg Gln Tyr Leu Ile Lys Ala Trp Glu Leu Met Tyr Leu Cys
                210                 215                 220 gcc tcc tct atg cct cct agc aaa gat atc ggt gga tat cta tct gag      895
Ala Ser Ser Met Pro Pro Ser Lys Asp Ile Gly Gly Tyr Leu Ser Glu
            225                 230                 235 tat att cat aat gtc gca cac gat gca act att gaa ccg gat gct cag      943
Tyr Ile His Asn Val Ala His Asp Ala Thr Ile Glu Pro Asp Ala Gln
        240                 245                 250 gtt ctt gct gtt aac act ttg aaa gct tta aag cgc tct atc aaa gct      991
Val Leu Ala Val Asn Thr Leu Lys Ala Leu Lys Arg Ser Ile Lys Ala
    255                 260                 265 ggt cct agg cac acc aca cct ggt cgt gaa gaa att gaa gcc ctt ttg     1039
Gly Pro Arg His Thr Thr Pro Gly Arg Glu Glu Ile Glu Ala Leu Leu
270                 275                 280                 285 acc ggt aga aag ctc aca acc att gtc ttc ttt ctc gat gaa act ttt     1087
Thr Gly Arg Lys Leu Thr Thr Ile Val Phe Phe Leu Asp Glu Thr Phe
                290                 295                 300 gaa gaa att tca tat gac atg gct acc aca gtg tct gat gct gtt gag     1135
Glu Glu Ile Ser Tyr Asp Met Ala Thr Thr Val Ser Asp Ala Val Glu
            305                 310                 315 gtatcttctt gctttctttt ttcataattt accgctgatc atattcttgt ccctttttct   1195
ctcactgcat tgacatctgt ttcaggag cta gct gga aca att aaa cta tca     1247
                                Leu Ala Gly Thr Ile Lys Leu Ser
                                            320                 325 gct ttc tct agc ttt agt ttg ttt gaa tgt cgt aaa gtt gtt tca agt     1295
Ala Phe Ser Ser Phe Ser Leu Phe Glu Cys Arg Lys Val Val Ser Ser
                330                 335                 340 tct aaa tca tct gat ccc gga aat ggt atgctttcat atgactggct           1342
Ser Lys Ser Ser Asp Pro Gly Asn Gly
            345                 350 tcgtcatata ttgtgaagta atacaacatt atcgatcatt tttctatctg tgcacttgca  1402 g agg aat ata tag gat tgg atg ata aca agt ata ttg gag atc tcc tcg  1451
  Arg Asn Ile     Asp Trp Met Ile Thr Ser Ile Leu Glu Ile Ser Ser
                            355                 360                 365 cag aat tta aag cta tta aag acc gaa ata aag gag aga tac tac act     1499
Gln Asn Leu Lys Leu Leu Lys Thr Glu Ile Lys Glu Arg Tyr Tyr Thr
                370                 375                 380 gca aac tgg tat tta aaa aaa aat tat tcc gag agt ctg atg aag ctg     1547
Ala Asn Trp Tyr Leu Lys Lys Asn Tyr Ser Glu Ser Leu Met Lys Leu
            385                 390                 395 taa cag atc tga tgt ttg tgc aac ttt cgt atg ttc aag tgagcatttt     1596
    Gln Ile     Cys Leu Cys Asn Phe Arg Met Phe Lys
        400                 405                 410 cttcattggt gacatttatt tccacacaaa aggcttgcct ttcgttgctg acacacatat  1656 atgcag ctg caa cat gac tat ttg cta gga aac tat cct gtt ggg agg     1704
       Leu Gln His Asp Tyr Leu Leu Gly Asn Tyr Pro Val Gly Arg
                415                 420                 425 gac gat gct gca cag ctt tgt gcc ttg caa att ctt gtt ggg att ggg    1752
Asp Asp Ala Ala Gln Leu Cys Ala Leu Gln Ile Leu Val Gly Ile Gly
```

```
                  430             435             440
ttt gtc aat agt cca gag tca tgc atg ttagttttct taagctccgc      1799
Phe Val Asn Ser Pro Glu Ser Cys Met
            445             450 cattgacttt attttagttg tccgatactt tattttccca attttcctcc cttaacaata 1859 tcatttcctt tctcaatgta tcacatatca g tga ttg gac atc act tct tga   1911
                                   Leu Asp Ile Thr Ser
                                               455 gcg gtt ttt gcc aag aca aat agc aat aac ccg agc aaa gcg tga atg  1959
Ala Val Phe Ala Lys Thr Asn Ser Asn Asn Pro Ser Lys Ala     Met
            460             465             470 gga att gga tat cct tgc tcg cta ccg ttc aat ggt aggaatagtt       2005
Gly Ile Gly Tyr Pro Cys Ser Leu Pro Phe Asn Gly
    475             480             485 ctatgcatgt ggattgtctt cccctttcta gatacctttg gcaaataaaa acccattgaa 2065 gtgatggcat ggtaaaatga tatttcgtat gtgtatgtgg gcatgtag gag aac gtg 2122
                                                    Glu Asn Val acc aaa gat gat gca aga caa caa ttt cta cgg ata ctg aag gca ctg  2170
Thr Lys Asp Asp Ala Arg Gln Gln Phe Leu Arg Ile Leu Lys Ala Leu
        490             495             500 cca tac ggg aat tca gtt ttt ttt agc gta cgc aag ata gat gat ccg  2218
Pro Tyr Gly Asn Ser Val Phe Phe Ser Val Arg Lys Ile Asp Asp Pro
505             510             515             520 atc ggt ctt tta cct ggg cga atc att ttg ggt atc aac aaa cgt ggg  2266
Ile Gly Leu Leu Pro Gly Arg Ile Ile Leu Gly Ile Asn Lys Arg Gly
            525             530             535 gttgtctcaa tataaatgtt atacattatg actttaaaaa aactgttatt gttgtttgga 2326 attcaaatct atgttgttgg atttgaattt gttgtttgct ttcttgtag gtt cac ttt 2384
                                                     Val His Phe ttt cga ccg gtt cct aaa gaa tat ctg cac tct gct gaa cta cgt gac  2432
Phe Arg Pro Val Pro Lys Glu Tyr Leu His Ser Ala Glu Leu Arg Asp
540             545             550             555 atc atg caa ttt ggc agc agt aac act gct gtc ttt ttc aaa atg aga  2480
Ile Met Gln Phe Gly Ser Ser Asn Thr Ala Val Phe Phe Lys Met Arg
            560             565             570 gtc gct ggt gtt ctt cac ata ttt cag ttc gag aca aaa cag           2522
Val Ala Gly Val Leu His Ile Phe Gln Phe Glu Thr Lys Gln
575             580             585 gtttaaacat cactatttgt ggatcattat attatgaagc aattcctat gagatattca 2582 atttgggtaa cttgtatgtt tgtag gga gaa gaa att tgt gtt gct ttg caa  2634
                              Gly Glu Glu Ile Cys Val Ala Leu Gln
                                              590 aca cat ata aat gat gtc atg ttg cgt cgt tac tcc aaa gct cga tct  2682
Thr His Ile Asn Asp Val Met Leu Arg Arg Tyr Ser Lys Ala Arg Ser
595             600             605             610 gct gcc aat tgc ttg gtt aat gga gat att tct tgt tgt tct aag ccg  2730
Ala Ala Asn Cys Leu Val Asn Gly Asp Ile Ser Cys Cys Ser Lys Pro
            615             620             625 caa aat ttt gaa gtg tat gaa aaa cgt ttg caa gat ttg tct aag gct  2778
Gln Asn Phe Glu Val Tyr Glu Lys Arg Leu Gln Asp Leu Ser Lys Ala
                630             635             640 tat gaa gag tcc caa aag aag att gag aag gtacacattc taacaaattt    2828
Tyr Glu Glu Ser Gln Lys Lys Ile Glu Lys
            645             650 cttatttatt cttcaatgta aaattgaata taatagaggg aggctgatct ttgtttaaat 2888 acatgaaata acttattgta gttggatttt ttcatggttt ttatgcttgg tagtcttgag 2948
```

```
atatttcagt atatatcacc ctcctatctt atgttattgt atgtagaatg ttataccatg   3008
acctcttttg ttttagagtg gcatgctgat gaactattcg tatgttttat gttgttgtat   3068 ag ttg atg gat gaa caa caa gag aaa aat cag caa gaa gtt act ctg      3115
   Leu Met Asp Glu Gln Gln Glu Lys Asn Gln Gln Glu Val Thr Leu
           655                 660                 665 cgt gaa gag tta gaa gct ata cac aat ggt ttg gag ctt gaa agg aga     3163
Arg Glu Glu Leu Glu Ala Ile His Asn Gly Leu Glu Leu Glu Arg Arg
        670                 675                 680 aaa ttg ttg gag gtt act tta gac cga gat aaa ctt agg tca ttg tgt     3211
Lys Leu Leu Glu Val Thr Leu Asp Arg Asp Lys Leu Arg Ser Leu Cys
685                 690                 695 gac gag aag gga acc cct att caa gttagttata acctaacttt tgtctttctt   3265
Asp Glu Lys Gly Thr Pro Ile Gln
700                 705 ttgatgcttg gttgaagtta tttaatgatt tattctatat atgctatag tcc ttg atg   3323
                                                       Ser Leu Met
                                                              710 tct gaa ctg cga gga atg gaa gca agg ttg gca aag tcg ggc aac acc     3371
Ser Glu Leu Arg Gly Met Glu Ala Arg Leu Ala Lys Ser Gly Asn Thr
        715                 720                 725 aaa tca agt aaa gag acc aaa tca gaa tta gcc gaa atg aat aat cag     3419
Lys Ser Ser Lys Glu Thr Lys Ser Glu Leu Ala Glu Met Asn Asn Gln
730                 735                 740 gtgaatatta tgtgtttaaa tctaattcat tgtaatcatt gagttgttgt tttttgttcc   3479
caattctgct ttcctttgac aatgaatttt aagtcacag ata tta tac aag atc      3533
                                          Ile Leu Tyr Lys Ile
                                                          745 caa aag gag tta gaa gtt cga aat aag gaa ttg cat gtc gca gtt gat     3581
Gln Lys Glu Leu Glu Val Arg Asn Lys Glu Leu His Val Ala Val Asp
        750                 755                 760 aat tca aag agg ttg ttg agt gaa aac aag ata ttg gag caa aat ctc     3629
Asn Ser Lys Arg Leu Leu Ser Glu Asn Lys Ile Leu Glu Gln Asn Leu
765                 770                 775 aat att gaa aag aag aaa aaa gag gag gtgaattcta tgtattagat           3676
Asn Ile Glu Lys Lys Lys Lys Glu Glu
780                 785 ttattgaaga tttcaaattg agaagtatca aatacttgcg tattgttgac atctcattat   3736 ttcag gtt gaa att cat caa aag aga tat gaa caa gaa aaa aag gtg tta  3786
      Val Glu Ile His Gln Lys Arg Tyr Glu Gln Glu Lys Lys Val Leu
          790                 795                 800 aag ctt cga gtt tct gaa ctt gaa aat aag ctt gaa gta ctt gct caa     3834
Lys Leu Arg Val Ser Glu Leu Glu Asn Lys Leu Glu Val Leu Ala Gln
805                 810                 815 gac ttg gat agt gct gag tct acg att gaa agt aag aat tct gac atg     3882
Asp Leu Asp Ser Ala Glu Ser Thr Ile Glu Ser Lys Asn Ser Asp Met
820                 825                 830                 835 ctg ctg ttg caa aat aac ttg aaa gaa ctt gag gag tta aga gaa atg     3930
Leu Leu Leu Gln Asn Asn Leu Lys Glu Leu Glu Glu Leu Arg Glu Met
                840                 845                 850 aaa gag gtaatggtac tcttttgtct tcttcattat ttaattttgt ttctgtttga     3986
Lys Glu atgatgataa tgtattttcg cgattccaaa ttgaagtaga gggatgtgtt tacattccaa   4046 tttcatttc ttag gac att gac aga aaa aat gag caa aca gct gcc att      4096
             Asp Ile Asp Arg Lys Asn Glu Gln Thr Ala Ala Ile
                                 855                 860                 865 ttg aaa atg caa gga gcc caa ctt gct gag cta gaa ata ctt tat aag     4144
```

```
                                                        -continued

Leu Lys Met Gln Gly Ala Gln Leu Ala Glu Leu Glu Ile Leu Tyr Lys
            870                 875                 880 gaa gaa caa gtt tta agg aaa aga tac tat aat acc ata gaa ggt        4189
Glu Glu Gln Val Leu Arg Lys Arg Tyr Tyr Asn Thr Ile Glu Gly
            885                 890                 895 aacataatgc tcaagtatgt acaatgatgt tcattgcttt taaaaagaa ttttactaac   4249 atttttattt gattgtag ata tga aag gga aga tta gag ttt att gtc gaa    4300
                    Ile     Lys Gly Arg Leu Glu Phe Ile Val Glu
                                        900             905 taa gac ctc taa atg aaa aag aga gtt cag aga ggg aaa aac aaa tgc    4348
    Asp Leu     Met Lys Lys Arg Val Gln Arg Gly Lys Asn Lys Cys
        910             915                 920 tga caa ctg tgg atg agt tta ctg ttg aac atg cat gga aag acg aca   4396
    Gln Leu Trp Met Ser Leu Leu Leu Asn Met His Gly Lys Thr Thr
        925                 930                 935 aaa gaa agc aac aca tat atg atc gcg tat ttg aca tgc gtg cta gtc   4444
Lys Glu Ser Asn Thr Tyr Met Ile Ala Tyr Leu Thr Cys Val Leu Val
940                 945                 950                 955 aag atg ata tct ttg aag aca caa agg tattattgat atgtaactgt          4491
Lys Met Ile Ser Leu Lys Thr Gln Arg
                960 gttcatttac ctttcatcct ttgttatttt cttgtggtta ctaacatcgt tttccttta   4551 acag tat ttg gta cag tcg gct gta gat ggg tat aac gtt tgc atc ttt  4600
     Tyr Leu Val Gln Ser Ala Val Asp Gly Tyr Asn Val Cys Ile Phe
         965                 970                 975 gca tat ggt caa act ggt tct gga aaa act ttc act ata tat ggg cat   4648
Ala Tyr Gly Gln Thr Gly Ser Gly Lys Thr Phe Thr Ile Tyr Gly His
980                 985                 990                 995 gag agc aat cct gga ctc aca cct cga gct aca aag gaa ctg ttc aac   4696
Glu Ser Asn Pro Gly Leu Thr Pro Arg Ala Thr Lys Glu Leu Phe Asn
                1000                1005                1010 ata tta aag cga gat agc aag aga ttt tca ttt tct cta aag           4738
Ile Leu Lys Arg Asp Ser Lys Arg Phe Ser Phe Ser Leu Lys
                1015                1020                1025 gtaatttgtt atcctaatag atgatgtgat aaaagattat gacatcaact gactacaaaa  4798
agttatgcag gca tat atg gtg gaa ctt tat caa gac aca ctt gta gac    4847
            Ala Tyr Met Val Glu Leu Tyr Gln Asp Thr Leu Val Asp
                    1030                1035 ctt ttg tta cca aaa agt gca aga cgc ttg aaa cta gag att aaa aaa   4895
Leu Leu Leu Pro Lys Ser Ala Arg Arg Leu Lys Leu Glu Ile Lys Lys
    1040                1045                1050 gat tca aag gta ttg tga gat ata tct att tta act agg tta taa cta   4943
Asp Ser Lys Val Leu     Asp Ile Ser Ile Leu Thr Arg Leu     Leu
1055                1060                1065                1070 gat tgt aga cac gta agt ttg atc tta tgc ata aaa tat ttt ctc agg   4991
Asp Cys Arg His Val Ser Leu Ile Leu Cys Ile Lys Tyr Phe Leu Arg
                1075                1080                1085 gaa tgg tct ttg tag aga atg tga caa cta ttc cta tat caa ctt tgg  5039
Glu Trp Ser Leu     Arg Met     Gln Leu Phe Leu Tyr Gln Leu Trp
        1090                1095                1100 agg aac tgc gaa tga ttc ttg aac ggg gat cgg aac gac gac atg ttt   5087
Arg Asn Cys Glu     Phe Leu Asn Gly Asp Arg Asn Asp Asp Met Phe
        1105                1110                1115 ctg gaa caa ata tga atg aag aaa gct caa gat ctc acc tca tat tat  5135
Leu Glu Gln Ile     Met Lys Lys Ala Gln Asp Leu Thr Ser Tyr Tyr
1120                1125                1130 cag ttg tta ttg aaa gta ttg atc ttc aaa ccc agt ctg ctg cga ggg   5183
Gln Leu Leu Leu Lys Val Leu Ile Phe Lys Pro Ser Leu Leu Arg Gly
```

```
                1135            1140            1145            1150
gca agg tgacaaaatt cactatgttt ttctttattg actcattatc attttttcaca      5239
Ala Arg ggatttagta gcatttaggg attttaagga aataggagtt tctttagatt ttcatgctta    5299
gtctaccgaa gaaaaatata gtaacattaa tcttgtttaa gagagatatt attttacagc    5359
tcaaatcttt ggtctggtac aaaatgttaa acctttatgt acacaatcca tattattagt    5419
caatgatatg ccctccattg ttaaacccat atcacctgat catggtggta tcttctacaa    5479
tattctgaat ttttgtttgt tatttgcag ctg agt ttt gtg gat ctt gct ggt      5532
                                  Leu Ser Phe Val Asp Leu Ala Gly
                                         1155                1160 tct gag aga gtt aaa aag tcg ggc tca gct ggt tgc caa ctc aaa gaa      5580
Ser Glu Arg Val Lys Lys Ser Gly Ser Ala Gly Cys Gln Leu Lys Glu
        1165                1170                1175 gct caa agt atc aac aaa tca ctt tct gca tta ggt gat gtt att ggt      5628
Ala Gln Ser Ile Asn Lys Ser Leu Ser Ala Leu Gly Asp Val Ile Gly
    1180                1185                1190 gct tta tct tct ggc aac cag cat att cct tat agg aat cac aag cta      5676
Ala Leu Ser Ser Gly Asn Gln His Ile Pro Tyr Arg Asn His Lys Leu
        1195                1200                1205 acg atg ttg atg agc gat tca ttg ggc ggc aat gcc aag acg tta atg      5724
Thr Met Leu Met Ser Asp Ser Leu Gly Gly Asn Ala Lys Thr Leu Met
    1210                1215                1220 ttt gtt aat gtg tct cca gcc gaa tca aat ttg gac gag acg tac aat      5772
Phe Val Asn Val Ser Pro Ala Glu Ser Asn Leu Asp Glu Thr Tyr Asn
1225                1230                1235                1240 tct ctt ctg taagtcatga gttcccatat atatataaca taaatcaaat               5821
Ser Leu Leu atgcttagtg taaaaatgga taatcccatat tgttttttttt tcctcctttg attccag     5878 ata tgc atc gag agt gag aac gat cgt gaa tga tcc cag caa aca tat      5926
Ile Cys Ile Glu Ser Glu Asn Asp Arg Glu     Ser Gln Gln Thr Tyr
        1245                1250                1255 atc atc caa aga gat ggt gcg att gaa gaa gtt ggt agc ata ctg gaa      5974
Ile Ile Gln Arg Asp Gly Ala Ile Glu Glu Val Gly Ser Ile Leu Glu
1260                1265                1270                1275 aga gca agc cgg taa aaa agg tga gga aga aga ctt ggt gga tat tga      6022
Arg Ala Ser Arg     Lys Arg     Gly Arg Arg Leu Gly Gly Tyr
        1280                1285                1290 gga aga tcg tac acg aaa aga tga ggc aga tag ttg aag aaagctgac        6070
Gly Arg Ser Tyr Thr Lys Arg     Gly Arg     Leu Lys
        1295                1300
```

<210> SEQ ID NO 62
<211> LENGTH: 1269
<212> TYPE: PRT
<213> ORGANISM: Arabidopsis thaliana

<400> SEQUENCE: 62

```
Met Glu Gly Gln Arg Gly Ser Asn Ser Ser Leu Ser Ser Gly Asn Gly
  1               5                  10                  15

Thr Glu Val Ala Thr Asp Val Ser Ser Cys Phe Tyr Val Pro Asn Pro
            20                  25                  30

Ser Gly Thr Asp Phe Asp Ala Glu Ser Ser Ser Leu Pro Pro Leu Ser
        35                  40                  45

Pro Ala Pro Gln Val Ala Leu Ser Ile Pro Ala Glu Leu Ala Ala Ala
    50                  55                  60

Ile Pro Leu Ile Asp Arg Phe Gln Val Glu Ala Phe Leu Arg Leu Met
```

-continued

```
                65                  70                  75                  80
        Gln Lys Gln Ile Gln Ser Ala Gly Lys Arg Gly Phe Phe Tyr Ser Lys
                        85                  90                  95
        Lys Ser Ser Gly Ser Asn Val Arg Glu Arg Phe Thr Phe Glu Asp Met
                       100                 105                 110
        Leu Cys Phe Gln Lys Asn Met Ser Leu Ser Pro Ser Phe Leu Gln Asp
                       115                 120                 125
        Pro Ile Pro Thr Ser Leu Leu Lys Ile Asn Ser Asp Leu Val Ser Arg
                       130                 135                 140
        Ala Thr Lys Leu Phe His Leu Ile Leu Lys Tyr Met Gly Val Asp Ser
        145                 150                 155                 160
        Ser Asp Arg Ser Thr Pro Pro Ser Leu Asp Glu Arg Ile Asp Leu Val
                       165                 170                 175
        Gly Lys Leu Phe Lys Lys Thr Leu Lys Arg Val Glu Leu Arg Asp Glu
                       180                 185                 190
        Leu Phe Ala Gln Ile Ser Lys Gln Thr Arg His Asn Pro Asp Arg Gln
                       195                 200                 205
        Tyr Leu Ile Lys Ala Trp Glu Leu Met Tyr Leu Cys Ala Ser Ser Met
                       210                 215                 220
        Pro Pro Ser Lys Asp Ile Gly Gly Tyr Leu Ser Glu Tyr Ile His Asn
        225                 230                 235                 240
        Val Ala His Asp Ala Thr Ile Glu Pro Asp Ala Gln Val Leu Ala Val
                       245                 250                 255
        Asn Thr Leu Lys Ala Leu Lys Arg Ser Ile Lys Ala Gly Pro Arg His
                       260                 265                 270
        Thr Thr Pro Gly Arg Glu Glu Ile Glu Ala Leu Leu Thr Gly Arg Lys
                       275                 280                 285
        Leu Thr Thr Ile Val Phe Phe Leu Asp Glu Thr Phe Glu Glu Ile Ser
                       290                 295                 300
        Tyr Asp Met Ala Thr Thr Val Ser Asp Ala Val Glu Leu Ala Gly Thr
        305                 310                 315                 320
        Ile Lys Leu Ser Ala Phe Ser Ser Phe Ser Leu Phe Glu Cys Arg Lys
                       325                 330                 335
        Val Val Ser Ser Ser Lys Ser Ser Asp Pro Gly Asn Glu Glu Tyr Ile
                       340                 345                 350
        Gly Leu Asp Asp Asn Lys Tyr Ile Gly Asp Leu Leu Ala Glu Phe Lys
                       355                 360                 365
        Ala Ile Lys Asp Arg Asn Lys Gly Glu Ile Leu His Cys Lys Leu Val
                       370                 375                 380
        Phe Lys Lys Lys Leu Phe Arg Glu Ser Asp Glu Ala Val Thr Asp Leu
        385                 390                 395                 400
        Met Phe Val Gln Leu Ser Tyr Val Gln Leu Gln His Asp Tyr Leu Leu
                       405                 410                 415
        Gly Asn Tyr Pro Val Gly Arg Asp Ala Ala Gln Leu Cys Ala Leu
                       420                 425                 430
        Gln Ile Leu Val Gly Ile Gly Phe Val Asn Ser Pro Glu Ser Cys Ile
                       435                 440                 445
        Asp Trp Thr Ser Leu Leu Glu Arg Phe Leu Pro Arg Gln Ile Ala Ile
                       450                 455                 460
        Thr Arg Ala Lys Arg Glu Trp Glu Leu Asp Ile Leu Ala Arg Tyr Arg
        465                 470                 475                 480
        Ser Met Glu Asn Val Thr Lys Asp Asp Ala Arg Gln Gln Phe Leu Arg
                       485                 490                 495
```

```
Ile Leu Lys Ala Leu Pro Tyr Gly Asn Ser Val Phe Ser Val Arg
            500                 505                 510
Lys Ile Asp Asp Pro Ile Gly Leu Leu Pro Gly Arg Ile Ile Leu Gly
        515                 520                 525
Ile Asn Lys Arg Gly Val His Phe Phe Arg Pro Val Pro Lys Glu Tyr
    530                 535                 540
Leu His Ser Ala Glu Leu Arg Asp Ile Met Gln Phe Gly Ser Ser Asn
545                 550                 555                 560
Thr Ala Val Phe Phe Lys Met Arg Val Ala Gly Val Leu His Ile Phe
                565                 570                 575
Gln Phe Glu Thr Lys Gln Gly Glu Glu Ile Cys Val Ala Leu Gln Thr
            580                 585                 590
His Ile Asn Asp Val Met Leu Arg Arg Tyr Ser Lys Ala Arg Ser Ala
        595                 600                 605
Ala Asn Cys Leu Val Asn Gly Asp Ile Ser Cys Cys Ser Lys Pro Gln
    610                 615                 620
Asn Phe Glu Val Tyr Glu Lys Arg Leu Gln Asp Leu Ser Lys Ala Tyr
625                 630                 635                 640
Glu Glu Ser Gln Lys Lys Ile Glu Lys Leu Met Asp Glu Gln Gln Glu
                645                 650                 655
Lys Asn Gln Gln Glu Val Thr Leu Arg Glu Glu Leu Glu Ala Ile His
            660                 665                 670
Asn Gly Leu Glu Leu Glu Arg Arg Lys Leu Leu Glu Val Thr Leu Asp
        675                 680                 685
Arg Asp Lys Leu Arg Ser Leu Cys Asp Glu Lys Gly Thr Pro Ile Gln
    690                 695                 700
Ser Leu Met Ser Glu Leu Arg Gly Met Glu Ala Arg Leu Ala Lys Ser
705                 710                 715                 720
Gly Asn Thr Lys Ser Ser Lys Glu Thr Lys Ser Glu Leu Ala Glu Met
                725                 730                 735
Asn Asn Gln Ile Leu Tyr Lys Ile Gln Lys Glu Leu Glu Val Arg Asn
            740                 745                 750
Lys Glu Leu His Val Ala Val Asp Asn Ser Lys Arg Leu Leu Ser Glu
        755                 760                 765
Asn Lys Ile Leu Glu Gln Asn Leu Asn Ile Glu Lys Lys Lys Lys Glu
    770                 775                 780
Glu Val Glu Ile His Gln Lys Arg Tyr Glu Gln Glu Lys Lys Val Leu
785                 790                 795                 800
Lys Leu Arg Val Ser Glu Leu Glu Asn Lys Leu Glu Val Leu Ala Gln
                805                 810                 815
Asp Leu Asp Ser Ala Glu Ser Thr Ile Glu Ser Lys Asn Ser Asp Met
            820                 825                 830
Leu Leu Leu Gln Asn Asn Leu Lys Glu Leu Glu Leu Arg Glu Met
        835                 840                 845
Lys Glu Asp Ile Asp Arg Lys Asn Glu Gln Thr Ala Ala Ile Leu Lys
    850                 855                 860
Met Gln Gly Ala Gln Leu Ala Glu Leu Glu Ile Leu Tyr Lys Glu Glu
865                 870                 875                 880
Gln Val Leu Arg Lys Arg Tyr Tyr Asn Thr Ile Glu Asp Met Lys Gly
                885                 890                 895
Lys Ile Arg Val Tyr Cys Arg Ile Arg Pro Leu Asn Glu Lys Glu Ser
            900                 905                 910
```

Ser Glu Arg Glu Lys Gln Met Leu Thr Thr Val Asp Glu Phe Thr Val
        915                 920                 925

Glu His Ala Trp Lys Asp Asp Lys Arg Lys Gln His Ile Tyr Asp Arg
        930                 935                 940

Val Phe Asp Met Arg Ala Ser Gln Asp Ile Phe Glu Asp Thr Lys
945                 950                 955                 960

Tyr Leu Val Gln Ser Ala Val Asp Gly Tyr Asn Val Cys Ile Phe Ala
                965                 970                 975

Tyr Gly Gln Thr Gly Ser Gly Lys Thr Phe Thr Ile Tyr Gly His Glu
                980                 985                 990

Ser Asn Pro Gly Leu Thr Pro Arg Ala Thr Lys Glu Leu Phe Asn Ile
        995                 1000                1005

Leu Lys Arg Asp Ser Lys Arg Phe Ser Phe Ser Leu Lys Ala Tyr Met
        1010                1015                1020

Val Glu Leu Tyr Gln Asp Thr Leu Val Asp Leu Leu Leu Pro Lys Ser
1025                1030                1035                1040

Ala Arg Arg Leu Lys Leu Glu Ile Lys Lys Asp Ser Lys Gly Met Val
                1045                1050                1055

Phe Val Glu Asn Val Thr Thr Ile Pro Ile Ser Thr Leu Glu Glu Leu
                1060                1065                1070

Arg Met Ile Leu Glu Arg Gly Ser Glu Arg His Val Ser Gly Thr
        1075                1080                1085

Asn Met Asn Glu Glu Ser Ser Arg Ser His Leu Ile Leu Ser Val Val
        1090                1095                1100

Ile Glu Ser Ile Asp Leu Gln Thr Gln Ser Ala Ala Arg Gly Lys Leu
1105                1110                1115                1120

Ser Phe Val Asp Leu Ala Gly Ser Glu Arg Val Lys Lys Ser Gly Ser
                1125                1130                1135

Ala Gly Cys Gln Leu Lys Glu Ala Gln Ser Ile Asn Lys Ser Leu Ser
                1140                1145                1150

Ala Leu Gly Asp Val Ile Gly Ala Leu Ser Ser Gly Asn Gln His Ile
                1155                1160                1165

Pro Tyr Arg Asn His Lys Leu Thr Met Leu Met Ser Asp Ser Leu Gly
        1170                1175                1180

Gly Asn Ala Lys Thr Leu Met Phe Val Asn Val Ser Pro Ala Glu Ser
1185                1190                1195                1200

Asn Leu Asp Glu Thr Tyr Asn Ser Leu Leu Tyr Ala Ser Arg Val Arg
                1205                1210                1215

Thr Ile Val Asn Asp Pro Ser Lys His Ile Ser Ser Lys Glu Met Val
                1220                1225                1230

Arg Leu Lys Lys Leu Val Ala Tyr Trp Lys Glu Gln Ala Gly Lys Lys
        1235                1240                1245

Gly Glu Glu Glu Asp Leu Val Asp Ile Glu Glu Asp Arg Thr Arg Lys
        1250                1255                1260

Asp Glu Ala Asp Ser
1265

<210> SEQ ID NO 63
<211> LENGTH: 2105
<212> TYPE: DNA
<213> ORGANISM: Arabidopsis thaliana
<220> FEATURE:
<221> NAME/KEY: CDS
<222> LOCATION: (1)...(1947)

<400> SEQUENCE: 63

```
atg aat aca gat aaa atg acc aag atg gat cta acg ggg tcc aat aac      48
Met Asn Thr Asp Lys Met Thr Lys Met Asp Leu Thr Gly Ser Asn Asn
 1               5                  10                  15 gtg ccc att aat cca ccg act act aag cgt gat ctt aga cag aat gat      96
Val Pro Ile Asn Pro Pro Thr Thr Lys Arg Asp Leu Arg Gln Asn Asp
             20                  25                  30 aat aat aac cct aag agt cat aat agt cat aat agc aat ggg atg act     144
Asn Asn Asn Pro Lys Ser His Asn Ser His Asn Ser Asn Gly Met Thr
         35                  40                  45 ggt aac agg aac aat aat aat aaa aat gcc ggc gga gtt gaa act agt     192
Gly Asn Arg Asn Asn Asn Asn Lys Asn Ala Gly Gly Val Glu Thr Ser
 50                  55                  60 aaa aaa gcg cgc tca cga ctg gaa aca cat ccc cga gat aat gag aat     240
Lys Lys Ala Arg Ser Arg Leu Glu Thr His Pro Arg Asp Asn Glu Asn
 65                  70                  75                  80 aat tac aga cta gct aca agt gcc ggt acg aaa gga ggt gcg cga acc     288
Asn Tyr Arg Leu Ala Thr Ser Ala Gly Thr Lys Gly Gly Ala Arg Thr
             85                  90                  95 gtt gac gta cca gtc ata tta agt acc cgg gaa tca caa ggc aca cgt     336
Val Asp Val Pro Val Ile Leu Ser Thr Arg Glu Ser Gln Gly Thr Arg
            100                 105                 110 tca gta aat gca aca agt aaa att aga tgc ccg gat tcc act gca att     384
Ser Val Asn Ala Thr Ser Lys Ile Arg Cys Pro Asp Ser Thr Ala Ile
        115                 120                 125 tgc gag tgg ttc gcc acg ccc acg gat cct caa aga cca gga gtt tat     432
Cys Glu Trp Phe Ala Thr Pro Thr Asp Pro Gln Arg Pro Gly Val Tyr
130                 135                 140 aac cac aag aac ggc gac aaa aac aac aga gat acc ggg aac att aat     480
Asn His Lys Asn Gly Asp Lys Asn Asn Arg Asp Thr Gly Asn Ile Asn
145                 150                 155                 160 acc gtt agc agt cta atg gat aat gct agg ggt ccg aac ccg cga tct     528
Thr Val Ser Ser Leu Met Asp Asn Ala Arg Gly Pro Asn Pro Arg Ser
                165                 170                 175 ggg att tca ata ccg aca cca acc tct aga caa tcc cca agt gag aca     576
Gly Ile Ser Ile Pro Thr Pro Thr Ser Arg Gln Ser Pro Ser Glu Thr
            180                 185                 190 cct cca gat cca ctg cag aat cct aat aat tat act agg tat cat aat     624
Pro Pro Asp Pro Leu Gln Asn Pro Asn Asn Tyr Thr Arg Tyr His Asn
        195                 200                 205 gat aaa aac agc aag aat agt aac aga aac tac aat aag aga aat aag     672
Asp Lys Asn Ser Lys Asn Ser Asn Arg Asn Tyr Asn Lys Arg Asn Lys
210                 215                 220 aac tcg acg acc ttt aat aac tcg gac ctt cct ggt cat aat aga agc     720
Asn Ser Thr Thr Phe Asn Asn Ser Asp Leu Pro Gly His Asn Arg Ser
225                 230                 235                 240 tcc cct gcg att aat gca gta aaa tca gca tca aat cga tca tct gct     768
Ser Pro Ala Ile Asn Ala Val Lys Ser Ala Ser Asn Arg Ser Ser Ala
                245                 250                 255 ata ggt agt cga aac agt gat tta aac aat gct gct aat gat gaa cgc     816
Ile Gly Ser Arg Asn Ser Asp Leu Asn Asn Ala Ala Asn Asp Glu Arg
            260                 265                 270 cat tac gct aga tcg gga aca tat cag ata aac gct gta aca gta ctt     864
His Tyr Ala Arg Ser Gly Thr Tyr Gln Ile Asn Ala Val Thr Val Leu
        275                 280                 285 aga gta tta gga aga gga gca cgg cgt gat gta aag tca gca tat cat     912
Arg Val Leu Gly Arg Gly Ala Arg Arg Asp Val Lys Ser Ala Tyr His
290                 295                 300 ggc acc tgt ggt aca ggt ccc cgg atg aaa gtg ata aca ttg gct gtt     960
Gly Thr Cys Gly Thr Gly Pro Arg Met Lys Val Ile Thr Leu Ala Val
```

-continued

| | | | | | | | | | | | | | | | |
|---|---|---|---|---|---|---|---|---|---|---|---|---|---|---|---|
| 305 | | | | | 310 | | | | | 315 | | | | | 320 | caa gag aat att aga aac cga att ata ttg gag cta cgg aca tta cac   1008
Gln Glu Asn Ile Arg Asn Arg Ile Ile Leu Glu Leu Arg Thr Leu His
                  325                             330                             335 aag acc tct tat caa tat atc gtt ccg tat tat gat ggg atc tat aca   1056
Lys Thr Ser Tyr Gln Tyr Ile Val Pro Tyr Tyr Asp Gly Ile Tyr Thr
                  340                             345                             350 gag ggc tca att ttc att cgg atg gtg gaa ctt gga tgg gta acg aat   1104
Glu Gly Ser Ile Phe Ile Arg Met Val Glu Leu Gly Trp Val Thr Asn
                  355                             360                             365 atc atg aac aaa acg gcg acc ata cgt gcg ccg gtt ttg ggt acg atg   1152
Ile Met Asn Lys Thr Ala Thr Ile Arg Ala Pro Val Leu Gly Thr Met
        370                             375                             380 gca ttt cta gtg tta caa ggt cgg att tac gtt cac aga aag ttc gat   1200
Ala Phe Leu Val Leu Gln Gly Arg Ile Tyr Val His Arg Lys Phe Asp
385                             390                             395                       400 aaa tgc ccg agc aag cgt gat ata aaa cct tca gat att ctg gta aac   1248
Lys Cys Pro Ser Lys Arg Asp Ile Lys Pro Ser Asp Ile Leu Val Asn
                        405                             410                       415 aat gaa ggt cga gca aag atc gca ggt ttc ggt gta agc gga cag tta   1296
Asn Glu Gly Arg Ala Lys Ile Ala Gly Phe Gly Val Ser Gly Gln Leu
                  420                             425                             430 caa cat act ctc tca aag gat gta act tcg gtg gag tct cct gaa cgt   1344
Gln His Thr Leu Ser Lys Asp Val Thr Ser Val Glu Ser Pro Glu Arg
        435                           440                             445 cgt agt ggt agg tct tat ggt ttc gat cga gat att tgg agt gat ggt   1392
Arg Ser Gly Arg Ser Tyr Gly Phe Asp Arg Asp Ile Trp Ser Asp Gly
                  450                             455                             460 ata aca cgt gta tca tgc gca atc ggg aga ttc cct tat gct tgt aat   1440
Ile Thr Arg Val Ser Cys Ala Ile Gly Arg Phe Pro Tyr Ala Cys Asn
465                             470                             475                       480 tac cca caa cag ctc cca caa gca tca caa cac cag cta cag caa cag   1488
Tyr Pro Gln Gln Leu Pro Gln Ala Ser Gln His Gln Leu Gln Gln Gln
                  485                             490                             495 caa caa aaa cga ccg gcg tta caa cca aag caa gaa caa ccg gaa gta   1536
Gln Gln Lys Arg Pro Ala Leu Gln Pro Lys Gln Glu Gln Pro Glu Val
        500                           505                             510 gag aaa cac cga tta caa ata cca cgt caa aat tta gct gta tat aat   1584
Glu Lys His Arg Leu Gln Ile Pro Arg Gln Asn Leu Ala Val Tyr Asn
                  515                             520                             525 agt aat cac gat ata tgg aat aat cgc aat aga gat aaa tat att att   1632
Ser Asn His Asp Ile Trp Asn Asn Arg Asn Arg Asp Lys Tyr Ile Ile
        530                           535                             540 agt aac aat cct aat aat agg aat gat aat aat act gta tgc gat   1680
Ser Asn Asn Pro Asn Asn Arg Asn Asp Asn Asn Thr Val Cys Asp
545                             550                             555                       560 cta agc agt ggc gag tta ggt gaa agt cgt gag gtt gtg cca gac ggt   1728
Leu Ser Ser Gly Glu Leu Gly Glu Ser Arg Glu Val Val Pro Asp Gly
                  565                             570                             575 atc ggg ttg gag gta ctt cta gat tct atc gta aaa gaa gag gta cga   1776
Ile Gly Leu Glu Val Leu Leu Asp Ser Ile Val Lys Glu Glu Val Arg
        580                           585                             590 atg gaa cca tca aca gtt tcg aag gaa ttt agg tcg atc att tct gaa   1824
Met Glu Pro Ser Thr Val Ser Lys Glu Phe Arg Ser Ile Ile Ser Glu
                  595                             600                       605 tgt tta cga aac gat gca act gaa aga caa aca gct tca aac tta gta   1872
Cys Leu Arg Asn Asp Ala Thr Glu Arg Gln Thr Ala Ser Asn Leu Val
        610                           615                             620 aat cac gaa ttt gta aag aaa tat caa aag tac aat cgt gaa aaa tgg   1920

```
Asn His Glu Phe Val Lys Lys Tyr Gln Lys Tyr Asn Arg Glu Lys Trp
625                 630                 635                 640 acc gca gat tta caa agg tgg caa taa aaatcgcctt cacgcctgat           1967
Thr Ala Asp Leu Gln Arg Trp Gln *
                645 cgctgacgct cgacgcctgc ccccagcctg cagctcgccc agctcgccca ggctcgccca   2027 gcctgcccac cagcctgccc caccgctcca cgcctaaata ataaaaattt ttaaaaaaaa   2087 aaaaaaaaaa aaaccgct                                                 2105

<210> SEQ ID NO 64
<211> LENGTH: 648
<212> TYPE: PRT
<213> ORGANISM: Arabidopsis thaliana

<400> SEQUENCE: 64

Met Asn Thr Asp Lys Met Thr Lys Met Asp Leu Thr Gly Ser Asn Asn
1               5                   10                  15

Val Pro Ile Asn Pro Pro Thr Thr Lys Arg Asp Leu Arg Gln Asn Asp
                20                  25                  30

Asn Asn Asn Pro Lys Ser His Asn Ser His Asn Ser Asn Gly Met Thr
            35                  40                  45

Gly Asn Arg Asn Asn Asn Lys Asn Ala Gly Gly Val Glu Thr Ser
        50                  55                  60

Lys Lys Ala Arg Ser Arg Leu Glu Thr His Pro Arg Asp Asn Glu Asn
65                  70                  75                  80

Asn Tyr Arg Leu Ala Thr Ser Ala Gly Thr Lys Gly Gly Ala Arg Thr
                85                  90                  95

Val Asp Val Pro Val Ile Leu Ser Thr Arg Glu Ser Gln Gly Thr Arg
            100                 105                 110

Ser Val Asn Ala Thr Ser Lys Ile Arg Cys Pro Asp Ser Thr Ala Ile
        115                 120                 125

Cys Glu Trp Phe Ala Thr Pro Thr Asp Pro Gln Arg Pro Gly Val Tyr
130                 135                 140

Asn His Lys Asn Gly Asp Lys Asn Asn Arg Asp Thr Gly Asn Ile Asn
145                 150                 155                 160

Thr Val Ser Ser Leu Met Asp Asn Ala Arg Gly Pro Asn Pro Arg Ser
                165                 170                 175

Gly Ile Ser Ile Pro Thr Pro Thr Ser Arg Gln Ser Pro Ser Glu Thr
            180                 185                 190

Pro Pro Asp Pro Leu Gln Asn Pro Asn Asn Tyr Thr Arg Tyr His Asn
        195                 200                 205

Asp Lys Asn Ser Lys Asn Ser Asn Arg Asn Tyr Asn Lys Arg Asn Lys
210                 215                 220

Asn Ser Thr Thr Phe Asn Asn Ser Asp Leu Pro Gly His Asn Arg Ser
225                 230                 235                 240

Ser Pro Ala Ile Asn Ala Val Lys Ser Ala Ser Asn Arg Ser Ala
                245                 250                 255

Ile Gly Ser Arg Asn Ser Asp Leu Asn Asn Ala Ala Asn Asp Glu Arg
            260                 265                 270

His Tyr Ala Arg Ser Gly Thr Tyr Gln Ile Asn Ala Val Thr Val Leu
        275                 280                 285

Arg Val Leu Gly Arg Gly Ala Arg Arg Asp Val Lys Ser Ala Tyr His
290                 295                 300

Gly Thr Cys Gly Thr Gly Pro Arg Met Lys Val Ile Thr Leu Ala Val
```

```
            305                 310                 315                 320
    Gln Glu Asn Ile Arg Asn Arg Ile Ile Leu Glu Leu Arg Thr Leu His
                    325                 330                 335

Lys Thr Ser Tyr Gln Tyr Ile Val Pro Tyr Tyr Asp Gly Ile Tyr Thr
                    340                 345                 350

Glu Gly Ser Ile Phe Ile Arg Met Val Glu Leu Gly Trp Val Thr Asn
                    355                 360                 365

Ile Met Asn Lys Thr Ala Thr Ile Arg Ala Pro Val Leu Gly Thr Met
                370                 375                 380

Ala Phe Leu Val Leu Gln Gly Arg Ile Tyr Val His Arg Lys Phe Asp
    385                 390                 395                 400

Lys Cys Pro Ser Lys Arg Asp Ile Lys Pro Ser Asp Ile Leu Val Asn
                    405                 410                 415

Asn Glu Gly Arg Ala Lys Ile Ala Gly Phe Gly Val Ser Gly Gln Leu
                    420                 425                 430

Gln His Thr Leu Ser Lys Asp Val Thr Ser Val Glu Ser Pro Glu Arg
                    435                 440                 445

Arg Ser Gly Arg Ser Tyr Gly Phe Asp Arg Asp Ile Trp Ser Asp Gly
    450                 455                 460

Ile Thr Arg Val Ser Cys Ala Ile Gly Arg Phe Pro Tyr Ala Cys Asn
    465                 470                 475                 480

Tyr Pro Gln Gln Leu Pro Gln Ala Ser Gln His Gln Leu Gln Gln Gln
                    485                 490                 495

Gln Gln Lys Arg Pro Ala Leu Gln Pro Lys Gln Glu Gln Pro Glu Val
                    500                 505                 510

Glu Lys His Arg Leu Gln Ile Pro Arg Gln Asn Leu Ala Val Tyr Asn
                    515                 520                 525

Ser Asn His Asp Ile Trp Asn Asn Arg Asn Arg Asp Lys Tyr Ile Ile
                530                 535                 540

Ser Asn Asn Pro Asn Asn Arg Asn Asp Asn Asn Thr Val Cys Asp
    545                 550                 555                 560

Leu Ser Ser Gly Glu Leu Gly Glu Ser Arg Glu Val Val Pro Asp Gly
                    565                 570                 575

Ile Gly Leu Glu Val Leu Leu Asp Ser Ile Val Lys Glu Val Arg
                580                 585                 590

Met Glu Pro Ser Thr Val Ser Lys Glu Phe Arg Ser Ile Ile Ser Glu
                    595                 600                 605

Cys Leu Arg Asn Asp Ala Thr Glu Arg Gln Thr Ala Ser Asn Leu Val
                    610                 615                 620

Asn His Glu Phe Val Lys Lys Tyr Gln Lys Tyr Asn Arg Glu Lys Trp
    625                 630                 635                 640

Thr Ala Asp Leu Gln Arg Trp Gln
                    645

<210> SEQ ID NO 65
<211> LENGTH: 920
<212> TYPE: DNA
<213> ORGANISM: Arabidopsis thaliana
<220> FEATURE:
<221> NAME/KEY: CDS
<222> LOCATION: (26)...(907)

<400> SEQUENCE: 65
acacagttat tggccgtcgg attca atg gaa gga tta gct atc aga gca tct      52
                           Met Glu Gly Leu Ala Ile Arg Ala Ser
                             1               5
```

```
cga ccg tcg gtt ttc tgt tct att cca ggt ctc ggc ggc gat tcc cac    100
Arg Pro Ser Val Phe Cys Ser Ile Pro Gly Leu Gly Gly Asp Ser His
 10              15                  20                  25 cga aaa cct cca agt gac ggt ttc ctc aag ctg cct gcg tcg tct att    148
Arg Lys Pro Pro Ser Asp Gly Phe Leu Lys Leu Pro Ala Ser Ser Ile
             30                  35                  40 ccg gcg gac agc cga aaa tta gta gcg aat tct act tcc ttt cat cca    196
Pro Ala Asp Ser Arg Lys Leu Val Ala Asn Ser Thr Ser Phe His Pro
                 45                  50                  55 atc tca gcc gtt aac gtc tct gct caa gct tcc ctc acc gct gat ttt    244
Ile Ser Ala Val Asn Val Ser Ala Gln Ala Ser Leu Thr Ala Asp Phe
         60                  65                  70 ccc gcc ctt tca gaa act ata ctg aaa gag gga aga aat aac gga aaa    292
Pro Ala Leu Ser Glu Thr Ile Leu Lys Glu Gly Arg Asn Asn Gly Lys
     75                  80                  85 gag aaa gca gag aac atc gtg tgg cac gag agt tcg ata tgc aga tgc    340
Glu Lys Ala Glu Asn Ile Val Trp His Glu Ser Ser Ile Cys Arg Cys
 90                  95                 100                 105 gac aga caa caa ctt ctt caa caa aag ggt tgt gtc gtt tgg atc act    388
Asp Arg Gln Gln Leu Leu Gln Gln Lys Gly Cys Val Val Trp Ile Thr
                110                 115                 120 ggt ctc agt ggt tca ggg aaa agc act gtt gct tgt gca cta agt aaa    436
Gly Leu Ser Gly Ser Gly Lys Ser Thr Val Ala Cys Ala Leu Ser Lys
            125                 130                 135 gca ttg ttt gaa aga ggc aaa ctt act tac aca ctc gac ggc gac aat    484
Ala Leu Phe Glu Arg Gly Lys Leu Thr Tyr Thr Leu Asp Gly Asp Asn
        140                 145                 150 gtc cgt cac ggc ctt aac cgt gac ctc act ttc aaa gca gag cac cgc    532
Val Arg His Gly Leu Asn Arg Asp Leu Thr Phe Lys Ala Glu His Arg
    155                 160                 165 acc gaa aac att aga aga att ggt gag gtg gct aag ttg ttt gct gac    580
Thr Glu Asn Ile Arg Arg Ile Gly Glu Val Ala Lys Leu Phe Ala Asp
170                 175                 180                 185 gtc gga gtc att tgt ata gca agt ttg att tct ccg tac cgg aga gac    628
Val Gly Val Ile Cys Ile Ala Ser Leu Ile Ser Pro Tyr Arg Arg Asp
                190                 195                 200 aga gac gcg tgc cgg tcc ttg tta cct gac ggc gat ttc gtc gag gtc    676
Arg Asp Ala Cys Arg Ser Leu Leu Pro Asp Gly Asp Phe Val Glu Val
            205                 210                 215 ttc atg gac gtt cct ctt cat gtg tgc gag tcg aga gat cca aag ggg    724
Phe Met Asp Val Pro Leu His Val Cys Glu Ser Arg Asp Pro Lys Gly
        220                 225                 230 ttg tac aag ctt gca cgt gca ggc aaa atc aaa ggc ttc act gga atc    772
Leu Tyr Lys Leu Ala Arg Ala Gly Lys Ile Lys Gly Phe Thr Gly Ile
    235                 240                 245 gac gac cct tac gag gca cca gtg aat tgc gag gta gtg ctg aaa cac    820
Asp Asp Pro Tyr Glu Ala Pro Val Asn Cys Glu Val Val Leu Lys His
250                 255                 260                 265 aca gga gac gac gag tcg tgt tcg cca cgt cag atg gct gag aac atc    868
Thr Gly Asp Asp Glu Ser Cys Ser Pro Arg Gln Met Ala Glu Asn Ile
                270                 275                 280 atc tct tac ctg caa aac aaa ggt tat ctt gag ggc taa gtcaaagtcg    917
Ile Ser Tyr Leu Gln Asn Lys Gly Tyr Leu Glu Gly *
            285                 290 gaa                                                                920

<210> SEQ ID NO 66
<211> LENGTH: 293
<212> TYPE: PRT
```

<213> ORGANISM: Arabidopsis thaliana

<400> SEQUENCE: 66

```
Met Glu Gly Leu Ala Ile Arg Ala Ser Arg Pro Ser Val Phe Cys Ser
 1               5                  10                  15

Ile Pro Gly Leu Gly Gly Asp Ser His Arg Lys Pro Pro Ser Asp Gly
             20                  25                  30

Phe Leu Lys Leu Pro Ala Ser Ser Ile Pro Ala Asp Ser Arg Lys Leu
         35                  40                  45

Val Ala Asn Ser Thr Ser Phe His Pro Ile Ser Ala Val Asn Val Ser
 50                  55                  60

Ala Gln Ala Ser Leu Thr Ala Asp Phe Pro Ala Leu Ser Glu Thr Ile
 65                  70                  75                  80

Leu Lys Glu Gly Arg Asn Asn Gly Lys Glu Lys Ala Glu Asn Ile Val
                 85                  90                  95

Trp His Glu Ser Ser Ile Cys Arg Cys Asp Arg Gln Gln Leu Leu Gln
            100                 105                 110

Gln Lys Gly Cys Val Val Trp Ile Thr Gly Leu Ser Gly Ser Gly Lys
        115                 120                 125

Ser Thr Val Ala Cys Ala Leu Ser Lys Ala Leu Phe Glu Arg Gly Lys
130                 135                 140

Leu Thr Tyr Thr Leu Asp Gly Asp Asn Val Arg His Gly Leu Asn Arg
145                 150                 155                 160

Asp Leu Thr Phe Lys Ala Glu His Arg Thr Glu Asn Ile Arg Arg Ile
                165                 170                 175

Gly Glu Val Ala Lys Leu Phe Ala Asp Val Gly Val Ile Cys Ile Ala
            180                 185                 190

Ser Leu Ile Ser Pro Tyr Arg Arg Asp Arg Asp Ala Cys Arg Ser Leu
        195                 200                 205

Leu Pro Asp Gly Asp Phe Val Glu Val Phe Met Asp Val Pro Leu His
210                 215                 220

Val Cys Glu Ser Arg Asp Pro Lys Gly Leu Tyr Lys Leu Ala Arg Ala
225                 230                 235                 240

Gly Lys Ile Lys Gly Phe Thr Gly Ile Asp Asp Pro Tyr Glu Ala Pro
                245                 250                 255

Val Asn Cys Glu Val Val Leu Lys His Thr Gly Asp Asp Glu Ser Cys
            260                 265                 270

Ser Pro Arg Gln Met Ala Glu Asn Ile Ile Ser Tyr Leu Gln Asn Lys
        275                 280                 285

Gly Tyr Leu Glu Gly
    290
```

<210> SEQ ID NO 67
<211> LENGTH: 1257
<212> TYPE: DNA
<213> ORGANISM: Arabidopsis thaliana
<220> FEATURE:
<221> NAME/KEY: CDS
<222> LOCATION: (13)...(1245)

<400> SEQUENCE: 67

```
aattactcaa tc atg ggg att tgc ttg agt gct cag gtc aaa gct gag agc      51
              Met Gly Ile Cys Leu Ser Ala Gln Val Lys Ala Glu Ser
                1               5                  10 tca gga gcg agt acg aag tat gac gcc aaa gat ata gga agt ctt ggg       99
Ser Gly Ala Ser Thr Lys Tyr Asp Ala Lys Asp Ile Gly Ser Leu Gly
 15                  20                  25
```

-continued

```
agc aag gct tcg tct gtg tct gta aga cca agc cct cga act gag ggt        147
Ser Lys Ala Ser Ser Val Ser Val Arg Pro Ser Pro Arg Thr Glu Gly
 30              35                  40                  45 gag atc tta cag tct cca aat ctc aag agt ttt agc ttt gct gag ctt        195
Glu Ile Leu Gln Ser Pro Asn Leu Lys Ser Phe Ser Phe Ala Glu Leu
             50                  55                  60 aaa tca gca acc agg aat ttt aga cca gac agt gtg ctt ggt gaa ggt        243
Lys Ser Ala Thr Arg Asn Phe Arg Pro Asp Ser Val Leu Gly Glu Gly
 65                  70                  75 gga ttc ggt tgt gtt ttc aaa gga tgg att gat gag aag tct ctc act        291
Gly Phe Gly Cys Val Phe Lys Gly Trp Ile Asp Glu Lys Ser Leu Thr
         80                  85                  90 gcc tca aga cca ggc acg ggt ttg gtt att gcc gtc aaa aag ctt aac        339
Ala Ser Arg Pro Gly Thr Gly Leu Val Ile Ala Val Lys Lys Leu Asn
     95                 100                 105 caa gat ggt tgg caa ggt cac cag gag tgg ctg gct gaa gtg aat tac        387
Gln Asp Gly Trp Gln Gly His Gln Glu Trp Leu Ala Glu Val Asn Tyr
110                 115                 120                 125 ctt ggt cag ttt tct cac cgt cac ctt gtg aag ctg att ggt tat tgc        435
Leu Gly Gln Phe Ser His Arg His Leu Val Lys Leu Ile Gly Tyr Cys
                130                 135                 140 cta gag gat gag cac cgt ctt ctt gtt tac gag ttc atg cct cgg ggt        483
Leu Glu Asp Glu His Arg Leu Leu Val Tyr Glu Phe Met Pro Arg Gly
            145                 150                 155 agc ttg gag aat cat ctt ttc agg aga ggt ttg tac ttc caa ccg tta        531
Ser Leu Glu Asn His Leu Phe Arg Arg Gly Leu Tyr Phe Gln Pro Leu
        160                 165                 170 tct tgg aaa ctt cgg ttg aaa gtt gct ctt ggt gct gca aag gga ctt        579
Ser Trp Lys Leu Arg Leu Lys Val Ala Leu Gly Ala Ala Lys Gly Leu
175                 180                 185 gct ttt ctt cac agt tcc gag aca aga gtg ata tac cga gat ttc aag        627
Ala Phe Leu His Ser Ser Glu Thr Arg Val Ile Tyr Arg Asp Phe Lys
190                 195                 200                 205 act tct aat atc ctt ctt gac tcg gag tac aac gca aag ctt tct gat        675
Thr Ser Asn Ile Leu Leu Asp Ser Glu Tyr Asn Ala Lys Leu Ser Asp
                210                 215                 220 ttt ggg ttg gct aag gat ggg cca ata ggt gat aaa agt cat gtc tct        723
Phe Gly Leu Ala Lys Asp Gly Pro Ile Gly Asp Lys Ser His Val Ser
            225                 230                 235 aca cga gtc atg ggt aca cac gga tat gca gct cct gaa tac ctt gca        771
Thr Arg Val Met Gly Thr His Gly Tyr Ala Ala Pro Glu Tyr Leu Ala
        240                 245                 250 acc ggt cat cta aca aca aag agt gat gtc tat agc ttc ggg gtt gtc        819
Thr Gly His Leu Thr Thr Lys Ser Asp Val Tyr Ser Phe Gly Val Val
255                 260                 265 ctt ctg gag ctg ttg tct ggt cgt cga gca gtg gac aag aac cgc cca        867
Leu Leu Glu Leu Leu Ser Gly Arg Arg Ala Val Asp Lys Asn Arg Pro
270                 275                 280                 285 tct gga gag agg aac ctt gtg gag tgg gct aaa cca tac ctc gta aac        915
Ser Gly Glu Arg Asn Leu Val Glu Trp Ala Lys Pro Tyr Leu Val Asn
                290                 295                 300 aaa aga aag ata ttc cga gtc att gat aat cgt ctt cag gac cag tac        963
Lys Arg Lys Ile Phe Arg Val Ile Asp Asn Arg Leu Gln Asp Gln Tyr
            305                 310                 315 tct atg gaa gaa gca tgt aaa gtg gct act ctg tct ctg aga tgt ctc       1011
Ser Met Glu Glu Ala Cys Lys Val Ala Thr Leu Ser Leu Arg Cys Leu
        320                 325                 330 acc aca gag att aag ctg aga cca aac atg agc gag gtt gtt tcg cac       1059
Thr Thr Glu Ile Lys Leu Arg Pro Asn Met Ser Glu Val Val Ser His
```

```
                335                 340                 345
ctc gaa cac att cag tct tta aat gct gct ata gga gga aat atg gat    1107
Leu Glu His Ile Gln Ser Leu Asn Ala Ala Ile Gly Gly Asn Met Asp
350                 355                 360                 365 aaa aca gat aga aga atg cgt agg aga agt gac agt gtt gtc agc aaa    1155
Lys Thr Asp Arg Arg Met Arg Arg Arg Ser Asp Ser Val Val Ser Lys
                370                 375                 380 aaa gtg aat gca ggt ttt gct cga cag act gct gtt ggc agt aca gtt    1203
Lys Val Asn Ala Gly Phe Ala Arg Gln Thr Ala Val Gly Ser Thr Val
            385                 390                 395 gtt gct tat cct cgc cca tca gcc tcg cca ctg tat gtt tga            1245
Val Ala Tyr Pro Arg Pro Ser Ala Ser Pro Leu Tyr Val *
                400                 405                 410 atagggttaa ac                                                       1257
```

<210> SEQ ID NO 68
<211> LENGTH: 410
<212> TYPE: PRT
<213> ORGANISM: Arabidopsis thaliana

<400> SEQUENCE: 68

```
Met Gly Ile Cys Leu Ser Ala Gln Val Lys Ala Glu Ser Ser Gly Ala
 1               5                  10                  15

Ser Thr Lys Tyr Asp Ala Lys Asp Ile Gly Ser Leu Gly Ser Lys Ala
            20                  25                  30

Ser Ser Val Ser Val Arg Pro Ser Pro Arg Thr Glu Gly Glu Ile Leu
        35                  40                  45

Gln Ser Pro Asn Leu Lys Ser Phe Ser Phe Ala Glu Leu Lys Ser Ala
    50                  55                  60

Thr Arg Asn Phe Arg Pro Asp Ser Val Leu Gly Glu Gly Gly Phe Gly
65                  70                  75                  80

Cys Val Phe Lys Gly Trp Ile Asp Glu Lys Ser Leu Thr Ala Ser Arg
                85                  90                  95

Pro Gly Thr Gly Leu Val Ile Ala Val Lys Lys Leu Asn Gln Asp Gly
            100                 105                 110

Trp Gln Gly His Gln Glu Trp Leu Ala Glu Val Asn Tyr Leu Gly Gln
        115                 120                 125

Phe Ser His Arg His Leu Val Lys Leu Ile Gly Tyr Cys Leu Glu Asp
    130                 135                 140

Glu His Arg Leu Leu Val Tyr Glu Phe Met Pro Arg Gly Ser Leu Glu
145                 150                 155                 160

Asn His Leu Phe Arg Arg Gly Leu Tyr Phe Gln Pro Leu Ser Trp Lys
                165                 170                 175

Leu Arg Leu Lys Val Ala Leu Gly Ala Ala Lys Gly Leu Ala Phe Leu
            180                 185                 190

His Ser Ser Glu Thr Arg Val Ile Tyr Arg Asp Phe Lys Thr Ser Asn
        195                 200                 205

Ile Leu Leu Asp Ser Glu Tyr Asn Ala Lys Leu Ser Asp Phe Gly Leu
    210                 215                 220

Ala Lys Asp Gly Pro Ile Gly Asp Lys Ser His Val Ser Thr Arg Val
225                 230                 235                 240

Met Gly Thr His Gly Tyr Ala Ala Pro Glu Tyr Leu Ala Thr Gly His
                245                 250                 255

Leu Thr Thr Lys Ser Asp Val Tyr Ser Phe Gly Val Val Leu Leu Glu
            260                 265                 270
```

```
Leu Leu Ser Gly Arg Arg Ala Val Asp Lys Asn Arg Pro Ser Gly Glu
        275                 280                 285

Arg Asn Leu Val Glu Trp Ala Lys Pro Tyr Leu Val Asn Lys Arg Lys
        290                 295                 300

Ile Phe Arg Val Ile Asp Asn Arg Leu Gln Asp Gln Tyr Ser Met Glu
305                 310                 315                 320

Glu Ala Cys Lys Val Ala Thr Leu Ser Leu Arg Cys Leu Thr Thr Glu
                325                 330                 335

Ile Lys Leu Arg Pro Asn Met Ser Glu Val Val Ser His Leu Glu His
                340                 345                 350

Ile Gln Ser Leu Asn Ala Ala Ile Gly Gly Asn Met Asp Lys Thr Asp
        355                 360                 365

Arg Arg Met Arg Arg Ser Asp Ser Val Val Ser Lys Lys Val Asn
370                 375                 380

Ala Gly Phe Ala Arg Gln Thr Ala Val Gly Ser Thr Val Val Ala Tyr
385                 390                 395                 400

Pro Arg Pro Ser Ala Ser Pro Leu Tyr Val
                405                 410

<210> SEQ ID NO 69
<211> LENGTH: 3240
<212> TYPE: DNA
<213> ORGANISM: Arabidopsis thaliana
<220> FEATURE:
<221> NAME/KEY: CDS
<222> LOCATION: (69)...(236)
<220> FEATURE:
<221> NAME/KEY: CDS
<222> LOCATION: (420)...(506)
<220> FEATURE:
<221> NAME/KEY: CDS
<222> LOCATION: (581)...(822)
<220> FEATURE:
<221> NAME/KEY: CDS
<222> LOCATION: (907)...(1126)
<220> FEATURE:
<221> NAME/KEY: CDS
<222> LOCATION: (1276)...(1355)
<220> FEATURE:
<221> NAME/KEY: CDS
<222> LOCATION: (1442)...(1526)
<220> FEATURE:
<221> NAME/KEY: CDS
<222> LOCATION: (1684)...(1815)
<220> FEATURE:
<221> NAME/KEY: CDS
<222> LOCATION: (1911)...(2024)
<220> FEATURE:
<221> NAME/KEY: CDS
<222> LOCATION: (2196)...(2243)
<220> FEATURE:
<221> NAME/KEY: CDS
<222> LOCATION: (2734)...(2818)
<220> FEATURE:
<221> NAME/KEY: CDS
<222> LOCATION: (2928)...(2984)
<220> FEATURE:
<221> NAME/KEY: CDS
<222> LOCATION: (3079)...(3191)

<400> SEQUENCE: 69
ctttcgtgtg aacttccgtc catatcctta gctctttgtt tggtatttac atttcataca      60 gacgcaaa atg cta gag aaa aaa tta gct gct gca gaa gtc tct gag gaa     110
         Met Leu Glu Lys Lys Leu Ala Ala Ala Glu Val Ser Glu Glu
          1               5                  10 gag caa aat aac ttg cta aag gat ttg gag atg aag gaa act gaa tat     158
Glu Gln Asn Asn Leu Leu Lys Asp Leu Glu Met Lys Glu Thr Glu Tyr
```

```
                    15                  20                  25                  30
atg cgc cgt cag agg cat aaa atg gga gct gat gac ttt gag cca ttg              206
Met Arg Arg Gln Arg His Lys Met Gly Ala Asp Asp Phe Glu Pro Leu
                35                  40                  45 aca atg att ggg aag ggt gca ttc gga gag gtaacatctc ttttatagat                256
Thr Met Ile Gly Lys Gly Ala Phe Gly Glu
                50                  55 catagtctgt tactctgttt tctcagcctc tcattggcat gcatcatctt gaaatgttct            316
ctgtgatgca tccttcttga aaggtcttct taggccattt ttttaccac agctaatttt             376 tcaaaaagt atggcatgct aattttctc tttctctttg cag gtt agg atc tgt                431
                                                  Val Arg Ile Cys
                                                              60 agg gag aag gga aca ggc aat gtc tat gca atg aag aag ctt aag aaa              479
Arg Glu Lys Gly Thr Gly Asn Val Tyr Ala Met Lys Lys Leu Lys Lys
                65                  70                  75 tct gag atg ctt cgc aga ggc cag gta tttaaattcc ttcaagtggc                    526
Ser Glu Met Leu Arg Arg Gly Gln Val
            80                  85 tttcgtttga catttgttta gttggttgat gtgaatgtgg aatctgattt tcag gtg              583
                                                              Val gaa cat gta aaa gca gag aga aat tta ctt gca gaa gtt gat agc aat              631
Glu His Val Lys Ala Glu Arg Asn Leu Leu Ala Glu Val Asp Ser Asn 90                  95                  100 tgc att gtc aaa ctg tat tgt tct ttc caa gat gaa gag tac ttg tat              679
Cys Ile Val Lys Leu Tyr Cys Ser Phe Gln Asp Glu Glu Tyr Leu Tyr
            105                 110                 115 ctc ata atg gag tat tta cct ggt ggg gat atg atg act tta ctt atg              727
Leu Ile Met Glu Tyr Leu Pro Gly Gly Asp Met Met Thr Leu Leu Met
    120                 125                 130 agg aaa gac acc ctc act gaa gac gag gcc agg ttt tat att ggg gaa              775
Arg Lys Asp Thr Leu Thr Glu Asp Glu Ala Arg Phe Tyr Ile Gly Glu
135                 140                 145                 150 act gtc ctg gct att gag tcc att cat aag cac aac tac att cac ag               822
Thr Val Leu Ala Ile Glu Ser Ile His Lys His Asn Tyr Ile His Arg
                155                 160                 165 gtcagtgaag cagaatatat gatttagttc tagctcccat tgttattttg ttctaaacgt            882 cttttttct ccaatgtgat acag a gat atc aag cct gat aat ctg cta ctt              934
                            Asp Ile Lys Pro Asp Asn Leu Leu Leu
                                            170                 175 gac aaa gac ggc cac atg aaa ttg tca gat ttt gga tta tgt aaa cca              982
Asp Lys Asp Gly His Met Lys Leu Ser Asp Phe Gly Leu Cys Lys Pro
        180                 185                 190 tta gac tgt agt aat ctt caa gag aaa gac ttt aca gtt gca aga aac              1030
Leu Asp Cys Ser Asn Leu Gln Glu Lys Asp Phe Thr Val Ala Arg Asn
                195                 200                 205 gtt agt ggg gct tta caa agt gat ggt cgc cct gtg gcg aca aga cgc              1078
Val Ser Gly Ala Leu Gln Ser Asp Gly Arg Pro Val Ala Thr Arg Arg
            210                 215                 220 acc caa caa gag caa tta cta aac tgg cag aga aat aga agg atg ctt              1126
Thr Gln Gln Glu Gln Leu Leu Asn Trp Gln Arg Asn Arg Arg Met Leu
    225                 230                 235 gtaagtttca cttattcctc atcttttctt ccagagatgt ggagtagtcc acagtatcca            1186
gtatatttcg ttattgaaag caaattctct ccattgatat agacatctat gttagatatg            1246
acttactagg ttaaggtcat tactttcag gct tat tcc aca gtt ggc act cct              1299
                                Ala Tyr Ser Thr Val Gly Thr Pro
                                                240                 245
```

```
gac tat att gcc cca gaa gtt ctg ttg aaa aaa gga tat gga atg gaa         1347
Asp Tyr Ile Ala Pro Glu Val Leu Leu Lys Lys Gly Tyr Gly Met Glu
        250                 255                 260 tgt gat tg gtaggtgaag ccaacctatt cctatttgtg gtctttgatt tctttggtgt       1405
Cys Asp Trp
        265 aaataaataa tatgggtgaa taatcttgag atttag g tgg tct ctt ggc gcc att        1460
                                         Trp Ser Leu Gly Ala Ile
                                                             270 atg tat gaa atg ctt gtg ggg ttt ccg ccc ttt tat tca gat gac cca         1508
Met Tyr Glu Met Leu Val Gly Phe Pro Pro Phe Tyr Ser Asp Asp Pro
        275                 280                 285 atg aca act tgt agg aag gtaattaatc cattcctttt tgaatctttc                1556
Met Thr Thr Cys Arg Lys
        290 attttaatat tgaaggcaga ctggcgattt caagtcttac atttaatttt agtctttttg       1616 tatctctttg gtaattctaa tgtggaaact tacctcttct cgattcatta tcttccccct       1676 tatgcag ata gta aat tgg aga aat tac ttg aaa ttc cca gat gag gtt         1725
        Ile Val Asn Trp Arg Asn Tyr Leu Lys Phe Pro Asp Glu Val
            295                 300                 305 aga cta tca cca gaa gcc aag gat ctt att tgt agg ctt tta tgc aat         1773
Arg Leu Ser Pro Glu Ala Lys Asp Leu Ile Cys Arg Leu Leu Cys Asn
        310                 315                 320 gtt gaa caa agg ctt gga aca aaa gga gca gat gaa att aag                 1815
Val Glu Gln Arg Leu Gly Thr Lys Gly Ala Asp Glu Ile Lys
325                 330                 335 gtgttgtatg cgttgttcaa ctttgagatt caaagttccc ttatgtaaga tcattgtgtg       1875
caattcttaa aaacgatttg actggtttct ttcag ggt cac cct tgg ttt aga          1928
                                        Gly His Pro Trp Phe Arg
                                                            340 ggc aca gaa tgg gga aaa ttg tat caa atg aaa gct gcc ttt att ccc         1976
Gly Thr Glu Trp Gly Lys Leu Tyr Gln Met Lys Ala Ala Phe Ile Pro
345                 350                 355                 360 caa gtt aat gat gag ttg gac acc caa aat ttt gag aaa ttt gaa gag         2024
Gln Val Asn Asp Glu Leu Asp Thr Gln Asn Phe Glu Lys Phe Glu Glu
                365                 370                 375 gtaacacact gatactatca gctaatgatg tctatagtga aatattggtg caatatatgc       2084
caccaaatga tgtggcatga tgtatatact gaaatattgg tatcacagat gatttttatg       2144
ctcctgataa ggaaaataat gtatactctt ctttgattcc ttctggaaca g act gac        2201
                                                        Thr Asp aag caa gtt cca aag tca gcc aag tca ggt cca tgg aga aag                 2243
Lys Gln Val Pro Lys Ser Ala Lys Ser Gly Pro Trp Arg Lys
        380                 385                 390 gtacagcata agcactgact ttttggcatt atgtaccatc aagcttttt tttttatcta        2303 atagaagagt gatcatactt caaatttat ctataagtgg gttccttgag atatgttgtt        2363
ctttgatgat actacagacg tagcttaaaa tattacatgc aacaaagagc tcagaatgat       2423
gaaattggct cagtttctgt cacaggcgtt tctatctttg tactatattc acaaaaacgt       2483
gattcactct tttaggttca aatttttctta tggtaattta gaatttggag ctgattggga     2543
tgctactaac agaattatgt tgttaatctg ccagttctgc atgttgacgt gtgttagatg      2603
aatcacttat ctttttggac caacatgata taacttagaa cctgttctgt caatagaatt      2663
tatgtcatga accaaaagga ttcttgtgaa tttcataaca tgacgctggc tttcttttt       2723 tcttctccag atg ctc tca tcc aaa gac att aac ttt gtt ggt tat act         2772
            Met Leu Ser Ser Lys Asp Ile Asn Phe Val Gly Tyr Thr
```

```
                Met Leu Ser Ser Lys Asp Ile Asn Phe Val Gly Tyr Thr
                            395                 400                 405 tac aag aac gta gaa atc gta aat gat gac caa ata cca ggg ata g          2818
Tyr Lys Asn Val Glu Ile Val Asn Asp Asp Gln Ile Pro Gly Ile
                410                 415                 420 gtaattcact taaccccct tccgttgctg aggaagaagc aacaatacta gattaccttg        2878
tgattatcat cgcatgtttg ctgcatttgt aatttgtttt attgtgcag ct gag ttg       2935
                                                         Ala Glu Leu aag aag aag agc aat aag cca aaa agg ccg tct att aaa tct ctc ttt        2983
Lys Lys Lys Ser Asn Lys Pro Lys Arg Pro Ser Ile Lys Ser Leu Phe
425                 430                 435 g gtaaatcatc tgtttgtatg ctatttgtaa atcaagatg attacgatcc                3034 atgtttgatt ctctctaacc aaactgtgga aactaaatta acag aa gac gaa aca        3089
                                                Glu Asp Glu Thr
                                                        440 tct ggt ggg aca aca acc cac caa gga agc ttt ttg aat cta cta ccg        3137
Ser Gly Gly Thr Thr Thr His Gln Gly Ser Phe Leu Asn Leu Leu Pro
445                 450                 455 acg cag att gaa gat cca gag aaa gaa ggt agt aag tcg agc tca tcc        3185
Thr Gln Ile Glu Asp Pro Glu Lys Glu Gly Ser Lys Ser Ser Ser Ser
460                 465                 470                 475 ggg tga atttcatttg acacattgca cagcctgaac cagaagactc ttgttatat          3240
Gly  *

<210> SEQ ID NO 70
<211> LENGTH: 476
<212> TYPE: PRT
<213> ORGANISM: Arabidopsis thaliana

<400> SEQUENCE: 70

Met Leu Glu Lys Lys Leu Ala Ala Glu Val Ser Glu Glu Gln
 1               5                   10                  15

Asn Asn Leu Leu Lys Asp Leu Glu Met Lys Glu Thr Glu Tyr Met Arg
            20                  25                  30

Arg Gln Arg His Lys Met Gly Ala Asp Asp Phe Glu Pro Leu Thr Met
        35                  40                  45

Ile Gly Lys Gly Ala Phe Gly Glu Val Arg Ile Cys Arg Glu Lys Gly
    50                  55                  60

Thr Gly Asn Val Tyr Ala Met Lys Lys Leu Lys Lys Ser Glu Met Leu
65                  70                  75                  80

Arg Arg Gly Gln Val Val Glu His Val Lys Ala Glu Arg Asn Leu Leu
                85                  90                  95

Ala Glu Val Asp Ser Asn Cys Ile Val Lys Leu Tyr Cys Ser Phe Gln
            100                 105                 110

Asp Glu Glu Tyr Leu Tyr Leu Ile Met Glu Tyr Leu Pro Gly Gly Asp
        115                 120                 125

Met Met Thr Leu Leu Met Arg Lys Asp Thr Leu Thr Glu Asp Glu Ala
    130                 135                 140

Arg Phe Tyr Ile Gly Glu Thr Val Leu Ala Ile Glu Ser Ile His Lys
145                 150                 155                 160

His Asn Tyr Ile His Arg Asp Ile Lys Pro Asp Asn Leu Leu Asp
                165                 170                 175

Lys Asp Gly His Met Lys Leu Ser Asp Phe Gly Leu Cys Lys Pro Leu
            180                 185                 190

Asp Cys Ser Asn Leu Gln Glu Lys Asp Phe Thr Val Ala Arg Asn Val
        195                 200                 205
```

```
Ser Gly Ala Leu Gln Ser Asp Gly Arg Pro Val Ala Thr Arg Arg Thr
    210                 215                 220

Gln Gln Glu Gln Leu Leu Asn Trp Gln Arg Asn Arg Arg Met Leu Ala
225                 230                 235                 240

Tyr Ser Thr Val Gly Thr Pro Asp Tyr Ile Ala Pro Glu Val Leu Leu
                245                 250                 255

Lys Lys Gly Tyr Gly Met Glu Cys Asp Trp Trp Ser Leu Gly Ala Ile
                260                 265                 270

Met Tyr Glu Met Leu Val Gly Phe Pro Pro Phe Tyr Ser Asp Asp Pro
        275                 280                 285

Met Thr Thr Cys Arg Lys Ile Val Asn Trp Arg Asn Tyr Leu Lys Phe
    290                 295                 300

Pro Asp Glu Val Arg Leu Ser Pro Glu Ala Lys Asp Leu Ile Cys Arg
305                 310                 315                 320

Leu Leu Cys Asn Val Glu Gln Arg Leu Gly Thr Lys Gly Ala Asp Glu
                325                 330                 335

Ile Lys Gly His Pro Trp Phe Arg Gly Thr Glu Trp Gly Lys Leu Tyr
                340                 345                 350

Gln Met Lys Ala Ala Phe Ile Pro Gln Val Asn Asp Glu Leu Asp Thr
        355                 360                 365

Gln Asn Phe Glu Lys Phe Glu Glu Thr Asp Lys Gln Val Pro Lys Ser
    370                 375                 380

Ala Lys Ser Gly Pro Trp Arg Lys Met Leu Ser Ser Lys Asp Ile Asn
385                 390                 395                 400

Phe Val Gly Tyr Thr Tyr Lys Asn Val Glu Ile Val Asn Asp Asp Gln
                405                 410                 415

Ile Pro Gly Ile Ala Glu Leu Lys Lys Lys Ser Asn Lys Pro Lys Arg
                420                 425                 430

Pro Ser Ile Lys Ser Leu Phe Glu Asp Glu Thr Ser Gly Gly Thr Thr
        435                 440                 445

Thr His Gln Gly Ser Phe Leu Asn Leu Leu Pro Thr Gln Ile Glu Asp
    450                 455                 460

Pro Glu Lys Glu Gly Ser Lys Ser Ser Ser Ser Gly
465                 470                 475

<210> SEQ ID NO 71
<211> LENGTH: 979
<212> TYPE: DNA
<213> ORGANISM: Arabidopsis thaliana
<220> FEATURE:
<221> NAME/KEY: CDS
<222> LOCATION: (28)...(843)

<400> SEQUENCE: 71
acgaaaacca ccgttagcta taggctg atg ata tgt agg atc cga ctc ggg tcg    54
                            Met Ile Cys Arg Ile Arg Leu Gly Ser
                              1               5 atg aac ggt gac gaa tgc gcg aac gtt gcg acg tgc tgg gtt act tct    102
Met Asn Gly Asp Glu Cys Ala Asn Val Ala Thr Cys Trp Val Thr Ser
 10                  15                  20                  25 cta gct tgt gta gtt gac gcc gga cga tat acg aaa aag gta tcc cac    150
Leu Ala Cys Val Val Asp Ala Gly Arg Tyr Thr Lys Lys Val Ser His
                 30                  35                  40 gac cgg cga acg agg tgg ccc gcc tgg aaa gca cga cgg gat cgt cat    198
Asp Arg Arg Thr Arg Trp Pro Ala Trp Lys Ala Arg Arg Asp Arg His
             45                  50                  55
```

```
agt gtc cga agt gat agc ggc cta gac agt cat gca ctt gaa ggt gga    246
Ser Val Arg Ser Asp Ser Gly Leu Asp Ser His Ala Leu Glu Gly Gly
         60              65              70 aaa cga cgt gag tca tgc gta tca cta gct cac gaa cga gat tat gca    294
Lys Arg Arg Glu Ser Cys Val Ser Leu Ala His Glu Arg Asp Tyr Ala
 75              80              85 cta acg gca cgg tgg gat cgt agc att gca atg acg gat gac acg aac    342
Leu Thr Ala Arg Trp Asp Arg Ser Ile Ala Met Thr Asp Asp Thr Asn
 90              95             100             105 cca caa acc caa cgt aaa ttt gag aaa cat act cgg gat gta gaa gct    390
Pro Gln Thr Gln Arg Lys Phe Glu Lys His Thr Arg Asp Val Glu Ala
                110             115             120 gtt cga ttt tct cca cga gat cgt cta att gta tct gcg ggt gca gat    438
Val Arg Phe Ser Pro Arg Asp Arg Leu Ile Val Ser Ala Gly Ala Asp
        125             130             135 ggg gta att gca gta tgt ccg gtt gct ggt gaa tgt gat gat gac gat    486
Gly Val Ile Ala Val Cys Pro Val Ala Gly Glu Cys Asp Asp Asp Asp
        140             145             150 gcc cgt gat ggt cat gaa gat tgt gtt agt agt att tgc ttt tca cca    534
Ala Arg Asp Gly His Glu Asp Cys Val Ser Ser Ile Cys Phe Ser Pro
155             160             165 tca cta gaa cac ccg atc ctc ttt tct ggt agt tgt atc tac ttt att    582
Ser Leu Glu His Pro Ile Leu Phe Ser Gly Ser Cys Ile Tyr Phe Ile
170             175             180             185 aaa gtg tgg aat gtc aat gga aag aaa tgt agg acg ccg cta aaa aag    630
Lys Val Trp Asn Val Asn Gly Lys Lys Cys Arg Thr Pro Leu Lys Lys
                190             195             200 cat agt aat ccc gta tct aca cgg aca cag tca gaa gag gga agg cta    678
His Ser Asn Pro Val Ser Thr Arg Thr Gln Ser Glu Glu Gly Arg Leu
        205             210             215 tgt gca aaa ggt ggt aaa agc ggt gca cgg cta cta ccc gat cta agt    726
Cys Ala Lys Gly Gly Lys Ser Gly Ala Arg Leu Leu Pro Asp Leu Ser
        220             225             230 act cag gaa caa cta ccc aaa att aat caa gaa aac cct att aat caa    774
Thr Gln Glu Gln Leu Pro Lys Ile Asn Gln Glu Asn Pro Ile Asn Gln
235             240             245 att gct ttt tca cct agt ccg ttc gtc gtc acg tgc caa acg gaa aga    822
Ile Ala Phe Ser Pro Ser Pro Phe Val Val Thr Cys Gln Thr Glu Arg
250             255             260             265 tcc cta tct caa acg tgg tga ccgtgcaccg gcacggtgaa aaagtcgacc        873
Ser Leu Ser Gln Thr Trp  *
                270 ggatcgaccg accgaaagcc tgctcgctgg acaaaaaaag agcttttag gcctttcgct    933 tttttgaag aaaaaggct cgcgaaaaaa aaaagctcg aaatca                     979
```

<210> SEQ ID NO 72
<211> LENGTH: 271
<212> TYPE: PRT
<213> ORGANISM: Arabidopsis thaliana

<400> SEQUENCE: 72

```
Met Ile Cys Arg Ile Arg Leu Gly Ser Met Asn Gly Asp Glu Cys Ala
 1               5                  10                  15

Asn Val Ala Thr Cys Trp Val Thr Ser Leu Ala Cys Val Val Asp Ala
                20                  25                  30

Gly Arg Tyr Thr Lys Lys Val Ser His Asp Arg Arg Thr Arg Trp Pro
            35                  40                  45

Ala Trp Lys Ala Arg Arg Asp Arg His Ser Val Arg Ser Asp Ser Gly
        50                  55                  60
```

```
Leu Asp Ser His Ala Leu Glu Gly Gly Lys Arg Arg Glu Ser Cys Val
 65                  70                  75                  80

Ser Leu Ala His Glu Arg Asp Tyr Ala Leu Thr Ala Arg Trp Asp Arg
                 85                  90                  95

Ser Ile Ala Met Thr Asp Thr Asn Pro Gln Thr Gln Arg Lys Phe
            100                 105                 110

Glu Lys His Thr Arg Asp Val Glu Ala Val Arg Phe Ser Pro Arg Asp
            115                 120                 125

Arg Leu Ile Val Ser Ala Gly Asp Gly Val Ile Ala Val Cys Pro
130                 135                 140

Val Ala Gly Glu Cys Asp Asp Asp Ala Arg Asp Gly His Glu Asp
145                 150                 155                 160

Cys Val Ser Ser Ile Cys Phe Ser Pro Ser Leu Glu His Pro Ile Leu
                165                 170                 175

Phe Ser Gly Ser Cys Ile Tyr Phe Ile Lys Val Trp Asn Val Asn Gly
            180                 185                 190

Lys Lys Cys Arg Thr Pro Leu Lys Lys His Ser Asn Pro Val Ser Thr
            195                 200                 205

Arg Thr Gln Ser Glu Glu Gly Arg Leu Cys Ala Lys Gly Gly Lys Ser
210                 215                 220

Gly Ala Arg Leu Leu Pro Asp Leu Ser Thr Gln Glu Gln Leu Pro Lys
225                 230                 235                 240

Ile Asn Gln Glu Asn Pro Ile Asn Gln Ile Ala Phe Ser Pro Ser Pro
                245                 250                 255

Phe Val Val Thr Cys Gln Thr Glu Arg Ser Leu Ser Gln Thr Trp
            260                 265                 270

<210> SEQ ID NO 73
<211> LENGTH: 1260
<212> TYPE: DNA
<213> ORGANISM: Arabidopsis thaliana
<220> FEATURE:
<221> NAME/KEY: CDS
<222> LOCATION: (101)...(155)
<220> FEATURE:
<221> NAME/KEY: CDS
<222> LOCATION: (254)...(660)
<220> FEATURE:
<221> NAME/KEY: CDS
<222> LOCATION: (750)...(1193)

<400> SEQUENCE: 73
gctcaattat gtttacaaca ttgttgtaat ttcaaaactt cataagaatt tctctgataa      60
taaagaaaaa gctggagtag aactatttta aagtgtcatc atg aag aga cta agc     115
                                             Met Lys Arg Leu Ser
                                               1               5 agc tca gat tca atg tgt ggt cta atc tcc act tct aca g gttcttatta     165
Ser Ser Asp Ser Met Cys Gly Leu Ile Ser Thr Ser Thr
            10                  15 ccatctttgt tctttctact ttttgctaat gtcagacaaa acccatgtga tcctttcttc    225
actttccact gtttctttta ttgacaag at tca ttt ggt tac aca aca gat gaa   279
                             Asp Ser Phe Gly Tyr Thr Thr Asp Glu
                                     20                  25 cag agt cca aga ggg tac gga agt aat tac caa tct atg ctt gaa ggt     327
Gln Ser Pro Arg Gly Tyr Gly Ser Asn Tyr Gln Ser Met Leu Glu Gly
        30                  35                  40 tac gat gaa gat gct aca cta atc gag gaa tat tcc ggc aac cac cac     375
Tyr Asp Glu Asp Ala Thr Leu Ile Glu Glu Tyr Ser Gly Asn His His
```

```
                45                    50                    55
cac atg ggt cta tcg gag aag aag aga aga tta aaa gtt gac caa gtc    423
His Met Gly Leu Ser Glu Lys Lys Arg Arg Leu Lys Val Asp Gln Val
 60                  65                  70                  75 aaa gct ctt gag aag aat ttc gaa ctt gag aat aaa ctc gaa cct gag    471
Lys Ala Leu Glu Lys Asn Phe Glu Leu Glu Asn Lys Leu Glu Pro Glu
                 80                  85                  90 agg aaa act aaa tta gca caa gag ctt gga ctt caa cct cgt caa gta    519
Arg Lys Thr Lys Leu Ala Gln Glu Leu Gly Leu Gln Pro Arg Gln Val
                     95                 100                 105 gct gtt tgg ttt cag aac cgt cgt gca cgg tgg aaa aca aaa cag ctt    567
Ala Val Trp Phe Gln Asn Arg Arg Ala Arg Trp Lys Thr Lys Gln Leu
            110                 115                 120 gaa aaa gat tac ggt gtt ctt aag ggt caa tac gat tct ctc cgc cac    615
Glu Lys Asp Tyr Gly Val Leu Lys Gly Gln Tyr Asp Ser Leu Arg His
        125                 130                 135 aat ttc gat tct ctc cgc cgt gac aat gat tcc ctt ctc caa gag        660
Asn Phe Asp Ser Leu Arg Arg Asp Asn Asp Ser Leu Leu Gln Glu
140                 145                 150 gtacaatatt agagacttta aaccataaaa attgaaactt cagagacgaa aatgcaaaaa   720
ggtttgattt ttaaagtttt tggttgcag att agt aaa atc aaa gct aag gta    773
                                Ile Ser Lys Ile Lys Ala Lys Val
                                        155                 160 aac ggt gaa gaa gat aac aac aac aac aaa gct att acg gag ggt gtt    821
Asn Gly Glu Glu Asp Asn Asn Asn Asn Lys Ala Ile Thr Glu Gly Val
            165                 170                 175 aag gaa gag gaa gtt cac aag acg gat tcg att cct tcg tct cct ctg    869
Lys Glu Glu Glu Val His Lys Thr Asp Ser Ile Pro Ser Ser Pro Leu
        180                 185                 190 cag ttt cta gaa cat tcc tct ggt ttt aac tac cgg cga agc ttc act    917
Gln Phe Leu Glu His Ser Ser Gly Phe Asn Tyr Arg Arg Ser Phe Thr
195                 200                 205                 210 gac ctc cgt gac ctt cta ccg aat tcc acc gtt gtc gag gct gga tct    965
Asp Leu Arg Asp Leu Leu Pro Asn Ser Thr Val Val Glu Ala Gly Ser
            215                 220                 225 tcc gat agt tgc gat tca agc gcc gtt ctt aac gac gaa aca agt tct   1013
Ser Asp Ser Cys Asp Ser Ser Ala Val Leu Asn Asp Glu Thr Ser Ser
        230                 235                 240 gat aac gga aga ttg acg ccg cct gtg acg gtt act ggc ggg agt ttc   1061
Asp Asn Gly Arg Leu Thr Pro Pro Val Thr Val Thr Gly Gly Ser Phe
            245                 250                 255 tta cag ttt gtg aaa aca gag caa aca gag gat cac gag gat ttt cta   1109
Leu Gln Phe Val Lys Thr Glu Gln Thr Glu Asp His Glu Asp Phe Leu
260                 265                 270 agc ggt gaa gaa gct tgt ggt ttc ttc tcc gat gaa cag ccg ccg tca   1157
Ser Gly Glu Glu Ala Cys Gly Phe Phe Ser Asp Glu Gln Pro Pro Ser
275                 280                 285                 290 ctt cat tgg tac tct gct tca gat cat tgg act tga gaattgttta        1203
Leu His Trp Tyr Ser Ala Ser Asp His Trp Thr *
            295                 300 tcaaattggt gctctgttta gtctcaatgg gaaaacagag aagagggcaa aggtgga    1260

<210> SEQ ID NO 74
<211> LENGTH: 301
<212> TYPE: PRT
<213> ORGANISM: Arabidopsis thaliana

<400> SEQUENCE: 74

Met Lys Arg Leu Ser Ser Ser Asp Ser Met Cys Gly Leu Ile Ser Thr
```

```
  1               5                  10                 15
Ser Thr Asp Ser Phe Gly Tyr Thr Thr Asp Glu Gln Ser Pro Arg Gly
                20                 25                 30

Tyr Gly Ser Asn Tyr Gln Ser Met Leu Glu Gly Tyr Asp Glu Asp Ala
                35                 40                 45

Thr Leu Ile Glu Glu Tyr Ser Gly Asn His His Met Gly Leu Ser
 50                 55                 60

Glu Lys Lys Arg Arg Leu Lys Val Asp Gln Val Lys Ala Leu Glu Lys
 65                 70                 75                 80

Asn Phe Glu Leu Glu Asn Lys Leu Glu Pro Glu Arg Lys Thr Lys Leu
                85                 90                 95

Ala Gln Glu Leu Gly Leu Gln Pro Arg Gln Val Ala Val Trp Phe Gln
                100                105                110

Asn Arg Arg Ala Arg Trp Lys Thr Lys Gln Leu Glu Lys Asp Tyr Gly
                115                120                125

Val Leu Lys Gly Gln Tyr Asp Ser Leu Arg His Asn Phe Asp Ser Leu
                130                135                140

Arg Arg Asp Asn Asp Ser Leu Leu Gln Glu Ile Ser Lys Ile Lys Ala
145                150                155                160

Lys Val Asn Gly Glu Glu Asp Asn Asn Asn Lys Ala Ile Thr Glu
                165                170                175

Gly Val Lys Glu Glu Val His Lys Thr Asp Ser Ile Pro Ser Ser
                180                185                190

Pro Leu Gln Phe Leu Glu His Ser Ser Gly Phe Asn Tyr Arg Arg Ser
                195                200                205

Phe Thr Asp Leu Arg Asp Leu Leu Pro Asn Ser Thr Val Val Glu Ala
                210                215                220

Gly Ser Ser Asp Ser Cys Asp Ser Ser Ala Val Leu Asn Asp Glu Thr
225                230                235                240

Ser Ser Asp Asn Gly Arg Leu Thr Pro Pro Val Thr Val Thr Gly Gly
                245                250                255

Ser Phe Leu Gln Phe Val Lys Thr Glu Gln Thr Glu Asp His Glu Asp
                260                265                270

Phe Leu Ser Gly Glu Glu Ala Cys Gly Phe Phe Ser Asp Glu Gln Pro
                275                280                285

Pro Ser Leu His Trp Tyr Ser Ala Ser Asp His Trp Thr
                290                295                300

<210> SEQ ID NO 75
<211> LENGTH: 1122
<212> TYPE: DNA
<213> ORGANISM: Arabidopsis thaliana
<220> FEATURE:
<221> NAME/KEY: CDS
<222> LOCATION: (22)...(1122)

<400> SEQUENCE: 75
acgtagctaa agtccgtttg a atg aac caa cgt gct gac cgt gac cgt gct      51
                       Met Asn Gln Arg Ala Asp Arg Asp Arg Ala
                        1               5                  10 agc tcg atc cgt tgg ttt gcc aac cga tta gtg agt ggt agc ctg tta      99
Ser Ser Ile Arg Trp Phe Ala Asn Arg Leu Val Ser Gly Ser Leu Leu
               15                  20                  25 ttg tgt gct aac gcc tac agt cgt cgt act ccc gcg tcc ggg gcc gca     147
Leu Cys Ala Asn Ala Tyr Ser Arg Arg Thr Pro Ala Ser Gly Ala Ala
           30                  35                  40
```

-continued

| | | |
|---|---|---|
| tta cag cag atg aac cgt gcc agt cag tca gtg aat tac cga cga cgt<br>Leu Gln Gln Met Asn Arg Ala Ser Gln Ser Val Asn Tyr Arg Arg Arg<br>                45                            50                          55 | | 195 |
| gag ctg tca tta atc agc ggc cgg aaa cag ggt gtc cag tct ctg ggt<br>Glu Leu Ser Leu Ile Ser Gly Arg Lys Gln Gly Val Gln Ser Leu Gly<br>        60                          65                                  70 | | 243 |
| tat aga ctt gca cgc ctc gat aac cgc gct ctt gca caa ttg ttg cac<br>Tyr Arg Leu Ala Arg Leu Asp Asn Arg Ala Leu Ala Gln Leu Leu His<br>75                       80                         85                            90 | | 291 |
| agg gat ggc cag ccc gag gaa gtg gta cag cgc ggc aat gaa atc agc<br>Arg Asp Gly Gln Pro Glu Glu Val Val Gln Arg Gly Asn Glu Ile Ser<br>                95                            100                         105 | | 339 |
| tat ttc gaa acg gga ctt gaa ccg acc acg ctt aga cgt gtg cgc gat<br>Tyr Phe Glu Thr Gly Leu Glu Pro Thr Thr Leu Arg Arg Val Arg Asp<br>                     110                           115                         120 | | 387 |
| tgt gtt gtt gcc gct ctg cca acc gtt atc tat acc gga ttc aaa cgt<br>Cys Val Val Ala Ala Leu Pro Thr Val Ile Tyr Thr Gly Phe Lys Arg<br>                  125                            130                        135 | | 435 |
| gtt tct cct tac tac gaa ttt atc tcc gtc ggg cgc acg agg gtt gct<br>Val Ser Pro Tyr Tyr Glu Phe Ile Ser Val Gly Arg Thr Arg Val Ala<br>      140                         145                             150 | | 483 |
| gat cgt ctt agc gaa gtc acg caa gtg gtt ccc cga gat gat aca cgc<br>Asp Arg Leu Ser Glu Val Thr Gln Val Val Pro Arg Asp Asp Thr Arg<br>155                     160                       165                         170 | | 531 |
| tac gtc tac atc gtg tgg cgg gaa tcc gaa cga tcg aaa tta gag gcg<br>Tyr Val Tyr Ile Val Trp Arg Glu Ser Glu Arg Ser Lys Leu Glu Ala<br>                  175                            180                        185 | | 579 |
| cgg ggg gat ctc cgt gat cgc gat ggt gaa acg ctg gaa aag ttt cgc<br>Arg Gly Asp Leu Arg Asp Arg Asp Gly Glu Thr Leu Glu Lys Phe Arg<br>                    190                           195                        200 | | 627 |
| gtg att gct ttt aac gtc acg ctg gat atc agc agc agt atg gag ccg<br>Val Ile Ala Phe Asn Val Thr Leu Asp Ile Ser Ser Ser Met Glu Pro<br>                205                            210                        215 | | 675 |
| ctg gcg aag gga gat ttg ccg ccg ttg ctt gct gtt cct gta ggt gaa<br>Leu Ala Lys Gly Asp Leu Pro Pro Leu Leu Ala Val Pro Val Gly Glu<br>     220                        225                          230 | | 723 |
| caa gct aga ttc agc ttg acg cca acc tgg ttg cca cag ggt cgt agc<br>Gln Ala Arg Phe Ser Leu Thr Pro Thr Trp Leu Pro Gln Gly Arg Ser<br>235                     240                       245                         250 | | 771 |
| gat gtt tcc agt agt cga cgt ggg cta ccg cgg atg gac aaa gtg cct<br>Asp Val Ser Ser Ser Arg Arg Gly Leu Pro Arg Met Asp Lys Val Pro<br>                255                            260                        265 | | 819 |
| atc gaa tcc cgt ctc tcg acc gac gga gta ttc agc ttc tcg gta aac<br>Ile Glu Ser Arg Leu Ser Thr Asp Gly Val Phe Ser Phe Ser Val Asn<br>                    270                          275                        280 | | 867 |
| gtt aac ggc gct acg cca tcg agg tgg gat cag atg ttg cgc acc gga<br>Val Asn Gly Ala Thr Pro Ser Arg Trp Asp Gln Met Leu Arg Thr Gly<br>              285                            290                        295 | | 915 |
| cgc agg ccc gtc agt aga agc gta cgt gat gtc gcc gaa aac acc att<br>Arg Arg Pro Val Ser Arg Ser Val Arg Asp Val Ala Glu Asn Thr Ile<br>     300                        305                          310 | | 963 |
| ggc ggt gaa ctg ccg ccg cgt agc tgc tcg cga ccc gat ccg ttg acc<br>Gly Gly Glu Leu Pro Pro Arg Ser Cys Ser Arg Pro Asp Pro Leu Thr<br>315                     320                       325                         330 | | 1011 |
| gct gac cgc cga cgc tgc gct agc ctg agc ctg ccc agc ctg cca gct<br>Ala Asp Arg Arg Arg Cys Ala Ser Leu Ser Leu Pro Ser Leu Pro Ala<br>                    335                            340                        345 | | 1059 |
| cga cag ccc tcc caa acg gag aaa cgc att gtc gag aat att aag tac<br>Arg Gln Pro Ser Gln Thr Glu Lys Arg Ile Val Glu Asn Ile Lys Tyr<br>                350                            355                        360 | | 1107 |

```
ggg gca gcg cca tga                                              1122
Gly Ala Ala Pro *
        365
```

<210> SEQ ID NO 76
<211> LENGTH: 366
<212> TYPE: PRT
<213> ORGANISM: Arabidopsis thaliana

<400> SEQUENCE: 76

| | | | | | | | | | | | | | | |
|---|---|---|---|---|---|---|---|---|---|---|---|---|---|---|
| Met | Asn | Gln | Arg | Ala | Asp | Arg | Asp | Arg | Ala | Ser | Ser | Ile | Arg | Trp | Phe |
| 1 | | | | 5 | | | | | 10 | | | | | 15 | |
| Ala | Asn | Arg | Leu | Val | Ser | Gly | Ser | Leu | Leu | Cys | Ala | Asn | Ala | Tyr |
| | | | 20 | | | | 25 | | | | | 30 | | |
| Ser | Arg | Arg | Thr | Pro | Ala | Ser | Gly | Ala | Ala | Leu | Gln | Gln | Met | Asn | Arg |
| | | 35 | | | | | 40 | | | | | 45 | | | |
| Ala | Ser | Gln | Ser | Val | Asn | Tyr | Arg | Arg | Arg | Glu | Leu | Ser | Leu | Ile | Ser |
| | 50 | | | | | 55 | | | | | 60 | | | | |
| Gly | Arg | Lys | Gln | Gly | Val | Gln | Ser | Leu | Gly | Tyr | Arg | Leu | Ala | Arg | Leu |
| 65 | | | | | 70 | | | | | 75 | | | | | 80 |
| Asp | Asn | Arg | Ala | Leu | Ala | Gln | Leu | Leu | His | Arg | Asp | Gly | Gln | Pro | Glu |
| | | | | 85 | | | | | 90 | | | | | 95 | |
| Glu | Val | Val | Gln | Arg | Gly | Asn | Glu | Ile | Ser | Tyr | Phe | Glu | Thr | Gly | Leu |
| | | | | 100 | | | | | 105 | | | | | 110 | |
| Glu | Pro | Thr | Thr | Leu | Arg | Arg | Val | Arg | Asp | Cys | Val | Val | Ala | Ala | Leu |
| | | | 115 | | | | | 120 | | | | | 125 | | |
| Pro | Thr | Val | Ile | Tyr | Thr | Gly | Phe | Lys | Arg | Val | Ser | Pro | Tyr | Tyr | Glu |
| | 130 | | | | | 135 | | | | | 140 | | | | |
| Phe | Ile | Ser | Val | Gly | Arg | Thr | Arg | Val | Ala | Asp | Arg | Leu | Ser | Glu | Val |
| 145 | | | | | 150 | | | | | 155 | | | | | 160 |
| Thr | Gln | Val | Val | Pro | Arg | Asp | Asp | Thr | Arg | Tyr | Val | Tyr | Ile | Val | Trp |
| | | | | 165 | | | | | 170 | | | | | 175 | |
| Arg | Glu | Ser | Glu | Arg | Ser | Lys | Leu | Glu | Ala | Arg | Gly | Asp | Leu | Arg | Asp |
| | | | | 180 | | | | | 185 | | | | | 190 | |
| Arg | Asp | Gly | Glu | Thr | Leu | Glu | Lys | Phe | Arg | Val | Ile | Ala | Phe | Asn | Val |
| | | | 195 | | | | | 200 | | | | | 205 | | |
| Thr | Leu | Asp | Ile | Ser | Ser | Ser | Met | Glu | Pro | Leu | Ala | Lys | Gly | Asp | Leu |
| | 210 | | | | | 215 | | | | | 220 | | | | |
| Pro | Pro | Leu | Leu | Ala | Val | Pro | Val | Gly | Glu | Gln | Ala | Arg | Phe | Ser | Leu |
| 225 | | | | | 230 | | | | | 235 | | | | | 240 |
| Thr | Pro | Thr | Trp | Leu | Pro | Gln | Gly | Arg | Ser | Asp | Val | Ser | Ser | Arg |
| | | | | 245 | | | | | 250 | | | | | 255 | |
| Arg | Gly | Leu | Pro | Arg | Met | Asp | Lys | Val | Pro | Ile | Glu | Ser | Arg | Leu | Ser |
| | | | | 260 | | | | | 265 | | | | | 270 | |
| Thr | Asp | Gly | Val | Phe | Ser | Phe | Ser | Val | Asn | Val | Asn | Gly | Ala | Thr | Pro |
| | | | 275 | | | | | 280 | | | | | 285 | | |
| Ser | Arg | Trp | Asp | Gln | Met | Leu | Arg | Thr | Gly | Arg | Arg | Pro | Val | Ser | Arg |
| | 290 | | | | | 295 | | | | | 300 | | | | |
| Ser | Val | Arg | Asp | Val | Ala | Glu | Asn | Thr | Ile | Gly | Gly | Glu | Leu | Pro | Pro |
| 305 | | | | | 310 | | | | | 315 | | | | | 320 |
| Arg | Ser | Cys | Ser | Arg | Pro | Asp | Pro | Leu | Thr | Ala | Asp | Arg | Arg | Cys |
| | | | | 325 | | | | | 330 | | | | | 335 | |
| Ala | Ser | Leu | Ser | Leu | Pro | Ser | Leu | Pro | Ala | Arg | Gln | Pro | Ser | Gln | Thr |
| | | | | 340 | | | | | 345 | | | | | 350 | |

-continued

```
Glu Lys Arg Ile Val Glu Asn Ile Lys Tyr Gly Ala Ala Pro
        355                 360                 365

<210> SEQ ID NO 77
<211> LENGTH: 1650
<212> TYPE: DNA
<213> ORGANISM: Arabidopsis thaliana
<220> FEATURE:
<221> NAME/KEY: CDS
<222> LOCATION: (21)...(203)
<220> FEATURE:
<221> NAME/KEY: CDS
<222> LOCATION: (291)...(482)
<220> FEATURE:
<221> NAME/KEY: CDS
<222> LOCATION: (633)...(838)
<220> FEATURE:
<221> NAME/KEY: CDS
<222> LOCATION: (1044)...(1605)

<400> SEQUENCE: 77
attcagagaa gaactcaccg atg agt atg gat ttt tca cct ttg tta acg gtt       53
                     Met Ser Met Asp Phe Ser Pro Leu Leu Thr Val
                      1               5                      10 ctt gag gga gat ttc aac aag gat aat act tct tct gca aca gaa att       101
Leu Glu Gly Asp Phe Asn Lys Asp Asn Thr Ser Ser Ala Thr Glu Ile
            15                  20                  25 gat act tta gag aac tta gat gac act agg cag ata agt aaa gga aaa       149
Asp Thr Leu Glu Asn Leu Asp Asp Thr Arg Gln Ile Ser Lys Gly Lys
        30                  35                  40 cct ccg agg cac ctc aca agc agt gct act agg ctg cag ctt gca gcc       197
Pro Pro Arg His Leu Thr Ser Ser Ala Thr Arg Leu Gln Leu Ala Ala
    45                  50                  55 aat gcg gtaatatact tgaccctgct ttttcttttt cctttctttt gttacaatgg       253
Asn Ala
 60 gattcgaatg atgtaactgg tttctgtttg tgcgcag gat gtg gat gtt tgt aac    308
                                        Asp Val Asp Val Cys Asn
                                                             65 ttg gtt atg aag tca ctt gat gac aaa tca gag ttt cta cct gta tac       356
Leu Val Met Lys Ser Leu Asp Asp Lys Ser Glu Phe Leu Pro Val Tyr
        70                  75                  80 cga tca gga agt tgt gct gag caa ggg gca aaa cag ttc atg gaa gat       404
Arg Ser Gly Ser Cys Ala Glu Gln Gly Ala Lys Gln Phe Met Glu Asp
    85                  90                  95 gaa cac att tgc atc gat gat ctt gtt aat cat ctt ggt gca gct att       452
Glu His Ile Cys Ile Asp Asp Leu Val Asn His Leu Gly Ala Ala Ile
100                 105                 110                 115 caa tgc tct tct ctt gga gcc ttc tat ggg gtgagtttat cttccaatct        502
Gln Cys Ser Ser Leu Gly Ala Phe Tyr Gly
                120                 125 tacccaaaga agcataaaag caattcacta gcctgattct tctttcttct cctcttttgt    562
actagtacga tataagaggt attacttcaa aaactcttct aacatttgtt gattgtgtgt    622
cctttggcag gta ttt gat ggc cac ggt ggc aca gat gca gca cac ttt       671
             Val Phe Asp Gly His Gly Gly Thr Asp Ala Ala His Phe
                 130                 135 gtt aga aag aac att ctg aga ttc att gta gag gac tcc tcc ttc cca       719
Val Arg Lys Asn Ile Leu Arg Phe Ile Val Glu Asp Ser Ser Phe Pro
140                 145                 150 cta tgc gta aag aaa gca att aag agt gct ttc tta aaa gct gat tat       767
Leu Cys Val Lys Lys Ala Ile Lys Ser Ala Phe Leu Lys Ala Asp Tyr
155                 160                 165                 170
```

-continued

```
gaa ttt gca gat gat tct tct ctt gac atc tct tct ggg acc act gcg         815
Glu Phe Ala Asp Asp Ser Ser Leu Asp Ile Ser Ser Gly Thr Thr Ala
            175                 180                 185 ctt aca gct ttt att ttt gga cg gtaagagcat ttaaattcgt atttatgaac          868
Leu Thr Ala Phe Ile Phe Gly Arg
            190 ttgggaagct atatatgtta tcacctgtat aatcatcaat acttatcagg ttgcctgtgt        928 gtataagata gagaataagg cttagtgtaa agacttatgt aacgggctgt tttaccatgt        988 ttctttgtag ttttgatgtg attttgaata gaattgctac tttctttctt tacag g agg      1047
                                                                Arg
                                                                195 ttg ata att gca aat gct ggt gat tgc cga gca gta ctg ggg aga aga        1095
Leu Ile Ile Ala Asn Ala Gly Asp Cys Arg Ala Val Leu Gly Arg Arg
                200                 205                 210 ggt agg gca att gag ttg tcc aaa gat cac aaa cca aac tgc aca gcc        1143
Gly Arg Ala Ile Glu Leu Ser Lys Asp His Lys Pro Asn Cys Thr Ala
            215                 220                 225 gag aaa gta aga ata gaa aag tta ggt gga gtt gtg tat gac ggt tac        1191
Glu Lys Val Arg Ile Glu Lys Leu Gly Gly Val Val Tyr Asp Gly Tyr
        230                 235                 240 ctc aac ggg caa cta tca gtt gca cgt gcc att gga gac tgg cac atg        1239
Leu Asn Gly Gln Leu Ser Val Ala Arg Ala Ile Gly Asp Trp His Met
    245                 250                 255 aaa ggt ccc aaa ggc tct gct tgt ccg cta agc cca gag cca gag ttg        1287
Lys Gly Pro Lys Gly Ser Ala Cys Pro Leu Ser Pro Glu Pro Glu Leu
260                 265                 270                 275 caa gag aca gac ctg agt gaa gac gac gag ttc ttg ata atg gga tgt        1335
Gln Glu Thr Asp Leu Ser Glu Asp Asp Glu Phe Leu Ile Met Gly Cys
                280                 285                 290 gat ggt ctg tgg gat gtg atg agc agc cag tgc gct gtg aca ata gct        1383
Asp Gly Leu Trp Asp Val Met Ser Ser Gln Cys Ala Val Thr Ile Ala
            295                 300                 305 agg aag gaa ctg atg att cat aat gat cca gag aga tgc tct aga gag        1431
Arg Lys Glu Leu Met Ile His Asn Asp Pro Glu Arg Cys Ser Arg Glu
        310                 315                 320 ctt gtg agg gag gcc ctt aaa cgg aat aca tgt gac aat ttg aca gtg        1479
Leu Val Arg Glu Ala Leu Lys Arg Asn Thr Cys Asp Asn Leu Thr Val
    325                 330                 335 att gtt gtg tgc ttc tct ccg gat cct cca cag agg ata gag atc cga        1527
Ile Val Val Cys Phe Ser Pro Asp Pro Pro Gln Arg Ile Glu Ile Arg
340                 345                 350                 355 atg cag tca cgg gtg agg cgg agc ata tct gcg gaa ggg tta aac cta        1575
Met Gln Ser Arg Val Arg Arg Ser Ile Ser Ala Glu Gly Leu Asn Leu
                360                 365                 370 ctc aaa ggc gtg ctc gat ggc tat ccg tga gcatgttatg ttgtacgtta         1625
Leu Lys Gly Val Leu Asp Gly Tyr Pro *
            375                 380 ctttgtgaga ctattgccaa gttag                                            1650
```

<210> SEQ ID NO 78
<211> LENGTH: 380
<212> TYPE: PRT
<213> ORGANISM: Arabidopsis thaliana

<400> SEQUENCE: 78

```
Met Ser Met Asp Phe Ser Pro Leu Leu Thr Val Leu Glu Gly Asp Phe
1               5                   10                  15

Asn Lys Asp Asn Thr Ser Ser Ala Thr Glu Ile Asp Thr Leu Glu Asn
            20                  25                  30
```

| Leu | Asp | Asp | Thr | Arg | Gln | Ile | Ser | Lys | Gly | Lys | Pro | Pro | Arg | His | Leu |
|-----|-----|-----|-----|-----|-----|-----|-----|-----|-----|-----|-----|-----|-----|-----|-----|
|     |     |     | 35  |     |     |     |     | 40  |     |     |     | 45  |     |     |     |

Thr Ser Ser Ala Thr Arg Leu Gln Leu Ala Ala Asn Ala Asp Val Asp
        50                 55              60

Val Cys Asn Leu Val Met Lys Ser Leu Asp Asp Lys Ser Glu Phe Leu
65                 70                 75                      80

Pro Val Tyr Arg Ser Gly Ser Cys Ala Glu Gln Gly Ala Lys Gln Phe
                 85                 90                 95

Met Glu Asp Glu His Ile Cys Ile Asp Asp Leu Val Asn His Leu Gly
            100             105              110

Ala Ala Ile Gln Cys Ser Ser Leu Gly Ala Phe Tyr Gly Val Phe Asp
        115             120             125

Gly His Gly Gly Thr Asp Ala Ala His Phe Val Arg Lys Asn Ile Leu
    130                135                140

Arg Phe Ile Val Glu Asp Ser Ser Phe Pro Leu Cys Val Lys Lys Ala
145                 150                155                160

Ile Lys Ser Ala Phe Leu Lys Ala Asp Tyr Glu Phe Ala Asp Asp Ser
               165               170              175

Ser Leu Asp Ile Ser Ser Gly Thr Thr Ala Leu Thr Ala Phe Ile Phe
          180                185              190

Gly Arg Arg Leu Ile Ile Ala Asn Ala Gly Asp Cys Arg Ala Val Leu
            195             200              205

Gly Arg Arg Gly Arg Ala Ile Glu Leu Ser Lys Asp His Lys Pro Asn
    210                215                220

Cys Thr Ala Glu Lys Val Arg Ile Glu Lys Leu Gly Gly Val Val Tyr
225                 230                235                240

Asp Gly Tyr Leu Asn Gly Gln Leu Ser Val Ala Arg Ala Ile Gly Asp
               245               250              255

Trp His Met Lys Gly Pro Lys Gly Ser Ala Cys Pro Leu Ser Pro Glu
          260                265              270

Pro Glu Leu Gln Glu Thr Asp Leu Ser Glu Asp Glu Phe Leu Ile
        275             280              285

Met Gly Cys Asp Gly Leu Trp Asp Val Met Ser Ser Gln Cys Ala Val
    290                295              300

Thr Ile Ala Arg Lys Glu Leu Met Ile His Asn Asp Pro Glu Arg Cys
305                 310                315                320

Ser Arg Glu Leu Val Arg Glu Ala Leu Lys Arg Asn Thr Cys Asp Asn
               325               330              335

Leu Thr Val Ile Val Val Cys Phe Ser Pro Asp Pro Gln Arg Ile
          340                345              350

Glu Ile Arg Met Gln Ser Arg Val Arg Arg Ser Ile Ser Ala Glu Gly
        355             360              365

Leu Asn Leu Leu Lys Gly Val Leu Asp Gly Tyr Pro
    370                375                380

<210> SEQ ID NO 79
<211> LENGTH: 590
<212> TYPE: DNA
<213> ORGANISM: Arabidopsis thaliana
<220> FEATURE:
<221> NAME/KEY: CDS
<222> LOCATION: (18)...(575)

<400> SEQUENCE: 79 atcttttttcc gataact atg gct gag gaa atc aag aat gtt cct gaa cag     50

```
                Met Ala Glu Glu Ile Lys Asn Val Pro Glu Gln
                  1               5                  10 gag gtg cca aag gta gca aca gag gaa tca tcg gca gag gtt aca gat        98
Glu Val Pro Lys Val Ala Thr Glu Glu Ser Ser Ala Glu Val Thr Asp
             15                  20                  25 cgt gga ttg ttc gat ttc ttg gga aag aag aaa gac gaa aca aaa cca       146
Arg Gly Leu Phe Asp Phe Leu Gly Lys Lys Lys Asp Glu Thr Lys Pro
         30                  35                  40 gag gag act ccg atc gct tca gag ttt gag cag aag gtt cat att tca       194
Glu Glu Thr Pro Ile Ala Ser Glu Phe Glu Gln Lys Val His Ile Ser
     45                  50                  55 gag ccg gag cca gag gtt aaa cac gaa agt ctt ctt gaa aag ctt cac       242
Glu Pro Glu Pro Glu Val Lys His Glu Ser Leu Leu Glu Lys Leu His
 60                  65                  70                  75 cga agc gac agt tct tct agc tcc tca agt gag gaa gaa ggt tca gat       290
Arg Ser Asp Ser Ser Ser Ser Ser Ser Ser Glu Glu Glu Gly Ser Asp
                 80                  85                  90 ggt gag aag agg aag aag aag aag gag aag aag aag cca act act gaa       338
Gly Glu Lys Arg Lys Lys Lys Lys Glu Lys Lys Lys Pro Thr Thr Glu
             95                 100                 105 gtt gag gta aag gag gaa gag aag aaa ggg ttt atg gag aag ttg aaa       386
Val Glu Val Lys Glu Glu Glu Lys Lys Gly Phe Met Glu Lys Leu Lys
         110                 115                 120 gag aag ctt cct gga cac aag aaa cct gaa gac ggt tca gcc gtc gct       434
Glu Lys Leu Pro Gly His Lys Lys Pro Glu Asp Gly Ser Ala Val Ala
     125                 130                 135 gcg gca ccg gtg gtt gtt cct cct cct gtg gaa gaa gcg cat cca gtg       482
Ala Ala Pro Val Val Val Pro Pro Pro Val Glu Glu Ala His Pro Val
140                 145                 150                 155 gag aag aaa ggg att ctt gag aag att aag gag aag ctt cca gga tac       530
Glu Lys Lys Gly Ile Leu Glu Lys Ile Lys Glu Lys Leu Pro Gly Tyr
                 160                 165                 170 cac cct aag acc acc gta gag gag gag aag aaa gat aaa gaa taa            575
His Pro Lys Thr Thr Val Glu Glu Glu Lys Lys Asp Lys Glu  *
             175                 180                 185 gaagattatc attaa                                                       590
```

<210> SEQ ID NO 80
<211> LENGTH: 185
<212> TYPE: PRT
<213> ORGANISM: Arabidopsis thaliana

<400> SEQUENCE: 80

```
Met Ala Glu Glu Ile Lys Asn Val Pro Glu Gln Glu Val Pro Lys Val
  1               5                  10                  15

Ala Thr Glu Glu Ser Ser Ala Glu Val Thr Asp Arg Gly Leu Phe Asp
             20                  25                  30

Phe Leu Gly Lys Lys Lys Asp Glu Thr Lys Pro Glu Glu Thr Pro Ile
         35                  40                  45

Ala Ser Glu Phe Glu Gln Lys Val His Ile Ser Glu Pro Glu Pro Glu
     50                  55                  60

Val Lys His Glu Ser Leu Leu Glu Lys Leu His Arg Ser Asp Ser Ser
 65                  70                  75                  80

Ser Ser Ser Ser Glu Glu Glu Gly Ser Asp Gly Glu Lys Arg Lys Lys
                 85                  90                  95

Lys Lys Glu Lys Lys Lys Pro Thr Thr Glu Val Glu Val Lys Glu Glu
            100                 105                 110

Glu Lys Lys Gly Phe Met Glu Lys Leu Lys Glu Lys Leu Pro Gly
```

```
                115                  120                 125
His Lys Lys Pro Glu Asp Gly Ser Ala Val Ala Ala Pro Val Val
        130                 135                 140

Val Pro Pro Val Glu Glu Ala His Pro Val Glu Lys Lys Gly Ile
145                 150                 155                 160

Leu Glu Lys Ile Lys Glu Lys Leu Pro Gly Tyr His Pro Lys Thr Thr
                165                 170                 175

Val Glu Glu Glu Lys Lys Asp Lys Glu
            180                 185

<210> SEQ ID NO 81
<211> LENGTH: 1376
<212> TYPE: DNA
<213> ORGANISM: Arabidopsis thaliana
<220> FEATURE:
<221> NAME/KEY: CDS
<222> LOCATION: (20)...(1366)

<400> SEQUENCE: 81
agcaatcgag aaaaaagca atg gcg tca gac aaa caa aag gcg gag aga gcc        52
                    Met Ala Ser Asp Lys Gln Lys Ala Glu Arg Ala
                     1               5                  10 gag gtt gcg gcg agg cta gcg gct gag gac ttg cat gac att aac aaa       100
Glu Val Ala Ala Arg Leu Ala Ala Glu Asp Leu His Asp Ile Asn Lys
             15                  20                  25 tcc ggt ggt gct gat gtc aca atg tat aag gtg acg gag aga aca act       148
Ser Gly Gly Ala Asp Val Thr Met Tyr Lys Val Thr Glu Arg Thr Thr
         30                  35                  40 gaa cat cca ccg gag caa gat agg ccc ggt gtg ata ggt tca gtg ttc       196
Glu His Pro Pro Glu Gln Asp Arg Pro Gly Val Ile Gly Ser Val Phe
     45                  50                  55 agg gct gtc caa gga acg tat gag cat gcg aga gac gct gta gtt gga       244
Arg Ala Val Gln Gly Thr Tyr Glu His Ala Arg Asp Ala Val Val Gly
 60                  65                  70                  75 aaa acc cac gaa gcg gct gag tct acc aaa gaa gga gct cag ata gct       292
Lys Thr His Glu Ala Ala Glu Ser Thr Lys Glu Gly Ala Gln Ile Ala
                 80                  85                  90 tca gag aaa gcg gtt gga gca aag gac gca acc gtc gag aaa gct aag       340
Ser Glu Lys Ala Val Gly Ala Lys Asp Ala Thr Val Glu Lys Ala Lys
             95                 100                 105 gaa acc gct gat tat act gcg gag aag gtg ggt gag tat aaa gac tat       388
Glu Thr Ala Asp Tyr Thr Ala Glu Lys Val Gly Glu Tyr Lys Asp Tyr
         110                 115                 120 acg gtt gat aaa gct aaa gag gct aag gac aca act gca gag aag gcg       436
Thr Val Asp Lys Ala Lys Glu Ala Lys Asp Thr Thr Ala Glu Lys Ala
     125                 130                 135 aag gag act gct aat tat act gcg gat aag gcg gtg gaa gca aag gat       484
Lys Glu Thr Ala Asn Tyr Thr Ala Asp Lys Ala Val Glu Ala Lys Asp
140                 145                 150                 155 aag acg gcg gag aag att ggt gag tac aaa gac tat gcg gtg gat aag       532
Lys Thr Ala Glu Lys Ile Gly Glu Tyr Lys Asp Tyr Ala Val Asp Lys
                160                 165                 170 gca gta gaa gct aaa gat aag aca gcg gag aag gcg aag gag act tcg       580
Ala Val Glu Ala Lys Asp Lys Thr Ala Glu Lys Ala Lys Glu Thr Ser
            175                 180                 185 aat tat acg gcg gat aag gct aaa gag gct aag gac aag acg gct gag       628
Asn Tyr Thr Ala Asp Lys Ala Lys Glu Ala Lys Asp Lys Thr Ala Glu
        190                 195                 200 aag gtt ggt gag tat aag gat tac acg gtg gac aag gcc gtg gaa gct       676
Lys Val Gly Glu Tyr Lys Asp Tyr Thr Val Asp Lys Ala Val Glu Ala
```

| | | |
|---|---|---|
| agg gat tac aca gcg gag aag gct att gaa gca aag gat aag aca gct<br>Arg Asp Tyr Thr Ala Glu Lys Ala Ile Glu Ala Lys Asp Lys Thr Ala<br>220                       225                     230                     235 | 724 | |
| gag aag act gga gag tat aag gac tat acg gtg gag aag gcg acg gag<br>Glu Lys Thr Gly Glu Tyr Lys Asp Tyr Thr Val Glu Lys Ala Thr Glu<br>                240                     245                     250 | 772 | |
| ggg aaa gat gtt acg gtg agt aag cta gga gag ctg aag gat agt gcc<br>Gly Lys Asp Val Thr Val Ser Lys Leu Gly Glu Leu Lys Asp Ser Ala<br>                     255                     260                     265 | 820 | |
| gtt gag aca gcg aag aga gct atg ggt ttc ttg tcg ggg aag aca gag<br>Val Glu Thr Ala Lys Arg Ala Met Gly Phe Leu Ser Gly Lys Thr Glu<br>           270                     275                     280 | 868 | |
| gag gcc aaa gga aaa gct gtg gag acc aaa gat act gcc aag gaa aac<br>Glu Ala Lys Gly Lys Ala Val Glu Thr Lys Asp Thr Ala Lys Glu Asn<br>285                       290                     295 | 916 | |
| atg gag aaa gct gga gaa gta aca aga caa aag atg gag gaa atg aga<br>Met Glu Lys Ala Gly Glu Val Thr Arg Gln Lys Met Glu Glu Met Arg<br>300                       305                     310                     315 | 964 | |
| ttg gaa ggt aaa gag ctc aaa gaa gaa gct gga gca aaa gcc caa gag<br>Leu Glu Gly Lys Glu Leu Lys Glu Glu Ala Gly Ala Lys Ala Gln Glu<br>           320                     325                     330 | 1012 | |
| gca tct caa aag act agg gag agt act gag tcg gga gct caa aaa gcc<br>Ala Ser Gln Lys Thr Arg Glu Ser Thr Glu Ser Gly Ala Gln Lys Ala<br>                335                     340                     345 | 1060 | |
| gaa gag acc aaa gat tct cct gcc gtg agg gga aat gaa gcg aaa ggg<br>Glu Glu Thr Lys Asp Ser Pro Ala Val Arg Gly Asn Glu Ala Lys Gly<br>350                       355                     360 | 1108 | |
| act att ttt ggt gca tta ggg aat gta acg gaa gca ata aag agc aaa<br>Thr Ile Phe Gly Ala Leu Gly Asn Val Thr Glu Ala Ile Lys Ser Lys<br>365                       370                     375 | 1156 | |
| ctg aca atg cca tca gac att gtg gag gaa aca cgc gcg gca cgt gag<br>Leu Thr Met Pro Ser Asp Ile Val Glu Glu Thr Arg Ala Ala Arg Glu<br>380                       385                     390                     395 | 1204 | |
| cat gga ggg acg ggt agg act gtg gtt gaa gtc aag gtc gag gat tca<br>His Gly Gly Thr Gly Arg Thr Val Val Glu Val Lys Val Glu Asp Ser<br>                400                     405                     410 | 1252 | |
| aag ccg ggt aag gtg gcg act tca ctg aag gcg tcg gat caa atg acc<br>Lys Pro Gly Lys Val Ala Thr Ser Leu Lys Ala Ser Asp Gln Met Thr<br>                     415                     420                     425 | 1300 | |
| ggt caa aca ttc aac gac gtt gga cgg atg gat gat gat gct cgg aaa<br>Gly Gln Thr Phe Asn Asp Val Gly Arg Met Asp Asp Asp Ala Arg Lys<br>           430                     435                     440 | 1348 | |
| gat aag gga aag ctg tga gaatactaga<br>Asp Lys Gly Lys Leu *<br>    445 | 1376 | |

<210> SEQ ID NO 82
<211> LENGTH: 448
<212> TYPE: PRT
<213> ORGANISM: Arabidopsis thaliana

<400> SEQUENCE: 82

Met Ala Ser Asp Lys Gln Lys Ala Glu Arg Ala Glu Val Ala Ala Arg
1               5                   10                   15

Leu Ala Ala Glu Asp Leu His Asp Ile Asn Lys Ser Gly Gly Ala Asp
                20                   25                   30

Val Thr Met Tyr Lys Val Thr Glu Arg Thr Thr Glu His Pro Pro Glu
           35                     40                   45

-continued

```
Gln Asp Arg Pro Gly Val Ile Gly Ser Val Phe Arg Ala Val Gln Gly
     50                  55                  60
Thr Tyr Glu His Ala Arg Asp Ala Val Val Gly Lys Thr His Glu Ala
65                  70                  75                  80
Ala Glu Ser Thr Lys Glu Gly Ala Gln Ile Ala Ser Glu Lys Ala Val
             85                  90                  95
Gly Ala Lys Asp Ala Thr Val Glu Lys Ala Lys Glu Thr Ala Asp Tyr
         100                 105                 110
Thr Ala Glu Lys Val Gly Glu Tyr Lys Asp Tyr Thr Val Asp Lys Ala
             115                 120                 125
Lys Glu Ala Lys Asp Thr Thr Ala Glu Lys Ala Lys Glu Thr Ala Asn
    130                 135                 140
Tyr Thr Ala Asp Lys Ala Val Glu Ala Lys Asp Lys Thr Ala Glu Lys
145                 150                 155                 160
Ile Gly Glu Tyr Lys Asp Tyr Ala Val Asp Lys Ala Val Glu Ala Lys
                165                 170                 175
Asp Lys Thr Ala Glu Lys Ala Lys Glu Thr Ser Asn Tyr Thr Ala Asp
            180                 185                 190
Lys Ala Lys Glu Ala Lys Asp Lys Thr Ala Glu Lys Val Gly Glu Tyr
        195                 200                 205
Lys Asp Tyr Thr Val Asp Lys Ala Val Glu Ala Arg Asp Tyr Thr Ala
    210                 215                 220
Glu Lys Ala Ile Glu Ala Lys Asp Lys Thr Ala Glu Lys Thr Gly Glu
225                 230                 235                 240
Tyr Lys Asp Tyr Thr Val Glu Lys Ala Thr Glu Gly Lys Asp Val Thr
                245                 250                 255
Val Ser Lys Leu Gly Glu Leu Lys Asp Ser Ala Val Glu Thr Ala Lys
            260                 265                 270
Arg Ala Met Gly Phe Leu Ser Gly Lys Thr Glu Glu Ala Lys Gly Lys
        275                 280                 285
Ala Val Glu Thr Lys Asp Thr Ala Lys Glu Asn Met Glu Lys Ala Gly
    290                 295                 300
Glu Val Thr Arg Gln Lys Met Glu Glu Met Arg Leu Glu Gly Lys Glu
305                 310                 315                 320
Leu Lys Glu Glu Ala Gly Ala Lys Ala Gln Glu Ala Ser Gln Lys Thr
                325                 330                 335
Arg Glu Ser Thr Glu Ser Gly Ala Gln Lys Ala Glu Glu Thr Lys Asp
            340                 345                 350
Ser Pro Ala Val Arg Gly Asn Glu Ala Lys Gly Thr Ile Phe Gly Ala
        355                 360                 365
Leu Gly Asn Val Thr Glu Ala Ile Lys Ser Lys Leu Thr Met Pro Ser
    370                 375                 380
Asp Ile Val Glu Glu Thr Arg Ala Ala Arg Glu His Gly Gly Thr Gly
385                 390                 395                 400
Arg Thr Val Val Glu Val Lys Val Glu Asp Ser Lys Pro Gly Lys Val
                405                 410                 415
Ala Thr Ser Leu Lys Ala Ser Asp Gln Met Thr Gly Gln Thr Phe Asn
            420                 425                 430
Asp Val Gly Arg Met Asp Asp Ala Arg Lys Asp Lys Gly Lys Leu
        435                 440                 445

<210> SEQ ID NO 83
<211> LENGTH: 561
<212> TYPE: DNA
```

<213> ORGANISM: Arabidopsis thaliana
<220> FEATURE:
<221> NAME/KEY: CDS
<222> LOCATION: (18)...(548)

<400> SEQUENCE: 83

```
aaccacacaa atacaaa atg aat gaa atg tcg ttc ttt ggt tat agt ttc          50
                   Met Asn Glu Met Ser Phe Phe Gly Tyr Ser Phe
                    1               5                  10 atc gta gta gca tta ttc ttc gat tta act caa gcc tat cgt cac act         98
Ile Val Val Ala Leu Phe Phe Asp Leu Thr Gln Ala Tyr Arg His Thr
             15                  20                  25 ccc gct caa ccg cca aaa gca aac gca aac ggt gat gtc aaa ccg caa        146
Pro Ala Gln Pro Pro Lys Ala Asn Ala Asn Gly Asp Val Lys Pro Gln
         30                  35                  40 gaa acg ctc gtg gtt cac aac aag gcc cga gcc atg gtc gga gtc gga        194
Glu Thr Leu Val Val His Asn Lys Ala Arg Ala Met Val Gly Val Gly
     45                  50                  55 cca atg gtg tgg aac gaa act ctt gcg acc tat gca cag agc tac gca        242
Pro Met Val Trp Asn Glu Thr Leu Ala Thr Tyr Ala Gln Ser Tyr Ala
 60                  65                  70                  75 cat gaa cga gcc aga gac tgt gcc atg aag cat tcc ttg gga cca ttc        290
His Glu Arg Ala Arg Asp Cys Ala Met Lys His Ser Leu Gly Pro Phe
                 80                  85                  90 ggc gag aat cta gcc gcg ggt tgg gga acg atg agc ggt ccg gta gca        338
Gly Glu Asn Leu Ala Ala Gly Trp Gly Thr Met Ser Gly Pro Val Ala
             95                 100                 105 act gag tat tgg atg acg gag aag gaa aat tac gat tat gat agt aac        386
Thr Glu Tyr Trp Met Thr Glu Lys Glu Asn Tyr Asp Tyr Asp Ser Asn
        110                 115                 120 acg tgt ggt ggt gat ggt gtg tgt gga cac tac act cag atc gtg tgg        434
Thr Cys Gly Gly Asp Gly Val Cys Gly His Tyr Thr Gln Ile Val Trp
    125                 130                 135 cgt gac tcg gtt cga ctt ggt tgt gcc tcc gtg aga tgt aag aat gat        482
Arg Asp Ser Val Arg Leu Gly Cys Ala Ser Val Arg Cys Lys Asn Asp
140                 145                 150                 155 gag tat att tgg gtg att tgt agc tat gat cct ccg ggg aat tac atc        530
Glu Tyr Ile Trp Val Ile Cys Ser Tyr Asp Pro Pro Gly Asn Tyr Ile
                160                 165                 170 ggt caa cgt cca tat tag tgattggatt tta                                 561
Gly Gln Arg Pro Tyr *
            175
```

<210> SEQ ID NO 84
<211> LENGTH: 176
<212> TYPE: PRT
<213> ORGANISM: Arabidopsis thaliana

<400> SEQUENCE: 84

```
Met Asn Glu Met Ser Phe Phe Gly Tyr Ser Phe Ile Val Val Ala Leu
 1               5                  10                  15

Phe Phe Asp Leu Thr Gln Ala Tyr Arg His Thr Pro Ala Gln Pro Pro
             20                  25                  30

Lys Ala Asn Ala Asn Gly Asp Val Lys Pro Gln Glu Thr Leu Val Val
         35                  40                  45

His Asn Lys Ala Arg Ala Met Val Gly Val Gly Pro Met Val Trp Asn
     50                  55                  60

Glu Thr Leu Ala Thr Tyr Ala Gln Ser Tyr Ala His Glu Arg Ala Arg
 65                  70                  75                  80

Asp Cys Ala Met Lys His Ser Leu Gly Pro Phe Gly Glu Asn Leu Ala
```

-continued

```
                    85                  90                  95
Ala Gly Trp Gly Thr Met Ser Gly Pro Val Ala Thr Glu Tyr Trp Met
                100                 105                 110

Thr Glu Lys Glu Asn Tyr Asp Tyr Asp Ser Asn Thr Cys Gly Gly Asp
            115                 120                 125

Gly Val Cys Gly His Tyr Thr Gln Ile Val Trp Arg Asp Ser Val Arg
        130                 135                 140

Leu Gly Cys Ala Ser Val Arg Cys Lys Asn Asp Glu Tyr Ile Trp Val
145                 150                 155                 160

Ile Cys Ser Tyr Asp Pro Pro Gly Asn Tyr Ile Gly Gln Arg Pro Tyr
                165                 170                 175

<210> SEQ ID NO 85
<211> LENGTH: 989
<212> TYPE: DNA
<213> ORGANISM: Arabidopsis thaliana
<220> FEATURE:
<221> NAME/KEY: CDS
<222> LOCATION: (12)...(977)

<400> SEQUENCE: 85
tttttaagaa a atg gca gct tct aag cga cta gtt gtc tct tgc ttg ttc       50
            Met Ala Ala Ser Lys Arg Leu Val Val Ser Cys Leu Phe
              1               5                  10 tta gtt ttg ttg ttt gct caa gcc aat tcg caa ggt ttg aaa gta ggt       98
Leu Val Leu Leu Phe Ala Gln Ala Asn Ser Gln Gly Leu Lys Val Gly
     15                  20                  25 ttc tac agc aaa aca tgc cca caa ctc gag ggt ata gtt aaa aag gtc      146
Phe Tyr Ser Lys Thr Cys Pro Gln Leu Glu Gly Ile Val Lys Lys Val
 30                  35                  40                  45 gtg ttc gat gcg atg aac aaa gca cca aca ctt ggt gct cct ttg ctt      194
Val Phe Asp Ala Met Asn Lys Ala Pro Thr Leu Gly Ala Pro Leu Leu
                 50                  55                  60 aga atg ttc ttc cac gac tgc ttc gtt cgg gga tgt gac gga tca gtt      242
Arg Met Phe Phe His Asp Cys Phe Val Arg Gly Cys Asp Gly Ser Val
             65                  70                  75 ttg tta gat aaa cca aac aat caa ggt gag aag agt gca gtt cct aac      290
Leu Leu Asp Lys Pro Asn Asn Gln Gly Glu Lys Ser Ala Val Pro Asn
         80                  85                  90 cta agt ctt cga ggg ttt ggc atc ata gac gat tcc aag gcg gct cta      338
Leu Ser Leu Arg Gly Phe Gly Ile Ile Asp Asp Ser Lys Ala Ala Leu
     95                 100                 105 gaa aaa gtg tgt ccg gga att gtt tct tgc tct gat atc ttg gca ctt      386
Glu Lys Val Cys Pro Gly Ile Val Ser Cys Ser Asp Ile Leu Ala Leu
110                 115                 120                 125 gtc gct aga gac gca atg gtt gca ctt gaa gga cca tca tgg gaa gtt      434
Val Ala Arg Asp Ala Met Val Ala Leu Glu Gly Pro Ser Trp Glu Val
                130                 135                 140 gaa acg gga aga aga gac ggt agg gtt tct aac atc aac gaa gtc aac      482
Glu Thr Gly Arg Arg Asp Gly Arg Val Ser Asn Ile Asn Glu Val Asn
            145                 150                 155 ttg cca tca cct ttt gat aac atc acc aag ctt atc agc gat ttt cgc      530
Leu Pro Ser Pro Phe Asp Asn Ile Thr Lys Leu Ile Ser Asp Phe Arg
        160                 165                 170 tca aag ggc ctc aac gag aag gat cta gtc att ctc tcg ggt ggt cac      578
Ser Lys Gly Leu Asn Glu Lys Asp Leu Val Ile Leu Ser Gly Gly His
    175                 180                 185 aca att gga atg gga cat tgt cct tta ttg aca aac cgg ctt tac aac      626
Thr Ile Gly Met Gly His Cys Pro Leu Leu Thr Asn Arg Leu Tyr Asn
190                 195                 200                 205
```

```
ttc acc gga aaa gga gac agc gac cca agt ttg gac tcg gag tac gcc      674
Phe Thr Gly Lys Gly Asp Ser Asp Pro Ser Leu Asp Ser Glu Tyr Ala
            210                 215                 220 gct aag ctc agg aag aaa tgc aag ccc acc gat acg acg gct cta          722
Ala Lys Leu Arg Lys Lys Cys Lys Pro Thr Asp Thr Thr Ala Leu
        225                 230                 235 gag atg gat ccg ggg agt ttc aaa aca ttt gac ttg agc tac ttc acg      770
Glu Met Asp Pro Gly Ser Phe Lys Thr Phe Asp Leu Ser Tyr Phe Thr
            240                 245                 250 cta gtg gct aag aga aga gga ctt ttc cag tcg gat gct gct cta ctc      818
Leu Val Ala Lys Arg Arg Gly Leu Phe Gln Ser Asp Ala Ala Leu Leu
        255                 260                 265 gac aac tcc aag act agg gct tat gtc ttg caa cag ata aga act cat      866
Asp Asn Ser Lys Thr Arg Ala Tyr Val Leu Gln Gln Ile Arg Thr His
270                 275                 280                 285 ggg tca atg ttc ttt aac gac ttt ggt gtc tct atg gtg aaa atg ggt      914
Gly Ser Met Phe Phe Asn Asp Phe Gly Val Ser Met Val Lys Met Gly
                290                 295                 300 cgg act gga gtt ctt acg ggt aag gcc ggg gag atc cgt aag acg tgt      962
Arg Thr Gly Val Leu Thr Gly Lys Ala Gly Glu Ile Arg Lys Thr Cys
            305                 310                 315 cgg tct gct aat taa gagatataga aa                                    989
Arg Ser Ala Asn *
        320

<210> SEQ ID NO 86
<211> LENGTH: 321
<212> TYPE: PRT
<213> ORGANISM: Arabidopsis thaliana

<400> SEQUENCE: 86

Met Ala Ala Ser Lys Arg Leu Val Val Ser Cys Leu Phe Leu Val Leu
 1               5                  10                  15

Leu Phe Ala Gln Ala Asn Ser Gln Gly Leu Lys Val Gly Phe Tyr Ser
                20                  25                  30

Lys Thr Cys Pro Gln Leu Glu Gly Ile Val Lys Val Val Phe Asp
            35                  40                  45

Ala Met Asn Lys Ala Pro Thr Leu Gly Ala Pro Leu Leu Arg Met Phe
        50                  55                  60

Phe His Asp Cys Phe Val Arg Gly Cys Asp Gly Ser Val Leu Leu Asp
65                  70                  75                  80

Lys Pro Asn Asn Gln Gly Glu Lys Ser Ala Val Pro Asn Leu Ser Leu
                85                  90                  95

Arg Gly Phe Gly Ile Ile Asp Ser Lys Ala Ala Leu Glu Lys Val
            100                 105                 110

Cys Pro Gly Ile Val Ser Cys Ser Asp Ile Leu Ala Leu Val Ala Arg
        115                 120                 125

Asp Ala Met Val Ala Leu Glu Gly Pro Ser Trp Glu Val Glu Thr Gly
    130                 135                 140

Arg Arg Asp Gly Arg Val Ser Asn Ile Asn Glu Val Asn Leu Pro Ser
145                 150                 155                 160

Pro Phe Asp Asn Ile Thr Lys Leu Ile Ser Asp Phe Arg Ser Lys Gly
                165                 170                 175

Leu Asn Glu Lys Asp Leu Val Ile Leu Ser Gly Gly His Thr Ile Gly
            180                 185                 190

Met Gly His Cys Pro Leu Leu Thr Asn Arg Leu Tyr Asn Phe Thr Gly
        195                 200                 205
```

```
Lys Gly Asp Ser Asp Pro Ser Leu Asp Ser Glu Tyr Ala Ala Lys Leu
    210                 215                 220

Arg Lys Lys Cys Lys Pro Thr Asp Thr Thr Ala Leu Glu Met Asp
225                 230                 235                 240

Pro Gly Ser Phe Lys Thr Phe Asp Leu Ser Tyr Phe Thr Leu Val Ala
                245                 250                 255

Lys Arg Arg Gly Leu Phe Gln Ser Asp Ala Ala Leu Leu Asp Asn Ser
            260                 265                 270

Lys Thr Arg Ala Tyr Val Leu Gln Gln Ile Arg Thr His Gly Ser Met
        275                 280                 285

Phe Phe Asn Asp Phe Gly Val Ser Met Val Lys Met Gly Arg Thr Gly
    290                 295                 300

Val Leu Thr Gly Lys Ala Gly Glu Ile Arg Lys Thr Cys Arg Ser Ala
305                 310                 315                 320

Asn
```

<210> SEQ ID NO 87
<211> LENGTH: 650
<212> TYPE: DNA
<213> ORGANISM: Arabidopsis thaliana
<220> FEATURE:
<221> NAME/KEY: CDS
<222> LOCATION: (8)...(634)

<400> SEQUENCE: 87

```
agcgaca atg gcg tcg att acg aac ctc gcc tct tct ctc tct tca ctc        49
        Met Ala Ser Ile Thr Asn Leu Ala Ser Ser Leu Ser Ser Leu
        1               5                   10 tcg ttc tcc tcc caa gtt tct caa aga cct aac acc att tcc ttc ccc        97
Ser Phe Ser Ser Gln Val Ser Gln Arg Pro Asn Thr Ile Ser Phe Pro
15                  20                  25                  30 cgc gcg aat tca gta ttc gca tta ccg gcg aaa tcc gca cgc cgc gct       145
Arg Ala Asn Ser Val Phe Ala Leu Pro Ala Lys Ser Ala Arg Arg Ala
                35                  40                  45 tct cta tct atc acc gcc acg gta tct gct cca ccg gag gag gag gag       193
Ser Leu Ser Ile Thr Ala Thr Val Ser Ala Pro Pro Glu Glu Glu Glu
            50                  55                  60 ata gtt gaa ctg aag aaa tac gtc aaa tcg agg ctt ccc gga gga ttt       241
Ile Val Glu Leu Lys Lys Tyr Val Lys Ser Arg Leu Pro Gly Gly Phe
        65                  70                  75 gct gct cag aag att att ggc act gga cga cgt aag tgc gca atc gct       289
Ala Ala Gln Lys Ile Ile Gly Thr Gly Arg Arg Lys Cys Ala Ile Ala
    80                  85                  90 aga gtt gtt ctt cag gaa ggt act ggg aag gtt atc atc aac tat cgt       337
Arg Val Val Leu Gln Glu Gly Thr Gly Lys Val Ile Ile Asn Tyr Arg
95                  100                 105                 110 gat gcc aag gag tac ctt cag gga aat cca ttg tgg ctt cag tat gtt       385
Asp Ala Lys Glu Tyr Leu Gln Gly Asn Pro Leu Trp Leu Gln Tyr Val
                115                 120                 125 aaa gta cca ttg gtg act tta gga tat gag aat agc tac gac ata ttt       433
Lys Val Pro Leu Val Thr Leu Gly Tyr Glu Asn Ser Tyr Asp Ile Phe
            130                 135                 140 gtg aaa gcc cat gga ggc ggt ctc tca ggt caa gct caa gca att acc       481
Val Lys Ala His Gly Gly Gly Leu Ser Gly Gln Ala Gln Ala Ile Thr
        145                 150                 155 ttg gga gtc gca cgt gca ctc ctg aag gta agt gca gac cac aga tcg       529
Leu Gly Val Ala Arg Ala Leu Leu Lys Val Ser Ala Asp His Arg Ser
    160                 165                 170
```

| | | |
|---|---|---|
| cct ttg aag aag gaa ggt ttg ctc act aga gat gcg aga gtg gtt gaa<br>Pro Leu Lys Lys Glu Gly Leu Leu Thr Arg Asp Ala Arg Val Val Glu<br>175                            180                     185                        190 | | 577 |
| aga aag aag gcc ggg ctc aag aag gcg cgt aaa gcc cca caa ttc tcc<br>Arg Lys Lys Ala Gly Leu Lys Lys Ala Arg Lys Ala Pro Gln Phe Ser<br>                  195                         200                     205 | | 625 |
| aag cgt taa gagttttata tatcat<br>Lys Arg * | | 650 |

<210> SEQ ID NO 88
<211> LENGTH: 208
<212> TYPE: PRT
<213> ORGANISM: Arabidopsis thaliana

<400> SEQUENCE: 88

Met Ala Ser Ile Thr Asn Leu Ala Ser Ser Leu Ser Ser Leu Ser Phe
1               5                   10                  15

Ser Ser Gln Val Ser Gln Arg Pro Asn Thr Ile Ser Phe Pro Arg Ala
            20                  25                  30

Asn Ser Val Phe Ala Leu Pro Ala Lys Ser Ala Arg Arg Ala Ser Leu
        35                  40                  45

Ser Ile Thr Ala Thr Val Ser Ala Pro Pro Glu Glu Glu Ile Val
    50                  55                  60

Glu Leu Lys Lys Tyr Val Lys Ser Arg Leu Pro Gly Gly Phe Ala Ala
65                  70                  75                  80

Gln Lys Ile Ile Gly Thr Gly Arg Arg Lys Cys Ala Ile Ala Arg Val
                85                  90                  95

Val Leu Gln Glu Gly Thr Gly Lys Val Ile Ile Asn Tyr Arg Asp Ala
            100                 105                 110

Lys Glu Tyr Leu Gln Gly Asn Pro Leu Trp Leu Gln Tyr Val Lys Val
        115                 120                 125

Pro Leu Val Thr Leu Gly Tyr Glu Asn Ser Tyr Asp Ile Phe Val Lys
    130                 135                 140

Ala His Gly Gly Gly Leu Ser Gly Gln Ala Gln Ala Ile Thr Leu Gly
145                 150                 155                 160

Val Ala Arg Ala Leu Leu Lys Val Ser Ala Asp His Arg Ser Pro Leu
                165                 170                 175

Lys Lys Glu Gly Leu Leu Thr Arg Asp Ala Arg Val Val Glu Arg Lys
            180                 185                 190

Lys Ala Gly Leu Lys Lys Ala Arg Lys Ala Pro Gln Phe Ser Lys Arg
        195                 200                 205

<210> SEQ ID NO 89
<211> LENGTH: 1223
<212> TYPE: DNA
<213> ORGANISM: Arabidopsis thaliana
<220> FEATURE:
<221> NAME/KEY: CDS
<222> LOCATION: (16)...(1215)

<400> SEQUENCE: 89

| | | |
|---|---|---|
| aacaagtgaa gcaca atg ggg atc atc gaa agg att aaa gaa atc gag gcc<br>                     Met Gly Ile Ile Glu Arg Ile Lys Glu Ile Glu Ala<br>                      1               5                        10 | | 51 |
| gag atg gct cgg act cag aag aat aaa gct aca gag tat cat ctt ggt<br>Glu Met Ala Arg Thr Gln Lys Asn Lys Ala Thr Glu Tyr His Leu Gly<br>    15                     20                     25 | | 99 |
| cag ctc aag gca aag att gca aaa ctc agg aca caa ctg ttg gag cct<br>Gln Leu Lys Ala Lys Ile Ala Lys Leu Arg Thr Gln Leu Leu Glu Pro | | 147 |

```
              30                  35                  40
cca aaa ggt gct agt gga ggc ggg gaa ggt ttt gaa gtt acc aag tat       195
Pro Lys Gly Ala Ser Gly Gly Gly Glu Gly Phe Glu Val Thr Lys Tyr
 45                  50                  55                  60 ggt cat gga cgt gtt gca ctt ata gga ttt cct agt gtc gga aag tcc       243
Gly His Gly Arg Val Ala Leu Ile Gly Phe Pro Ser Val Gly Lys Ser
                     65                  70                  75 acg ctt ttg act atg tta act gga aca cat tct gaa gca gcc tca tat       291
Thr Leu Leu Thr Met Leu Thr Gly Thr His Ser Glu Ala Ala Ser Tyr
                 80                  85                  90 gaa ttt aca aca ctt aca tgc atc cct ggt gta att cac tac aac gac       339
Glu Phe Thr Thr Leu Thr Cys Ile Pro Gly Val Ile His Tyr Asn Asp
             95                 100                 105 aca aag att cag ctt ctc gat ctt cct ggg att att gaa ggt gct tcg       387
Thr Lys Ile Gln Leu Leu Asp Leu Pro Gly Ile Ile Glu Gly Ala Ser
        110                 115                 120 gaa gga aag ggg cga gga agg cag gtt att gct gtt gca aag tct tcc       435
Glu Gly Lys Gly Arg Gly Arg Gln Val Ile Ala Val Ala Lys Ser Ser
125                 130                 135                 140 gac ctt gta ttg atg gtt ctt gat gcc tca aaa agc gaa ggc cac agg       483
Asp Leu Val Leu Met Val Leu Asp Ala Ser Lys Ser Glu Gly His Arg
                    145                 150                 155 caa ata ttg act aag gaa ctt gag gca gtg ggc ttg cga cta aac aaa       531
Gln Ile Leu Thr Lys Glu Leu Glu Ala Val Gly Leu Arg Leu Asn Lys
                160                 165                 170 act cct ccg cag ata tac ttt aaa aag aaa aag act ggt gga atc tct       579
Thr Pro Pro Gln Ile Tyr Phe Lys Lys Lys Lys Thr Gly Gly Ile Ser
            175                 180                 185 ttc aac act aca gca ccc ttg act cac att gat gag aag ctc tgt tat       627
Phe Asn Thr Thr Ala Pro Leu Thr His Ile Asp Glu Lys Leu Cys Tyr
        190                 195                 200 caa atc ctg cat gaa tac aag att cac aat gct gag gtg cta ttt cgt       675
Gln Ile Leu His Glu Tyr Lys Ile His Asn Ala Glu Val Leu Phe Arg
205                 210                 215                 220 gag aat gcc aca gtg gat gac ttt att gat gtc att gaa ggc aac cgc       723
Glu Asn Ala Thr Val Asp Asp Phe Ile Asp Val Ile Glu Gly Asn Arg
                    225                 230                 235 aag tat att aag tgt gtt tat gtc tac atc aaa ata gat gtt gtt gga       771
Lys Tyr Ile Lys Cys Val Tyr Val Tyr Ile Lys Ile Asp Val Val Gly
                240                 245                 250 att gat gat gtg gat aga cta tcc cgg cag cca aat tcc att gtt att       819
Ile Asp Asp Val Asp Arg Leu Ser Arg Gln Pro Asn Ser Ile Val Ile
            255                 260                 265 agc tgc aat ctt aag ctt aac tta gac aga cta ctt gct agg atg tgg       867
Ser Cys Asn Leu Lys Leu Asn Leu Asp Arg Leu Leu Ala Arg Met Trp
        270                 275                 280 gac gaa atg ggc ctt gtg aga gtt tac tcg aag ccg caa ggc cag caa       915
Asp Glu Met Gly Leu Val Arg Val Tyr Ser Lys Pro Gln Gly Gln Gln
285                 290                 295                 300 cca gat ttc gat gag cct ttt gtc ctc tca tct gat cga ggt ggc tgc       963
Pro Asp Phe Asp Glu Pro Phe Val Leu Ser Ser Asp Arg Gly Gly Cys
                    305                 310                 315 aca gtg gaa gac ttc tgt aac cac gtc cac agg act ctg gtg aag gat      1011
Thr Val Glu Asp Phe Cys Asn His Val His Arg Thr Leu Val Lys Asp
                320                 325                 330 atg aag tat gca ctc gtt tgg ggc aca agc aca agg cac aat cca cag      1059
Met Lys Tyr Ala Leu Val Trp Gly Thr Ser Thr Arg His Asn Pro Gln
            335                 340                 345 aat tgt ggt ctt tct caa cat ctt gaa gac gaa gat gtt gtt cag atc      1107
```

| | | | | | | | | | | | | |
|---|---|---|---|---|---|---|---|---|---|---|---|---|
| Asn | Cys | Gly | Leu | Ser | Gln | His | Leu | Glu | Asp | Glu | Asp | Val | Val | Gln | Ile |
| | 350 | | | | | 355 | | | | | 360 | | | | |

```
gtc aag aaa aag gag aga gac gaa gga gga aga ggc cgg ttc aag tca    1155
Val Lys Lys Lys Glu Arg Asp Glu Gly Gly Arg Gly Arg Phe Lys Ser
365                 370                 375                 380 cac tca aac gcc cct gct aga att gca gac aga gag aaa aaa gct cct    1203
His Ser Asn Ala Pro Ala Arg Ile Ala Asp Arg Glu Lys Lys Ala Pro
                385                 390                 395 ctt aag caa taa gcttttag                                           1223
Leu Lys Gln *
```

<210> SEQ ID NO 90
<211> LENGTH: 399
<212> TYPE: PRT
<213> ORGANISM: Arabidopsis thaliana

<400> SEQUENCE: 90

Met Gly Ile Ile Glu Arg Ile Lys Glu Ile Glu Ala Glu Met Ala Arg
 1               5                  10                  15

Thr Gln Lys Asn Lys Ala Thr Glu Tyr His Leu Gly Gln Leu Lys Ala
             20                  25                  30

Lys Ile Ala Lys Leu Arg Thr Gln Leu Leu Glu Pro Pro Lys Gly Ala
         35                  40                  45

Ser Gly Gly Glu Gly Phe Glu Val Thr Lys Tyr Gly His Gly Arg
     50                  55                  60

Val Ala Leu Ile Gly Phe Pro Ser Val Gly Lys Ser Thr Leu Leu Thr
 65                  70                  75                  80

Met Leu Thr Gly Thr His Ser Glu Ala Ala Ser Tyr Glu Phe Thr Thr
                 85                  90                  95

Leu Thr Cys Ile Pro Gly Val Ile His Tyr Asn Asp Thr Lys Ile Gln
            100                 105                 110

Leu Leu Asp Leu Pro Gly Ile Ile Glu Gly Ala Ser Glu Gly Lys Gly
        115                 120                 125

Arg Gly Arg Gln Val Ile Ala Val Ala Lys Ser Ser Asp Leu Val Leu
    130                 135                 140

Met Val Leu Asp Ala Ser Lys Ser Glu Gly His Arg Gln Ile Leu Thr
145                 150                 155                 160

Lys Glu Leu Glu Ala Val Gly Leu Arg Leu Asn Lys Thr Pro Pro Gln
                165                 170                 175

Ile Tyr Phe Lys Lys Lys Thr Gly Gly Ile Ser Phe Asn Thr Thr
            180                 185                 190

Ala Pro Leu Thr His Ile Asp Glu Lys Leu Cys Tyr Gln Ile Leu His
        195                 200                 205

Glu Tyr Lys Ile His Asn Ala Glu Val Leu Phe Arg Glu Asn Ala Thr
    210                 215                 220

Val Asp Asp Phe Ile Asp Val Ile Glu Gly Asn Arg Lys Tyr Ile Lys
225                 230                 235                 240

Cys Val Tyr Val Tyr Ile Lys Ile Asp Val Val Gly Ile Asp Val
                245                 250                 255

Asp Arg Leu Ser Arg Gln Pro Asn Ser Ile Val Ile Ser Cys Asn Leu
            260                 265                 270

Lys Leu Asn Leu Asp Arg Leu Leu Ala Arg Met Trp Asp Glu Met Gly
        275                 280                 285

Leu Val Arg Val Tyr Ser Lys Pro Gln Gly Gln Gln Pro Asp Phe Asp
    290                 295                 300

-continued

```
Glu Pro Phe Val Leu Ser Ser Asp Arg Gly Gly Cys Thr Val Glu Asp
305                 310                 315                 320

Phe Cys Asn His Val His Arg Thr Leu Val Lys Asp Met Lys Tyr Ala
            325                 330                 335

Leu Val Trp Gly Thr Ser Thr Arg His Asn Pro Gln Asn Cys Gly Leu
        340                 345                 350

Ser Gln His Leu Glu Asp Glu Asp Val Val Gln Ile Val Lys Lys Lys
    355                 360                 365

Glu Arg Asp Glu Gly Gly Arg Gly Arg Phe Lys Ser His Ser Asn Ala
370                 375                 380

Pro Ala Arg Ile Ala Asp Arg Glu Lys Lys Ala Pro Leu Lys Gln
385                 390                 395
```

<210> SEQ ID NO 91
<211> LENGTH: 536
<212> TYPE: DNA
<213> ORGANISM: Arabidopsis thaliana
<220> FEATURE:
<221> NAME/KEY: CDS
<222> LOCATION: (12)...(524)

<400> SEQUENCE: 91

```
aaataaaaac a atg aca agc tcc gat caa tct cca tcg cac gac gtc ttc      50
             Met Thr Ser Ser Asp Gln Ser Pro Ser His Asp Val Phe
             1               5                   10 gtc tac ggc agt ttc caa gaa cca gcc gtt gtt aat tta att ctc gaa       98
Val Tyr Gly Ser Phe Gln Glu Pro Ala Val Val Asn Leu Ile Leu Glu
    15                  20                  25 tgt gct ccg gtc atg gtt tcc gct caa ctc cac ggc tat cac ttg tat      146
Cys Ala Pro Val Met Val Ser Ala Gln Leu His Gly Tyr His Leu Tyr
30                  35                  40                  45 aga ctt aaa ggt cgt ttg cat cca tgt att tct cct tcc gac aat gga      194
Arg Leu Lys Gly Arg Leu His Pro Cys Ile Ser Pro Ser Asp Asn Gly
                50                  55                  60 tta atc aat ggc aag ata cta act gga tta aca gat tct cag tta gag      242
Leu Ile Asn Gly Lys Ile Leu Thr Gly Leu Thr Asp Ser Gln Leu Glu
            65                  70                  75 agt tta gat atg att gaa gga act gaa tat gtg agg aag act gtt gaa      290
Ser Leu Asp Met Ile Glu Gly Thr Glu Tyr Val Arg Lys Thr Val Glu
        80                  85                  90 gtt gtt ttg act gat act ttg gag aag aag caa gtt gaa aca att gta      338
Val Val Leu Thr Asp Thr Leu Glu Lys Lys Gln Val Glu Thr Ile Val
    95                  100                 105 tgg gca aac aag gat gat cct aat atg tat gga gaa tgg gat ttc gag      386
Trp Ala Asn Lys Asp Asp Pro Asn Met Tyr Gly Glu Trp Asp Phe Glu
110                 115                 120                 125 gaa tgg aag agg ctt cat atg gag aaa ttt ata gag gcg gcg acg aaa      434
Glu Trp Lys Arg Leu His Met Glu Lys Phe Ile Glu Ala Ala Thr Lys
                130                 135                 140 ttc atg gag tgg aag aag aat ccg aat ggg aga agt agg gaa gag ttt      482
Phe Met Glu Trp Lys Lys Asn Pro Asn Gly Arg Ser Arg Glu Glu Phe
            145                 150                 155 gag aag ttt gta caa gat gat tct tct ccg gct tcg gct tga             524
Glu Lys Phe Val Gln Asp Asp Ser Ser Pro Ala Ser Ala *
        160                 165                 170 agaagttgtt ta                                                        536
```

<210> SEQ ID NO 92
<211> LENGTH: 170
<212> TYPE: PRT

-continued

<213> ORGANISM: Arabidopsis thaliana

<400> SEQUENCE: 92

```
Met Thr Ser Ser Asp Gln Ser Pro Ser His Asp Val Phe Val Tyr Gly
 1               5                  10                  15

Ser Phe Gln Glu Pro Ala Val Val Asn Leu Ile Leu Glu Cys Ala Pro
                20                  25                  30

Val Met Val Ser Ala Gln Leu His Gly Tyr His Leu Tyr Arg Leu Lys
             35                  40                  45

Gly Arg Leu His Pro Cys Ile Ser Pro Ser Asp Asn Gly Leu Ile Asn
 50                  55                  60

Gly Lys Ile Leu Thr Gly Leu Thr Asp Ser Gln Leu Glu Ser Leu Asp
 65                  70                  75                  80

Met Ile Glu Gly Thr Glu Tyr Val Arg Lys Thr Val Glu Val Val Leu
                 85                  90                  95

Thr Asp Thr Leu Glu Lys Lys Gln Val Glu Thr Ile Val Trp Ala Asn
                100                 105                 110

Lys Asp Pro Asn Met Tyr Gly Glu Trp Asp Phe Glu Glu Trp Lys
            115                 120                 125

Arg Leu His Met Glu Lys Phe Ile Glu Ala Ala Thr Lys Phe Met Glu
            130                 135                 140

Trp Lys Lys Asn Pro Asn Gly Arg Ser Arg Glu Glu Phe Glu Lys Phe
145                 150                 155                 160

Val Gln Asp Asp Ser Ser Pro Ala Ser Ala
                165                 170
```

<210> SEQ ID NO 93
<211> LENGTH: 293
<212> TYPE: DNA
<213> ORGANISM: Arabidopsis thaliana
<220> FEATURE:
<221> NAME/KEY: CDS
<222> LOCATION: (16)...(71)
<220> FEATURE:
<221> NAME/KEY: CDS
<222> LOCATION: (197)...(278)

<400> SEQUENCE: 93

```
agagaagtaa gagaa atg gca ggt tct aac tgt gga tgt ggc tcc tcc tgc         51
                 Met Ala Gly Ser Asn Cys Gly Cys Gly Ser Ser Cys
                  1               5                  10 aaa tgt ggt gat tcg tgc ag gtaaaccta gattctctct tcattaactt           101
Lys Cys Gly Asp Ser Cys Ser
         15 atcatgcata tatatcctaa tatacatgtg gttacatatt ccttaagata aattttgaaa     161 tcttatactt ctgttgtttt tttggtatga caaag t tgc gag aag aac tac aac      215
                                     Cys Glu Lys Asn Tyr Asn
                                                 20              25 aag gag tgt gat aac tgt agc tgt gga tca aac tgc agc tgc ggg tca      263
Lys Glu Cys Asp Asn Cys Ser Cys Gly Ser Asn Cys Ser Cys Gly Ser
            30                  35                  40 agc tgt aac tgt tga agaaattatc agcat                                  293
Ser Cys Asn Cys *
         45
```

<210> SEQ ID NO 94
<211> LENGTH: 45
<212> TYPE: PRT
<213> ORGANISM: Arabidopsis thaliana

```
<400> SEQUENCE: 94

Met Ala Gly Ser Asn Cys Gly Cys Gly Ser Ser Cys Lys Cys Gly Asp
 1               5                  10                  15

Ser Cys Ser Cys Glu Lys Asn Tyr Asn Lys Glu Cys Asp Asn Cys Ser
             20                  25                  30

Cys Gly Ser Asn Cys Ser Cys Gly Ser Ser Cys Asn Cys
         35                  40                  45

<210> SEQ ID NO 95
<211> LENGTH: 880
<212> TYPE: DNA
<213> ORGANISM: Arabidopsis thaliana
<220> FEATURE:
<221> NAME/KEY: CDS
<222> LOCATION: (14)...(868)

<400> SEQUENCE: 95
```

| | | |
|---|---|---|
| cacaccaaca cca atg tct gct tct tct tta ttt aat ctc cca ttg att<br>            Met Ser Ala Ser Ser Leu Phe Asn Leu Pro Leu Ile<br>             1               5                  10 | 49 |
| cgc ctc aga tct ctc gct ctt tcg tct tct ttt tct tct ttc cga ttt<br>Arg Leu Arg Ser Leu Ala Leu Ser Ser Ser Phe Ser Ser Phe Arg Phe<br>         15                  20                  25 | 97 |
| gcc cat cgt cct ctg tca tcg att tca ccg aga aag tta ccg aat ttt<br>Ala His Arg Pro Leu Ser Ser Ile Ser Pro Arg Lys Leu Pro Asn Phe<br> 30                  35                  40 | 145 |
| cgt gct ttc tct ggt acc gct atg aca gat act aaa gat gct ggt atg<br>Arg Ala Phe Ser Gly Thr Ala Met Thr Asp Thr Lys Asp Ala Gly Met<br>45                  50                  55                  60 | 193 |
| gat gct gtt cag aga cgt ctc atg ttt gag gat gaa tgc att ctt gtt<br>Asp Ala Val Gln Arg Arg Leu Met Phe Glu Asp Glu Cys Ile Leu Val<br>                 65                  70                  75 | 241 |
| gat gaa act gat cgt gtt gtg ggg cat gac agc aag tat aat tgt cat<br>Asp Glu Thr Asp Arg Val Val Gly His Asp Ser Lys Tyr Asn Cys His<br>             80                  85                  90 | 289 |
| ctg atg gaa aat att gaa gcc aag aat ttg ctg cac agg gct ttt agt<br>Leu Met Glu Asn Ile Glu Ala Lys Asn Leu Leu His Arg Ala Phe Ser<br>         95                  100                 105 | 337 |
| gta ttt tta ttc aac tcg aag tat gag ttg ctc ctc cag caa agg tca<br>Val Phe Leu Phe Asn Ser Lys Tyr Glu Leu Leu Leu Gln Gln Arg Ser<br>     110                 115                 120 | 385 |
| aac aca aag gtt acg ttc cct cta gtg tgg act aac act tgt tgc agc<br>Asn Thr Lys Val Thr Phe Pro Leu Val Trp Thr Asn Thr Cys Cys Ser<br>125                 130                 135                 140 | 433 |
| cat cct ctt tac cgt gaa tca gag ctt atc cag gac aat gca cta ggt<br>His Pro Leu Tyr Arg Glu Ser Glu Leu Ile Gln Asp Asn Ala Leu Gly<br>                 145                 150                 155 | 481 |
| gtg agg aat gct gca caa aga aag ctt ctc gat gag ctt ggt att gta<br>Val Arg Asn Ala Ala Gln Arg Lys Leu Leu Asp Glu Leu Gly Ile Val<br>             160                 165                 170 | 529 |
| gct gaa gat gta cca gtc gat gag ttc act ccc ttg gga cgt atg ctg<br>Ala Glu Asp Val Pro Val Asp Glu Phe Thr Pro Leu Gly Arg Met Leu<br>         175                 180                 185 | 577 |
| tac aag gct cct tct gat ggc aaa tgg gga gag cat gaa ctt gat tac<br>Tyr Lys Ala Pro Ser Asp Gly Lys Trp Gly Glu His Glu Leu Asp Tyr<br>     190                 195                 200 | 625 |
| ttg ctc ttc atc gtg cga gac gtg aag gtt caa cca aac cca gat gaa<br>Leu Leu Phe Ile Val Arg Asp Val Lys Val Gln Pro Asn Pro Asp Glu<br>205                 210                 215                 220 | 673 |
| gta gct gag atc aag tat gtg agc cgg gaa gag ctg aag gag ctg gtg | 721 |

| | | | | | | | | | | | | |
|---|---|---|---|---|---|---|---|---|---|---|---|---|
| Val | Ala | Glu | Ile | Lys | Tyr | Val | Ser | Arg | Glu | Glu | Leu | Lys | Glu | Leu | Val |
| | | | | 225 | | | | 230 | | | | 235 | |

```
aag aaa gca gat gca ggt gag gaa ggt ttg aaa ctg tca cca tgg ttc      769
Lys Lys Ala Asp Ala Gly Glu Glu Gly Leu Lys Leu Ser Pro Trp Phe
            240                 245                 250 aga ttg gtg gtg gac aat ttc ttg atg aag tgg tgg gat cat gta gag      817
Arg Leu Val Val Asp Asn Phe Leu Met Lys Trp Trp Asp His Val Glu
            255                 260                 265 aaa gga act ttg gtt gaa gct ata gac atg aaa acc atc cac aaa ctc      865
Lys Gly Thr Leu Val Glu Ala Ile Asp Met Lys Thr Ile His Lys Leu
    270                 275                 280 tga acatctttt tt                                                     880
 *
```

<210> SEQ ID NO 96
<211> LENGTH: 284
<212> TYPE: PRT
<213> ORGANISM: Arabidopsis thaliana

<400> SEQUENCE: 96

Met Ser Ala Ser Ser Leu Phe Asn Leu Pro Leu Ile Arg Leu Arg Ser
 1               5                  10                  15

Leu Ala Leu Ser Ser Ser Phe Ser Ser Phe Arg Phe Ala His Arg Pro
                20                  25                  30

Leu Ser Ser Ile Ser Pro Arg Lys Leu Pro Asn Phe Arg Ala Phe Ser
            35                  40                  45

Gly Thr Ala Met Thr Asp Thr Lys Asp Ala Gly Met Asp Ala Val Gln
 50                  55                  60

Arg Arg Leu Met Phe Glu Asp Glu Cys Ile Leu Val Asp Glu Thr Asp
65                  70                  75                  80

Arg Val Val Gly His Asp Ser Lys Tyr Asn Cys His Leu Met Glu Asn
                85                  90                  95

Ile Glu Ala Lys Asn Leu Leu His Arg Ala Phe Ser Val Phe Leu Phe
                100                 105                 110

Asn Ser Lys Tyr Glu Leu Leu Leu Gln Gln Arg Ser Asn Thr Lys Val
            115                 120                 125

Thr Phe Pro Leu Val Trp Thr Asn Thr Cys Cys Ser His Pro Leu Tyr
130                 135                 140

Arg Glu Ser Glu Leu Ile Gln Asp Asn Ala Leu Gly Val Arg Asn Ala
145                 150                 155                 160

Ala Gln Arg Lys Leu Leu Asp Glu Leu Gly Ile Val Ala Glu Asp Val
                165                 170                 175

Pro Val Asp Glu Phe Thr Pro Leu Gly Arg Met Leu Tyr Lys Ala Pro
            180                 185                 190

Ser Asp Gly Lys Trp Gly Glu His Glu Leu Asp Tyr Leu Leu Phe Ile
        195                 200                 205

Val Arg Asp Val Lys Val Gln Pro Asn Pro Asp Glu Val Ala Glu Ile
    210                 215                 220

Lys Tyr Val Ser Arg Glu Glu Leu Lys Glu Leu Val Lys Lys Ala Asp
225                 230                 235                 240

Ala Gly Glu Glu Gly Leu Lys Leu Ser Pro Trp Phe Arg Leu Val Val
                245                 250                 255

Asp Asn Phe Leu Met Lys Trp Trp Asp His Val Glu Lys Gly Thr Leu
            260                 265                 270

Val Glu Ala Ile Asp Met Lys Thr Ile His Lys Leu
        275                 280

<210> SEQ ID NO 97
<211> LENGTH: 831
<212> TYPE: DNA
<213> ORGANISM: Arabidopsis thaliana
<220> FEATURE:
<221> NAME/KEY: CDS
<222> LOCATION: (18)...(821)

<400> SEQUENCE: 97

```
tgcactactc aacctca atg gcc gcc tca aca atg gct ctc tcc tcc cct           50
                   Met Ala Ala Ser Thr Met Ala Leu Ser Ser Pro
                    1               5                  10 gcc ttc gcc ggt aag gcc gtc aag ctt tcc ccc gcg gca tca gaa gtc          98
Ala Phe Ala Gly Lys Ala Val Lys Leu Ser Pro Ala Ala Ser Glu Val
            15                  20                  25 ctt gga agc ggc cgt gtg aca atg agg aag act gtt gcc aag cca aag        146
Leu Gly Ser Gly Arg Val Thr Met Arg Lys Thr Val Ala Lys Pro Lys
         30                  35                  40 ggc cca tca ggc agc cca tgg tac gga tct gac cgt gtc aag tac ttg        194
Gly Pro Ser Gly Ser Pro Trp Tyr Gly Ser Asp Arg Val Lys Tyr Leu
     45                  50                  55 ggt cca ttc tct ggc gaa tca ccg agc tac ctt acc gga gag ttc ccc        242
Gly Pro Phe Ser Gly Glu Ser Pro Ser Tyr Leu Thr Gly Glu Phe Pro
 60                  65                  70                  75 gga gac tac gga tgg gac acc gcc gga ctt tca gct gac ccc gag aca        290
Gly Asp Tyr Gly Trp Asp Thr Ala Gly Leu Ser Ala Asp Pro Glu Thr
                 80                  85                  90 ttc gca agg aac cgt gaa cta gaa gtt atc cac agc agg tgg gct atg        338
Phe Ala Arg Asn Arg Glu Leu Glu Val Ile His Ser Arg Trp Ala Met
             95                 100                 105 ctc gga gcc cta ggc tgc gtc ttc cct gag ctt ttg gct aga aac gga        386
Leu Gly Ala Leu Gly Cys Val Phe Pro Glu Leu Leu Ala Arg Asn Gly
        110                 115                 120 gtc aag ttc gga gag gcg gtt tgg ttc aag gcc ggt tca cag atc ttc        434
Val Lys Phe Gly Glu Ala Val Trp Phe Lys Ala Gly Ser Gln Ile Phe
    125                 130                 135 agc gat gga ggg ctc gat tac ttg gga aac cct agc ttg gtt cac gct        482
Ser Asp Gly Gly Leu Asp Tyr Leu Gly Asn Pro Ser Leu Val His Ala
140                 145                 150                 155 cag agc att ttg gcc att tgg gcc aca caa gtt att ttg atg gga gcc        530
Gln Ser Ile Leu Ala Ile Trp Ala Thr Gln Val Ile Leu Met Gly Ala
                160                 165                 170 gtt gaa ggc tac aga gtc gca gga aat ggg cca ttg gga gag gcc gag        578
Val Glu Gly Tyr Arg Val Ala Gly Asn Gly Pro Leu Gly Glu Ala Glu
            175                 180                 185 gac ttg ctt tac ccc ggt ggc agc ttc gac cca ttg ggt ttg gct acc        626
Asp Leu Leu Tyr Pro Gly Gly Ser Phe Asp Pro Leu Gly Leu Ala Thr
        190                 195                 200 gac cca gag gca ttc gct gag ttg aag gtg aag gag ctc aag aac gga        674
Asp Pro Glu Ala Phe Ala Glu Leu Lys Val Lys Glu Leu Lys Asn Gly
    205                 210                 215 aga ttg gct atg ttc tct atg ttt gga ttc ttc gtt caa gcc atc gtc        722
Arg Leu Ala Met Phe Ser Met Phe Gly Phe Phe Val Gln Ala Ile Val
220                 225                 230                 235 act ggt aag gga ccg ata gag aac ctt gct gac cat ttg gcc gat cca        770
Thr Gly Lys Gly Pro Ile Glu Asn Leu Ala Asp His Leu Ala Asp Pro
                240                 245                 250 gtt aac aac aac gca tgg gcc ttc gcc acc aac ttt gtt ccc gga aag        818
Val Asn Asn Asn Ala Trp Ala Phe Ala Thr Asn Phe Val Pro Gly Lys
            255                 260                 265
```

```
tga gccaagtttt                                                    831
    *
```

<210> SEQ ID NO 98
<211> LENGTH: 267
<212> TYPE: PRT
<213> ORGANISM: Arabidopsis thaliana

<400> SEQUENCE: 98

```
Met Ala Ala Ser Thr Met Ala Leu Ser Ser Pro Ala Phe Ala Gly Lys
 1               5                  10                  15

Ala Val Lys Leu Ser Pro Ala Ala Ser Glu Val Leu Gly Ser Gly Arg
             20                  25                  30

Val Thr Met Arg Lys Thr Val Ala Lys Pro Lys Gly Pro Ser Gly Ser
         35                  40                  45

Pro Trp Tyr Gly Ser Asp Arg Val Lys Tyr Leu Gly Pro Phe Ser Gly
 50                  55                  60

Glu Ser Pro Ser Tyr Leu Thr Gly Glu Phe Pro Gly Asp Tyr Gly Trp
 65                  70                  75                  80

Asp Thr Ala Gly Leu Ser Ala Asp Pro Glu Thr Phe Ala Arg Asn Arg
                 85                  90                  95

Glu Leu Glu Val Ile His Ser Arg Trp Ala Met Leu Gly Ala Leu Gly
            100                 105                 110

Cys Val Phe Pro Glu Leu Leu Ala Arg Asn Gly Val Lys Phe Gly Glu
        115                 120                 125

Ala Val Trp Phe Lys Ala Gly Ser Gln Ile Phe Ser Asp Gly Gly Leu
    130                 135                 140

Asp Tyr Leu Gly Asn Pro Ser Leu Val His Ala Gln Ser Ile Leu Ala
145                 150                 155                 160

Ile Trp Ala Thr Gln Val Ile Leu Met Gly Ala Val Glu Gly Tyr Arg
                165                 170                 175

Val Ala Gly Asn Gly Pro Leu Gly Glu Ala Glu Asp Leu Leu Tyr Pro
            180                 185                 190

Gly Gly Ser Phe Asp Pro Leu Gly Leu Ala Thr Asp Pro Glu Ala Phe
        195                 200                 205

Ala Glu Leu Lys Val Lys Glu Leu Lys Asn Gly Arg Leu Ala Met Phe
    210                 215                 220

Ser Met Phe Gly Phe Phe Val Gln Ala Ile Val Thr Gly Lys Gly Pro
225                 230                 235                 240

Ile Glu Asn Leu Ala Asp His Leu Ala Asp Pro Val Asn Asn Asn Ala
                245                 250                 255

Trp Ala Phe Ala Thr Asn Phe Val Pro Gly Lys
            260                 265
```

<210> SEQ ID NO 99
<211> LENGTH: 855
<212> TYPE: DNA
<213> ORGANISM: Arabidopsis thaliana
<220> FEATURE:
<221> NAME/KEY: CDS
<222> LOCATION: (15)...(164)
<220> FEATURE:
<221> NAME/KEY: CDS
<222> LOCATION: (257)...(305)
<220> FEATURE:
<221> NAME/KEY: CDS
<222> LOCATION: (416)...(843)

<400> SEQUENCE: 99

```
cacagtatta acaa atg gca gga atc aaa gtt ttc ggt cac cca gct tcc        50
              Met Ala Gly Ile Lys Val Phe Gly His Pro Ala Ser
                1               5                  10 aca gcc act aga aga gtt ctc atc gct ctt cac gag aag aat gtc gac        98
Thr Ala Thr Arg Arg Val Leu Ile Ala Leu His Glu Lys Asn Val Asp
        15                  20                  25 ttt gaa ttc gtt cat gtc gag ctc aaa gat ggt gaa cac aag aaa gag       146
Phe Glu Phe Val His Val Glu Leu Lys Asp Gly Glu His Lys Lys Glu
    30                  35                  40 cct ttc atc ctt cgc aac gtgagtacat ataacatctg tcaagccaaa              194
Pro Phe Ile Leu Arg Asn
45                  50 atattgtatt tcatctagat actgaatctt ggtcttaaca atcttgaata atgttttgc       254 ag ccc ttt ggt aaa gtt cca gcc ttt gaa gat gga gac ttc aag att        301
   Pro Phe Gly Lys Val Pro Ala Phe Glu Asp Gly Asp Phe Lys Ile
             55                  60                  65 ttc g gtaaatacaa atatatatca ttatagtcat gtttacaaat ttttggtttt          355
Phe atgatcattg caataataga aagcagaaac actcaaaaat gttttttttt tggtgggcag      415 aa tca aga gca att act caa tac ata gct cat gaa ttc tca gac aaa        462
   Ser Arg Ala Ile Thr Gln Tyr Ile Ala His Glu Phe Ser Asp Lys
Glu
        70                  75                  80 gga aac aac ctt ctc tca act ggc aag gac atg gcg atc ata gcc atg       510
Gly Asn Asn Leu Leu Ser Thr Gly Lys Asp Met Ala Ile Ile Ala Met
        85                  90                  95 ggc att gaa att gag tcg cat gag ttt gac cca gtt ggt tca aag ctt       558
Gly Ile Glu Ile Glu Ser His Glu Phe Asp Pro Val Gly Ser Lys Leu
    100                 105                 110 gtt tgg gag caa gtc tta aag cct ttg tat ggt atg acc aca gac aaa       606
Val Trp Glu Gln Val Leu Lys Pro Leu Tyr Gly Met Thr Thr Asp Lys
115                 120                 125                 130 act gtt gtt gaa gaa gaa gag gct aag cta gcc aaa gtc ctc gat gtt       654
Thr Val Val Glu Glu Glu Glu Ala Lys Leu Ala Lys Val Leu Asp Val
            135                 140                 145 tac gaa cac agg ctt ggt gag tcc aag tat ttg gct tct gac cac ttc       702
Tyr Glu His Arg Leu Gly Glu Ser Lys Tyr Leu Ala Ser Asp His Phe
                150                 155                 160 act ttg gtc gat ctt cac act atc cct gtg att caa tac tta ctt gga      750
Thr Leu Val Asp Leu His Thr Ile Pro Val Ile Gln Tyr Leu Leu Gly
        165                 170                 175 act cca act aag aaa ctc ttc gac gag cgt cca cat gtg agt gct tgg       798
Thr Pro Thr Lys Lys Leu Phe Asp Glu Arg Pro His Val Ser Ala Trp
    180                 185                 190 gtt gct gac atc act tca agg cct tct gct cag aag gtt ctt taa          843
Val Ala Asp Ile Thr Ser Arg Pro Ser Ala Gln Lys Val Leu  *
195                 200                 205 gtgaatctca aa                                                         855

<210> SEQ ID NO 100
<211> LENGTH: 208
<212> TYPE: PRT
<213> ORGANISM: Arabidopsis thaliana

<400> SEQUENCE: 100

Met Ala Gly Ile Lys Val Phe Gly His Pro Ala Ser Thr Ala Thr Arg
1               5                  10                  15

Arg Val Leu Ile Ala Leu His Glu Lys Asn Val Asp Phe Glu Phe Val
            20                  25                  30
```

His Val Glu Leu Lys Asp Gly Glu His Lys Lys Glu Pro Phe Ile Leu
         35                  40                  45

Arg Asn Pro Phe Gly Lys Val Pro Ala Phe Glu Asp Gly Asp Phe Lys
 50                  55                  60

Ile Phe Glu Ser Arg Ala Ile Thr Gln Tyr Ile Ala His Glu Phe Ser
 65                  70                  75                  80

Asp Lys Gly Asn Asn Leu Leu Ser Thr Gly Lys Asp Met Ala Ile Ile
                 85                  90                  95

Ala Met Gly Ile Glu Ile Glu Ser His Glu Phe Asp Pro Val Gly Ser
             100                 105                 110

Lys Leu Val Trp Glu Gln Val Leu Lys Pro Leu Tyr Gly Met Thr Thr
         115                 120                 125

Asp Lys Thr Val Val Glu Glu Glu Ala Lys Leu Ala Lys Val Leu
 130                 135                 140

Asp Val Tyr Glu His Arg Leu Gly Glu Ser Lys Tyr Leu Ala Ser Asp
145                 150                 155                 160

His Phe Thr Leu Val Asp Leu His Thr Ile Pro Val Ile Gln Tyr Leu
                165                 170                 175

Leu Gly Thr Pro Thr Lys Lys Leu Phe Asp Glu Arg Pro His Val Ser
            180                 185                 190

Ala Trp Val Ala Asp Ile Thr Ser Arg Pro Ser Ala Gln Lys Val Leu
        195                 200                 205

<210> SEQ ID NO 101
<211> LENGTH: 512
<212> TYPE: DNA
<213> ORGANISM: Arabidopsis thaliana
<220> FEATURE:
<221> NAME/KEY: CDS
<222> LOCATION: (12)...(67)
<220> FEATURE:
<221> NAME/KEY: CDS
<222> LOCATION: (241)...(309)
<220> FEATURE:
<221> NAME/KEY: CDS
<222> LOCATION: (417)...(492)

<400> SEQUENCE: 101

```
tatctgaaaa a atg tca gag acc aac aag aat gcc ttc caa gcc ggt cag    50
           Met Ser Glu Thr Asn Lys Asn Ala Phe Gln Ala Gly Gln
             1               5                  10 acc gct ggc aaa gct ga ggtactactc tttctctctt tgacagaact             97
Thr Ala Gly Lys Ala Glu
         15 cttaaactgg aaaaattgtt gaagctataa ctctttgaaa acagttgaaa cttgatcatt   157 actagaaatt tcagttactt gtttaattta gtttgtcgta attatgtaat tgatgatttt   217 atggttacaa tggttgtcat gta g gag aag agc aat gtt ctg ctg gac aag    268
                        Glu Lys Ser Asn Val Leu Leu Asp Lys
                         20                  25 gcc aag gat gct gca gct ggt gct gga gct gga gca caa ca ggtaaacaat  319
Ala Lys Asp Ala Ala Ala Gly Ala Gly Ala Gly Ala Gln Gln
 30                  35                  40 ccatacacag acacataaca tataatatgt aacgaaataa acgtctttgt aagcttacat   379
gtacgcagat ttctgatatg gttatgtata tgttata g gcg gga aag agt gta     432
                                         Ala Gly Lys Ser Val
                                                         45 tcg gat gcg gca gcg gga ggt gtt aac ttc gtg aag gac aag acc ggc    480
Ser Asp Ala Ala Ala Gly Gly Val Asn Phe Val Lys Asp Lys Thr Gly
```

```
                   50                  55                  60
ctg aac aag tag agattcgggt caaatttggg                                    512
Leu Asn Lys *
     65

<210> SEQ ID NO 102
<211> LENGTH: 66
<212> TYPE: PRT
<213> ORGANISM: Arabidopsis thaliana

<400> SEQUENCE: 102

Met Ser Glu Thr Asn Lys Asn Ala Phe Gln Ala Gly Gln Thr Ala Gly
 1               5                  10                  15

Lys Ala Glu Lys Ser Asn Val Leu Leu Asp Lys Ala Lys Asp Ala
            20                  25                  30

Ala Ala Gly Ala Gly Ala Gly Ala Gln Gln Ala Gly Lys Ser Val Ser
        35                  40                  45

Asp Ala Ala Gly Gly Val Asn Phe Val Lys Asp Lys Thr Gly Leu
    50                  55                  60

Asn Lys
65

<210> SEQ ID NO 103
<211> LENGTH: 1138
<212> TYPE: DNA
<213> ORGANISM: Arabidopsis thaliana
<220> FEATURE:
<221> NAME/KEY: CDS
<222> LOCATION: (11)...(1123)

<400> SEQUENCE: 103
aaaacaaaaa atg gcg act ttg gtt gat cct cct aat ggg ata agg aat       49
            Met Ala Thr Leu Val Asp Pro Pro Asn Gly Ile Arg Asn
             1               5                  10 gaa ggg aag cat tac ttc tca atg tgg caa act ctg ttc gag atc gac      97
Glu Gly Lys His Tyr Phe Ser Met Trp Gln Thr Leu Phe Glu Ile Asp
     15                  20                  25 act aag tac atg cct atc aag cct att ggt cgt gga gct tac ggt gtt     145
Thr Lys Tyr Met Pro Ile Lys Pro Ile Gly Arg Gly Ala Tyr Gly Val
 30                  35                  40                  45 gtc tgc tcc tct gtt aac agt gac acc aac gag aaa gtt gct atc aag     193
Val Cys Ser Ser Val Asn Ser Asp Thr Asn Glu Lys Val Ala Ile Lys
                 50                  55                  60 aag att cac aat gtt tat gag aat agg atc gat gcg ttg agg act ctt     241
Lys Ile His Asn Val Tyr Glu Asn Arg Ile Asp Ala Leu Arg Thr Leu
             65                  70                  75 cgg gag ctc aag ctt cta cgc cat ctt cga cat gag aat gtc att gct     289
Arg Glu Leu Lys Leu Leu Arg His Leu Arg His Glu Asn Val Ile Ala
         80                  85                  90 ttg aaa gat gtc atg atg cca att cat aag atg agc ttc aag gat gtt     337
Leu Lys Asp Val Met Met Pro Ile His Lys Met Ser Phe Lys Asp Val
     95                 100                 105 tat ctt gtt tat gag ctc atg gac act gat ctc cac cag att atc aag     385
Tyr Leu Val Tyr Glu Leu Met Asp Thr Asp Leu His Gln Ile Ile Lys
110                 115                 120                 125 tct tct cag cgt ctt agt aac gat cat tgc caa tac ttc ttg ttc cag     433
Ser Ser Gln Arg Leu Ser Asn Asp His Cys Gln Tyr Phe Leu Phe Gln
                130                 135                 140 ttg ctt cga ggg ctc aag tat att cat tca gcc aat atc ctg cac cga     481
Leu Leu Arg Gly Leu Lys Tyr Ile His Ser Ala Asn Ile Leu His Arg
            145                 150                 155
```

```
gat ttg aaa cct ggt aac ctt ctt gtc aac gca aac tgc gat tta aag         529
Asp Leu Lys Pro Gly Asn Leu Leu Val Asn Ala Asn Cys Asp Leu Lys
            160                 165                 170 ata tgc gat ttt gga cta gcg cgt gcg agc aac acc aag ggt cag ttc         577
Ile Cys Asp Phe Gly Leu Ala Arg Ala Ser Asn Thr Lys Gly Gln Phe
175                 180                 185 atg act gaa tat gtt gtg act cgt tgg tac cga gcc cca gag ctt ctc         625
Met Thr Glu Tyr Val Val Thr Arg Trp Tyr Arg Ala Pro Glu Leu Leu
190                 195                 200                 205 ctc tgt tgt gac aac tat gga aca tcc att gat gtt tgg tct gtt ggt         673
Leu Cys Cys Asp Asn Tyr Gly Thr Ser Ile Asp Val Trp Ser Val Gly
                210                 215                 220 tgc att ttc gcc gag ctt ctt ggt agg aaa ccg ata ttc caa gga acg         721
Cys Ile Phe Ala Glu Leu Leu Gly Arg Lys Pro Ile Phe Gln Gly Thr
            225                 230                 235 gaa tgt ctt aac cag ctt aag ctc att gtc aac att atc gga agc caa         769
Glu Cys Leu Asn Gln Leu Lys Leu Ile Val Asn Ile Ile Gly Ser Gln
        240                 245                 250 aga gaa gaa gat ctt gag ttc ata gtt aac ccg aaa gct aaa aga tac         817
Arg Glu Glu Asp Leu Glu Phe Ile Val Asn Pro Lys Ala Lys Arg Tyr
    255                 260                 265 att aga tca ctt ccg tac tca cct ggg atg tct tta tcc aga ctt tac         865
Ile Arg Ser Leu Pro Tyr Ser Pro Gly Met Ser Leu Ser Arg Leu Tyr
270                 275                 280                 285 ccg tgc gct cat gta ttg gcc atc gac ctt ctg cag aaa atg ctt gtt         913
Pro Cys Ala His Val Leu Ala Ile Asp Leu Leu Gln Lys Met Leu Val
                290                 295                 300 ttt gat ccg tca aag agg att agt gcc tct gaa gca ctc cag cat cca         961
Phe Asp Pro Ser Lys Arg Ile Ser Ala Ser Glu Ala Leu Gln His Pro
            305                 310                 315 tac atg gcg cca cta tat gac ccg aat gca aac cct cct gct caa gtt        1009
Tyr Met Ala Pro Leu Tyr Asp Pro Asn Ala Asn Pro Pro Ala Gln Val
        320                 325                 330 cct atc gat ctc gat gta gat gag gat ttg aga gag gag atg ata aga        1057
Pro Ile Asp Leu Asp Val Asp Glu Asp Leu Arg Glu Glu Met Ile Arg
335                 340                 345 gaa atg ata tgg aat gag atg ctt cac tac cat cca caa gct tca acc        1105
Glu Met Ile Trp Asn Glu Met Leu His Tyr His Pro Gln Ala Ser Thr
350                 355                 360                 365 tta aac act gag ctc tga gctcaagtct tgttt                               1138
Leu Asn Thr Glu Leu *
        370
```

<210> SEQ ID NO 104
<211> LENGTH: 370
<212> TYPE: PRT
<213> ORGANISM: Arabidopsis thaliana

<400> SEQUENCE: 104

```
Met Ala Thr Leu Val Asp Pro Pro Asn Gly Ile Arg Asn Glu Gly Lys
1               5                   10                  15

His Tyr Phe Ser Met Trp Gln Thr Leu Phe Glu Ile Asp Thr Lys Tyr
            20                  25                  30

Met Pro Ile Lys Pro Ile Gly Arg Gly Ala Tyr Gly Val Val Cys Ser
        35                  40                  45

Ser Val Asn Ser Asp Thr Asn Glu Lys Val Ala Ile Lys Lys Ile His
    50                  55                  60

Asn Val Tyr Glu Asn Arg Ile Asp Ala Leu Arg Thr Leu Arg Glu Leu
65                  70                  75                  80
```

```
Lys Leu Leu Arg His Leu Arg His Glu Asn Val Ile Ala Leu Lys Asp
                85                  90                  95

Val Met Met Pro Ile His Lys Met Ser Phe Lys Asp Val Tyr Leu Val
            100                 105                 110

Tyr Glu Leu Met Asp Thr Asp Leu His Gln Ile Ile Lys Ser Ser Gln
        115                 120                 125

Arg Leu Ser Asn Asp His Cys Gln Tyr Phe Leu Phe Gln Leu Leu Arg
    130                 135                 140

Gly Leu Lys Tyr Ile His Ser Ala Asn Ile Leu His Arg Asp Leu Lys
145                 150                 155                 160

Pro Gly Asn Leu Leu Val Asn Ala Asn Cys Asp Leu Lys Ile Cys Asp
                165                 170                 175

Phe Gly Leu Ala Arg Ala Ser Asn Thr Lys Gly Gln Phe Met Thr Glu
            180                 185                 190

Tyr Val Val Thr Arg Trp Tyr Arg Ala Pro Glu Leu Leu Leu Cys Cys
        195                 200                 205

Asp Asn Tyr Gly Thr Ser Ile Asp Val Trp Ser Val Gly Cys Ile Phe
    210                 215                 220

Ala Glu Leu Leu Gly Arg Lys Pro Ile Phe Gln Gly Thr Glu Cys Leu
225                 230                 235                 240

Asn Gln Leu Lys Leu Ile Val Asn Ile Ile Gly Ser Gln Arg Glu Glu
                245                 250                 255

Asp Leu Glu Phe Ile Val Asn Pro Lys Ala Lys Arg Tyr Ile Arg Ser
            260                 265                 270

Leu Pro Tyr Ser Pro Gly Met Ser Leu Ser Arg Leu Tyr Pro Cys Ala
        275                 280                 285

His Val Leu Ala Ile Asp Leu Leu Gln Lys Met Leu Val Phe Asp Pro
    290                 295                 300

Ser Lys Arg Ile Ser Ala Ser Glu Ala Leu Gln His Pro Tyr Met Ala
305                 310                 315                 320

Pro Leu Tyr Asp Pro Asn Ala Asn Pro Pro Ala Gln Val Pro Ile Asp
                325                 330                 335

Leu Asp Val Asp Glu Asp Leu Arg Glu Glu Met Ile Arg Glu Met Ile
            340                 345                 350

Trp Asn Glu Met Leu His Tyr His Pro Gln Ala Ser Thr Leu Asn Thr
        355                 360                 365

Glu Leu
    370

<210> SEQ ID NO 105
<211> LENGTH: 445
<212> TYPE: DNA
<213> ORGANISM: Arabidopsis thaliana
<220> FEATURE:
<221> NAME/KEY: CDS
<222> LOCATION: (20)...(430)

<400> SEQUENCE: 105
aacaacaatt tcaagagac atg gca ggc aaa ggt gga aaa gga ctc gta gct        52
                    Met Ala Gly Lys Gly Gly Lys Gly Leu Val Ala
                     1               5                  10 gcg aag acg atg gct gct aac aag gac aaa gac aag gac aag aag aaa       100
Ala Lys Thr Met Ala Ala Asn Lys Asp Lys Asp Lys Asp Lys Lys Lys
         15                  20                  25 ccc atc tct cgc tct gct cgt gct ggt att cag ttt cca gtt gga cga       148
Pro Ile Ser Arg Ser Ala Arg Ala Gly Ile Gln Phe Pro Val Gly Arg
```

```
             30                  35                  40
att cac agg caa ctg aag acc cga gtc tcg gca cat ggc aga gtt ggt    196
Ile His Arg Gln Leu Lys Thr Arg Val Ser Ala His Gly Arg Val Gly
     45                  50                  55 gcc act gca gcc gtc tac aca gct tca atc ctg gag tat ctg aca gca    244
Ala Thr Ala Ala Val Tyr Thr Ala Ser Ile Leu Glu Tyr Leu Thr Ala
 60                  65                  70                  75 gag gtt ctt gag ttg gct ggg aat gcg agc aag gat ctc aaa gtg aag    292
Glu Val Leu Glu Leu Ala Gly Asn Ala Ser Lys Asp Leu Lys Val Lys
                 80                  85                  90 agg ata acg cca agg cat ctg cag ttg gcg att aga gga gat gag gag    340
Arg Ile Thr Pro Arg His Leu Gln Leu Ala Ile Arg Gly Asp Glu Glu
             95                 100                 105 ctg gac aca ctc atc aag gga acg att gct gga ggt ggt gtg atc cct    388
Leu Asp Thr Leu Ile Lys Gly Thr Ile Ala Gly Gly Gly Val Ile Pro
         110                 115                 120 cac atc cac aag tct ctc atc aac aaa acc acc aag gag tga             430
His Ile His Lys Ser Leu Ile Asn Lys Thr Thr Lys Glu *
     125                 130                 135 tgtgtagctt tttat                                                    445

<210> SEQ ID NO 106
<211> LENGTH: 136
<212> TYPE: PRT
<213> ORGANISM: Arabidopsis thaliana

<400> SEQUENCE: 106

Met Ala Gly Lys Gly Lys Gly Leu Val Ala Ala Lys Thr Met Ala
 1               5                  10                  15

Ala Asn Lys Asp Lys Asp Lys Asp Lys Lys Pro Ile Ser Arg Ser
             20                  25                  30

Ala Arg Ala Gly Ile Gln Phe Pro Val Gly Arg Ile His Arg Gln Leu
         35                  40                  45

Lys Thr Arg Val Ser Ala His Gly Arg Val Gly Ala Thr Ala Ala Val
     50                  55                  60

Tyr Thr Ala Ser Ile Leu Glu Tyr Leu Thr Ala Glu Val Leu Glu Leu
 65                  70                  75                  80

Ala Gly Asn Ala Ser Lys Asp Leu Lys Val Lys Arg Ile Thr Pro Arg
                 85                  90                  95

His Leu Gln Leu Ala Ile Arg Gly Asp Glu Glu Leu Asp Thr Leu Ile
            100                 105                 110

Lys Gly Thr Ile Ala Gly Gly Gly Val Ile Pro His Ile His Lys Ser
        115                 120                 125

Leu Ile Asn Lys Thr Thr Lys Glu
    130                 135

<210> SEQ ID NO 107
<211> LENGTH: 930
<212> TYPE: DNA
<213> ORGANISM: Arabidopsis thaliana
<220> FEATURE:
<221> NAME/KEY: CDS
<222> LOCATION: (14)...(916)

<400> SEQUENCE: 107
gcctccttgg ctt atg tac tta cca aaa cgt ggc aat ttg ttc gaa ctc     49
               Met Tyr Leu Pro Lys Arg Gly Asn Leu Phe Glu Leu
                1               5                  10 tat gat cca ttg cat cag aag atg tac aca ttg aat cta cct gag ctt    97
```

-continued

| | | |
|---|---|---|
| Tyr Asp Pro Leu His Gln Lys Met Tyr Thr Leu Asn Leu Pro Glu Leu<br>15                    20                    25 | | |
| gcc aaa tct acg gtt tgt tac tca aga gat gga tgg tta cta atg cgt<br>Ala Lys Ser Thr Val Cys Tyr Ser Arg Asp Gly Trp Leu Leu Met Arg<br>    30                    35                    40 | 145 |
| aaa acc att tca aga gaa atg ttc ttc ttc aac ccg ttt act cgt gag<br>Lys Thr Ile Ser Arg Glu Met Phe Phe Phe Asn Pro Phe Thr Arg Glu<br>45                    50                    55                    60 | 193 |
| ctc ata aac gta cca aaa tgt act tta tca tat gat gcg atc gct ttc<br>Leu Ile Asn Val Pro Lys Cys Thr Leu Ser Tyr Asp Ala Ile Ala Phe<br>                    65                    70                    75 | 241 |
| tct tgt gca cct aca tca ggt act tgc gtg ttg cta gca ttt aag cat<br>Ser Cys Ala Pro Thr Ser Gly Thr Cys Val Leu Leu Ala Phe Lys His<br>                80                    85                    90 | 289 |
| gtt tcg tat cgt atc acc act acg agc act tgc cat ccc aaa gca acc<br>Val Ser Tyr Arg Ile Thr Thr Thr Ser Thr Cys His Pro Lys Ala Thr<br>          95                    100                  105 | 337 |
| gag tgg gtt act gag gat cta caa ttc cat cgt cgc ttc cgc agt gaa<br>Glu Trp Val Thr Glu Asp Leu Gln Phe His Arg Arg Phe Arg Ser Glu<br>        110                    115                    120 | 385 |
| aca ctt aac cac agc aat gtt gtc tat gcc aaa cgt cgc ttc tat tgc<br>Thr Leu Asn His Ser Asn Val Val Tyr Ala Lys Arg Arg Phe Tyr Cys<br>125                    130                    135                    140 | 433 |
| ctt gac ggt caa gga agc tta tat tac ttt gat ccg tct tct cga aga<br>Leu Asp Gly Gln Gly Ser Leu Tyr Tyr Phe Asp Pro Ser Ser Arg Arg<br>                    145                    150                    155 | 481 |
| tgg gat ttt agt tac acc tat tta ctg cca tgt cct tat atc tcg gat<br>Trp Asp Phe Ser Tyr Thr Tyr Leu Leu Pro Cys Pro Tyr Ile Ser Asp<br>                160                    165                    170 | 529 |
| aga ttt agt tac cag tat gag cgg aag aag aag aga att ttc ttg gct<br>Arg Phe Ser Tyr Gln Tyr Glu Arg Lys Lys Lys Arg Ile Phe Leu Ala<br>        175                    180                    185 | 577 |
| gtg cgg aaa gga gtg ttc ttt aag ata ttt aca tgt gat ggt gag aag<br>Val Arg Lys Gly Val Phe Phe Lys Ile Phe Thr Cys Asp Gly Glu Lys<br>        190                    195                    200 | 625 |
| ccg ata gtg cat aag tta gaa gat atc aat tgg gag gag atc aat agt<br>Pro Ile Val His Lys Leu Glu Asp Ile Asn Trp Glu Glu Ile Asn Ser<br>205                    210                    215                    220 | 673 |
| act acg att gat gga ttg aca atc ttt acg ggt ctt tat tcc tct gag<br>Thr Thr Ile Asp Gly Leu Thr Ile Phe Thr Gly Leu Tyr Ser Ser Glu<br>                    225                    230                    235 | 721 |
| gtg aga ctt aat cta cca tgg atg agg aat agt gtt tac ttt cct aga<br>Val Arg Leu Asn Leu Pro Trp Met Arg Asn Ser Val Tyr Phe Pro Arg<br>        240                    245                    250 | 769 |
| ctt cgt ttt aat gtc aag cgt tgt gta tca tat tcg ctt gat gaa gag<br>Leu Arg Phe Asn Val Lys Arg Cys Val Ser Tyr Ser Leu Asp Glu Glu<br>        255                    260                    265 | 817 |
| agg tat tat ccg cgg aag cag tgg caa gaa cag gag gat tta tgt cct<br>Arg Tyr Tyr Pro Arg Lys Gln Trp Gln Glu Gln Glu Asp Leu Cys Pro<br>        270                    275                    280 | 865 |
| att gag aat ctt tgg att agg cca ccg aag aaa gct gta gat ttc atg<br>Ile Glu Asn Leu Trp Ile Arg Pro Pro Lys Lys Ala Val Asp Phe Met<br>285                    290                    295                    300 | 913 |
| tga agataaaagt aatg<br> *  | 930 |

<210> SEQ ID NO 108
<211> LENGTH: 300
<212> TYPE: PRT
<213> ORGANISM: Arabidopsis thaliana

<400> SEQUENCE: 108

| | | | | | | | | | | | | | | | |
|---|---|---|---|---|---|---|---|---|---|---|---|---|---|---|---|
|Met|Tyr|Leu|Pro|Lys|Arg|Gly|Asn|Leu|Phe|Glu|Leu|Tyr|Asp|Pro|Leu|
|1| | | |5| | | |10| | | |15| | | |

| | | | | | | | | | | | | | | | |
|---|---|---|---|---|---|---|---|---|---|---|---|---|---|---|---|
|His|Gln|Lys|Met|Tyr|Thr|Leu|Asn|Leu|Pro|Glu|Leu|Ala|Lys|Ser|Thr|
| | | |20| | | | |25| | | | |30| | |

| | | | | | | | | | | | | | | | |
|---|---|---|---|---|---|---|---|---|---|---|---|---|---|---|---|
|Val|Cys|Tyr|Ser|Arg|Asp|Gly|Trp|Leu|Leu|Met|Arg|Lys|Thr|Ile|Ser|
| | | |35| | | | |40| | | | |45| | |

| | | | | | | | | | | | | | | | |
|---|---|---|---|---|---|---|---|---|---|---|---|---|---|---|---|
|Arg|Glu|Met|Phe|Phe|Phe|Asn|Pro|Phe|Thr|Arg|Glu|Leu|Ile|Asn|Val|
| |50| | | | |55| | | | |60| | | | |

| | | | | | | | | | | | | | | | |
|---|---|---|---|---|---|---|---|---|---|---|---|---|---|---|---|
|Pro|Lys|Cys|Thr|Leu|Ser|Tyr|Asp|Ala|Ile|Ala|Phe|Ser|Cys|Ala|Pro|
|65| | | | |70| | | | |75| | | | |80|

| | | | | | | | | | | | | | | | |
|---|---|---|---|---|---|---|---|---|---|---|---|---|---|---|---|
|Thr|Ser|Gly|Thr|Cys|Val|Leu|Leu|Ala|Phe|Lys|His|Val|Ser|Tyr|Arg|
| | | | |85| | | | |90| | | | |95| |

| | | | | | | | | | | | | | | | |
|---|---|---|---|---|---|---|---|---|---|---|---|---|---|---|---|
|Ile|Thr|Thr|Thr|Ser|Thr|Cys|His|Pro|Lys|Ala|Thr|Glu|Trp|Val|Thr|
| | | | |100| | | | |105| | | | |110| |

| | | | | | | | | | | | | | | | |
|---|---|---|---|---|---|---|---|---|---|---|---|---|---|---|---|
|Glu|Asp|Leu|Gln|Phe|His|Arg|Arg|Phe|Arg|Ser|Glu|Thr|Leu|Asn|His|
| | | | |115| | | | |120| | | | |125| |

| | | | | | | | | | | | | | | | |
|---|---|---|---|---|---|---|---|---|---|---|---|---|---|---|---|
|Ser|Asn|Val|Val|Tyr|Ala|Lys|Arg|Arg|Phe|Tyr|Cys|Leu|Asp|Gly|Gln|
| |130| | | | |135| | | | |140| | | | |

| | | | | | | | | | | | | | | | |
|---|---|---|---|---|---|---|---|---|---|---|---|---|---|---|---|
|Gly|Ser|Leu|Tyr|Tyr|Phe|Asp|Pro|Ser|Ser|Arg|Arg|Trp|Asp|Phe|Ser|
|145| | | | |150| | | | |155| | | | |160|

| | | | | | | | | | | | | | | | |
|---|---|---|---|---|---|---|---|---|---|---|---|---|---|---|---|
|Tyr|Thr|Tyr|Leu|Leu|Pro|Cys|Pro|Tyr|Ile|Ser|Asp|Arg|Phe|Ser|Tyr|
| | | | |165| | | | |170| | | | |175| |

| | | | | | | | | | | | | | | | |
|---|---|---|---|---|---|---|---|---|---|---|---|---|---|---|---|
|Gln|Tyr|Glu|Arg|Lys|Lys|Arg|Ile|Phe|Leu|Ala|Val|Arg|Lys|Gly|
| | | | |180| | | | |185| | | | |190| |

| | | | | | | | | | | | | | | | |
|---|---|---|---|---|---|---|---|---|---|---|---|---|---|---|---|
|Val|Phe|Phe|Lys|Ile|Phe|Thr|Cys|Asp|Gly|Glu|Lys|Pro|Ile|Val|His|
| | | |195| | | | |200| | | | |205| | |

| | | | | | | | | | | | | | | | |
|---|---|---|---|---|---|---|---|---|---|---|---|---|---|---|---|
|Lys|Leu|Glu|Asp|Ile|Asn|Trp|Glu|Glu|Ile|Asn|Ser|Thr|Thr|Ile|Asp|
| |210| | | | |215| | | | |220| | | | |

| | | | | | | | | | | | | | | | |
|---|---|---|---|---|---|---|---|---|---|---|---|---|---|---|---|
|Gly|Leu|Thr|Ile|Phe|Thr|Gly|Leu|Tyr|Ser|Ser|Glu|Val|Arg|Leu|Asn|
|225| | | | |230| | | | |235| | | | |240|

| | | | | | | | | | | | | | | | |
|---|---|---|---|---|---|---|---|---|---|---|---|---|---|---|---|
|Leu|Pro|Trp|Met|Arg|Asn|Ser|Val|Tyr|Phe|Pro|Arg|Leu|Arg|Phe|Asn|
| | | | |245| | | | |250| | | | |255| |

| | | | | | | | | | | | | | | | |
|---|---|---|---|---|---|---|---|---|---|---|---|---|---|---|---|
|Val|Lys|Arg|Cys|Val|Ser|Tyr|Ser|Leu|Asp|Glu|Glu|Arg|Tyr|Tyr|Pro|
| | | |260| | | | |265| | | | |270| | |

| | | | | | | | | | | | | | | | |
|---|---|---|---|---|---|---|---|---|---|---|---|---|---|---|---|
|Arg|Lys|Gln|Trp|Gln|Glu|Gln|Glu|Asp|Leu|Cys|Pro|Ile|Glu|Asn|Leu|
| | |275| | | | |280| | | | |285| | | |

| | | | | | | | | |
|---|---|---|---|---|---|---|---|---|
|Trp|Ile|Arg|Pro|Pro|Lys|Lys|Ala|Val|Asp|Phe|Met|
| | |290| | | | |295| | | | |300|

<210> SEQ ID NO 109
<211> LENGTH: 2639
<212> TYPE: DNA
<213> ORGANISM: Arabidopsis thaliana
<220> FEATURE:
<221> NAME/KEY: CDS
<222> LOCATION: (145)...(981)
<220> FEATURE:
<221> NAME/KEY: CDS
<222> LOCATION: (1439)...(1727)
<220> FEATURE:
<221> NAME/KEY: CDS
<222> LOCATION: (1817)...(2126)
<220> FEATURE:
<221> NAME/KEY: CDS
<222> LOCATION: (2204)...(2330)
<220> FEATURE:
<221> NAME/KEY: CDS -continued

<222> LOCATION: (2405)...(2518)

<400> SEQUENCE: 109

| | | |
|---|---|---|
| tccacggcta caaaagaaca ttctcgacat acacaaaaaa attcgaaatt tcgagaactc | | 60 |
| tcttgtgcct tcttcttcat cttcctctgt ttttaaaaat gcaatcaagc agattctcac | | 120 |

| | | |
|---|---|---|
| gatacctaaa ccaaatccaa ttca atg gcg gaa gaa gca aaa tcc aaa gga | | 171 |
| Met Ala Glu Glu Ala Lys Ser Lys Gly | | |
| 1 5 | | |

| aac gca gct ttc tct tcc ggc gat tac gcc acc gca ata acc cat ttc | 219 |
|---|---|
| Asn Ala Ala Phe Ser Ser Gly Asp Tyr Ala Thr Ala Ile Thr His Phe | |
| 10 15 20 25 | |

| aca gaa gca atc aac ctt tca cca acc aat cac atc ctc tac tca aac | 267 |
|---|---|
| Thr Glu Ala Ile Asn Leu Ser Pro Thr Asn His Ile Leu Tyr Ser Asn | |
| 30 35 40 | |

| aga tcc gct tct tac gct tct ctc cac cgt tac gaa gaa gct tta tca | 315 |
|---|---|
| Arg Ser Ala Ser Tyr Ala Ser Leu His Arg Tyr Glu Glu Ala Leu Ser | |
| 45 50 55 | |

| gac gcg aag aag act ata gag ctt aaa cct gat tgg tct aaa gga tat | 363 |
|---|---|
| Asp Ala Lys Lys Thr Ile Glu Leu Lys Pro Asp Trp Ser Lys Gly Tyr | |
| 60 65 70 | |

| agc cga tta ggt gct gcg ttt att gga ttg tcc aag ttt gat gaa gcg | 411 |
|---|---|
| Ser Arg Leu Gly Ala Ala Phe Ile Gly Leu Ser Lys Phe Asp Glu Ala | |
| 75 80 85 | |

| gtt gat tcg tat aag aaa gga tta gag att gat ccg agt aat gag atg | 459 |
|---|---|
| Val Asp Ser Tyr Lys Lys Gly Leu Glu Ile Asp Pro Ser Asn Glu Met | |
| 90 95 100 105 | |

| ctt aaa tcg gga tta gct gat gct tcg aga tct agg gtt tcg tca aag | 507 |
|---|---|
| Leu Lys Ser Gly Leu Ala Asp Ala Ser Arg Ser Arg Val Ser Ser Lys | |
| 110 115 120 | |

| tcg aat cct ttt gtt gat gcg ttt caa ggg aag gag atg tgg gag aag | 555 |
|---|---|
| Ser Asn Pro Phe Val Asp Ala Phe Gln Gly Lys Glu Met Trp Glu Lys | |
| 125 130 135 | |

| ttg acg gcg gat ccg ggg act agg gtt tat ttg gag cag gat gat ttt | 603 |
|---|---|
| Leu Thr Ala Asp Pro Gly Thr Arg Val Tyr Leu Glu Gln Asp Asp Phe | |
| 140 145 150 | |

| gtt aag acg atg aag gag att cag agg aac cct aat aat ctt aat ttg | 651 |
|---|---|
| Val Lys Thr Met Lys Glu Ile Gln Arg Asn Pro Asn Asn Leu Asn Leu | |
| 155 160 165 | |

| tat atg aag gat aag aga gtt atg aag gct tta ggg gtt ttg ttg aat | 699 |
|---|---|
| Tyr Met Lys Asp Lys Arg Val Met Lys Ala Leu Gly Val Leu Leu Asn | |
| 170 175 180 185 | |

| gtg aag ttt ggt gga tct agt ggt gaa gat act gag atg aag gag gct | 747 |
|---|---|
| Val Lys Phe Gly Gly Ser Ser Gly Glu Asp Thr Glu Met Lys Glu Ala | |
| 190 195 200 | |

| gat gag agg aaa gag cct gaa ccg gag atg gaa cct atg gag ttg acg | 795 |
|---|---|
| Asp Glu Arg Lys Glu Pro Glu Pro Glu Met Glu Pro Met Glu Leu Thr | |
| 205 210 215 | |

| gag gag gag agg cag aag aag gag aga aag gag aag gct ttg aag gag | 843 |
|---|---|
| Glu Glu Glu Arg Gln Lys Lys Glu Arg Lys Glu Lys Ala Leu Lys Glu | |
| 220 225 230 | |

| aaa ggg gaa gga aat gtt gct tat aag aag aag gat ttt ggg aga gct | 891 |
|---|---|
| Lys Gly Glu Gly Asn Val Ala Tyr Lys Lys Lys Asp Phe Gly Arg Ala | |
| 235 240 245 | |

| gtt gaa cat tat act aag gcc atg gag ctc gat gat gag gat att tcg | 939 |
|---|---|
| Val Glu His Tyr Thr Lys Ala Met Glu Leu Asp Asp Glu Asp Ile Ser | |
| 250 255 260 265 | |

| tat ttg acg aat cgt gct gct gtt tat ctt gag atg ggg aag | 981 |
|---|---|
| Tyr Leu Thr Asn Arg Ala Ala Val Tyr Leu Glu Met Gly Lys | |
| 270 275 | |

-continued

```
gtattaagtc ttatacttgg cttaaaagtt aaacctttag gtactttaag attaaggagg       1041
agatcttggg ttcttgaagt agcttatctg tttagtatag cttgtcacta gttagtacat       1101
ttgtgatgac cttgatgggt tttgataact ttcatctgct tcttgttgga gatttaagag       1161
ttttgaactt aagttttcac ttgtgctgaa agtagttagc tttagatgag gtagaaattt       1221
agggtttatg gcttcatgat ggagtttatt cacttgttct gtagaagtgg ttatctttat       1281
tattactgga atcaattaat cttcaagtat cctgagtggt tcaattccat tggtctatgt       1341
gttcttgcat tagtcttgtt taattaacag ttggttcatc tggatcttac tgtatcttgt       1401
gtgatgtttt acttcatttc tcaaatgaaa ttatcag tac gag gag tgc att gaa        1456
                                           Tyr Glu Glu Cys Ile Glu
                                                   280         285 gac tgt gac aag gct gtt gaa aga ggc aga gaa ctt cgt tct gac ttc         1504
Asp Cys Asp Lys Ala Val Glu Arg Gly Arg Glu Leu Arg Ser Asp Phe
                290                 295                 300 aag atg ata gca aga gct ctg act aga aaa gga tct gct cta gtg aaa         1552
Lys Met Ile Ala Arg Ala Leu Thr Arg Lys Gly Ser Ala Leu Val Lys
            305                 310                 315 atg gcg aga tgc tcg aaa gac ttt gag cct gcg att gag act ttc cag         1600
Met Ala Arg Cys Ser Lys Asp Phe Glu Pro Ala Ile Glu Thr Phe Gln
        320                 325                 330 aaa gct ctt aca gag cat cgt aat cca gat aca ttg aag aaa ctg aac         1648
Lys Ala Leu Thr Glu His Arg Asn Pro Asp Thr Leu Lys Lys Leu Asn
    335                 340                 345 gat gct gag aaa gtc aag aaa gag ctg gag caa cag gag tac ttt gat         1696
Asp Ala Glu Lys Val Lys Lys Glu Leu Glu Gln Gln Glu Tyr Phe Asp
350                 355                 360                 365 cct acg ata gcc gag gag gag cga gag aaa g gtatatatac tgatcctcag         1747
Pro Thr Ile Ala Glu Glu Glu Arg Glu Lys
                370                 375 ttacacttac tatcttgaaa cgtgatttga ttttaggatt aagcatttga cacttcttca       1807 ttgatgcag gt aat gga ttc ttt aaa gaa caa aag tat cca gag gca gtg        1857
            Gly Asn Gly Phe Phe Lys Glu Gln Lys Tyr Pro Glu Ala Val
                380                         385 aag cat tat tca gaa gca atc aaa aga aac ccg aac gac gtg agg gca         1905
Lys His Tyr Ser Glu Ala Ile Lys Arg Asn Pro Asn Asp Val Arg Ala
390                 395                 400                 405 tat agc aac aga gct gct tgt tac aca aag tta gga gca tta cca gag         1953
Tyr Ser Asn Arg Ala Ala Cys Tyr Thr Lys Leu Gly Ala Leu Pro Glu
                410                 415                 420 gga ttg aaa gat gct gaa aaa tgc att gag ctg gac cca agt ttc acg         2001
Gly Leu Lys Asp Ala Glu Lys Cys Ile Glu Leu Asp Pro Ser Phe Thr
            425                 430                 435 aaa gga tac agt aga aaa gga gct att caa ttt ttc atg aag gaa tac         2049
Lys Gly Tyr Ser Arg Lys Gly Ala Ile Gln Phe Phe Met Lys Glu Tyr
        440                 445                 450 gat aaa gct atg gaa acg tat caa gaa ggg cta aaa cat gat cct aag         2097
Asp Lys Ala Met Glu Thr Tyr Gln Glu Gly Leu Lys His Asp Pro Lys
    455                 460                 465 aac cag gag ttc ctt gat ggt gtt aga ag gtttgcaaat tttggcattc            2146
Asn Gln Glu Phe Leu Asp Gly Val Arg Arg
470                 475 tctctttgtt gtttaacctt gcaaagatcg gtctagtgaa agtgttgttg ttttcag a        2204 tgt gtg gaa cag ata aac aaa gcg agc cgt ggt gat ctg act cca gaa         2252
Cys Val Glu Gln Ile Asn Lys Ala Ser Arg Gly Asp Leu Thr Pro Glu
480                 485                 490                 495
```

```
gaa ttg aag gag aga caa gca aag gca atg caa gat cct gaa gtt cag    2300
Glu Leu Lys Glu Arg Gln Ala Lys Ala Met Gln Asp Pro Glu Val Gln
            500                 505                 510 aac ata tta tcg gat cca gtg atg aga cag gtaaaagcag tggcaagcat      2350
Asn Ile Leu Ser Asp Pro Val Met Arg Gln
            515                 520 tgtgttctaa ctcgtaagct gtctgtgaga cttgtgtgat gatgtctatt gtag gta    2407
                                                             Val cta gtg gac ttt caa gag aat ccg aaa gct gca caa gag cat atg aag    2455
Leu Val Asp Phe Gln Glu Asn Pro Lys Ala Ala Gln Glu His Met Lys
            525                 530                 535 aac cca atg gta atg aac aag att cag aag ctg gtt agt gcc gga att    2503
Asn Pro Met Val Met Asn Lys Ile Gln Lys Leu Val Ser Ala Gly Ile
            540                 545                 550 gtt cag gtc cgg taa attgttatgc taaaccggag tggtatattg aatcaaaccg    2558
Val Gln Val Arg *
555 aagatgtttc caaattttca ctgcgttctt ttgggctttt gttaaactga tgaaactctg  2618 atttggtttg ggtcatgttt g                                            2639

<210> SEQ ID NO 110
<211> LENGTH: 558
<212> TYPE: PRT
<213> ORGANISM: Arabidopsis thaliana

<400> SEQUENCE: 110

Met Ala Glu Glu Ala Lys Ser Lys Gly Asn Ala Ala Phe Ser Ser Gly
 1               5                   10                  15

Asp Tyr Ala Thr Ala Ile Thr His Phe Thr Glu Ala Ile Asn Leu Ser
            20                  25                  30

Pro Thr Asn His Ile Leu Tyr Ser Asn Arg Ser Ala Ser Tyr Ala Ser
        35                  40                  45

Leu His Arg Tyr Glu Glu Ala Leu Ser Asp Ala Lys Lys Thr Ile Glu
    50                  55                  60

Leu Lys Pro Asp Trp Ser Lys Gly Tyr Ser Arg Leu Gly Ala Ala Phe
65                  70                  75                  80

Ile Gly Leu Ser Lys Phe Asp Glu Ala Val Asp Ser Tyr Lys Lys Gly
                85                  90                  95

Leu Glu Ile Asp Pro Ser Asn Glu Met Leu Lys Ser Gly Leu Ala Asp
            100                 105                 110

Ala Ser Arg Ser Arg Val Ser Ser Lys Ser Asn Pro Phe Val Asp Ala
        115                 120                 125

Phe Gln Gly Lys Glu Met Trp Glu Lys Leu Thr Ala Asp Pro Gly Thr
    130                 135                 140

Arg Val Tyr Leu Glu Gln Asp Phe Val Lys Thr Met Lys Glu Ile
145                 150                 155                 160

Gln Arg Asn Pro Asn Asn Leu Asn Leu Tyr Met Lys Asp Lys Arg Val
                165                 170                 175

Met Lys Ala Leu Gly Val Leu Leu Asn Val Lys Phe Gly Gly Ser Ser
            180                 185                 190

Gly Glu Asp Thr Glu Met Lys Glu Ala Asp Glu Arg Lys Glu Pro Glu
        195                 200                 205

Pro Glu Met Glu Pro Met Glu Leu Thr Glu Glu Arg Gln Lys Lys
    210                 215                 220

Glu Arg Lys Glu Lys Ala Leu Lys Glu Lys Gly Glu Gly Asn Val Ala
225                 230                 235                 240
```

```
Tyr Lys Lys Lys Asp Phe Gly Arg Ala Val Glu His Tyr Thr Lys Ala
            245                 250                 255
Met Glu Leu Asp Asp Glu Asp Ile Ser Tyr Leu Thr Asn Arg Ala Ala
            260                 265                 270
Val Tyr Leu Glu Met Gly Lys Tyr Glu Glu Cys Ile Glu Asp Cys Asp
            275                 280                 285
Lys Ala Val Glu Arg Gly Arg Glu Leu Arg Ser Asp Phe Lys Met Ile
            290                 295                 300
Ala Arg Ala Leu Thr Arg Lys Gly Ser Ala Leu Val Lys Met Ala Arg
305                 310                 315                 320
Cys Ser Lys Asp Phe Glu Pro Ala Ile Glu Thr Phe Gln Lys Ala Leu
            325                 330                 335
Thr Glu His Arg Asn Pro Asp Thr Leu Lys Lys Leu Asn Asp Ala Glu
            340                 345                 350
Lys Val Lys Lys Glu Leu Glu Gln Gln Glu Tyr Phe Asp Pro Thr Ile
            355                 360                 365
Ala Glu Glu Glu Arg Glu Lys Gly Asn Gly Phe Phe Lys Glu Gln Lys
            370                 375                 380
Tyr Pro Glu Ala Val Lys His Tyr Ser Glu Ala Ile Lys Arg Asn Pro
385                 390                 395                 400
Asn Asp Val Arg Ala Tyr Ser Asn Arg Ala Ala Cys Tyr Thr Lys Leu
            405                 410                 415
Gly Ala Leu Pro Glu Gly Leu Lys Asp Ala Glu Lys Cys Ile Glu Leu
            420                 425                 430
Asp Pro Ser Phe Thr Lys Gly Tyr Ser Arg Lys Gly Ala Ile Gln Phe
            435                 440                 445
Phe Met Lys Glu Tyr Asp Lys Ala Met Glu Thr Tyr Gln Glu Gly Leu
            450                 455                 460
Lys His Asp Pro Lys Asn Gln Glu Phe Leu Asp Gly Val Arg Arg Cys
465                 470                 475                 480
Val Glu Gln Ile Asn Lys Ala Ser Arg Gly Asp Leu Thr Pro Glu Glu
            485                 490                 495
Leu Lys Glu Arg Gln Ala Lys Ala Met Gln Asp Pro Glu Val Gln Asn
            500                 505                 510
Ile Leu Ser Asp Pro Val Met Arg Gln Val Leu Val Asp Phe Gln Glu
            515                 520                 525
Asn Pro Lys Ala Ala Gln Glu His Met Lys Asn Pro Met Val Met Asn
            530                 535                 540
Lys Ile Gln Lys Leu Val Ser Ala Gly Ile Val Gln Val Arg
545                 550                 555
```

<210> SEQ ID NO 111
<211> LENGTH: 1560
<212> TYPE: DNA
<213> ORGANISM: Arabidopsis thaliana
<220> FEATURE:
<221> NAME/KEY: CDS
<222> LOCATION: (130)...(265)
<220> FEATURE:
<221> NAME/KEY: CDS
<222> LOCATION: (386)...(515)
<220> FEATURE:
<221> NAME/KEY: CDS
<222> LOCATION: (622)...(1480)

<400> SEQUENCE: 111
tatataaacc tcacacacgc attatcatac accatcctcc tcattctctt catcatcaac    60

-continued

| | |
|---|---|
| ataagagaga gagaagaaaa aaagaattac aattaataag aacaagatca agaatcaaga | 120 |

| | | |
|---|---|---|
| atcaagaaa atg gga aga gca ccg tgt tgt gat aag gcc aac gtg aag aaa | | 171 |
| Met Gly Arg Ala Pro Cys Cys Asp Lys Ala Asn Val Lys Lys | | |
| 1 5 10 | | |

| | |
|---|---|
| ggg cct tgg tct cct gag gaa gac gcc aaa ctc aaa gat tac atc gag | 219 |
| Gly Pro Trp Ser Pro Glu Glu Asp Ala Lys Leu Lys Asp Tyr Ile Glu | |
| 15 20 25 30 | |

| | |
|---|---|
| aat agt ggc aca gga ggc aac tgg att gct ttg cct cag aaa att g | 265 |
| Asn Ser Gly Thr Gly Gly Asn Trp Ile Ala Leu Pro Gln Lys Ile | |
| 35 40 45 | |

| | |
|---|---|
| gtatgtatta cttaaaactc acttttgatt taaaattggc actgagagtt tccaaatagt | 325 |
| actttgagac cgtggtcgtg ttaaatttgt gtgttgatga tatttattta catggtatag | 385 |

| | |
|---|---|
| gt tta agg aga tgt ggg aag agt tgc agg cta agg tgg ctc aac tat | 432 |
| Gly Leu Arg Arg Cys Gly Lys Ser Cys Arg Leu Arg Trp Leu Asn Tyr | |
| 50 55 60 | |

| | |
|---|---|
| ttg aga cca aac atc aaa cat ggt ggc ttc tcc gag gaa gaa gac aac | 480 |
| Leu Arg Pro Asn Ile Lys His Gly Gly Phe Ser Glu Glu Glu Asp Asn | |
| 65 70 75 | |

| | |
|---|---|
| atc att tgt aac ctc tat gtt act att ggt agc ag gtactatata | 525 |
| Ile Ile Cys Asn Leu Tyr Val Thr Ile Gly Ser Arg | |
| 80 85 | |

| | |
|---|---|
| cttacatata tatcatcata tgcatggatg aaatattatta attgacacac ttattcttga | 585 |
| cttagagact cactatgtat ctttgtttaa ttctag g tgg tct ata att gct gca | 640 |
| Trp Ser Ile Ile Ala Ala | |
| 90 95 | |

| | |
|---|---|
| caa ttg ccg gga aga acc gac aac gat atc aaa aac tat tgg aac acg | 688 |
| Gln Leu Pro Gly Arg Thr Asp Asn Asp Ile Lys Asn Tyr Trp Asn Thr | |
| 100 105 110 | |

| | |
|---|---|
| agg ctg aag aag aag ctt ctg aac aaa caa agg aaa gag ttc caa gaa | 736 |
| Arg Leu Lys Lys Lys Leu Leu Asn Lys Gln Arg Lys Glu Phe Gln Glu | |
| 115 120 125 | |

| | |
|---|---|
| gcg cga atg aag caa gag atg gtg atg atg aaa agg caa caa caa gga | 784 |
| Ala Arg Met Lys Gln Glu Met Val Met Met Lys Arg Gln Gln Gln Gly | |
| 130 135 140 | |

| | |
|---|---|
| caa gga caa ggt caa agt aat ggt agt acg gat ctt tat ctt aac aac | 832 |
| Gln Gly Gln Gly Gln Ser Asn Gly Ser Thr Asp Leu Tyr Leu Asn Asn | |
| 145 150 155 | |

| | |
|---|---|
| atg ttt gga tca tca cca tgg cca tta cta cca caa ctt cct cct cca | 880 |
| Met Phe Gly Ser Ser Pro Trp Pro Leu Leu Pro Gln Leu Pro Pro Pro | |
| 160 165 170 175 | |

| | |
|---|---|
| cat cat caa ata cct ctt gga atg atg gaa cca aca agc tgt aac tac | 928 |
| His His Gln Ile Pro Leu Gly Met Met Glu Pro Thr Ser Cys Asn Tyr | |
| 180 185 190 | |

| | |
|---|---|
| tac caa acg aca ccg tct tgt aac cta gaa caa aag cca ttg atc aca | 976 |
| Tyr Gln Thr Thr Pro Ser Cys Asn Leu Glu Gln Lys Pro Leu Ile Thr | |
| 195 200 205 | |

| | |
|---|---|
| ctc aag aac atg gtc aag att gaa gaa gaa cag gaa agg aca aac cct | 1024 |
| Leu Lys Asn Met Val Lys Ile Glu Glu Glu Gln Glu Arg Thr Asn Pro | |
| 210 215 220 | |

| | |
|---|---|
| gat cat cat cat caa gat tct gtc aca aac cct ttt gat ttc tct ttc | 1072 |
| Asp His His His Gln Asp Ser Val Thr Asn Pro Phe Asp Phe Ser Phe | |
| 225 230 235 | |

| | |
|---|---|
| tct cag ctt ttg tta gat ccc aat tac tat ctg gga tca gga ggg gga | 1120 |
| Ser Gln Leu Leu Leu Asp Pro Asn Tyr Tyr Leu Gly Ser Gly Gly Gly | |
| 240 245 250 255 | |

| | |
|---|---|
| gga gaa gga gat ttt gct atc atg agc agc agc aca aac tca cca tta | 1168 |
| Gly Glu Gly Asp Phe Ala Ile Met Ser Ser Ser Thr Asn Ser Pro Leu | |

-continued

```
                   260                  265                   270
cca aac aca agt agt gat caa cat cca agt caa cag caa gag att ctt    1216
Pro Asn Thr Ser Ser Asp Gln His Pro Ser Gln Gln Gln Glu Ile Leu
            275                 280                 285 caa tgg ttt ggg agc agt aac ttt cag aca gaa gca atc aac gat atg    1264
Gln Trp Phe Gly Ser Ser Asn Phe Gln Thr Glu Ala Ile Asn Asp Met
        290                 295                 300 ttc ata aac aac aac aac ata gtg aat ctt gag acc atc gag aac        1312
Phe Ile Asn Asn Asn Asn Asn Ile Val Asn Leu Glu Thr Ile Glu Asn
    305                 310                 315 aca aaa gtc tat gga gac gcc tca gta gcc gga gcc gct gtc cga gca    1360
Thr Lys Val Tyr Gly Asp Ala Ser Val Ala Gly Ala Ala Val Arg Ala
320                 325                 330                 335 gct ttg ggc gga ggg aca acg agt aca tcg gcg gat caa agt aca ata    1408
Ala Leu Gly Gly Gly Thr Thr Ser Thr Ser Ala Asp Gln Ser Thr Ile
                340                 345                 350 agt tgg gag gat ata act tct cta gtt aat tcc gaa gat gca agt tac    1456
Ser Trp Glu Asp Ile Thr Ser Leu Val Asn Ser Glu Asp Ala Ser Tyr
            355                 360                 365 ttc aat gcg cca aat cat gtg taa cattttgttt aaactttat ttgtacttaa    1510
Phe Asn Ala Pro Asn His Val  *
        370 atacataaag agggttttc tattttgtat aaatctgtgt ctttagggag              1560

<210> SEQ ID NO 112
<211> LENGTH: 374
<212> TYPE: PRT
<213> ORGANISM: Arabidopsis thaliana

<400> SEQUENCE: 112

Met Gly Arg Ala Pro Cys Cys Asp Lys Ala Asn Val Lys Lys Gly Pro
 1               5                  10                  15

Trp Ser Pro Glu Glu Asp Ala Lys Leu Lys Asp Tyr Ile Glu Asn Ser
                20                  25                  30

Gly Thr Gly Gly Asn Trp Ile Ala Leu Pro Gln Lys Ile Gly Leu Arg
            35                  40                  45

Arg Cys Gly Lys Ser Cys Arg Leu Arg Trp Leu Asn Tyr Leu Arg Pro
        50                  55                  60

Asn Ile Lys His Gly Gly Phe Ser Glu Glu Asp Asn Ile Ile Cys
 65                  70                  75                  80

Asn Leu Tyr Val Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Asn Lys Gln Arg Lys Glu Phe Gln Glu Ala
        115                 120                 125

Arg Met Lys Gln Glu Met Val Met Met Lys Arg Gln Gln Gln Gly Gln
    130                 135                 140

Gly Gln Gly Gln Ser Asn Gly Ser Thr Asp Leu Tyr Leu Asn Asn Met
145                 150                 155                 160

Phe Gly Ser Ser Pro Trp Pro Leu Leu Pro Gln Leu Pro Pro Pro His
                165                 170                 175

His Gln Ile Pro Leu Gly Met Met Glu Pro Thr Ser Cys Asn Tyr Tyr
            180                 185                 190

Gln Thr Thr Pro Ser Cys Asn Leu Glu Gln Lys Pro Leu Ile Thr Leu
        195                 200                 205
```

-continued

```
Lys Asn Met Val Lys Ile Glu Glu Gln Glu Arg Thr Asn Pro Asp
210                 215                 220
His His His Gln Asp Ser Val Thr Asn Pro Phe Asp Phe Ser Phe Ser
225                 230                 235                 240
Gln Leu Leu Leu Asp Pro Asn Tyr Tyr Leu Gly Ser Gly Gly Gly
                245                 250                 255
Glu Gly Asp Phe Ala Ile Met Ser Ser Ser Thr Asn Ser Pro Leu Pro
            260                 265                 270
Asn Thr Ser Ser Asp Gln His Pro Ser Gln Gln Gln Glu Ile Leu Gln
                275                 280                 285
Trp Phe Gly Ser Ser Asn Phe Gln Thr Glu Ala Ile Asn Asp Met Phe
290                 295                 300
Ile Asn Asn Asn Asn Ile Val Asn Leu Glu Thr Ile Glu Asn Thr
305                 310                 315                 320
Lys Val Tyr Gly Asp Ala Ser Val Ala Gly Ala Ala Val Arg Ala Ala
                325                 330                 335
Leu Gly Gly Gly Thr Thr Ser Thr Ser Ala Asp Gln Ser Thr Ile Ser
                340                 345                 350
Trp Glu Asp Ile Thr Ser Leu Val Asn Ser Glu Asp Ala Ser Tyr Phe
            355                 360                 365
Asn Ala Pro Asn His Val
    370
```

<210> SEQ ID NO 113
<211> LENGTH: 3790
<212> TYPE: DNA
<213> ORGANISM: Arabidopsis thaliana
<220> FEATURE:
<221> NAME/KEY: CDS
<222> LOCATION: (38)...(1597)
<220> FEATURE:
<221> NAME/KEY: CDS
<222> LOCATION: (1717)...(1943)
<220> FEATURE:
<221> NAME/KEY: CDS
<222> LOCATION: (2052)...(2384)
<220> FEATURE:
<221> NAME/KEY: CDS
<222> LOCATION: (2468)...(2714)
<220> FEATURE:
<221> NAME/KEY: CDS
<222> LOCATION: (2800)...(2928)
<220> FEATURE:
<221> NAME/KEY: CDS
<222> LOCATION: (3020)...(3203)
<220> FEATURE:
<221> NAME/KEY: CDS
<222> LOCATION: (3532)...(3773)

<400> SEQUENCE: 113

```
ttgtatggtt cgttgttact gatagattac ttaagct atg gtt tgg ttt aga atc     55
                                        Met Val Trp Phe Arg Ile
                                          1               5 ggt tct tct gtg gca aag ctt gcc ata aga agg aca ctg tct cag tct    103
Gly Ser Ser Val Ala Lys Leu Ala Ile Arg Arg Thr Leu Ser Gln Ser
         10                  15                  20 cgt tgt ggt tca tat gcc act aga aca agg gtt ttg cct tgt caa acc    151
Arg Cys Gly Ser Tyr Ala Thr Arg Thr Arg Val Leu Pro Cys Gln Thr
     25                  30                  35 aga tgt ttt cac tct aca ata ctc aaa tca aag gca gag tct gct gca    199
Arg Cys Phe His Ser Thr Ile Leu Lys Ser Lys Ala Glu Ser Ala Ala
 40                  45                  50 cct gtt cca cgt cct gtc cca ctt tct aag cta act gat agc ttc tta    247
```

-continued

| | | |
|---|---|---|
| Pro Val Pro Arg Pro Val Pro Leu Ser Lys Leu Thr Asp Ser Phe Leu<br>55                         60                         65                       70 | | |
| gat gga aca agc agt gtg tat cta gag gag tta caa aga gct tgg gag<br>Asp Gly Thr Ser Ser Val Tyr Leu Glu Glu Leu Gln Arg Ala Trp Glu<br>                    75                         80                       85 | 295 | |
| gct gat ccc aac agt gtt gat gag tcg tgg gat aac ttt ttt agg aat<br>Ala Asp Pro Asn Ser Val Asp Glu Ser Trp Asp Asn Phe Phe Arg Asn<br>                    90                         95                     100 | 343 | |
| ttt gtg ggt cag gct tct aca tcg cct ggt atc tcg ggg caa acc att<br>Phe Val Gly Gln Ala Ser Thr Ser Pro Gly Ile Ser Gly Gln Thr Ile<br>                105                      110                     115 | 391 | |
| caa gaa agc atg cgt ttg ttg ttg cta gtt aga gct tac cag gtt aat<br>Gln Glu Ser Met Arg Leu Leu Leu Val Arg Ala Tyr Gln Val Asn<br>            120                      125                     130 | 439 | |
| ggc cac atg aag gcc aag ctt gat cct tta ggt cta gag aag aga gag<br>Gly His Met Lys Ala Lys Leu Asp Pro Leu Gly Leu Glu Lys Arg Glu<br>135                        140                      145                     150 | 487 | |
| att cca gag gat ctc acg cca ggt ctt tat ggg ttt act gag gct gat<br>Ile Pro Glu Asp Leu Thr Pro Gly Leu Tyr Gly Phe Thr Glu Ala Asp<br>                    155                      160                     165 | 535 | |
| ctt gat cgg gaa ttc ttt ctg ggt gta tgg agg atg tcg ggt ttt ctc<br>Leu Asp Arg Glu Phe Phe Leu Gly Val Trp Arg Met Ser Gly Phe Leu<br>            170                      175                     180 | 583 | |
| tct gag aac cgc ccg gtt caa aca ctg agg tcg ata ctg tcg agg ctt<br>Ser Glu Asn Arg Pro Val Gln Thr Leu Arg Ser Ile Leu Ser Arg Leu<br>              185                      190                     195 | 631 | |
| gag caa gct tac tgt ggg act ata ggg tat gag tac atg cac att gct<br>Glu Gln Ala Tyr Cys Gly Thr Ile Gly Tyr Glu Tyr Met His Ile Ala<br>        200                      205                     210 | 679 | |
| gat agg gat aaa tgt aac tgg ttg aga gac aag atc gag acc cca act<br>Asp Arg Asp Lys Cys Asn Trp Leu Arg Asp Lys Ile Glu Thr Pro Thr<br>215                        220                      225                     230 | 727 | |
| cct cga cag tac aat agt gag cgt cgg atg gtt att tat gat agg ctt<br>Pro Arg Gln Tyr Asn Ser Glu Arg Arg Met Val Ile Tyr Asp Arg Leu<br>                    235                      240                     245 | 775 | |
| acc tgg agc aca cag ttt gag aat ttc ttg gct act aag tgg acc acg<br>Thr Trp Ser Thr Gln Phe Glu Asn Phe Leu Ala Thr Lys Trp Thr Thr<br>              250                      255                     260 | 823 | |
| gct aaa agg ttt gga ctg gaa ggt gct gaa tct ttg att cct ggc atg<br>Ala Lys Arg Phe Gly Leu Glu Gly Ala Glu Ser Leu Ile Pro Gly Met<br>        265                      270                     275 | 871 | |
| aag gag atg ttc gat agg tct gca gat ctc ggg gta gag aac ata gtt<br>Lys Glu Met Phe Asp Arg Ser Ala Asp Leu Gly Val Glu Asn Ile Val<br>280                        285                      290 | 919 | |
| atc ggt atg ccc cat agg ggt cga ctt aat gtt ttg ggt aat gtt gtt<br>Ile Gly Met Pro His Arg Gly Arg Leu Asn Val Leu Gly Asn Val Val<br>295                        300                      305                     310 | 967 | |
| aga aaa cct cta cgc caa ata ttc agc gag ttt agc ggt ggt act agg<br>Arg Lys Pro Leu Arg Gln Ile Phe Ser Glu Phe Ser Gly Gly Thr Arg<br>              315                      320                     325 | 1015 | |
| cca gta gat gaa gtt ggg ctt tac acc gga aca ggt gat gtg aaa tac<br>Pro Val Asp Glu Val Gly Leu Tyr Thr Gly Thr Gly Asp Val Lys Tyr<br>        330                      335                     340 | 1063 | |
| cac ttg ggt aca tct tat gat cgt cca act aga gga ggc aaa cat ctc<br>His Leu Gly Thr Ser Tyr Asp Arg Pro Thr Arg Gly Gly Lys His Leu<br>              345                      350                     355 | 1111 | |
| cac ttg tct ttg gta gca aat ccc agt cac ttg gaa gca gta gat cct<br>His Leu Ser Leu Val Ala Asn Pro Ser His Leu Glu Ala Val Asp Pro<br>360                        365                      370 | 1159 | |

-continued

```
gtt gtg ata ggt aaa acc aga gcg aaa caa tat tac acg aaa gac gag      1207
Val Val Ile Gly Lys Thr Arg Ala Lys Gln Tyr Tyr Thr Lys Asp Glu
375                 380                 385                 390 aac aga aca aag aac atg ggt att ttg atc cat ggg gat ggt agc ttt      1255
Asn Arg Thr Lys Asn Met Gly Ile Leu Ile His Gly Asp Gly Ser Phe
                395                 400                 405 gcc gga caa gga gtg gtg tat gaa act ctc cat ctt agt gca ctt cct      1303
Ala Gly Gln Gly Val Val Tyr Glu Thr Leu His Leu Ser Ala Leu Pro
            410                 415                 420 aac tac tgt acc ggt gga aca gtg cac att gtg gtg aat aat caa gtg      1351
Asn Tyr Cys Thr Gly Gly Thr Val His Ile Val Val Asn Asn Gln Val
        425                 430                 435 gct ttc aca acc gat ccc agg gaa gga agg tct tca cag tat tgc act      1399
Ala Phe Thr Thr Asp Pro Arg Glu Gly Arg Ser Ser Gln Tyr Cys Thr
    440                 445                 450 gat gtt gca aag gct ttg agc gcc cca att ttc cat gtc aat gca gat      1447
Asp Val Ala Lys Ala Leu Ser Ala Pro Ile Phe His Val Asn Ala Asp
455                 460                 465                 470 gac att gaa gca gta gtg cat gct tgt gag ctt gct gct gag tgg cgc      1495
Asp Ile Glu Ala Val Val His Ala Cys Glu Leu Ala Ala Glu Trp Arg
                475                 480                 485 cag acg ttc cat tct gat gtt gtt gtt gat tta gta tgc tac cgt cgc      1543
Gln Thr Phe His Ser Asp Val Val Val Asp Leu Val Cys Tyr Arg Arg
                490                 495                 500 ttt ggg cat aac gag ata gac gaa ccg tca ttc aca caa cca aaa atg      1591
Phe Gly His Asn Glu Ile Asp Glu Pro Ser Phe Thr Gln Pro Lys Met
            505                 510                 515 tac aag gtctggctat tatatcatcc atctctgtga aataatctaa taaccaattc      1647
Tyr Lys
    520 aagtttccat ttcatacttt tcttgtactt ttttttttgtt taaaaacgga tgttacttgt      1707 tggtgatag gtg ata cgc agt cat ccc tcg tca ctt caa atc tac cag gag      1758
          Val Ile Arg Ser His Pro Ser Ser Leu Gln Ile Tyr Gln Glu
                  525                 530 aag ctc ttg caa tct gga cag gta acc caa gaa gat att gat aag att      1806
Lys Leu Leu Gln Ser Gly Gln Val Thr Gln Glu Asp Ile Asp Lys Ile
535                 540                 545                 550 caa aag aaa gta agc tct atc ctc aat gaa gaa tat gag gca agt aaa      1854
Gln Lys Lys Val Ser Ser Ile Leu Asn Glu Glu Tyr Glu Ala Ser Lys
                555                 560                 565 gat tat att cca caa aaa cgt gac tgg ctg gca agt cac tgg act gga      1902
Asp Tyr Ile Pro Gln Lys Arg Asp Trp Leu Ala Ser His Trp Thr Gly
            570                 575                 580 ttc aag tct ccg gag cag att tct agg att cga aac acc gg gtaaaaaaca      1953
Phe Lys Ser Pro Glu Gln Ile Ser Arg Ile Arg Asn Thr Gly
    585                 590                 595 tttttatttc atttagtttg tcaatgcctt ttggccttt ttcttttctt tttcaatgta      2013 acatttgct ggaaaactat tcccttgttc ttttgcag a gtg aag cca gag att      2067
                                          Val Lys Pro Glu Ile
                                                      600 ttg aag aat gtg gga aag gca atc tca acc ttc cct gag aac ttt aag      2115
Leu Lys Asn Val Gly Lys Ala Ile Ser Thr Phe Pro Glu Asn Phe Lys
                605                 610                 615 cca cac aga gga gtt aaa aga gtt tat gaa caa cgt gct caa atg att      2163
Pro His Arg Gly Val Lys Arg Val Tyr Glu Gln Arg Ala Gln Met Ile
            620                 625                 630 gaa tcg gga gaa ggc att gac tgg gga ctt gga gaa gca ctt gct ttt      2211
Glu Ser Gly Glu Gly Ile Asp Trp Gly Leu Gly Glu Ala Leu Ala Phe
    635                 640                 645
```

-continued

```
gct aca ctg gtt gtg gaa ggg aac cat gtt cgg cta agt ggt caa gat         2259
Ala Thr Leu Val Val Glu Gly Asn His Val Arg Leu Ser Gly Gln Asp
650                 655                 660                 665 gtt gaa aga gga act ttc agt cat aga cac tca gtg ctt cat gat caa         2307
Val Glu Arg Gly Thr Phe Ser His Arg His Ser Val Leu His Asp Gln
                670                 675                 680 gaa acc ggg gag gaa tat tgt ccc ctc gat cac cta atc aaa aac caa         2355
Glu Thr Gly Glu Glu Tyr Cys Pro Leu Asp His Leu Ile Lys Asn Gln
            685                 690                 695 gac cct gaa atg ttc act gtc agc aac ag gtatgcattt ttttttaatc            2404
Asp Pro Glu Met Phe Thr Val Ser Asn Ser
        700                 705 tctagagatg ataaccactc ttcaattgtt tttacatgat ctttacgttg tttgtgtatg       2464 cag c tcc ctt tca gaa ttt ggt gtt ctc ggt ttc gaa ctg ggt tat tcg       2513
    Ser Leu Ser Glu Phe Gly Val Leu Gly Phe Glu Leu Gly Tyr Ser
        710                 715                 720 atg gaa aat ccc aat tct ctg gtg ata tgg gaa gct cag ttt gga gac         2561
Met Glu Asn Pro Asn Ser Leu Val Ile Trp Glu Ala Gln Phe Gly Asp
            725                 730                 735 ttt gct aat ggc gca caa gtt atg ttt gat cag ttc ata agc agt ggg         2609
Phe Ala Asn Gly Ala Gln Val Met Phe Asp Gln Phe Ile Ser Ser Gly
        740                 745                 750 gaa gcc aaa tgg ctc cgt caa act ggt cta gta gtt tta ctt cct cat         2657
Glu Ala Lys Trp Leu Arg Gln Thr Gly Leu Val Val Leu Leu Pro His
755                 760                 765                 770 gga tat gat ggt cag ggt cct gaa cat tcc agt gga aga ttg gaa cgt         2705
Gly Tyr Asp Gly Gln Gly Pro Glu His Ser Ser Gly Arg Leu Glu Arg
                775                 780                 785 ttc ctt cag gtatattata tgaccgatac ttaccgttaa gattctctcc                 2754
Phe Leu Gln acttttgta tttgtttccc tctcatttga aaattttaac tgcag atg agt gat gac       2811
                                                Met Ser Asp Asp
                                                        790 aat cct tac gtt atc cct gag atg gac cca act ctt cga aag cag att        2859
Asn Pro Tyr Val Ile Pro Glu Met Asp Pro Thr Leu Arg Lys Gln Ile
        795                 800                 805 caa gaa tgt aat tgg caa gtt gtt aat gtt act aca cct gcc aac tat        2907
Gln Glu Cys Asn Trp Gln Val Val Asn Val Thr Thr Pro Ala Asn Tyr
810                 815                 820                 825 ttc cat gtt ctg cgt cgg cag gtaaaatatc tatttatccc aagttcgtaa           2958
Phe His Val Leu Arg Arg Gln
                830 aatgttgtta cttaattttc gtattcttca cactcacatg cttgatatca tccatttgca      3018 g ata cac agg gac ttt cgc aag cct ctt ata gtg atg gcc ccc aaa aac      3067
  Ile His Arg Asp Phe Arg Lys Pro Leu Ile Val Met Ala Pro Lys Asn
        835                 840                 845 ttg ctt cgt cac aaa cag tgt gta tct aat ctc tcg gaa ttc gat gat        3115
Leu Leu Arg His Lys Gln Cys Val Ser Asn Leu Ser Glu Phe Asp Asp
850                 855                 860 gtt aaa gga cat cct gga ttt gac aag caa gga act cga ttt aaa cgg        3163
Val Lys Gly His Pro Gly Phe Asp Lys Gln Gly Thr Arg Phe Lys Arg
865                 870                 875                 880 ttg atc aaa gat caa agt ggc cac tct gat ctt gaa gaa g gtatcagacg       3213
Leu Ile Lys Asp Gln Ser Gly His Ser Asp Leu Glu Glu
                885                 890 tctagtcctc tgctctggga aggtataaaa aaaaagatcc acttttttccg tcattaacta     3273 acaaagttcc cacattctga aatttaatac tttaaatgtc aatgaatcag gtctactatg      3333
```

```
agcttgacga agagcgaaag aagtctgaaa caaaggatgt agccatttgc agagtagagc    3393
agctttgccc atttccatat gatctcatcc aaagagaact aaagcgatat ccaagtaggc    3453
gtcgaaaact caagtttgtg ttcaatagtt ttggttgatt atggaattct ttgaaacttt    3513
tgttcttgtg tttaacag at gca gag atc gtg tgg tgt caa gaa gag ccg      3563
                     Asp Ala Glu Ile Val Trp Cys Gln Glu Glu Pro
                                 895                 900 atg aac atg gga gga tac caa tac ata gcc cta agg ctt tgc acc gcg     3611
Met Asn Met Gly Gly Tyr Gln Tyr Ile Ala Leu Arg Leu Cys Thr Ala
905                 910                 915                 920 atg aaa gca ctg caa aga gga aac ttc aac gac atc aaa tac gtt ggt     3659
Met Lys Ala Leu Gln Arg Gly Asn Phe Asn Asp Ile Lys Tyr Val Gly
                925                 930                 935 cgt ctt ccc tca gct gct aca gcc aca gga ttt tac cag ctt cat gtt     3707
Arg Leu Pro Ser Ala Ala Thr Ala Thr Gly Phe Tyr Gln Leu His Val
                940                 945                 950 aag gag cag act gat ctt gtg aag aaa gct ctt caa cct gac ccc atc     3755
Lys Glu Gln Thr Asp Leu Val Lys Lys Ala Leu Gln Pro Asp Pro Ile
                955                 960                 965 acc ccc gtc atc cct taa aaaaacacag cttgaga                          3790
Thr Pro Val Ile Pro *
    970

<210> SEQ ID NO 114
<211> LENGTH: 973
<212> TYPE: PRT
<213> ORGANISM: Arabidopsis thaliana

<400> SEQUENCE: 114

Met Val Trp Phe Arg Ile Gly Ser Ser Val Ala Lys Leu Ala Ile Arg
1               5                   10                  15

Arg Thr Leu Ser Gln Ser Arg Cys Gly Ser Tyr Ala Thr Arg Thr Arg
            20                  25                  30

Val Leu Pro Cys Gln Thr Arg Cys Phe His Ser Thr Ile Leu Lys Ser
        35                  40                  45

Lys Ala Glu Ser Ala Ala Pro Val Pro Arg Pro Val Pro Leu Ser Lys
    50                  55                  60

Leu Thr Asp Ser Phe Leu Asp Gly Thr Ser Ser Val Tyr Leu Glu Glu
65                  70                  75                  80

Leu Gln Arg Ala Trp Glu Ala Asp Pro Asn Ser Val Asp Glu Ser Trp
                85                  90                  95

Asp Asn Phe Phe Arg Asn Phe Val Gly Gln Ala Ser Thr Ser Pro Gly
            100                 105                 110

Ile Ser Gly Gln Thr Ile Gln Glu Ser Met Arg Leu Leu Leu Leu Val
        115                 120                 125

Arg Ala Tyr Gln Val Asn Gly His Met Lys Ala Lys Leu Asp Pro Leu
    130                 135                 140

Gly Leu Glu Lys Arg Glu Ile Pro Glu Asp Leu Thr Pro Gly Leu Tyr
145                 150                 155                 160

Gly Phe Thr Glu Ala Asp Leu Asp Arg Glu Phe Phe Leu Gly Val Trp
                165                 170                 175

Arg Met Ser Gly Phe Leu Ser Glu Asn Arg Pro Val Gln Thr Leu Arg
            180                 185                 190

Ser Ile Leu Ser Arg Leu Glu Gln Ala Tyr Cys Gly Thr Ile Gly Tyr
        195                 200                 205

Glu Tyr Met His Ile Ala Asp Arg Asp Lys Cys Asn Trp Leu Arg Asp
```

```
                210                 215                 220
Lys Ile Glu Thr Pro Thr Pro Arg Gln Tyr Asn Ser Glu Arg Arg Met
225                 230                 235                 240

Val Ile Tyr Asp Arg Leu Thr Trp Ser Thr Gln Phe Glu Asn Phe Leu
                245                 250                 255

Ala Thr Lys Trp Thr Thr Ala Lys Arg Phe Gly Leu Glu Gly Ala Glu
                260                 265                 270

Ser Leu Ile Pro Gly Met Lys Glu Met Phe Asp Arg Ser Ala Asp Leu
                275                 280                 285

Gly Val Glu Asn Ile Val Ile Gly Met Pro His Arg Gly Arg Leu Asn
290                 295                 300

Val Leu Gly Asn Val Val Arg Lys Pro Leu Arg Gln Ile Phe Ser Glu
305                 310                 315                 320

Phe Ser Gly Gly Thr Arg Pro Val Asp Glu Val Gly Leu Tyr Thr Gly
                325                 330                 335

Thr Gly Asp Val Lys Tyr His Leu Gly Thr Ser Tyr Asp Arg Pro Thr
                340                 345                 350

Arg Gly Gly Lys His Leu His Leu Ser Leu Val Ala Asn Pro Ser His
                355                 360                 365

Leu Glu Ala Val Asp Pro Val Val Ile Gly Lys Thr Arg Ala Lys Gln
370                 375                 380

Tyr Tyr Thr Lys Asp Glu Asn Arg Thr Lys Asn Met Gly Ile Leu Ile
385                 390                 395                 400

His Gly Asp Gly Ser Phe Ala Gly Gln Gly Val Val Tyr Glu Thr Leu
                405                 410                 415

His Leu Ser Ala Leu Pro Asn Tyr Cys Thr Gly Gly Thr Val His Ile
                420                 425                 430

Val Val Asn Asn Gln Val Ala Phe Thr Thr Asp Pro Arg Glu Gly Arg
                435                 440                 445

Ser Ser Gln Tyr Cys Thr Asp Val Ala Lys Ala Leu Ser Ala Pro Ile
                450                 455                 460

Phe His Val Asn Ala Asp Asp Ile Glu Ala Val Val His Ala Cys Glu
465                 470                 475                 480

Leu Ala Ala Glu Trp Arg Gln Thr Phe His Ser Asp Val Val Asp
                485                 490                 495

Leu Val Cys Tyr Arg Arg Phe Gly His Asn Glu Ile Asp Glu Pro Ser
                500                 505                 510

Phe Thr Gln Pro Lys Met Tyr Lys Val Ile Arg Ser His Pro Ser Ser
                515                 520                 525

Leu Gln Ile Tyr Gln Glu Lys Leu Leu Gln Ser Gly Gln Val Thr Gln
                530                 535                 540

Glu Asp Ile Asp Lys Ile Gln Lys Lys Val Ser Ser Ile Leu Asn Glu
545                 550                 555                 560

Glu Tyr Glu Ala Ser Lys Asp Tyr Ile Pro Gln Lys Arg Asp Trp Leu
                565                 570                 575

Ala Ser His Trp Thr Gly Phe Lys Ser Pro Glu Gln Ile Ser Arg Ile
                580                 585                 590

Arg Asn Thr Gly Val Lys Pro Glu Ile Leu Lys Asn Val Gly Lys Ala
                595                 600                 605

Ile Ser Thr Phe Pro Glu Asn Phe Lys Pro His Arg Gly Val Lys Arg
                610                 615                 620

Val Tyr Glu Gln Arg Ala Gln Met Ile Glu Ser Gly Glu Gly Ile Asp
625                 630                 635                 640
```

-continued

```
Trp Gly Leu Gly Glu Ala Leu Ala Phe Ala Thr Leu Val Val Glu Gly
            645                 650                 655

Asn His Val Arg Leu Ser Gly Gln Asp Val Glu Arg Gly Thr Phe Ser
            660                 665                 670

His Arg His Ser Val Leu His Asp Gln Glu Thr Gly Glu Glu Tyr Cys
            675                 680                 685

Pro Leu Asp His Leu Ile Lys Asn Gln Asp Pro Glu Met Phe Thr Val
            690                 695                 700

Ser Asn Ser Ser Leu Ser Glu Phe Gly Val Leu Gly Phe Glu Leu Gly
705                 710                 715                 720

Tyr Ser Met Glu Asn Pro Asn Ser Leu Val Ile Trp Glu Ala Gln Phe
                725                 730                 735

Gly Asp Phe Ala Asn Gly Ala Gln Val Met Phe Asp Gln Phe Ile Ser
            740                 745                 750

Ser Gly Glu Ala Lys Trp Leu Arg Gln Thr Gly Leu Val Val Leu Leu
            755                 760                 765

Pro His Gly Tyr Asp Gly Gln Gly Pro Glu His Ser Ser Gly Arg Leu
            770                 775                 780

Glu Arg Phe Leu Gln Met Ser Asp Asp Asn Pro Tyr Val Ile Pro Glu
785                 790                 795                 800

Met Asp Pro Thr Leu Arg Lys Gln Ile Gln Glu Cys Asn Trp Gln Val
                805                 810                 815

Val Asn Val Thr Thr Pro Ala Asn Trp Phe His Val Leu Arg Arg Gln
            820                 825                 830

Ile His Arg Asp Phe Arg Lys Pro Leu Ile Val Met Ala Pro Lys Asn
            835                 840                 845

Leu Leu Arg His Lys Gln Cys Val Ser Asn Leu Ser Glu Phe Asp Asp
            850                 855                 860

Val Lys Gly His Pro Gly Phe Asp Lys Gln Gly Thr Arg Phe Lys Arg
865                 870                 875                 880

Leu Ile Lys Asp Gln Ser Gly His Ser Asp Leu Glu Glu Asp Ala Glu
                885                 890                 895

Ile Val Trp Cys Gln Glu Glu Pro Met Asn Met Gly Gly Tyr Gln Tyr
            900                 905                 910

Ile Ala Leu Arg Leu Cys Thr Ala Met Lys Ala Leu Gln Arg Gly Asn
            915                 920                 925

Phe Asn Asp Ile Lys Tyr Val Gly Arg Leu Pro Ser Ala Ala Thr Ala
            930                 935                 940

Thr Gly Phe Tyr Gln Leu His Val Lys Glu Gln Thr Asp Leu Val Lys
945                 950                 955                 960

Lys Ala Leu Gln Pro Asp Pro Ile Thr Pro Val Ile Pro
                965                 970

<210> SEQ ID NO 115
<211> LENGTH: 1200
<212> TYPE: DNA
<213> ORGANISM: Arabidopsis thaliana
<220> FEATURE:
<221> NAME/KEY: CDS
<222> LOCATION: (25)...(151)
<220> FEATURE:
<221> NAME/KEY: CDS
<222> LOCATION: (257)...(357)
<220> FEATURE:
<221> NAME/KEY: CDS
<222> LOCATION: (465)...(662)
<220> FEATURE:
```

<221> NAME/KEY: CDS
<222> LOCATION: (783)...(1166)

<400> SEQUENCE: 115

| | |
|---|---:|
| tgcattttta ctctcttgac gcta atg ttc att cgg gtt tcc gct cga ccc<br>                                       Met Phe Ile Arg Val Ser Ala Arg Pro<br>                                          1              5 | 51 |
| gcg aca ttc gtc gag gat ttc aaa gcc gcc tgg tcg gaa tct cac atc<br>Ala Thr Phe Val Glu Asp Phe Lys Ala Ala Trp Ser Glu Ser His Ile<br> 10                 15                20                25 | 99 |
| cgt caa atg gaa gac gga aaa gct atc cag ctc gtc ctt gat cag agc<br>Arg Gln Met Glu Asp Gly Lys Ala Ile Gln Leu Val Leu Asp Gln Ser<br>           30                35                40 | 147 |
| act g gtacaccaac gccacagtta tatttttaaa cggaaacatt ttgaaattaa<br>Thr | 201 |
| tggtgttttt atgtaatata ctctcactgt acatgttcat atttgtcttt taaag ga<br>                                                                                   Gly | 258 |
| tgt gga ttt gct tcc aaa aga aaa tat cta ttc gga cga gtg agc atg<br>Cys Gly Phe Ala Ser Lys Arg Lys Tyr Leu Phe Gly Arg Val Ser Met<br>    45                     50                   55 | 306 |
| aag atc aaa ctc att ccc gga gac tct gcc ggt acg gtc acc gct ttc<br>Lys Ile Lys Leu Ile Pro Gly Asp Ser Ala Gly Thr Val Thr Ala Phe<br> 60                 65                70                75 | 354 |
| tac gtaagtctat cattttactc cactagtttt gaaattttac acattcacac<br>Tyr | 407 |
| aataaaaaat aacattttct tgaaacacta acggtcaaat cattgatatg tctatag atg<br>                                                                                             Met | 467 |
| aac tcc gat acg gcc acg gtg aga gac gag cta gat ttt gag ttc ttg<br>Asn Ser Asp Thr Ala Thr Val Arg Asp Glu Leu Asp Phe Glu Phe Leu<br>           80                85                90 | 515 |
| gga aac aga agt ggt caa cct tac tca gtg caa aca aac ata ttt gct<br>Gly Asn Arg Ser Gly Gln Pro Tyr Ser Val Gln Thr Asn Ile Phe Ala<br>        95                  100                105 | 563 |
| cat ggc aaa gga gat aga gaa caa aga gtt aat ctt tgg ttc gac cca<br>His Gly Lys Gly Asp Arg Glu Gln Arg Val Asn Leu Trp Phe Asp Pro<br>110                115                120                125 | 611 |
| tct atg gat tac cac act tac act atc tta tgg tca cac aaa cac att<br>Ser Met Asp Tyr His Thr Tyr Thr Ile Leu Trp Ser His Lys His Ile<br>                130                135                140 | 659 |
| gtg taagcttttc tctaattgta ctttcaacta gaatcaacat ttactgtttc<br>Val | 712 |
| aaaacaaaaa atcaccattt actgtttaaa aaaaccttag tttaacgtgg ggttgttttg | 772 |
| gttactcagt ttt tac gta gac gat gtg cca ata aga gaa tac aaa aac<br>                 Phe Tyr Val Asp Asp Val Pro Ile Arg Glu Tyr Lys Asn<br>                          145                      150                      155 | 821 |
| aac gaa gcc aag aac ata gct tac cca aca tca caa cct atg gga gta<br>Asn Glu Ala Lys Asn Ile Ala Tyr Pro Thr Ser Gln Pro Met Gly Val<br>                160                    165                    170 | 869 |
| tac tca aca tta tgg gaa gca gat gac tgg gca aca cgt ggt gga tta<br>Tyr Ser Thr Leu Trp Glu Ala Asp Asp Trp Ala Thr Arg Gly Gly Leu<br>                   175                    180                    185 | 917 |
| gag aaa att gat tgg agc aaa gct cca ttt tat gct tat tac aaa gat<br>Glu Lys Ile Asp Trp Ser Lys Ala Pro Phe Tyr Ala Tyr Tyr Lys Asp<br>                190                195                200 | 965 |
| ttc gac atc gaa ggt tgt cct gtt cct gga cca acc ttt tgt cca tcg<br>Phe Asp Ile Glu Gly Cys Pro Val Pro Gly Pro Thr Phe Cys Pro Ser<br>205                210                215 | 1013 |
| aac cct cat aat tgg tgg gaa ggt tat gcc tat cag tct ctt aac gcc | 1061 |

```
Asn Pro His Asn Trp Trp Glu Gly Tyr Ala Tyr Gln Ser Leu Asn Ala
220                 225                 230                 235 gtt gaa gct cga cgt tac cgg tgg gtt aga gta aac cat atg gtt tat      1109
Val Glu Ala Arg Arg Tyr Arg Trp Val Arg Val Asn His Met Val Tyr
                240                 245                 250 gat tat tgt act gac cgg tct agg ttt cct gtc cca cca ccc gag tgt      1157
Asp Tyr Cys Thr Asp Arg Ser Arg Phe Pro Val Pro Pro Pro Glu Cys
            255                 260                 265 cgt gct tga aaataattgc atacgtacgt tgcaatgatc atgt                    1200
Arg Ala  *

<210> SEQ ID NO 116
<211> LENGTH: 269
<212> TYPE: PRT
<213> ORGANISM: Arabidopsis thaliana

<400> SEQUENCE: 116

Met Phe Ile Arg Val Ser Ala Arg Pro Ala Thr Phe Val Glu Asp Phe
  1               5                  10                  15

Lys Ala Ala Trp Ser Glu Ser His Ile Arg Gln Met Glu Asp Gly Lys
             20                  25                  30

Ala Ile Gln Leu Val Leu Asp Gln Ser Thr Gly Cys Gly Phe Ala Ser
         35                  40                  45

Lys Arg Lys Tyr Leu Phe Gly Arg Val Ser Met Lys Ile Lys Leu Ile
     50                  55                  60

Pro Gly Asp Ser Ala Gly Thr Val Thr Ala Phe Tyr Met Asn Ser Asp
 65                  70                  75                  80

Thr Ala Thr Val Arg Asp Glu Leu Asp Phe Glu Phe Leu Gly Asn Arg
                 85                  90                  95

Ser Gly Gln Pro Tyr Ser Val Gln Thr Asn Ile Phe Ala His Gly Lys
            100                 105                 110

Gly Asp Arg Glu Gln Arg Val Asn Leu Trp Phe Asp Pro Ser Met Asp
        115                 120                 125

Tyr His Thr Tyr Thr Ile Leu Trp Ser His Lys His Ile Val Phe Tyr
    130                 135                 140

Val Asp Asp Val Pro Ile Arg Glu Tyr Lys Asn Asn Glu Ala Lys Asn
145                 150                 155                 160

Ile Ala Tyr Pro Thr Ser Gln Pro Met Gly Val Tyr Ser Thr Leu Trp
                165                 170                 175

Glu Ala Asp Asp Trp Ala Thr Arg Gly Gly Leu Glu Lys Ile Asp Trp
            180                 185                 190

Ser Lys Ala Pro Phe Tyr Ala Tyr Tyr Lys Asp Phe Asp Ile Glu Gly
        195                 200                 205

Cys Pro Val Pro Gly Pro Thr Phe Cys Pro Ser Asn Pro His Asn Trp
    210                 215                 220

Trp Glu Gly Tyr Ala Tyr Gln Ser Leu Asn Ala Val Glu Ala Arg Arg
225                 230                 235                 240

Tyr Arg Trp Val Arg Val Asn His Met Val Tyr Asp Tyr Cys Thr Asp
                245                 250                 255

Arg Ser Arg Phe Pro Val Pro Pro Glu Cys Arg Ala
            260                 265

<210> SEQ ID NO 117
<211> LENGTH: 1399
<212> TYPE: DNA
<213> ORGANISM: Arabidopsis thaliana
<220> FEATURE:
```

<221> NAME/KEY: CDS
<222> LOCATION: (25)...(1386)

<400> SEQUENCE: 117

```
aacacaaacc gaggttttag aaac atg gcg tct aag gta atc tct gcc aca        51
                          Met Ala Ser Lys Val Ile Ser Ala Thr
                            1               5 atc cgc aga acc cta acc aaa cca cac ggc act ttt tcc cgg tgt cgc       99
Ile Arg Arg Thr Leu Thr Lys Pro His Gly Thr Phe Ser Arg Cys Arg
 10              15                  20                  25 tac tta tca acc gcc gct gct gcg acg gag gtg aat tac gag gat gaa      147
Tyr Leu Ser Thr Ala Ala Ala Thr Glu Val Asn Tyr Glu Asp Glu
             30                  35                  40 tcg att atg atg aaa gga gtt cga att tca ggt aga cct ctt tac tta      195
Ser Ile Met Met Lys Gly Val Arg Ile Ser Gly Arg Pro Leu Tyr Leu
                 45                  50                  55 gat atg caa gcg acg act ccg att gat cct aga gta ttc gat gcg atg      243
Asp Met Gln Ala Thr Thr Pro Ile Asp Pro Arg Val Phe Asp Ala Met
             60                  65                  70 aat gct tca cag atc cat gag tat ggg aat cct cac tcg cga acg cat      291
Asn Ala Ser Gln Ile His Glu Tyr Gly Asn Pro His Ser Arg Thr His
 75                  80                  85 ctc tac ggc tgg gaa gct gag aac gcc gtc gag aac gca cga aac cag      339
Leu Tyr Gly Trp Glu Ala Glu Asn Ala Val Glu Asn Ala Arg Asn Gln
 90                  95                 100                 105 gtc gcg aaa ctg atc gaa gct tca ccg aag gag atc gta ttc gtg tcc      387
Val Ala Lys Leu Ile Glu Ala Ser Pro Lys Glu Ile Val Phe Val Ser
                110                 115                 120 ggt gca acg gag gcg aac aat atg gcg gtg aaa gga gtg atg cac ttt      435
Gly Ala Thr Glu Ala Asn Asn Met Ala Val Lys Gly Val Met His Phe
                125                 130                 135 tac aag gac acg aag aaa cat gtg ata act aca cag act gag cat aag      483
Tyr Lys Asp Thr Lys Lys His Val Ile Thr Thr Gln Thr Glu His Lys
                140                 145                 150 tgt gtg ctt gat tcg tgt agg cat ttg cag caa gaa gga ttt gag gta      531
Cys Val Leu Asp Ser Cys Arg His Leu Gln Gln Glu Gly Phe Glu Val
                155                 160                 165 act tat tta cct gtg aaa act gat gga ttg gtt gat tta gag atg ttg      579
Thr Tyr Leu Pro Val Lys Thr Asp Gly Leu Val Asp Leu Glu Met Leu
170                 175                 180                 185 aga gaa gct att agg cca gac aca ggg cta gtt tct att atg gct gtg      627
Arg Glu Ala Ile Arg Pro Asp Thr Gly Leu Val Ser Ile Met Ala Val
                190                 195                 200 aac aat gag att ggt gtg gtt caa cct atg gag gag att ggt atg att      675
Asn Asn Glu Ile Gly Val Val Gln Pro Met Glu Glu Ile Gly Met Ile
                205                 210                 215 tgc aaa gag cat aat gtt ccg ttt cat act gat gct gct caa gct att      723
Cys Lys Glu His Asn Val Pro Phe His Thr Asp Ala Ala Gln Ala Ile
                220                 225                 230 ggg aag ata cct gtt gat gtt aag aag tgg aat gtt gct ttg atg tct      771
Gly Lys Ile Pro Val Asp Val Lys Lys Trp Asn Val Ala Leu Met Ser
                235                 240                 245 atg agt gct cac aag atc tat gga ccg aaa ggt gtt ggt gct ttg tat      819
Met Ser Ala His Lys Ile Tyr Gly Pro Lys Gly Val Gly Ala Leu Tyr
250                 255                 260                 265 gtg agg agg agg ccg aga atc agg ctt gag ccg ttg atg aat ggt gga      867
Val Arg Arg Arg Pro Arg Ile Arg Leu Glu Pro Leu Met Asn Gly Gly
                270                 275                 280 ggt cag gag agg gga ttg cgt agt ggt acg ggg gct acg cag cag att      915
Gly Gln Glu Arg Gly Leu Arg Ser Gly Thr Gly Ala Thr Gln Gln Ile
```

```
                    285                 290                 295
gtt ggg ttc ggg gct gct tgt gag ttg gct atg aag gag atg gag tat    963
Val Gly Phe Gly Ala Ala Cys Glu Leu Ala Met Lys Glu Met Glu Tyr
            300                 305                 310 gat gag aag tgg att aag ggg tta cag gag agg ttg ctg aat ggg gtt   1011
Asp Glu Lys Trp Ile Lys Gly Leu Gln Glu Arg Leu Leu Asn Gly Val
315                 320                 325 aga gag aag ctt gat ggt gtt gtg gtg aat ggt tca atg gat agt cga   1059
Arg Glu Lys Leu Asp Gly Val Val Val Asn Gly Ser Met Asp Ser Arg
330                 335                 340                 345 tat gta ggg aat ttg aat ttg tcg ttt gct tat gtt gaa gga gag agt   1107
Tyr Val Gly Asn Leu Asn Leu Ser Phe Ala Tyr Val Glu Gly Glu Ser
            350                 355                 360 ttg ttg atg gga ttg aag gaa gtt gca gtg tct agt gga agt gct tgt   1155
Leu Leu Met Gly Leu Lys Glu Val Ala Val Ser Ser Gly Ser Ala Cys
            365                 370                 375 act agt gcg agt ttg gag cct tct tat gtg ttg aga gct ttg ggt gtg   1203
Thr Ser Ala Ser Leu Glu Pro Ser Tyr Val Leu Arg Ala Leu Gly Val
            380                 385                 390 gat gaa gac atg gct cac act tcg att agg ttt ggg att ggt agg ttt   1251
Asp Glu Asp Met Ala His Thr Ser Ile Arg Phe Gly Ile Gly Arg Phe
395                 400                 405 acc acg aag gaa gag att gat aaa gcg gtc gag ctt acg gtt aaa caa   1299
Thr Thr Lys Glu Glu Ile Asp Lys Ala Val Glu Leu Thr Val Lys Gln
410                 415                 420                 425 gtt gag aag ttg agg gaa atg agc ccg ctt tat gaa atg gtt aaa gaa   1347
Val Glu Lys Leu Arg Glu Met Ser Pro Leu Tyr Glu Met Val Lys Glu
            430                 435                 440 ggt atc gat atc aag aac att caa tgg tct caa cac tga ttcaacagtt   1396
Gly Ile Asp Ile Lys Asn Ile Gln Trp Ser Gln His *
            445                 450 cca                                                                1399

<210> SEQ ID NO 118
<211> LENGTH: 453
<212> TYPE: PRT
<213> ORGANISM: Arabidopsis thaliana

<400> SEQUENCE: 118

Met Ala Ser Lys Val Ile Ser Ala Thr Ile Arg Arg Thr Leu Thr Lys
1               5                   10                  15

Pro His Gly Thr Phe Ser Arg Cys Arg Tyr Leu Ser Thr Ala Ala Ala
            20                  25                  30

Ala Thr Glu Val Asn Tyr Glu Asp Glu Ser Ile Met Met Lys Gly Val
        35                  40                  45

Arg Ile Ser Gly Arg Pro Leu Tyr Leu Asp Met Gln Ala Thr Thr Pro
    50                  55                  60

Ile Asp Pro Arg Val Phe Asp Ala Met Asn Ala Ser Gln Ile His Glu
65                  70                  75                  80

Tyr Gly Asn Pro His Ser Arg Thr His Leu Tyr Gly Trp Glu Ala Glu
                85                  90                  95

Asn Ala Val Glu Asn Ala Arg Asn Gln Val Ala Lys Leu Ile Glu Ala
            100                 105                 110

Ser Pro Lys Glu Ile Val Phe Val Ser Gly Ala Thr Glu Ala Asn Asn
        115                 120                 125

Met Ala Val Lys Gly Val Met His Phe Tyr Lys Asp Thr Lys Lys His
    130                 135                 140
```

-continued

```
Val Ile Thr Thr Gln Thr Glu His Lys Cys Val Leu Asp Ser Cys Arg
145                 150                 155                 160

His Leu Gln Gln Glu Gly Phe Glu Val Thr Tyr Leu Pro Val Lys Thr
                165                 170                 175

Asp Gly Leu Val Asp Leu Glu Met Leu Arg Glu Ala Ile Arg Pro Asp
            180                 185                 190

Thr Gly Leu Val Ser Ile Met Ala Val Asn Asn Glu Ile Gly Val Val
        195                 200                 205

Gln Pro Met Glu Glu Ile Gly Met Ile Cys Lys Glu His Asn Val Pro
    210                 215                 220

Phe His Thr Asp Ala Ala Gln Ala Ile Gly Lys Ile Pro Val Asp Val
225                 230                 235                 240

Lys Lys Trp Asn Val Ala Leu Met Ser Met Ser Ala His Lys Ile Tyr
                245                 250                 255

Gly Pro Lys Gly Val Gly Ala Leu Tyr Val Arg Arg Arg Pro Arg Ile
            260                 265                 270

Arg Leu Glu Pro Leu Met Asn Gly Gly Gln Glu Arg Gly Leu Arg
        275                 280                 285

Ser Gly Thr Gly Ala Thr Gln Gln Ile Val Gly Phe Gly Ala Ala Cys
    290                 295                 300

Glu Leu Ala Met Lys Glu Met Glu Tyr Asp Glu Lys Trp Ile Lys Gly
305                 310                 315                 320

Leu Gln Glu Arg Leu Leu Asn Gly Val Arg Glu Lys Leu Asp Gly Val
                325                 330                 335

Val Val Asn Gly Ser Met Asp Ser Arg Tyr Val Gly Asn Leu Asn Leu
            340                 345                 350

Ser Phe Ala Tyr Val Glu Gly Glu Ser Leu Leu Met Gly Leu Lys Glu
        355                 360                 365

Val Ala Val Ser Ser Gly Ser Ala Cys Thr Ser Ala Ser Leu Glu Pro
    370                 375                 380

Ser Tyr Val Leu Arg Ala Leu Gly Val Asp Glu Asp Met Ala His Thr
385                 390                 395                 400

Ser Ile Arg Phe Gly Ile Gly Arg Phe Thr Thr Lys Glu Glu Ile Asp
                405                 410                 415

Lys Ala Val Glu Leu Thr Val Lys Gln Val Glu Lys Leu Arg Glu Met
            420                 425                 430

Ser Pro Leu Tyr Glu Met Val Lys Glu Gly Ile Asp Ile Lys Asn Ile
        435                 440                 445

Gln Trp Ser Gln His
    450
```

```
<210> SEQ ID NO 119
<211> LENGTH: 3180
<212> TYPE: DNA
<213> ORGANISM: Arabidopsis thaliana
<220> FEATURE:
<221> NAME/KEY: CDS
<222> LOCATION: (8)...(1781)
<220> FEATURE:
<221> NAME/KEY: CDS
<222> LOCATION: (1833)...(2609)
<220> FEATURE:
<221> NAME/KEY: CDS
<222> LOCATION: (2697)...(3076)

<400> SEQUENCE: 119 caacacg atg ctc acc aat act aat ctc ttc ttc ttt ctc tct tta ctt        49
        Met Leu Thr Asn Thr Asn Leu Phe Phe Phe Leu Ser Leu Leu
```

```
              1               5                    10
ctt ctt tct tgt ttt ctc caa gtt tct tcc aat gga gac gct gag ata    97
Leu Leu Ser Cys Phe Leu Gln Val Ser Ser Asn Gly Asp Ala Glu Ile
 15                  20                  25                  30 ttg agt aga gtt aaa aag acc cga ctt ttc gac ccc gat gga aat tta   145
Leu Ser Arg Val Lys Lys Thr Arg Leu Phe Asp Pro Asp Gly Asn Leu
                 35                  40                  45 caa gat tgg gtc ata acc gga gat aat cgg agt cca tgt aat tgg acg   193
Gln Asp Trp Val Ile Thr Gly Asp Asn Arg Ser Pro Cys Asn Trp Thr
             50                  55                  60 gga atc aca tgc cac atc aga aaa ggt agc tcc ctc gcc gtc act acc   241
Gly Ile Thr Cys His Ile Arg Lys Gly Ser Ser Leu Ala Val Thr Thr
                 65                  70                  75 att gat ctc tcc ggc tat aat atc tcc ggt ggc ttt ccc tac gga ttc   289
Ile Asp Leu Ser Gly Tyr Asn Ile Ser Gly Gly Phe Pro Tyr Gly Phe
         80                  85                  90 tgt cgt atc cgt aca ctc atc aac atc act ctt tct caa aac aat ctc   337
Cys Arg Ile Arg Thr Leu Ile Asn Ile Thr Leu Ser Gln Asn Asn Leu
 95                 100                 105                 110 aat ggt acg att gat tct gct cct ctc tcc ctc tgt tct aaa ctt cag   385
Asn Gly Thr Ile Asp Ser Ala Pro Leu Ser Leu Cys Ser Lys Leu Gln
                115                 120                 125 aat ttg att ctc aat caa aac aac ttc tcc ggt aaa tta ccg gaa ttc   433
Asn Leu Ile Leu Asn Gln Asn Asn Phe Ser Gly Lys Leu Pro Glu Phe
            130                 135                 140 tca ccg gag ttt cgt aaa tta cga gtc ctc gaa ttg gaa tca aac ctc   481
Ser Pro Glu Phe Arg Lys Leu Arg Val Leu Glu Leu Glu Ser Asn Leu
                145                 150                 155 ttc acc ggt gag att cct caa agt tac ggg aga ctc act gct ctg caa   529
Phe Thr Gly Glu Ile Pro Gln Ser Tyr Gly Arg Leu Thr Ala Leu Gln
160                 165                 170 gtt ctg aat ctt aat ggt aac ccg ctc agt gga atc gtt ccg gcg ttt   577
Val Leu Asn Leu Asn Gly Asn Pro Leu Ser Gly Ile Val Pro Ala Phe
175                 180                 185                 190 ttg ggt tat ctg act gag tta act cgt ctt gat ctc gct tac atc agt   625
Leu Gly Tyr Leu Thr Glu Leu Thr Arg Leu Asp Leu Ala Tyr Ile Ser
                195                 200                 205 ttt gat cct agt ccg att cca tca acc ttg ggg aac ttg tcg aat ctg   673
Phe Asp Pro Ser Pro Ile Pro Ser Thr Leu Gly Asn Leu Ser Asn Leu
            210                 215                 220 act gat ctt cgg cta act cac tcg aac ctc gtc gga gaa att cct gat   721
Thr Asp Leu Arg Leu Thr His Ser Asn Leu Val Gly Glu Ile Pro Asp
                225                 230                 235 tcg atc atg aat ctg gtg ttg tta gag aat ctt gat tta gct atg aat   769
Ser Ile Met Asn Leu Val Leu Leu Glu Asn Leu Asp Leu Ala Met Asn
240                 245                 250 agt ctc acc gga gaa ata cct gag agt atc gga aga ctc gaa tcg gtt   817
Ser Leu Thr Gly Glu Ile Pro Glu Ser Ile Gly Arg Leu Glu Ser Val
255                 260                 265                 270 tac cag att gag ctc tac gat aac cgg tta tct gga aaa tta ccg gag   865
Tyr Gln Ile Glu Leu Tyr Asp Asn Arg Leu Ser Gly Lys Leu Pro Glu
                275                 280                 285 agt atc gga aat tta acc gaa ttg agg aat ttt gat gtc tcg cag aat   913
Ser Ile Gly Asn Leu Thr Glu Leu Arg Asn Phe Asp Val Ser Gln Asn
            290                 295                 300 aat cta acc ggt gaa cta ccg gaa aag atc gct gct ctg caa ctt atc   961
Asn Leu Thr Gly Glu Leu Pro Glu Lys Ile Ala Ala Leu Gln Leu Ile
                305                 310                 315 tct ttc aat ctc aat gat aat ttc ttc acc gga gga tta cca gat gtc  1009
```

```
Ser Phe Asn Leu Asn Asp Asn Phe Phe Thr Gly Gly Leu Pro Asp Val
    320                 325                 330 gta gct ttg aat cct aat ctc gtt gaa ttc aaa atc ttc aac aac agt      1057
Val Ala Leu Asn Pro Asn Leu Val Glu Phe Lys Ile Phe Asn Asn Ser
335                 340                 345                 350 ttc acg ggg acg tta cca agg aat ctc ggg aaa ttc tca gaa atc tct      1105
Phe Thr Gly Thr Leu Pro Arg Asn Leu Gly Lys Phe Ser Glu Ile Ser
                355                 360                 365 gaa ttc gat gtc tcg acg aac aga ttc tcc ggt gaa ttg ccg ccg tat      1153
Glu Phe Asp Val Ser Thr Asn Arg Phe Ser Gly Glu Leu Pro Pro Tyr
            370                 375                 380 ttg tgc tac aga aga aaa ctt cag aag att atc acc ttc agc aat caa      1201
Leu Cys Tyr Arg Arg Lys Leu Gln Lys Ile Ile Thr Phe Ser Asn Gln
        385                 390                 395 tta agc ggc gaa att ccg gaa tct tac ggc gat tgt cat tcg ctt aat      1249
Leu Ser Gly Glu Ile Pro Glu Ser Tyr Gly Asp Cys His Ser Leu Asn
    400                 405                 410 tac att cgt atg gcg gat aac aaa ctc tcc ggc gaa gtt ccg gct agg      1297
Tyr Ile Arg Met Ala Asp Asn Lys Leu Ser Gly Glu Val Pro Ala Arg
415                 420                 425                 430 ttt tgg gaa ctt cct ctt act cgt ctt gag cta gcc aac aac aat caa      1345
Phe Trp Glu Leu Pro Leu Thr Arg Leu Glu Leu Ala Asn Asn Asn Gln
                435                 440                 445 tta caa ggt tcg att cct cct tcg att tcc aaa gct cgt cat cta tct      1393
Leu Gln Gly Ser Ile Pro Pro Ser Ile Ser Lys Ala Arg His Leu Ser
            450                 455                 460 cag ctt gaa atc tcc gct aac aac ttc tcc ggt gtg att ccc gtc aaa      1441
Gln Leu Glu Ile Ser Ala Asn Asn Phe Ser Gly Val Ile Pro Val Lys
        465                 470                 475 ctt tgt gat ctc cgt gat ctc aga gtc atc gat ctt agc cgc aac agt      1489
Leu Cys Asp Leu Arg Asp Leu Arg Val Ile Asp Leu Ser Arg Asn Ser
    480                 485                 490 ttc tta gga tca att ccg tct tgc atc aac aaa ttg aag aat cta gag      1537
Phe Leu Gly Ser Ile Pro Ser Cys Ile Asn Lys Leu Lys Asn Leu Glu
495                 500                 505                 510 aga gta gag atg cag gag aac atg ctc gac ggc gag att ccg agt tca      1585
Arg Val Glu Met Gln Glu Asn Met Leu Asp Gly Glu Ile Pro Ser Ser
                515                 520                 525 gtg agt tcg tgc acc gag tta acc gaa tta aat ctc tcc aac aac cgt      1633
Val Ser Ser Cys Thr Glu Leu Thr Glu Leu Asn Leu Ser Asn Asn Arg
            530                 535                 540 tta cga ggc ggg ata cca ccg gaa ctc ggt gat tta ccg gtt tta aac      1681
Leu Arg Gly Gly Ile Pro Pro Glu Leu Gly Asp Leu Pro Val Leu Asn
        545                 550                 555 tac ctg gat ctc tct aac aac caa ctc acc ggt gag att ccg gcg gag      1729
Tyr Leu Asp Leu Ser Asn Asn Gln Leu Thr Gly Glu Ile Pro Ala Glu
    560                 565                 570 ctg ttg agg ctc aag ctt aat caa ttc aac gtc tcc gat aac aaa ctc      1777
Leu Leu Arg Leu Lys Leu Asn Gln Phe Asn Val Ser Asp Asn Lys Leu
575                 580                 585                 590 tat g gtaagattcc ttctggattt cagcaagata tttttcgacc cagtttctta        1831
Tyr g gt aac ccg aat ctc tgt gcc cca aat ttg gat ccg att aga cct tgc    1879
  Gly Asn Pro Asn Leu Cys Ala Pro Asn Leu Asp Pro Ile Arg Pro Cys
                  595                 600                 605 cga tcc aaa cgg gaa acc cgg tac att ctc cca atc tca atc ctc tgc     1927
Arg Ser Lys Arg Glu Thr Arg Tyr Ile Leu Pro Ile Ser Ile Leu Cys
            610                 615                 620 atc gtt gca cta acc gga gct ttg gtt tgg cta ttc atc aaa acc aaa     1975
```

-continued

```
                Ile Val Ala Leu Thr Gly Ala Leu Val Trp Leu Phe Ile Lys Thr Lys
                    625                 630                 635 ccg tta ttc aag aga aaa ccg aaa cgg acc aac aaa ata acc atc ttc          2023
Pro Leu Phe Lys Arg Lys Pro Lys Arg Thr Asn Lys Ile Thr Ile Phe
640                 645                 650                 655 cag cgg gtc ggg ttc acg gag gaa gac ata tac ccg caa tta aca gaa          2071
Gln Arg Val Gly Phe Thr Glu Glu Asp Ile Tyr Pro Gln Leu Thr Glu
                    660                 665                 670 gat aac ata att ggg tcg ggc ggg tcg ggt ttg gtt tat aga gtg aaa          2119
Asp Asn Ile Ile Gly Ser Gly Gly Ser Gly Leu Val Tyr Arg Val Lys
675                 680                 685 ctc aaa tca ggt caa acg ctt gcg gtg aag aaa ctc tgg gga gaa acg          2167
Leu Lys Ser Gly Gln Thr Leu Ala Val Lys Lys Leu Trp Gly Glu Thr
        690                 695                 700 ggt caa aaa acg gaa tct gaa tct gtt ttt cga tcc gaa gta gag acg          2215
Gly Gln Lys Thr Glu Ser Glu Ser Val Phe Arg Ser Glu Val Glu Thr
705                 710                 715 ttg ggt cgg gtc aga cat gga aac atc gtg aaa ctt ctt atg tgc tgc          2263
Leu Gly Arg Val Arg His Gly Asn Ile Val Lys Leu Leu Met Cys Cys
720                 725                 730                 735 aac ggc gag gag ttt cgg ttc tta gtg tac gag ttc atg gaa aac ggc          2311
Asn Gly Glu Glu Phe Arg Phe Leu Val Tyr Glu Phe Met Glu Asn Gly
                    740                 745                 750 agc tta ggt gac gtt ttg cat tcg gag aaa gaa cat cgt gcc gtt tct          2359
Ser Leu Gly Asp Val Leu His Ser Glu Lys Glu His Arg Ala Val Ser
                755                 760                 765 cca ctt gat tgg acg aca cga ttt tcg atc gcg gtt ggt gct gct caa          2407
Pro Leu Asp Trp Thr Thr Arg Phe Ser Ile Ala Val Gly Ala Ala Gln
            770                 775                 780 gga ctt tct tat cta cat cat gac tct gtt ccg cct att gtt cac cgt          2455
Gly Leu Ser Tyr Leu His His Asp Ser Val Pro Pro Ile Val His Arg
785                 790                 795 gac gtc aaa agc aat aat ata ttg ttg gac cat gag atg aag cca cgt          2503
Asp Val Lys Ser Asn Asn Ile Leu Leu Asp His Glu Met Lys Pro Arg
800                 805                 810                 815 gtc gcc gat ttc ggt tta gct aaa ccg ttg aag aga gaa gac aat gat          2551
Val Ala Asp Phe Gly Leu Ala Lys Pro Leu Lys Arg Glu Asp Asn Asp
                    820                 825                 830 ggt gtc tcc gat gtt tca atg tct tgt gtt gct gga tcc tac ggc tac          2599
Gly Val Ser Asp Val Ser Met Ser Cys Val Ala Gly Ser Tyr Gly Tyr
                835                 840                 845 att gct ccg g gttcgaattc ttagctctac aatatcaaat cgttaaaacc               2649
Ile Ala Pro
        850 ctatacgcaa gcgttttagt aacattactg ttcttctgtg gatgcag aa tat ggt          2704
                                                        Glu Tyr Gly tat acg tca aaa gtg aat gag aag agc gat gtc tat agc ttc ggg gtg          2752
Tyr Thr Ser Lys Val Asn Glu Lys Ser Asp Val Tyr Ser Phe Gly Val
        855                 860                 865 gtt tta ctc gaa ctg att acg gga aaa aga ccg aac gat tcg tct ttt          2800
Val Leu Leu Glu Leu Ile Thr Gly Lys Arg Pro Asn Asp Ser Ser Phe
870                 875                 880                 885 ggg gag aat aag gac att gtt aag ttt gca atg gaa gca gct ttg tgt          2848
Gly Glu Asn Lys Asp Ile Val Lys Phe Ala Met Glu Ala Ala Leu Cys
                    890                 895                 900 tac cct tct cca tca gca gaa gac gga gcc atg aat caa gat tca ctt          2896
Tyr Pro Ser Pro Ser Ala Glu Asp Gly Ala Met Asn Gln Asp Ser Leu
                905                 910                 915 gga aac tat cga gat ctt agc aag ctt gtt gat cca aag atg aaa ctt          2944
```

```
Gly Asn Tyr Arg Asp Leu Ser Lys Leu Val Asp Pro Lys Met Lys Leu
            920                 925                 930 tcg acg aga gag tat gaa gag ata gag aaa gtt ctt gac gtt gca ttg      2992
Ser Thr Arg Glu Tyr Glu Glu Ile Glu Lys Val Leu Asp Val Ala Leu
935                 940                 945 ctc tgt acg tcg tct ttt cct atc aac agg ccg acc atg agg aaa gta      3040
Leu Cys Thr Ser Ser Phe Pro Ile Asn Arg Pro Thr Met Arg Lys Val
950                 955                 960                 965 gta gag ttg ctt aaa gag aag aaa tca cta gag tga tattaatcct           3086
Val Glu Leu Leu Lys Glu Lys Lys Ser Leu Glu *
                970                 975 aggcttttaa ttattaggct tctataatgt acaaaatccg actaggattg ttactcatta    3146
ttatagccat aggttggact ttgctttaaa gttt                                3180

<210> SEQ ID NO 120
<211> LENGTH: 976
<212> TYPE: PRT
<213> ORGANISM: Arabidopsis thaliana

<400> SEQUENCE: 120

Met Leu Thr Asn Thr Asn Leu Phe Phe Leu Ser Leu Leu Leu
 1               5                  10                  15

Ser Cys Phe Leu Gln Val Ser Ser Asn Gly Asp Ala Glu Ile Leu Ser
            20                  25                  30

Arg Val Lys Lys Thr Arg Leu Phe Asp Pro Asp Gly Asn Leu Gln Asp
        35                  40                  45

Trp Val Ile Thr Gly Asp Asn Arg Ser Pro Cys Asn Trp Thr Gly Ile
    50                  55                  60

Thr Cys His Ile Arg Lys Gly Ser Ser Leu Ala Val Thr Thr Ile Asp
65                  70                  75                  80

Leu Ser Gly Tyr Asn Ile Ser Gly Gly Phe Pro Tyr Gly Phe Cys Arg
                85                  90                  95

Ile Arg Thr Leu Ile Asn Ile Thr Leu Ser Gln Asn Asn Leu Asn Gly
            100                 105                 110

Thr Ile Asp Ser Ala Pro Leu Ser Leu Cys Ser Lys Leu Gln Asn Leu
        115                 120                 125

Ile Leu Asn Gln Asn Asn Phe Ser Gly Lys Leu Pro Glu Phe Ser Pro
    130                 135                 140

Glu Phe Arg Lys Leu Arg Val Leu Glu Leu Ser Asn Leu Phe Thr
145                 150                 155                 160

Gly Glu Ile Pro Gln Ser Tyr Gly Arg Leu Thr Ala Leu Gln Val Leu
                165                 170                 175

Asn Leu Asn Gly Asn Pro Leu Ser Gly Ile Val Pro Ala Phe Leu Gly
            180                 185                 190

Tyr Leu Thr Glu Leu Thr Arg Leu Asp Leu Ala Tyr Ile Ser Phe Asp
        195                 200                 205

Pro Ser Pro Ile Pro Ser Thr Leu Gly Asn Leu Ser Asn Leu Thr Asp
    210                 215                 220

Leu Arg Leu Thr His Ser Asn Leu Val Gly Glu Ile Pro Asp Ser Ile
225                 230                 235                 240

Met Asn Leu Val Leu Leu Glu Asn Leu Asp Leu Ala Met Asn Ser Leu
                245                 250                 255

Thr Gly Glu Ile Pro Glu Ser Ile Gly Arg Leu Glu Ser Val Tyr Gln
            260                 265                 270

Ile Glu Leu Tyr Asp Asn Arg Leu Ser Gly Lys Leu Pro Glu Ser Ile
```

-continued

```
                275                 280                 285
Gly Asn Leu Thr Glu Leu Arg Asn Phe Asp Val Ser Gln Asn Asn Leu
    290                 295                 300
Thr Gly Glu Leu Pro Glu Lys Ile Ala Ala Leu Gln Leu Ile Ser Phe
305                 310                 315                 320
Asn Leu Asn Asp Asn Phe Phe Thr Gly Gly Leu Pro Asp Val Val Ala
                325                 330                 335
Leu Asn Pro Asn Leu Val Glu Phe Lys Ile Phe Asn Asn Ser Phe Thr
                340                 345                 350
Gly Thr Leu Pro Arg Asn Leu Gly Lys Phe Ser Glu Ile Ser Glu Phe
                355                 360                 365
Asp Val Ser Thr Asn Arg Phe Ser Gly Glu Leu Pro Pro Tyr Leu Cys
                370                 375                 380
Tyr Arg Arg Lys Leu Gln Lys Ile Ile Thr Phe Ser Asn Gln Leu Ser
385                 390                 395                 400
Gly Glu Ile Pro Glu Ser Tyr Gly Asp Cys His Ser Leu Asn Tyr Ile
                405                 410                 415
Arg Met Ala Asp Asn Lys Leu Ser Gly Glu Val Pro Ala Arg Phe Trp
                420                 425                 430
Glu Leu Pro Leu Thr Arg Leu Glu Leu Ala Asn Asn Gln Leu Gln
                435                 440                 445
Gly Ser Ile Pro Pro Ser Ile Ser Lys Ala Arg His Leu Ser Gln Leu
                450                 455                 460
Glu Ile Ser Ala Asn Asn Phe Ser Gly Val Ile Pro Val Lys Leu Cys
465                 470                 475                 480
Asp Leu Arg Asp Leu Arg Val Ile Asp Leu Ser Arg Asn Ser Phe Leu
                485                 490                 495
Gly Ser Ile Pro Ser Cys Ile Asn Lys Leu Lys Asn Leu Glu Arg Val
                500                 505                 510
Glu Met Gln Glu Asn Met Leu Asp Gly Glu Ile Pro Ser Ser Val Ser
                515                 520                 525
Ser Cys Thr Glu Leu Thr Glu Leu Asn Leu Ser Asn Asn Arg Leu Arg
                530                 535                 540
Gly Gly Ile Pro Pro Glu Leu Gly Asp Leu Pro Val Leu Asn Tyr Leu
545                 550                 555                 560
Asp Leu Ser Asn Asn Gln Leu Thr Gly Glu Ile Pro Ala Glu Leu Leu
                565                 570                 575
Arg Leu Lys Leu Asn Gln Phe Asn Val Ser Asp Asn Lys Leu Tyr Gly
                580                 585                 590
Asn Pro Asn Leu Cys Ala Pro Asn Leu Asp Pro Ile Arg Pro Cys Arg
                595                 600                 605
Ser Lys Arg Glu Thr Arg Tyr Ile Leu Pro Ile Ser Ile Leu Cys Ile
                610                 615                 620
Val Ala Leu Thr Gly Ala Leu Val Trp Leu Phe Ile Lys Thr Lys Pro
625                 630                 635                 640
Leu Phe Lys Arg Lys Pro Lys Arg Thr Asn Lys Ile Thr Ile Phe Gln
                645                 650                 655
Arg Val Gly Phe Thr Glu Glu Asp Ile Tyr Pro Gln Leu Thr Glu Asp
                660                 665                 670
Asn Ile Ile Gly Ser Gly Gly Ser Gly Leu Val Tyr Arg Val Lys Leu
                675                 680                 685
Lys Ser Gly Gln Thr Leu Ala Val Lys Lys Leu Trp Gly Glu Thr Gly
                690                 695                 700
```

| | | | | | | | | | | | |
|---|---|---|---|---|---|---|---|---|---|---|---|
|Gln|Lys|Thr|Glu|Ser|Glu|Ser|Val|Phe|Arg|Ser|Glu|Val|Glu|Thr|Leu|
|705| | | |710| | | |715| | | |720| | | |

Gly Arg Val Arg His Gly Asn Ile Val Lys Leu Leu Met Cys Cys Asn
                    725                    730                  735

Gly Glu Glu Phe Arg Phe Leu Val Tyr Glu Phe Met Glu Asn Gly Ser
           740                    745                    750

Leu Gly Asp Val Leu His Ser Glu Lys Glu His Arg Ala Val Ser Pro
        755                    760                765

Leu Asp Trp Thr Thr Arg Phe Ser Ile Ala Val Gly Ala Ala Gln Gly
770                    775                    780

Leu Ser Tyr Leu His His Asp Ser Val Pro Pro Ile Val His Arg Asp
785                  790                    795                800

Val Lys Ser Asn Asn Ile Leu Leu Asp His Glu Met Lys Pro Arg Val
            805                    810                815

Ala Asp Phe Gly Leu Ala Lys Pro Leu Lys Arg Glu Asp Asn Asp Gly
        820                    825                830

Val Ser Asp Val Ser Met Ser Cys Val Ala Gly Ser Tyr Gly Tyr Ile
        835                    840                845

Ala Pro Glu Tyr Gly Tyr Thr Ser Lys Val Asn Glu Lys Ser Asp Val
850                    855                    860

Tyr Ser Phe Gly Val Val Leu Leu Glu Leu Ile Thr Gly Lys Arg Pro
865                  870                  875                880

Asn Asp Ser Ser Phe Gly Glu Asn Lys Asp Ile Val Lys Phe Ala Met
           885                    890                895

Glu Ala Ala Leu Cys Tyr Pro Ser Pro Ser Ala Glu Asp Gly Ala Met
        900                    905                910

Asn Gln Asp Ser Leu Gly Asn Tyr Arg Asp Leu Ser Lys Leu Val Asp
           915                    920                925

Pro Lys Met Lys Leu Ser Thr Arg Glu Tyr Glu Glu Ile Glu Lys Val
        930                    935                940

Leu Asp Val Ala Leu Leu Cys Thr Ser Ser Phe Pro Ile Asn Arg Pro
945                    950                  955                960

Thr Met Arg Lys Val Val Glu Leu Leu Lys Glu Lys Ser Leu Glu
           965                    970                975

<210> SEQ ID NO 121
<211> LENGTH: 731
<212> TYPE: DNA
<213> ORGANISM: Arabidopsis thaliana

<400> SEQUENCE: 121

```
aagtcgagta tgattgtccg tacgtgctcg acggtgcgac cgtacgtacc ctggcagtcg      60
ccctgacgca acttcgaatc tgccctgcgc cctgctcctc ctatggcagt actgcgtact     120
tcgacgagca ggagctgaag ctgactataa cgtgcctggt cgaaaagcat gccagcccat     180
gaaaaggag atcgagaacg gtatctcgga cttcggcgag acggctccg ggaacgtcga      240
tttcgagaag tccgtgcaaa tcggtacggc gcggaacggc gagcgccacg cacgcgacga     300
ggtcataaac gaaacccgcc tgttcggcgc acgccaaacc gggacgataa cctgcaacag     360
cctaaaacgc ccggccgagg agctaggcca ggggcggac ccggaggaga tcccgggaac      420
ccgcgacgag gccgacaggc agggcgacgg cgagaccaag aacgaacgtg ccgtcagctg     480
tagaccggac gggcgacccca tccagccctga ccgcttggac ccgtacccgt tgcctgaaat     540
gcctgaattc gcctcgcctt ggatgcctgc tctgaaatgc tcgcctgttg cctgaattcg     600
```

```
                                        -continued ctctgaaatc cgttcccccg cctccgcagc tcgtgaccgt ccgaaccgct cgaaccctgc      660
aaaaaaagcc tcgaaaaaaa aaaaaggctc aaaaaaaaaa aaaaaacagt ccaaaaaaaa      720
aaacgcctcg c                                                           731

<210> SEQ ID NO 122
<211> LENGTH: 21
<212> TYPE: DNA
<213> ORGANISM: Arabidopsis thaliana

<400> SEQUENCE: 122
aaaaaacaca tacaggaatt c                                                 21

<210> SEQ ID NO 123
<211> LENGTH: 21
<212> TYPE: DNA
<213> ORGANISM: Arabidopsis thaliana

<400> SEQUENCE: 123
agttagctag ctgagctcga g                                                 21
```

GENES INVOLVED IN TOLERANCE TO ENVIRONMENTAL STRESS

This application is a continuation application of application Ser. No. 09/762,154 filed on Feb. 2, 2001 now abandoned, which in turn claims priority to PCT Application No. PCT/EP99/05652 filed on Aug. 4, 1999 and European Application No. 98202634.0 filed on Aug. 4, 1998. The contents of all of the aforementioned application(s) are hereby incorporated by reference.

The present invention relates to molecular biology, in particular plant molecular biology. In particular, the invention relates to improvements of crop productivity of useful plants. One of the major limitations of crop productivity is the effect of environmental stress conditions on plant growth and development. An important goal of molecular biology is the identification and isolation of genes that can provide resistance or tolerance to such stresses. For agriculture, the creation of transgenic plants containing such genes provides the potential for improving the stress resistance or tolerance of plants.

Drought, salt loading, and freezing are stresses that cause adverse effects on the growth of plants and the productivity of crops. The physiological response to these stresses arises out of changes in cellular gene expression. Expression of a number of genes has been demonstrated to be induced by these stresses (Zhu et al., 1997; Shinozaki et al., 1996; Thomashow, 1994). The products of these genes can be classified into two groups: those that directly protect against environmental stresses and those that regulate gene expression and signal transduction in the stress response. The first group includes proteins that likely function by protecting cells from dehydration, such as the enzymes required for biosynthesis of various osmoprotectants, late-embryogenesis-abundant (LEA) proteins, antifreeze proteins, chaperones, and detoxitication enzymes (Shinozaki et al., 1997; Ingram et al., 1996, Bray et al., 1997). The second group of gene products includes transcription factors, protein kinases, and enzymes involved in phosphoinositide metabolism (Shinozaki et al., 1997). An overview of the methods known to improve stress tolerance in plants is also given in Holmberg & Bülow, (1998).

Further studies are definitely needed to give an insight into the mechanisms involved in the plant response to environmental stress conditions.

The study of plants naturally adapted to extreme desiccation has led to the hypothesis that the genetic information for tolerance to environmental stress conditions exists in all higher plants. In glycophytes, this information would only be expressed in seeds and pollen grains which undergo a desiccation process.

The induction of osmotolerance in plants is very important to crop productivity: 30 to 50% of the land under irrigation is presently affected by salinity. Several lines of evidence also demonstrate that even mild environmental stress conditions throughout the growth season have a negative impact on plant growth and crop productivity. It is for instance known that even minor limitations in water availability cause a reduced photosynthetic rate. Unpredictable rainfall, increase in soil salinity at the beginning and the end of the growing season often result in decreased plant growth and crop productivity. These environmental factors share at least one element of stress and that is water deficit or dehydration. Drought is a significant problem in agriculture today. Over the last 40 years, for example, drought accounted for 74% of the total US crop losses of corn. To sustain productivity under adverse environmental conditions, it is important to provide crops with a genetic basis for coping with water deficit, for example by breeding water retention and tolerance mechanisms into crops so that they can grow and yield under these adverse conditions.

It is an aim of the present invention to provide a new method for screening for plant genes involved in tolerance or resistance to environmental stress.

It is an aim of the present invention to provide new plant genes, more particularly plant genes providing the potential of improving the tolerance to environmental stress conditions in plants.

It is also an aim of the present invention to provide polypeptides encoded by said new plant genes.

It is further an aim of the present invention to provide methods for producing plants with enhanced tolerance or resistance to environmental stress conditions based on said new genes.

It is also an aim of the present invention to provide recombinant polynucleic acids comprising said new genes.

It is further an aim of the present invention to provide plant cells and plants transformed with said new genes.

It is further an aim of the present invention to provide plant cells and plants with enhanced tolerance or resistance to environmental stress conditions.

The present invention relates more particularly to a method for obtaining polynucleic acids comprising coding sequences and/or genes involved in environmental stress in plants, comprising the preparation of a cDNA library comprising coding sequences from siliques, introducing said coding sequences in yeast cells in a functional format and screening for polynucleic acids leading to an enhanced tolerance or resistance to environmental stress conditions in said transformed yeast cells.

It has been found that the transfer of genes from plants which are often difficult to assay for certain characteristics, to lower eukaryotes, such as yeasts and fungi, but in particular yeast, especially Saccharomyces, is relatively-easy to achieve, whereby it has now been shown that the results of testing for tolerance or resistance to environmental conditions in the resulting yeast cells gives a relatively reliable measure of the capability of the inserted coding sequence or gene to induce tolerance or resistance to environmental stress in plants. Thus the expression of polynucleic acid sequences comprising the gene or coding sequence which are responsible for inducing tolerance or resistance to environmental stress conditions can be enhanced in the plant species from which it originates or in any other plant species.

In the present context the term "enhancing" must be understood to mean that the levels of molecules correlated with stress protection in a transformed plant cell, plant tissue or plant part will be "substantially increased" or "elevated" meaning that this level will be greater than the levels in an untransformed plant.

This may be achieved by inducing overexpression of suitable genetic information which is already present, or by any other suitable means of introducing into the plant cell heterologous information resulting in a capability to tolerate or resist environmental stress.

The term "environmental stress" has been defined in different ways in the prior art and largely overlaps with the term "osmotic stress". Holmberg et al., 1998 for instance define different environmental stress factors which result in abiotic stress. Salinity, drought, heat, chilling and freezing are all described as examples of conditions which induce osmotic stress. The term "environmental stress" as used in the present invention refers to any adverse effect on metabolism, growth or viability of the cell, tissue, seed, organ or whole plant which is produced by an non-living or non-biological environmental stressor. More particularly, it also encompasses environmental factors such as water stress (flooding, drought, dehydration), anaerobic (low level of oxygen, $CO_2$ etc.), aerobic stress, osmotic stress, salt stress, temperature stress (hot/heat, cold, freezing, frost) or nutrients/pollutants stress.

The term "anaerobic stress" means any reduction in oxygen levels sufficient to produce a stress as hereinbefore defined, including hypoxia and anoxia.

The term "flooding stress" refers to any stress which is associated with or induced by prolonged or transient immersion of a plant, plant part, tissue or isolated cell in a liquid medium such as occurs during monsoon, wet season, flash flooding or excessive irrigation of plants, etc.

"Cold stress" and "heat stress" are stresses induced by temperatures which are respectively, below or above, the optimum range of growth temperatures for a particular plant species. Such optimum growth temperature ranges are readily determined or known to those skilled in the art.

"Dehydration stress" is any stress which is associated with or induced by the loss of water, reduced turgor or reduced water content of a cell, tissue, organ or whole plant.

"Drought stress" refers to any stress which is induced by or associated with the deprivation of water or reduced supply of water to a cell, tissue, organ or organism.

"Oxidative stress" refers to any stress which increases the intracellular level of reactive oxygen species.

The terms "salinity-induced stress", "salt-stress" or similar term refer to any stress which is associated with or induced by elevated concentrations of salt and which result in a perturbation in the osmotic potential of the intracellular or extracellular environment of a cell.

Said salt can be for example, water soluble inorganic salts such as sodium sulfate, magnesium sulfate, calcium sulfate, sodium chloride, magnesium chloride, calcium chloride, potassium chloride etc., salts of agricultural fertilizers and salts associated with alkaline or acid soil conditions.

The transgenic plants obtained in accordance with the method of the present invention, upon the presence of the polynucleic acid and/or regulatory sequence introduced into said plant, attain resistance, tolerance or improved tolerance or resistance against environmental stress which the corresponding wild-type plant was susceptible to.

The terms "tolerance" and "resistance" cover the range of protection from a delay to complete inhibition of alteration in cellular metabolism, reduced cell growth and/or cell death caused by the environmental stress conditions defined herein before. Preferably, the transgenic plant obtained in accordance with the method of the present invention is tolerant or resistant to environmental stress conditions in the sense that said plant is capable of growing substantially normal under environmental conditions where the corresponding wild-type plant shows reduced growth, metabolism, viability, productivity and/or male or female sterility. Methodologies to determine plant growth or response to stress include, but are not limited to height measurements, leaf area, plant water relations, ability to flower, ability to generate progeny and yield or any other methodology known to those skilled in the art.

The terms "tolerance" and "resistance" may be used interchangeably in the present invention.

The methods according to the invention as set out below can be applied to any, higher plant, preferably important crops, preferably to all cells of a plant leading to an enhanced osmotic or any other form of environmental stress tolerance. By means of the embodiments as set out below, it now becomes possible to grow crops with improved yield, growth, development and productivity under environmental stress conditions, it may even become possible for instance to grow crops in areas where they cannot grow without the induced osmotolerance according to the invention.

In order to do a thorough screening for relevant plant genes and/or coding sequences, it is preferred to apply a method according to the invention whereby said cDNA library comprises copies of essentially all mRNA of said plant cell. Probably only coding sequences are sufficient. For the screening of genes involved in environmental stress, it is preferred to use a cDNA library from siliques (fruits, containing the maturing seeds), such as the siliques from *Arabidopsis*, because genes involved in for instance osmotolerance are preferentially expressed in these organs.

Although the genetic information may be introduced into yeast for screening by any suitable method, as long as it is in a functional format long enough for testing of tolerance or resistance to environmental stress conditions, it is preferred for ease of operation to use a well known vector such as a 2μ plasmid. It is to be preferred to have the coding sequence or the gene under control of a strong constitutive yeast promoter, to enhance good expression of the gene or coding sequence of interest. Strong constitutive yeast promoters are well known in the art and include, but are not limited to the yeast TPI promoter.

The term "gene" as used herein refers to any DNA sequence comprising several operably linked DNA fragments such as a promoter and a 5' untranslated region (the 5'UTR), a coding region (which may or may not code for a protein), and an untranslated 3' region (3'UTR) comprising a polyadenylation site. Typically in plant cells, the 5'UTR, the coding region and the 3'UTR (together referred to as the transcribed DNA region) are transcribed into an RNA which, in the case of a protein encoding gene, is translated into a protein. A gene may include additional DNA fragments such as, for example, introns. As used herein, a genetic locus is the position of a given gene in the genome of a plant.

The present invention more particularly relates to an isolated polynucleic acid obtainable by a method comprising the preparation of a cDNA as set out above comprising coding sequences from siliques, introducing said coding sequences in yeast cells in a functional format and screening for polynucleic acids leading to an enhanced tolerance or resistance to environmental stress conditions in said transformed yeast cells.

The term "polynucleic acid" refers to DNA or RNA, or amplified versions thereof, or the complement thereof.

The present invention more particularly provides an isolated polynucleic acid obtainable by a method as defined above which encodes a polypeptide as listed in Table 1.

The capacity of an isolated polynucleic acid to confer tolerance or resistance to environmental stress conditions can be tested according to methods well-known in the art, see for example, Grillo et al. (1996), Peassarakli et al. (Editor), Nilsen et al. (1996), Shinozaki et al. (1999), Jones et al. (1989), Fowden et al. (1993) or as described in the appended examples.

The present invention more particularly relates to an isolated polynucleic acid which encodes a homolog of any of the polypeptides as listed in Table 1, which is chosen from:
  (a) any of SEQ ID NO 1, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, or 121, or the complementary strands thereof;
  (b) polynucleic acid sequences which hybridize to sequences defined in (a) or fragments thereof;
  (c) polynucleic acid sequences which are degenerated as a result of the genetic code to the polynucleic acid sequences defined in (a) or (b), or,
  (d) polynucleic acid sequences encoding a fragment of a protein encoded by a polynucleic acid of any one of (a) to (c).

Preferably said sequences according to part (b) hybridize under stringent conditions to the sequences of part (a).

Said fragment as defined above are preferably unique fragments of said sequences.

The term "hybridizing" refers to hybridization conditions as described in Sambrook (1989), preferably specific or stringent hybridization conditions are aimed at.

Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, genomic DNA or cDNA comprising the polynucleic acids of the invention can be identified in standard Southern blots under stringent conditions using the cDNA sequence shown. The preparation of both genomic and cDNA libraries is within the skill of the art. Examples of hybridization conditions are also given in the Examples section.

The present invention also relates to the isolated polynucleic acids which encode polypeptides which are a homolog of the polypeptides as set out in Table 1 useful for the production of plants which are resistant or tolerant to environmental stress conditions.

The present invention also relates to a polynucleic acid comprising at least part of any of SEQ ID NO 1, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 or 121, or at least part of a gene that is at least 50% identical, preferentially at least 55%, 60%, 65% or 70% identical, more preferably at least 75%, 80% or 85% identical, and most preferably at least 90% or 95% identical to any of SEQ ID NO 1, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77 or 121. Preferably, said gene encodes a protein having substantially the same biological activity as the protein having the sequence of SEQ ID NO 2, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76 or 78. Said part of said gene is preferably a unique part.

The present invention preferably relates to the use of a polynucleic acid comprising at least part of any of SEQ ID NO 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, or 121, or at least part of a gene that is at least 50% identical, preferentially at least 55%, 60%, 65% or 70% identical, more preferably at least 75%, 80% or 85% identical, and most preferably at least 90% or 95% identical to any of SEQ ID NO 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, or 121 for the production of transgenic plants having enhanced tolerance or resistance to environmental stress conditions.

Preferably, said gene encodes a protein having substantially the same biological activity as the protein having the sequence of SEQ ID NO 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, or 120. Said part of said gene is preferably a unique part.

The present invention particularly relates to an isolated polynucleic acid as defined above, which encodes a plant homolog of yeast DBF2 kinase, more particularly a DBF2 kinase homolog from *Arabidopsis thaliana* termed At-DBF2, which can at least be used to confer enhanced environmental stress tolerance or resistance in plants and yeast.

More preferably, the present invention relates to an isolated polynucleic acid encoding a plant DFB2 kinase, which is chosen from:
  (a) SEQ ID NO 1, or the complementary strand thereof;
  (b) polynucleic acid sequences which hybridize to sequences defined in (a) or fragments thereof;
  (e) polynucleic acid sequences which are degenerated as a result of the genetic code to the polynucleic acid sequences defined in (a) or (b), or,
  (c) polynucleic acid sequences encoding a fragment of a protein encoded by a polynucleic acid of any one of (a) to (c).

Preferably said sequences according to part (b) hybridize under stringent conditions to the sequences of part (a).

Alternatively, the present invention relates to a polynucleic acid derived from a plant comprising at least part of SEQ ID NO 1, or at least part of a gene having a sequence that is at least 50% identical, preferentially at least 55%, 60%, 65% or 70% identical, more preferably at least 75%, 80% or 85% identical, and most preferably at least 90% or 95% identical to SEQ ID NO 1. Preferably said gene encodes a protein having substantially the same biological activity as the protein having the sequence of SEQ ID NO 2.

The present invention also relates to the use of an isolated polynucleic acid as defined above which encodes a plant HSP 17.6A protein for the production of transgenic plants, more particularly a homolog from *Arabidopsis thaliana*, which at least can be used to confer enhanced environmental stress tolerance in plants and yeast.

More preferably, the present invention relates to the use of an isolated polynucleic acid as defined above which is chosen from:
(a) SEQ ID NO 3, or the complementary strand thereof;
(b) polynucleic acid sequences which hybridize to sequences defined in (a) or fragments thereof;
(c) polynucleic acid sequences which are degenerated as a result of the genetic code to the polynucleic acid sequences defined in (a) or (b) or,
(d) polynucleic acid sequences encoding a fragment of a protein encoded by a polynucleic acid of any one of (a) to (c), for the production of transgenic plants having an enhanced tolerance or resistance to environmental stress conditions.

Preferably said sequences according to part (b) hybridize under stringent conditions to the sequences of part (a).

The present invention also relates to the use of a polynucleic acid comprising at least part of SEQ ID NO 3, or at least part of a gene having a sequence that is at least 50% identical, preferentially at least 55%, 60%, 65% or 70% identical, more preferably at least 75%, 80% or 85% identical, and most preferably at least 90% or 95% identical to SEQ ID NO 3. Preferably said gene encodes a protein having substantially the same biological activity as the protein having the sequence of SEQ ID NO 4, for the production of transgenic plants having enhanced tolerance or resistance to environmental stress conditions.

More preferably, the present invention relates to the use of an isolated polynucleic acid as defined above which is chosen from:
(a) any of SEQ ID NO 79, 81, 83, 85, 87, 89, 91, 93, 95, 97, 99, 101, 103, 105, 107, 109, 111, 113, 115, 117, or 119, or the complementary strand thereof;
(b) polynucleic acid sequences which hybridize to sequences defined in (a) or fragments thereof;
(c) polynucleic acid sequences which are degenerated as a result of the genetic code to the polynucleic acid sequences defined in (a) or (b) or,
(d) polynucleic acid sequences encoding a fragment of a protein encoded by a polynucleic acid of any one of (a) to (c), for the production of transgenic plants-having an enhanced tolerance or resistance to environmental stress conditions.

The present invention preferably relates to the use of a polynucleic acid comprising at least part of any of SEQ ID NO 79, 81, 83, 85, 87, 89, 91, 93, 95, 97, 99, 101, 103, 105, 107, 109, 111, 113, 115, 117, or 119, or at least part of a gene that is at least 50% identical, preferentially at least 55%, 60%, 65% or 70% identical, more preferably at least 75%, 80% or 85% identical, and most preferably at least 90% or 95% identical to any of SEQ ID NO 79, 81, 83, 85, 87, 89, 91, 93, 95, 97, 99, 101, 103, 105, 107, 109, 111, 113, 115, 117, or 119, for the production of transgenic plants having enhanced tolerance or resistance to environmental stress conditions.

Preferably, said gene encodes a protein having substantially the same biological activity as the protein having the sequence of SEQ ID NO 80, 82, 84, 86, 88, 90, 92, 94, 96, 98, 100, 102, 104, 106, 108, 110, 112, 114, 116, 118, or 120. Said part of said gene is preferably a unique part.

According to another preferred embodiment, the present invention relates to an isolated polynucleic acid as defined above, which encodes a protein termed c74, more particularly a plant homolog of c74, even more preferably a c74 from *Arabidopsis thaliana*, which at least can be used to confer enhanced environmental stress tolerance in plants and yeast.

More particularly, the present invention relates to an isolated polynucleic acid as defined above, which is chosen from:
(a) SEQ ID NO 5, or the complementary strand thereof;
(b) polynucleic acid sequences which hybridize to sequences defined in (a) or fragments thereof;
(c) polynucleic acid sequences which are degenerated as a result of the genetic code to the polynucleic acid sequences defined in (a) or (b) or,
(d) polynucleic acid sequences encoding a fragment of a protein encoded by a polynucleic acid of any one of (a) to (c).

Preferably said sequences according to part (b) hybridize under stringent conditions to the sequences of part (a).

The present invention also relates to a polynucleic acid comprising at least part of SEQ ID NO 5, or at least part of a gene having a sequence that is at least 50% identical, preferentially at least 55%, 60%, 65% or 70% identical, more preferably at least 75%, 80% or 85% identical, and most preferably at least 90% or 95% identical to SEQ ID NO 5. Preferably said gene encodes a protein having substantially the same biological activity as the protein having the sequence of SEQ ID NO 6.

Two nucleic acid sequences or polypeptides are said to be "identical" according to the present invention if the sequence of nucleotides or amino acid residues, respectively, in the two sequences is the same when aligned for maximum correspondence as described below. The term "complementary to" is used herein to mean that the complementary sequence hybridizes to all or a portion of a given polynucleotide sequence.

Sequence comparisons between two (or more) polynucleic acid or polypeptide sequences are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by visual inspection.

"Percentage of sequence identity" is determined by comparing two optimally aligned sequences over a comparison window, wherein the portion of the polynucleic acid or polypeptide sequences in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleic acid or polypeptide sequences means that a polynucleotide sequence comprises a sequence that has at least 60%, 65%, 70% or 75% sequence identity, preferably at least 80% or 85%, more preferably at least 90% and most preferably at least 95%, compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, 45%, 50% or 55% preferably at least 60%, 65%, 70%, 75%, 80% or 85% more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other, or a third nucleic acid, under stringent conditions.

More particularly, the polynucleic acids as used herein will comprise at least part of a DNA sequence which is essentially similar, or, preferentially, essentially identical or identical to one or both of the nucleotide or amino acid sequences corresponding to SEQ ID NO 1 to 121 disclosed herein, more specifically in the nucleotide sequence encoding, or the amino-acid sequence corresponding to the "active domain" of the respective protein or polypeptide.

The polynucleic acid sequences according to the present invention can be produced by means of any nucleic acid amplification technique known in the art such as PCR or conventional chemical synthesis.

For a general overview of PCR see PCR Protocols (Innis et al. (1990)).

Polynucleotides may also be synthesized by well-known techniques as described in the technical literature. See, e.g., Carruthers et al. (1982) and Adams et al. (1983). Double stranded DNA fragments may then be obtained either by synthesizing the complementary strand and annealing the strands together under appropriate conditions, or by adding the complementary strand using DNA polymerase with an appropriate primer sequence.

The present invention more particularly relates to an isolated polypeptide encoded by a polynucleic acid according to any of the polynucleic acids as defined above, or a functional fragment thereof.

The present invention preferably relates to an isolated polypeptide as listed in Table 1 or to an isolated polypeptide encoded by a polynucleic acid isolated as defined above. Preferably, the present invention relates to polypeptides or peptides having at least part of the sequence of any of SEQ ID NO NO 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, or 120. Preferably, said part is a unique part and preferably includes the active domain of said polypeptide. Preferably said polypeptide is a recombinant polypeptide.

The term "isolated" distinguishes the protein or polynucleic acid according to the invention from the naturally occuring one.

The present invention also relates to a polypeptide comprising at least part of a polypeptide which is at least 50%, 55%, 60%, 65% identical, preferentially at least 70%, 75% identical, more preferably at least 80% or 85% identical, and most preferably at least 90% or 95% identical to any of SEQ ID NO NO 2, 4, 6, 8, 10, 12, 14,16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, or 120.

The terms "polypeptide" and "protein" are used interchangeably throughout the present description.

Said polypeptide preferably has the ability to confer tolerance or resistance to environmental stress conditions in at least plants, plant parts, plant tissues, plant cells, plant calli or yeast.

The term "functional fragment" refers to a fragment having substantially the biological activity of the protein from which it is derived.

The polypeptides of the present invention may be produced by recombinant expression in prokaryotic and eukaryotic engineered cells such as bacteria, yeast or fungi. It is expected that those of skill in the art are knowledgeable in the numerous expression systems available for expression in these systems.

The present invention more particularly relates to a method for producing a plant with enhanced environmental stress resistance or tolerance, said method comprising transiently introducing into a plant cell a recombinant DNA comprising any of the polynucleic acids as defined above which when (over)expressed in a plant cell enhances tolerance or resistance to environmental stress of said plant.

The term "plant cell" as defined above also comprises plant tissue or a plant as a whole. The present invention more particularly relates to a method for producing a plant with enhanced environmental stress resistance or tolerance, said method comprising transiently introducing into a plant cell a recombinant DNA comprising any of the polynucleic acids encoding a protein as listed in Table 1 which when (over) expressed in a plant cell enhances tolerance or resistance to environmental stress in said plant.

The term "(over)expression" refers to the fact that the polypeptides of the invention encoded by said polynucleic acid are preferably expressed in an amount effective to confer tolerance or resistance to the transformed plant, to an amount of salt, heat, cold, (or other stress factors) that inhibits the growth of the corresponding untransformed plant.

Several methods to obtain transient introduction and expression of a recombinant DNA in a plant are known to the art. For example, plant virus vectors can be used to obtain such purpose. Examples conferring to the use of plant viral vectors are described in Porta and Lomonossoff (1996), WO9320217 and U.S. Pat. No. 5,589,367.

The present invention also relates to a method for producing a plant with enhanced environmental stress resistance or tolerance, said method comprising stably introducing into the genome of a plant cell a recombinant DNA comprising any of the polynucleic acids as defined above which when (over)expressed in a plant cell enhances the environmental stress tolerance or resistance of a plant.

The present invention also relates to a method for producing a plant with enhanced tolerance or resistance to environmental stress conditions, said method comprising introducing into the genome of a plant cell a recombinant DNA comprising any of the polynucleic acids encoding a protein as listed Table 1 which when (over)expressed in a plant cell enhances the environmental stress resistance of said plant.

According to a preferred embodiment, the present invention relates to a method for producing a plant with enhanced tolerance or resistance to environmental stress, said method comprising introducing into said plant a polynucleic acid as defined above encoding a DBF2 kinase, preferably a plant DBF2 kinase, most preferably an *Arabidopsis* DBF2 kinase.

According to another preferred embodiment, the present invention relates to a method as defined above for producing a plant with enhanced tolerance or resistance to environmental stress, said method comprising introducing into said plant a polynucleic acid as defined above encoding an HSP 17.6A protein, preferably a plant HSP 17.6A protein, most preferably an *Arabidopsis* HSP 17.6A.

According to a preferred embodiment, the present invention relates to a method as defined above for producing a plant with enhanced tolerance or resistance to environmental stress, said method comprising introducing into said plant a polynucleic acid as defined above encoding a c74 protein, preferably a plant c74 protein, most preferably a *Arabidopsis* c74 protein.

Preferably, the present invention relates to a method as defined above, comprising:
(a) introducing into the genome of a plant cell one or more recombinant DNA molecules, said recombinant DNA molecules comprising:
   a polynucleic acid as defined above, and,
   a plant expressible promoter, whereby said polynucleic acid is in the same transcriptional unit and under the control of said plant-expressible promoter, and,
(b) regenerating said plant from said plant cell.

The present invention also relates to a method for producing a plant with enhanced tolerance or resistance to environmental stress, said method comprising indirectly increasing of inducing the expression of an endogenous gene in said plant comprised within a polynucleic acid as defined above or indirectly increasing of inducing te activity of a protein as defined above.

The present invention also relates to a method as defined above, comprising:
(a) introducing into the genome of a plant cell one or more recombinant DNA molecules, said recombinant DNA molecules comprising:
   a DNA encoding a protein which when expressed in said plant cell at an effective amount indirectly increases or induces the expression of an endogenous polynucleic acid or indirectly increases or induces the protein activity of a protein encoded by said polynucleic acid of the present invention, and,
   a plant expressible promoter, whereby said DNA is in the same transcriptional unit and under the control of said plant-expressible promoter, and,
(b) regenerating said plant from said plant cell.

A "recombinant" DNA molecule will comprise a "heterologous sequence" meaning that said recombinant DNA molecule will comprise a sequence originating from a foreign species, or, if from the same species, may be substantially modified from its original form. For example, a promoter operably linked to a structural gene which is from a species different from which the structural gene was derived, or, if from the same species, may be substantially modified from its original form.

The present invention also relates to a method as defined above for producing a plant with enhanced tolerance or resistance to environmental stress conditions, said method comprising indirectly increasing or inducing the expression of an endogenous gene in said plant comprised within a polynucleic acid as defined above or indirectly increasing or inducing the activity of a protein of the invention as defined above. According to this embodiment, other polynucleic acids modulating the expression or the activity of a protein according to the present invention may be introduced transiently or stably into the genome of said plants. The term "modulating" means enhancing, inducing, increasing, decreasing or inhibiting.

Increase or induction of expression or induction or increase of protein activity is required when said regulator protein is a positive regulator of the expression or the activity of at least one of the polynucleic acids or protein of the present invention.

Decrease or inhibition of expression or decrease or inhibition of protein activity is required when said regulator protein is a negative regulator of the expression or activity of at least one of the polynucleic acids or proteins of the present invention.

Increase of the activity of said polypeptide according to the present invention is obtained, according to one embodiment of the invention, by influencing endogenous gene expression in the plant. This is preferably achieved by the introduction of one or more polynucleic acid sequences according to the invention into the plant genome, in a suitable conformation for gene expression (e.g. under control of a plant-expressible promoter). This will result in increased or induced expression (overexpression) or increased or induced activity of the protein in the plant cells, and, in the presence of an adequate substrate, in an increase of tolerance or resistance to environmental stress conditions in a transgenic plant or plant cell as compared to a non-transgenic plant or plant cell. This increase in tolerance can be measured by measuring mRNA levels, or where appropriate, the level or activity of the respective protein (e.g. by means of ELISA, activity of the enzyme as measured by any technique known in the art). Endogenous gene expression refers to the expression of a protein which is naturally found in the plant, plant part or plant cell concerned.

Alternatively, said enhanced tolerance or resistance to environmental stress conditions may be achieved by introducing into the genome of the plant, one or more transgenes which interact with the expression of endogenous genes (polynucleic acids) according to the present invention, by anti-sense RNA, co-suppression or ribozyme suppression of genes which normally inhibit the expression of the polynucleic acids of the present invention or by suppression of genes which normally inhibit the activity of the polypeptides of the invention as defined above.

For inhibition of expression, the nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA.

Generally, higher homology can be used to compensate for the use of a shorter sequence.

Furthermore, the introduced sequence need not have the same intron or exon pattern, and homology of non-coding segments may be equally effective. Normally, a sequence of between about 30 or 40 nucleotides up to the full length sequence should be used, though a sequence of at least about 100 nucleotides is preferred, a sequence of at least about 200 nucleotides is more preferred, and a sequence of about 500 to about 1700 nucleotides is especially preferred.

Catalytic RNA molecules or ribozymes can also be used to inhibit expression of genes as explained above. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of selfcleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. (1988).

Another method of suppression of gene expression is sense suppression. Introduction of nucleic acid configured in the sense orientation has been shown to be an effective means by which to block the transcription of target genes. For an example of the use of this method to modulate expression of endogenous genes see, Napoli et al. (1990), and U.S. Pat. Nos. 5,034,323, 5,231,020, and 5,283,184.

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Other methods for altering or replacing genes known in the art can also be used to inhibit expression of a gene. For instance, insertional mutants using T-DNA or transposons can be generated. See, e.g., Haring et al. (1991) and Walbot (1992). Another strategy in genetic engineering of plants and animals is targeted gene replacement. Homologous recombination has typically been used for this purpose (see, Capecchi (1989)).

Alternatively, the present invention also relates to a method as defined above wherein said DNA encodes a sense or antisense RNA or a ribozyme capable of indirectly increasing or inducing the expression of an endogenous polynucleic acid sequence according to the invention as defined above or increasing or inducing the activity of a protein of the invention as defined above. Preferably said endogenous polynucleic acid encodes a protein as listed in Table 1.

The present invention also relates to a recombinant polynucleic acid comprising: a polynucleic acid as defined above, and, a plant expressible promoter, whereby said polynucleic acid is in the same transcriptional unit and under the control of said plant-expressible promoter.

The present invention also relates to a recombinant polynucleic acid comprising:
(a) a DNA encoding a protein which when expressed in said plant at an effective amount indirectly increases or induces the expression of an endogenous polynucleic acid as defined above or indirectly increases or induces the protein activity of a polypeptide as defined above, and,
(b) a plant expressible promoter, whereby said DNA is in the same transcriptional unit and under the control of said plant-expressible promoter.

An "endogenous" polynucleic acid refers to a polynucleic acid that is already present in the plant species before transformation.

Said recombinant polynucleic acid as described here above is generally also referred to as a "recombinant vector" or an "expression cassette". An expression cassette of the invention can be cloned into an expression vector by standard methods. The expression vector can then be introduced into host cells by currently available DNA transfer methods.

The present invention also relates to the recombinant polynucleic acid as defined above, comprising a DNA which encodes an anti-sense RNA, a ribozyme or a sense RNA which increases or induces the activity of a protein as defined above in said cell. Preferably said protein is listed in Table 1.

More particularly, the present invention relates to a recombinant polynucleic acid comprising at least part of the nucleotide sequence of any of SEQ ID NO 1, 3, 5, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101,103, 105,107, 109, 111, 113, 115, 117,119, or 121.

Preferably, the present invention relates to a recombinant polynucleic acid comprising at least part of the coding sequence of a gene encoding a protein as listed in Table 1. Preferably, said "part" is a unique part of any of said nucleotide sequences. (26-28) As used herein, the term a "plant-expressible promoter" refers to a promoter that is capable of driving transcription in a plant cell. This includes any promoter of plant origin, including the natural promoter of the transcribed DNA sequence, but also any promoter of non-plant origin which is capable of directing transcription in a plant cell. The promoter may also be an artificial or synthetic promoter. The term "plant-expressible promoter" includes, but is not restricted to, constitutive, inducible, organ-, tissue-specific or developmentally regulated promoters.

According to the invention, production and/or activity of a polypeptide according to the present invention in a plant or in plant parts is increased by introducing one or more polynucleic acids according to the invention into the genome of the plant. More specifically, the constitutive promoter can be, but is not restricted to, one of the following: a 35S promoter (Odell et al. (1985)), a 35S'3 promoter (Hull and Howell (1987)), the promoter of the nopaline synthase gene ("PNOS") of the Ti-plasmid (Herrera-Estrella, (1983)) or the promoter of the octopine synthase gene ("POCS", De Greve et al. (1982)). It is clear that other constitutive promoters can be used to obtain similar effects. A list of plant-expressible promoters that can be used according to the present invention is given in Table 2.

For specific embodiments of this invention, the use of inducible promoters can provide certain advantages. Modulation of protein levels or protein activity may be required in certain parts of the plant, making it possible to limit modulation to a certain period of culture or developmental stage of the plant.

For specific embodiments of this invention, the use of organ- or tissue-specific or chemical inducible promoters can provide certain advantages. Thus, in specific embodiments of the invention, the gene(s) or part thereof is (are) placed under the control of a promoter directing expression in specific plant tissues or organs, such as for instance roots, leaves, harvestable parts, etc.

It is also possible to use a promoter that can be induced upon the environmental stress conditions. Such promoters can be taken for example from stress-related genes which are regulated directly by an environmental, i.e. preferable abiotic, stress in a plant cell, including genes for which expression is increased, reduced or otherwise altered. These stress related genes comprise genes the expression of which is either induced or repressed by anaerobic stress, flooding stress, cold stress, dehydration stress, drought stress, heat stress or salinity. An exemplary list of such promoters is given in Table 3.

The recombinant polynucleic acids according to the present invention may include further regulatory or other sequences from other genes, such as leader sequences (e.g. the cab22 leader from Petunia), 3' transcription termination and polyadenylation signals (e.g. from the octopine synthase gene or the nopaline synthase gene), plant translation initiation consensus sequences, introns, transcription enhancers and other regulatory elements such as adh intron 1, etc, which is or are operably linked to the gene or a fragment thereof. Additionally, the recombinant polynucleic acid can be constructed and employed to target the gene product of the polynucleic acid of the invention to a specific intracellular compartment within a plant cell on to direct a protein to the extracellular environment. This can generally be obtained by operably joining a DNA sequence encoding a transit or signal peptide to the recombinant polynucleic acid.

The recombinant DNA comprising one or more polynucleic acids according to the present invention may be accompanied by a chimeric marker gene (Hansen et al., 1999 and references therein). The chimeric marker gene can comprise a marker DNA that is operably linked at its 5' end to a plant-expressible promoter, preferably a constitutive promoter, such as the CaMV 35S promoter, or a light inducible promoter such as the promoter of the gene encoding the small subunit of Rubisco; and operably linked at its 3' end to suitable plant transcription 3' end formation and polyadenylation signals. It is expected that the choice of the marker DNA is not critical, and any suitable marker DNA can be used. For example, a marker DNA can encode a protein that provides a distinguishable color to the transformed plant cell, such as the A1 gene (Meyer et al., (1987)), can provide herbicide resistance to the transformed plant cell, such as the bar gene, encoding resistance to phosphinothricin (EP 0 242 246), or can provide antibiotic resistance to the transformed cells, such as the aac(6') gene, encoding resistance to gentamycin (WO94/01560).

According to another embodiment, the present invention invention relates to the use of the polynucleic acids above as selectable marker gene. More preferably, the present invention also relates to the use of the plant DBF2 gene as defined above as selectable marker gene, selection taking place with treatment with a stress condition.

The recombinant DNA vectors according to the present invention comprising the sequences from genes of the invention will typically also comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulforon or Basta.

The present invention also relates to a recombinant host cell transformed with an isolated polynucleic acid as defined above. Said host can be any host known in the art. Preferably said recombinant host cell is a plant cell, yeast, fungi, insect cell, etc. In order to be efficiently expressed in said host, said polynucleic acids can be combined with any promoter known to function in said host system. Methods for transforming said host cells are also well known in the art.

The present invention particularly also relates to a plant cell transformed with at least one recombinant polynucleic acid as defined above.

The present invention also relates to a plant consisting essentially of plant cells transformed with at least one recombinant polynucleic acid as defined above.

A "Transgenic plant" refers to a plant comprising a transgene in the genome of essentially all of its cells.

DNA constructs of the invention may be introduced into the genome of the desired plant host by a variety of conventional techniques (see for example Hansen et al., 1999 for review and WO 99/05902). For example, DNA constructs of the invention may be introduced into the genome of the desired plant host by using techniques such as protoplast transformation, biolistics or microprojectile bombardment or Agrobacterium mediated transformation.

Microinjection techniques are known in the art and well described in the scientific and patent literature. The introduction of DNA constructs using polyethylene glycol precipitation is described in Paszkowski et al. (1984).

Electroporation techniques are described in Fromm et al. (1985). Biolistic transformation techniques are described in Klein et al. (1987).

Alternatively, the DNA constructs may be combined with suitable T-DNA flanking regions and introduced into a conventional Agrobacterium host vector. The virulence functions of the Agrobacterium host will direct the insertion of the construct and adjacent marker into the plant cell DNA when the cell is infected by the bacteria. Agrobacterium tumefaciens-mediated transformation techniques, including disarming and use of binary vectors, are well described in the scientific literature. See, for example Horsch et al. (1984), and Fraley et al. (1983).

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium. Plant regeneration from cultured protoplasts is described in Evans et al. (1983); and Binding (1985). Regeneration can also be obtained from plant callus, explants, organs, or parts thereof. Such regeneration techniques are described generally in Klee et al. (1987).

The polynucleic acids and polypeptides of the invention can be used to confer desired traits on a broad range of plants, including monocotyledonous or dicotyledonous plants, preferably they belong to a plant species of interest in agriculture, wood culture or horticulture, such as a crop plant, root plant, oil producing plant, wood producing plant, fruit producing plant, fodder or forage legume, companion or ornamental or horticultured plant. The plants can include species from the genera Actinidia, Apium, Allium, Ananas, Arachis, Arisaema, Asparagus, Atropa, Avena, Beta, Brassica, Carica, Cichorium, Citrus, Citrullus, Capsicum, Cucumis, Cucurbita, Cydonia, Daucus, Diospyros, Fragaria, Glycine, Gossypium, Helianthus, Heterocallis, Hordeum, Hyoscyamus, Ipomoea, Lactuca, Linum, Lolium, Lycopersicon, Malus, Mangifera, Manihot, Majorana, Medicago, Musa, Nicotiana, Oryza, Panicum, Pannesetum, Persea, Petroselinum, Phaseolus, Pisum, Pyrus, Prunus, Raphanus, Rheum, Ribes, Rubus, Saccharum, Secale, Senecio, Sinapis, Solanum, Sorghum, Spinacia, Trigoneila, Triticum, Vaccinium, Vitis, Vigna, Zea, and Zingiber. Additional species are not excluded. Crops grown on cultivated lands in arid and semi-arid areas in which irrigation with ground water is needed may advantageously benefit from the invention.

One of skill will recognize that after the recombinant polynucleic acid is stably incorporated in transgenic plants and confirmed to be operable, it can be introduced into other plants by sexual crossing. Any of a number of standard breeding techniques can be used, depending upon the species to be crossed. As described before, the plant cells, plant tissue, in particular, transgenic plants of the invention display a certain higher or enhanced degree of tolerance (or even resistance) to environmental stress conditions compared to the corresponding wild-type plants. For the meaning of "environmental stress", see supra. In a preferred embodiment of the present invention, the transgenic plant displays increased tolerance to osmotic stress, salt stress, cold and/or heat stress. An increase in tolerance to such environmental stress is understood to refer to a tolerance to a level of such stress which inhibits the growth and productivity of the corresponding untransformed plant, as determined by methodologies known to the art. Such increased tolerance in transgenic plants is related to an increased expression level in the transgenic plant or parts thereof of one ore more of the polynucleic acids of the present invention and/or to an increased level of activity of the polypeptide(s) encoded by said polynucleic acid, as determined by methodologies known to the art. In comparison with their untransformed counterparts, and determined according to methodologies known in the art, a transgenic plant according to the present invention shows an increased growth, viability, metabolism, fertility and/or productivity under mild environmental stress conditions. In the alternative, a transgenic plant according to the invention can grow under environmental stress conditions wherein the untransformed counterparts can not grow. An increase in tolerance to salt stress is understood to refer to the capability of the transgenic plant to grow under stress conditions which inhibit the growth of at least 95% of the parent, non-stress tolerant plants from which the stress tolerant transgenic plants are derived. Typically, the growth rate of stress tolerant plants of the invention will be inhibited by less than 50%, preferably less than 30%, and most preferably will have a growth rate which is not significantly inhibited by growth conditions which inhibit the growth of at least 95% of the parental, non-stress tolerant plants. In an alternative example, under mild environmental stress conditions, the growth and/or productivity of the transgenic plants is statistically at least 1% higher than for their untransformed counterparts, preferably more than 5% higher and most preferably more than 10% higher.

Any transformed plant obtained according to the invention can be used in a conventional breeding scheme or in in vitro plant propagation to produce more transformed plants with the same characteristics and/or can be used to introduce the same characteristic in other varieties of the same or related species.

Furthermore, the characteristic of the transgenic plants of the present invention to maintain normal/rapid/high growth rates under environmental stress conditions can be combined with various approaches to confer environmental stress tolerance with the use of other stress tolerance genes. Some examples of such stress tolerant genes are provided in Holmberg and Bülow (1998). Most prior art approaches which include the introduction of various stress tolerance genes have the drawback that they result in reduced or abnormal growth (compared to non-transgenic controls) under normal, non-stressed conditions, namely stress tolerance comes at the expense of growth and productivity (Kasuga et al., 1999). This correlation between constitutive expression of stress-responsive genes and reduced growth rates under normal growth conditions indicates the presence of cross talk mechanisms between stress response control and growth control.

Furthermore, the characteristic of the transgenic plants of the present invention to display tolerance to environmental stress conditions can be combined with various approaches to confer to plants other stress tolerance genes, e.g., osmotic protectants such as mannitol, proline; glycine-betaine, water-channeling proteins, etc. Thus, the approach of the present invention to confer tolerance to environmental stress conditions to plants can be combined with prior art approaches which include introduction of various stress tolerance genes. Combination of these approaches may have additive and/or synergistic effects in enhancing tolerance or resistance to environmental stress.

Thus, it is immediately evident to the person skilled in the art that the method of the present invention can be employed to produce transgenic stress tolerant plant with any further desired trait (see for review TIPTEC Plant Product & Crop Biotechnology 13 (1995), 312-397) comprising:
 (i) herbicide tolerance (DE-A 3701623; Stalker (1988)),
 (ii) insect resistance (Vaek (1987)),
 (iii) virus resistance (Powell (1986), Pappu (1995), Lawson (1996)),
 (iv) ozone resistance (Van Camp (1994)),
 (v) improving the preserving of fruits (Oeller (1991)),
 (vi) improvement of starch composition and/or production (Stark (1992), Visser (1991)),
 (vii) altering lipid composition (Voelker (1992)),
 (viii) production of (bio)polymers (Poirer (1992)),
 (ix) alteration of the flower color, e.g., bu manipulating the anthocyanin and flavonoid biosynthetic pathway (Meyer (1987), WO90/12084),
 (x) resistance to bacteria, insects and fungi (Duering (1996), Strittmatter (1995), Estruch (1997)),
 (xi) alteration of alkaloid and/or cardia glycoside composition,
 (xii) inducing maintaining male and/or female sterility (EP-A1 0 412 006; EP-A1 0 223 399; WO93(25695);
 (xiii) higher longevity of the inflorescences/flowers, and
 (xvi) stress resistance.

Thus, the present invention relates to any plant cell, plant tissue, or plant which due to genetic engineering displays an enhanced tolerance or resistance to environmental stress obtainable in accordance with the method of the present invention and comprising a further nucleic acid molecule conferring a novel phenotype to the plant such as one of those described above.

The present invention also relates to a callus or calli consisting essentially of plant cells as defined here above. Such transgenic calli can be preferably used for the production of secondary metabolites in plant cell suspension cultures.

The present invention also relates to any other harvestable part, organ or tissue or propagation material of the plant as defined here above.

The present invention also relates to the seed of a transgenic plant as defined here above, comprising said recombinant DNA.

The present invention also relates to the use of any isolated polynucleic acid as defined above to produce transgenic plants.

The present invention also relates to the use of a recombinant polynucleic acid as defined above, to produce transgenic plants, preferably transgenic plants having an enhanced tolerance or resistance to environmental stress conditions. Preferably said polynucleic acid encodes a polypeptide as listed in Table 1.

The present invention also relates to the use of an isolated polynucleic acid as defined above, to produce transgenic callus having an enhanced tolerance or resistance to environmental stress conditions. Preferably said polynucleic acid encodes a polypeptide as listed in Table 1.

The present invention also relates to probes and primers derived from the genes of the invention that are useful for instance for the isolation of additional genes having sequences which are similar to but differ from any of SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, or 121, but which encode a protein having substantially the same biological activity as a protein having the amino acids sequence of any of SEQ ID NO 2 to 120 (even numbers) by techniques known in the art, such as PCR. The presence of a homologous gene in another plant species can for instance be verified by means of Northern of Southern blotting experiments.

The present invention also relates to the cloning of the genomic counterpart of any of the cDNA sequences as represented in SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, or 121. These genomic counterparts can be selected from a genomic library using these cDNA sequences as a probe. The present invention also relates to the coding region as well as the promoter region of any of said genomic clones.

The term "probe" according to the present invention refers to a single-stranded oligonucleotide sequence which is designed to specifically hybridize to any of the polynucleic acids of the invention.

The term "primer" refers to a single stranded oligonucleotide sequence capable of acting as a point of initiation for synthesis of a primer extension product which is complementary to the nucleic acid strand to be copied. Preferably the primer is about 5-50 nucleotides long. The term "target region" of a probe or a primer according to the present invention is a sequence within the polynucleic acid(s) to which the probe or the primer is completely complementary or partially complementary (i.e. with some degree of mismatch). It is to be understood that the complement of said target sequence is also a suitable target sequence in some cases.

"Specific hybridization" of a probe to a target region of the polynucleic acid(s) means that the probe forms a duplex with part of this region or with the entire region under the experimental conditions used, and that under those conditions this probe does substantially not form a duplex with other regions of the polynucleic acids present in the sample to be analysed.

"Specific hybridization" of a primer to a target region of the polynucleic acid(s) means that, during the amplification step, said primer forms a duplex with part of this region or with the entire region under the experimental conditions used, and that under those conditions the primer does not form a duplex with other regions of the polynucleic acids present in the sample to be analysed. It is to be understood that "duplex" as used hereby, means a duplex that will lead to specific amplification.

Preferably, the probes of the invention are about 5 nucleotides to about 1 Kb long, more preferably from about 10 to 25 nucleotides. The nucleotides as used in the present invention may be ribonucleotides, deoxyribonucleotides and modified nucleotides such as inosine or nucleotides containing modified groups which do not essentially alter their hybridization characteristics. The probes according to the present invention preferably include parts of the cDNA sequences of any of the polynucleic acids as defined above.

The present invention also relates to a composition comprising a polynucleic acid sequence as defined above, a polypeptide as defined above, a probe as defined above or a primer as defined above.

The present invention also relates to a pharmaceutical or agrochemical composition comprising said polynucleic acid, a polypeptide of the invention as defined above.

The present invention also relates to antibodies specifically reacting with a protein or polypeptide according to the present invention.

The following Examples describe by way of example the tolerance and/or resistance to several environmental stress conditions observed for transgenic plants and yeast overexpressing some of the polynucleic acids according to the present invention. Unless stated otherwise in the Examples, all recombinant DNA techniques are carried out according to standard protocols as described in Sambrook et al. (1989) and in volumes 1 and 2 of Ausubel et al. (1994). Standard materials and methods for plant molecular work are described in Plant Molecular Biology Labfax (1993) by R. D. D. Croy, jointly published by BIOS Scientific Publications Ltd. (UK) and Blackwell Scientific Publications, UK.

These examples and figures are not to be construed as limiting to any of the embodiments of the present invention as set out above. All of the references mentioned herein are incorporated by reference.

BRIEF DESCRIPTION OF THE FIGURES AND TABLES

FIG. 1. At-DBF2 encodes a functional homolog of the yeast Dbf2 (A) Comparison of the deduced amino acid sequence of At-DBF2 with that of yeast DBF2. Gaps were introduced to optimize the alignment. Roman numerals above the At-DBF2 sequence indicate the protein kinase catalytic subdomains defined by Hanks et al. (1988). (B) Complementation of dbf2. The dbf2 mutant S7-4A [MATa dbf2Δ::URA3 ura3 leu2 ade5 trp1 his7] (Toyn and Johnston, 1994) (B1) forms swollen pairs of daughter cells (dumbbells) at restrictive temperature (37° C.). The defective morphology of the dbf2 mutant can be complemented by transformation with the pYX112 centromeric plasmid (Ingenius, R&D system) containing the At-DBF2 cDNA (B2) or DBF2 (B3); wild type (CG378 strain, MATa ade5 leu2 trp1 ura3) (B4). Log phase cultures were shifted from 28° C. to 37° C. and photographed after 16 hours. After 16 hours, 98% of the S7-4A cells arrested with a dumbbell morphology (B1) whereas 6,1 and 0% of dumbbells were observed in B1, B3 and B4. Strains were kindly provided by (Dr Lindl, Max Planck Institut fur Zuchtungsforschung, Koln, Germany).

FIG. 2. Overexpression of DBF2 or At-DBF2 enhances tolerance to osmotic, salt, heat and cold stress. Yeast cells were grown in YPD and cell density was adjusted to OD600 at 2. (1) DY, (2) DY transformed with pYX212 containing DBF2, pYX-YDBF2, (3) DY transformed with vector alone or (4) with vector containing At-DBF2, pYX-AtDBF2. Serial dilutions were made in step 1:10. Ten µl of each dilution was spotted on solid YPD medium (control) supplemented with 2M sorbitol (osmotic stress) or 1.2 M NaCl (salt stress) or 4 µl $H_2O_2$ (oxidative stress) and incubated at 28° C. or at 42° C. (heat stress) or at 4° C. (cold stress) for 3 days.

FIG. 3. DBF2 and At-DBF2 are induced by stress. (a) Northern analysis showing the kinetics of At-DBF2 induction in plants treated with PEG 6000 20% and the one of DBF2 in yeast treated with sorbitol 2M for the time indicated. (b) Northern analysis of At-DBF2 in 10 day-old-plants grown for 5 hours in control conditions (as described in Verbruggen et al. 1993) (1), at 37° C. (2), with PEG 6000 20% (3), NaCl 1% (4), at 4° C. (5) or with 0.4 mM $H_2O_2$ (6); and of DBF2 in yeast cells grown for 11/2 hour in YPD (1), at 37 C. (2), with sorbitol 2M (3), with NaCl 1.2 M (4), at 4° C. (5) or with 0.4 mM $H_2O_2$ (6). Control of loading has been done with EtBr staining and is shown under each Northern analysis.

(c) Western analysis of At-DBF2 in *Arabidopsis*. Samples are similar to those analysed in (b). Antibodies used were raised against yeast Dbf2 and kindly provided by Dr L. Leindl (Max Planck Institut fur Zuchtungsforschung, Koln, Germany).

FIG. 4. DBF2 overexpression can suppress hog1 osmosensitivity. The hog1 mutant (4) [W303-1A, MATa, hog1Δ::TRP1] and wild type (W303) (1) were kindly provided by Dr Thevelein (Katholieke Universiteit Leuven, Belgium). The hog1 mutant was transformed with pYX-YDBF2 (2) or pYX-AtDBF2 (3). Each of the 4 strains was grown for 16 hours in YPD (rich medium), and cell density was adjusted to OD600 at 2. Serial dilutions, 1:10 were made at five consecutive steps. Ten microliter of each dilution was spotted on solid YPD medium (control) or solid YPD medium supplemented with 0.9 M NaCl and incubated at 28° C. for 3 days.

FIG. 5. T-DBF2 (*Nicotiana tabacum* DBF2) is periodically expressed during plant cell cycle. Tobacco DBF2 expression has been followed in BY2 cells synchronised with aphidicolin (a & b) or with propyzamide (c & d) with At-DBF2 as probe. The measure of relative rate of DNA synthesis and of the mitotic index, the use of the cell cycle markers CYCB1.2 and H4 markers have been previously described (Reicheld et al., 1995). T-DBF2 transcript levels were quantified from the blots shown in b and d using a PhosphorImager (Molecular Dynamics).

FIG. 6. shows the results of a comparison of the growth of *A. thaliana* plants transformed with the following constructs: P35S-At-DBF2 (upper left and bottom right section), P35S control (upper right section) and P35S-antisense At-DBF2 (bottom left section) upon applying a salt stress of 200 mM NaCl overnight.

Figure 10:
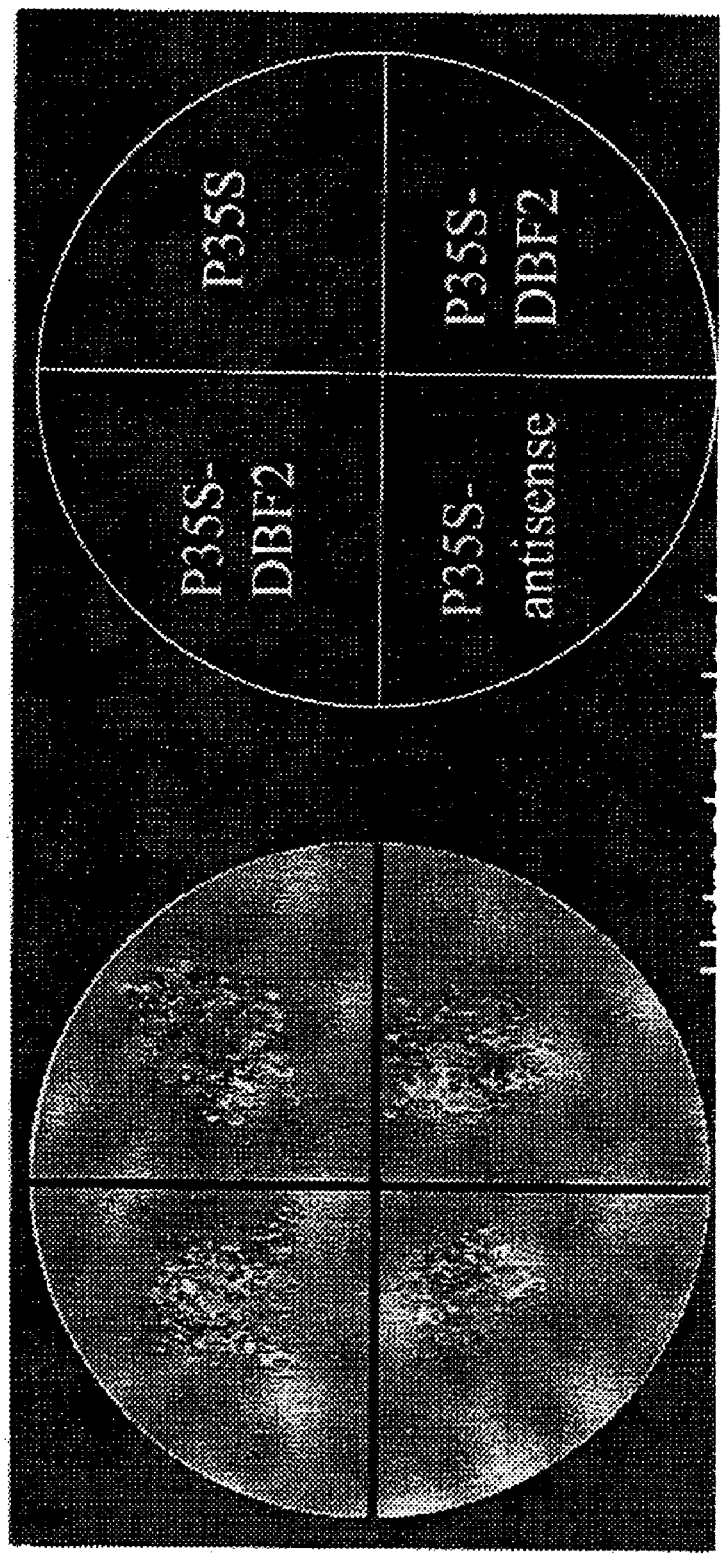

FIG. 10 shows the results of a comparison of the growth of *A. thaliana* plants transformed with the following constructs: P35S-At-DBF2 (upper left and bottom right section), P35S control (upper right section) and P35S-antisense At-DBF2 (bottom left section). It can be concluded that the P35S-At-DBF2 transformed plants do not show morphological abnormalities compared to the control transgenic plants.

Figure 11:

FIG. 11 shows the results of a salt stress tolerance test with transgenic *A. thaliana* plants overexpressing HSP 17.6A (A) or c74 (B). The control plants (bottom left in A en B) is a transgenic line tranformed with pBIN-35S-CaMVter. The other sections in A are 5 independently obtained transgenic lines overexpressing HSP17.6A. The other sections in B are 5 independently obtained transgenic lines overexpressing c74.

FIG. 12 shows the influence of At-DBF2 expression in sense and antisense orientations on stress tolerance. BY2 cells were transformed by *A. tumefaciens* with recombinant T-DNA vectors containing At-DBF2 driven by CaMV 35S RNA promoter, pBIN-35S-At-DBF2 (upper left and right sections in A or diamonds in B), the CaMV 35S promoter and terminator pBIN-35S-CaMVter (bottom left sections in A or triangles in B), or antisense At-DBF2 under the control of the CaMV 35S promoter pBIN-35S-ASAt-DBF2 (bottom right sections in A or circles in B). (A) Picture of the same amounts of transgenic cells after 3 weeks of growth on solid medium supplemented with 300 mM NaCl, 25% PEG, 2 mM $H_2O_2$, or at 47° C. (heat). (B) Growth of suspension cells in liquid medium. Upon stress, growth was measured as fresh weigth and expressed as a percentage of unstressed growth (control) (a). Stresses were applied after subculturing (=day 0) at indicated temperatures (e) and concentrations of NaCl (b) PEG (c), and $H_2O_2$ (f). For the cold shock (d), cells were maintained at 0° C. for 2 days before the 2-week culture at 22° C. For each construction data of three independent transgenic lines were pooled. To not overload the figure, SDs are not shown (maximum 15% of measured values). (C) Northern analysis of At-DBF2+TDBF2, kin1, and HSP17.6. Total RNAs were extracted from independent lines transformed with pBIN-35S-At-DBF2 (1) and (2), pBIN-35S-CaMter (3), and pBIN-35S-ASAt-DBF2 (4). Osmotic stress was induced with 10% PEG treatment for 5 hr (stressed).

Figure 13:

FIG. 13 shows the results of the growth of *A. thaliana* plants transformed with p35S-AtHSP17.6A and P35S control (upper right section) upon applying an osmotic stress induced by 20% PEG overnight. The results of two independent experiments are shown, each performed with 3 independently obtained transgenic lines overexpressing At-HSP17.6A (upper left and bottom left and right).

Figure 14:
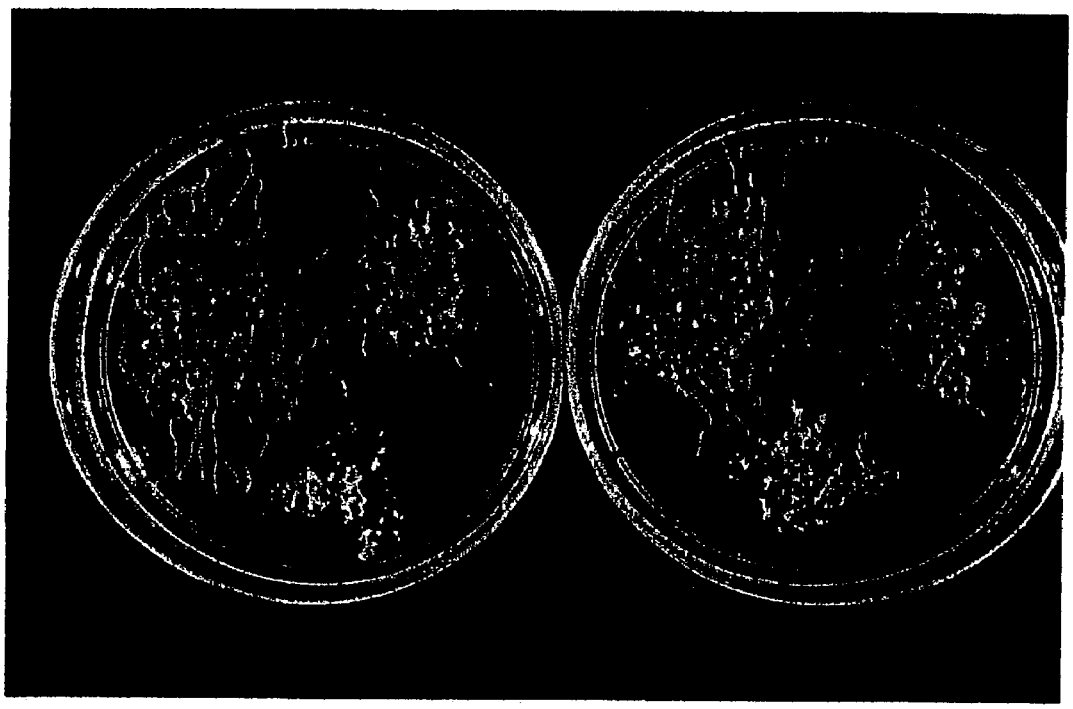

FIG. 14 shows the results of the germination of *A. thaliana* plants transformed with p35S-Atc74 and P35S control (bottom section) on mineral medium supplemented with 125 mM NaCl. The results of two independent experiments are shown, each performed with 2 independently obtained transgenic lines overexpressing Atc74 (2 upper sections).

Table 1. Classification of the *Arabidopsis thaliana* clones isolated in Example 2. Clones isolated according to the description in example 2 have been analyzed on their potential to confer tolerance. According to the method described in example 2, the tolerance of different yeast transformants expressing an *Arabidopsis* cDNA to osmotic stress and salt stress was compared with the tolerance of DY wild type cells.

+: similar growth to the DY wild type cells;
++: growth of the transformant is visible at a 10-fold higher dilution (1:10) than control (1:1);
+++: growth of the transformant is visible at a 100-fold higher dilution (1:100) than control (1:1);
++++: growth of the transformant is visible at a 1000-fold higher dilution (1:1000) than control (1:1).

Table 2. Exemplary plant-expressible promoters for use in the performance of the present invention.

Table 3. Exemplary stress-inducible promoters for use in the performance of the present invention.

EXAMPLES

Example 1

Construction of the cDNA Library

Total RNA has been isolated from green siliques from *Arabidopsis thaliana* by grinding 1 g of siliques in 4 ml extraction buffer (100 mM tris-Hcl, pH 8, 10 mM EDTA, 100 mM LiCl) at 4° C., followed by phenolisation and chloroform: isoamylalcohol (24:1) extraction. To the aqueous phase, LiCl was added up to a final concentration of 2M, and the total RNA was allowed to precipitate overnight at 4° C. After centrifugation, the pellet was redissolved in 400 µl $H_2O$ and reprecipitated with ethanol. Poly(A) messenger RNA was isolated from the total RNA by binding it to an oligo-dT cellulose spun column (Pharmacia), washing the column three times with 10 mM Tris-HCl, pH 7.5, 1 mM EDTA , 0.5 M NaCl and eluting the mRNA with 10 mM Tris-HCl, pH 7.5, 1 mM EDTA at 65° C.

The eluate was precipitated with ethanol, and cDNA was synthesized using MMLV-reverse transcriptase (Pharmacia) and a $d(T)_{14}$-XhoI primer for the first strand and *E. coli* DNA polymerase I (Pharmacia) for the second strand.

Example 2

Yeast Transformation and Selection for Osmotolerance

The cDNA was cloned into pYX vectors (Ingenius, R&D systems; 2 µ based pYX 212 for bank 1, ARSICEN based pYX112 for bank 2) as EcoRI-XhoI fragments, using an Eco RI/Not I adaptor.

In these constructs, the cDNA is under the control of the strong constitutive TPI promoter. The yeast strain DY (MATa, his3, can1-100, ade2, leu2, trp1, ura3::3×SV40AP1-lacZ; kindly provided by N. Jones, Imperial Cancer Research Fund, London, UK) has been transformed with these cDNA libraries, using the Lithium Acetate transformation procedure (Gietz and Schietsl, 1995). After transformation with the *Arabidopsis* cDNA bank, transformants have been selected for the ability to grow in the presence of 100 mM LiCl in a stepwise selection (Lee et al., 1999). LiCl is commonly used for salt tolerance screening in yeast (Haro et al. 1991). Several *A. thaliana* genes, conferring osmotolerance to the yeast, have been isolated (Table 1). To further analyse the potential of the selected *Arabidopsis* cDNA's to confer tolerance to environmental stress in yeast, each yeast transformant expressing such selected *Arabidopsis* cDNA's has been exposed to osmotic stress and salt stress. Each of the transformants was therefore grown for 16 hours in YPD (rich medium), and cell density was adjusted to $OD_{600}$ at 2. Serial dilutions, 1:10, were made at three consecutive steps. Ten microliters of each dilution was spotted on solid YPD medium (control) supplemented with 2 M sorbitol (osmotis stress) or 1.2 M NaCl (salt stress) and incubated at 28° C. for 3 days. The results of this drop growth test (see also Lee et al., 1999) are shown in Table 1.

Example 3

Characterization of At-DBF2

Figure 1B:
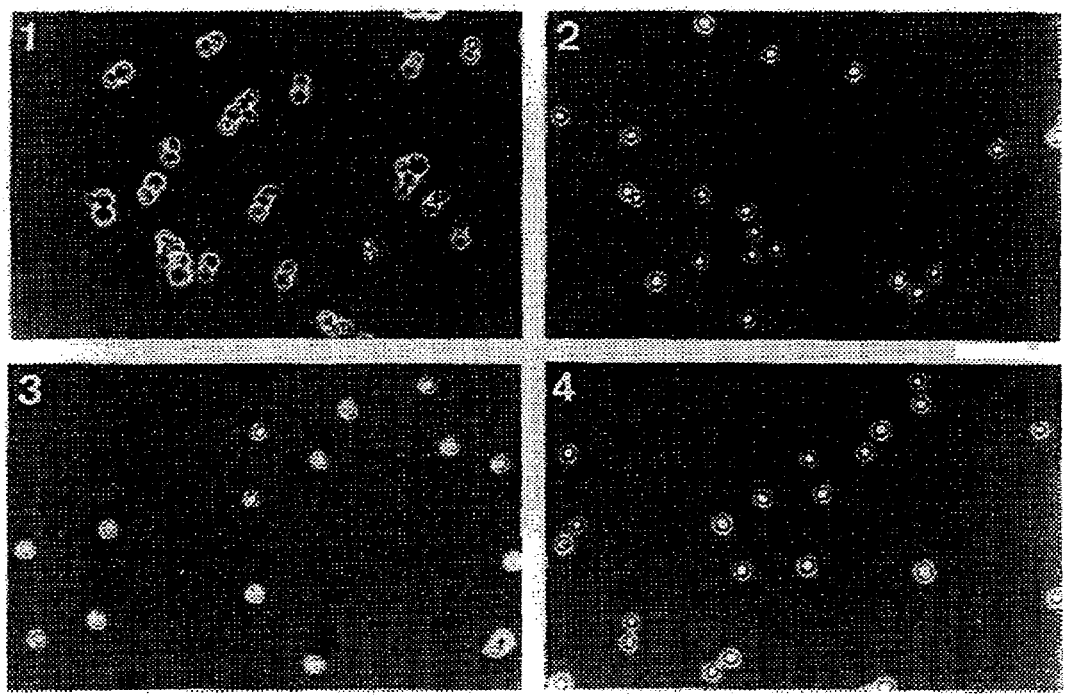

At-DBF2, a 1.8 kb cDNA (SEQ ID NO 1) has been identified in this screening that encodes a predicted 60.2 kDa protein showing 81% similarity with the yeast Dbf2 transcriptional regulator. Homology (less than 40% similarity) has also be found with the putative Dbf2 homologues in human, *C. elegans* and Drosophila (named Ndr for nulear Dbf2 related, Millward et al. 1995). The At-DBF2 deduced protein sequence (SEQ ID NO 2) contains the 11 domains of protein kinases (FIG. 1A). Amino acids lying between the invariant residues D and N of domain VI do not match the features of serine/threonine specificity (LKPE) defined by Hanks et al. (1988) but the GSPDYIALE peptide in domain VIII does well indicate serine/threonine specificity and At-DBF2 can complement the yeast dbf2 mutant (FIG. 1B).

Figure 2:
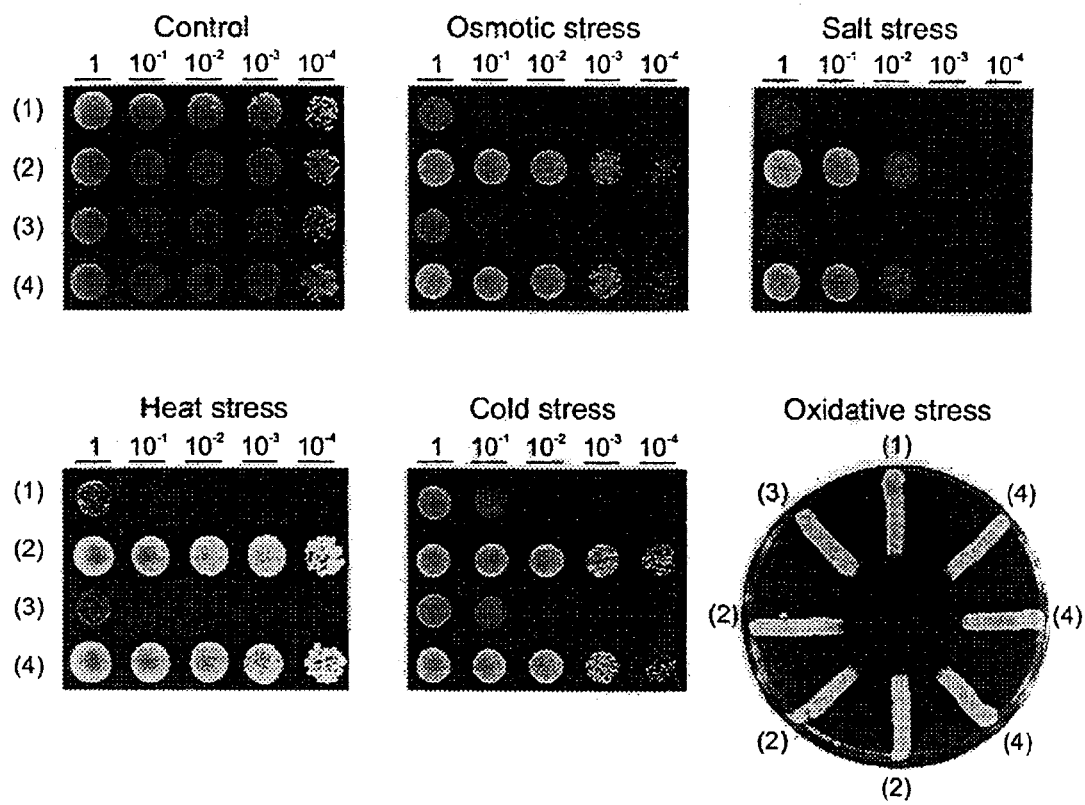

In mature *Arabidopsis* plants, At-DBF2 is expressed in all tested organs. The highest abundance of transcripts has been found in siliques. A Southern analysis in *Arabidopsis*, tobacco and tomato has revealed that DBF2 seems to be conserved in plants (see Example 13 below). As At-DBF2 has been identified in a screening for LiCl tolerance, its effect in other stress situations has been tested in yeast (FIG. 2).

Example 4

Figure 3:
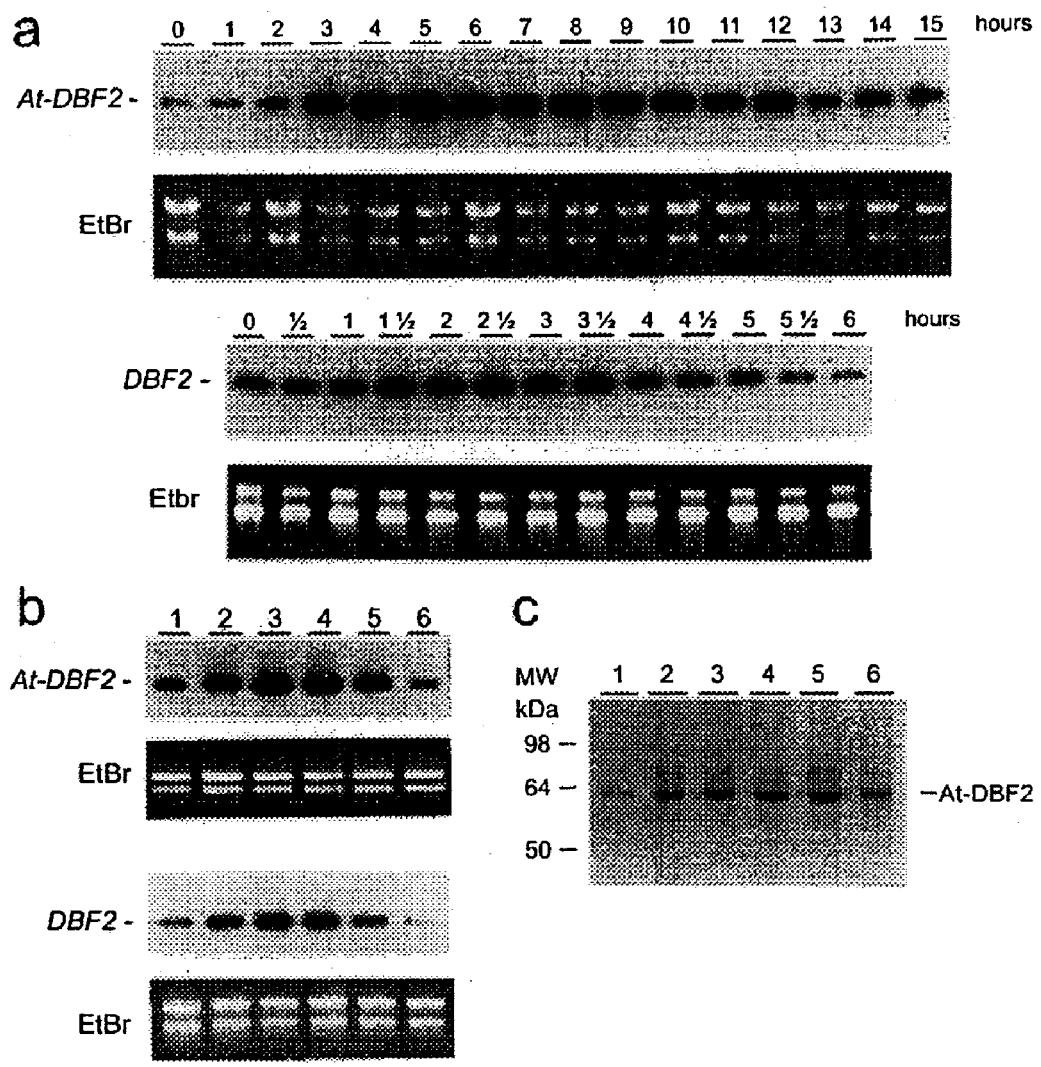

Overexpression of *Arabidopsis* and *Saccharomyces cerevislae* DBF2 Enhances Cold, Heat, Salt and Drought Tolerance in Yeast In order to test whether the effect was specific to the plant gene, the yeast DBF2 gene has been overexpressed in the same vector. Upon a drop growth test (FIG. 2 and Lee et al., 1999). A remarkable enhancement of stress tolerance can be seen at 42° C., during osmotic stress (sorbitol), and after salt and cold treatments in yeast. There is no difference between stress tolerance afforded by the plant or the yeast gene. The enhancement of stress tolerance due to the overexpression of At-DBF2 or DBF2 reflects a role for these genes in stress situations. Therefore yeast and *Arabidopsis* plants have been exposed to sorbitol- and PEG-induced osmotic stress. At-DBF2 as well as DBF2 is induced rapidly (1 to 2 hours) and transiently upon osmotic stress (FIG. 3A). The expression of At-DBF2 and DBF2 has been analyzed during other environmental stresses in *Arabidopsis* plants or in yeast cells after the time corresponding to the highest induction seen in FIG. 3A (FIG. 3B). In plant as in yeast, there is a clear induction after heat, salt, osmotic and to a lesser extent after cold, which perfectly correlates with stresses to which the overexpression enhances tolerance. However, many genes are induced upon stress without relevant adaptive role, amongst others because post-transcriptional mechanisms inhibit subsequent translation. Here At-DBF2 protein amount, as detected by anti-Dbf2 antibodies, clearly increased upon stress (FIG. 3C).

Example 5

Both At-DBF2 and DBF2 Can Functionally Complement the Hog1 Mutation

Figure 4:
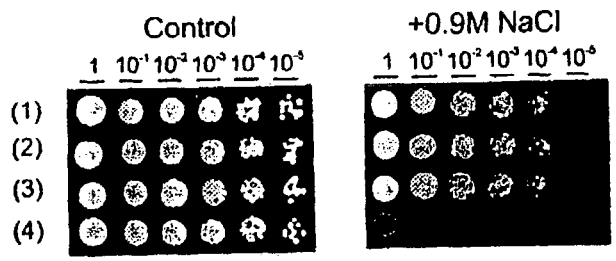

To investigate a possible interaction between stress signaling pathways and DBF2, the salt sensitive hog1 mutant was transformed with At-BDF2 and DBF2. The HOG1 MAP kinase pathway regulates osmotic induction of transcription in yeast (Schuller et al. 1994). The osmosensitivity of the mutant could be recovered by the overexpression of both DBF2 and At-DBF2 (FIG. 4).

Example 6

At-DBF2 is Cell Cycle Regulated

Figure 5:
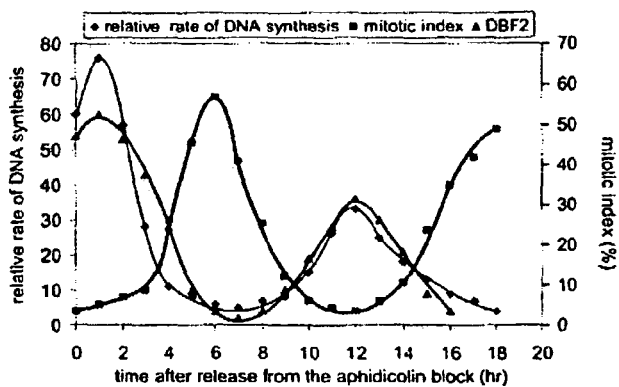
Figure 5:
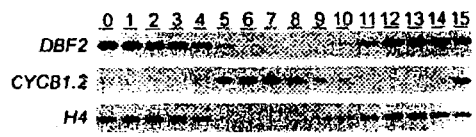
Figure 5:
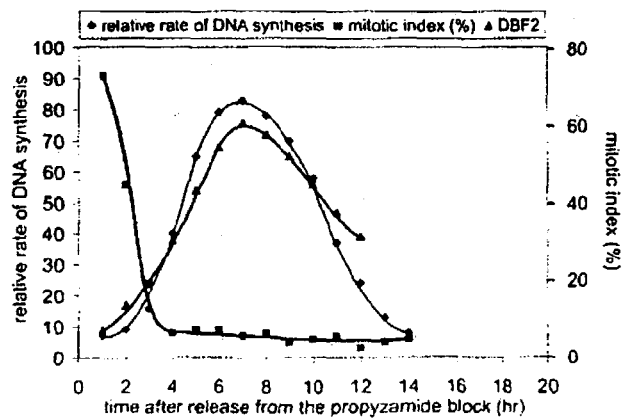

DBF2 expression is cell cycle regulated where it plays a role in DNA synthesis initiation but also in nuclear division through its association with the CCR4 complex (Komamitsky et al. 1998, Johnston et al. 1990). This regulation was investigated in plants. A tobacco BY-2 cell line in which the highest level of culture synchronization, compared with other plant cell lines has been achieved so far (Shaul et al. 1996, Reicheld et al. 1995) was used. Stationary phase cells were diluted into fresh medium and treated with aphidicolin (blocking cells in the beginning of the S phase) for 24 hours, then washed. The percentage of synchronous mitosis after release from the aphidicolin block was about 65% (FIGS. 5A-B). A 1.6-Kb tobacco DBF2 homologue (T-DBF2) could be detected on Northern blot with the At-DBF2 as a probe. T-DBF2 steady-state transcript level clearly oscillates during the cell cycle and is mainly present during S, decreases during G2 until late M from where it increases until a peak in S phase. T-DBF2 expression occurs clearly before CYCB1.2 (a marker of G2-M phases), but parallels the one of H4 (a S phase marker) except at the S/G2 transition, where T-DBF2 transcripts decline earlier, and at the M/G1 transition, where T-DBF2 expression increases earlier. The use of the cell cycle markers CYCB1.2 and H4 is described in Reicheld et al.

To follow unperturbed G1 and S phases, BY2 cell suspension was synchronized using a double blocking procedure (Nagata et al., 1992). After the release from the aphidicoline block, cells are treated for 4 hours with propyzamide in the beginning of the preprophase. The percentage of synchronous mitosis after the release from the propyzamide block was higher than 75%. T-DBF2 was periodically expressed with an undetectable expression until late M, a sharp increase in G1 and a peak in mid S (FIGS. 5C-D) which confirms results of FIGS. 5A-B. However a function for the plant DBF2 in cell cycle can only be assigned with measurement of the kinase activity. In yeast, DBF2 transcript levels do not correlate with kinase activation which occurs by dephosphorylation (Toyn and Johnson, 1994). The precise function of Dbf2 in regulation of the cell cycle is not known. An essential role has been proposed during anaphase or telophase. No activity has been measured in G1 despite evidence for a role for Dbf2 in initiation of DNA synthesis.

As other proteins recently identified, Dbf2 controls the M/G1 transition which is a major cell cycle transition in yeast (Aerne et al. 1998). The existence of a M/G1 control checkpoint has been suggested in plant cells (Hemmerlin and Bach 1998) but its importance compared to G1/S and G2/M has not been investigated.

Overexpression of DBF2 in yeast results in kinase activity throughout the cell cycle, which may be due to the saturation of a post-translational deactivating mechanism (Toyn and Johnston, 1994). Overexpression of the functionnally conserved At-DBF2 has most probably the same effect. However, the presence of Dbf2 kinase activity at the wrong time in the cell cycle does apparently not affect its progression. In marked contrast constitutive activity has a marked effect on stress tolerance. The role played by At-DBF2 or DBF2 in stress is most probably independent from the cell division cycle. At-DBF2 expression is present in all plant organs (abundant expression is observed in stems where only 1-2% cells have a mitotic activity) and can be rapidly induced upon stress. However, a link with the cell cycle is not excluded. Higher stress tolerance in yeast overexpressing DBF2 or At-DBF2 may be correlated to the overproduction of the kinase in G1 where yeast cells are particularly sensitive to stress. Most plant cells are also thought to be blocked in G1 but the relationship with stress response is poorly known.

Example 7

Tobacco Cell Transformation and Recombinant T-DNA Vector Construction

BY2 cells were stably transformed as described (Shaul et al., 1996) by Agrobacterium tumefaciens C58C1 Rif$^R$ (pGV2260) strain (Deblaere et al., 1985) carrying pBIN-35S-At-DBF2 or pBIN-35S-ASAt-DBF2 recombinant binary vectors. PBIN-35S-At-DBF2 is the plant binary vector pBIN m-gfp4 in which the BamHI-SacI fragment containing the gfp reporter gene was replaced with a BamHI-SacI fragment containing the At-DBF2 cDNA from pYX-At-DBF2. p-Bin-35S-CaMVter is the plant binary vector pBIN19 in the HindIII-SacI restriction sites of which the hindIII-SacI fragment of pDH51 containing the cauliflower mosaic virus (CaMV) 35S RNA promoter and terminator was cloned. pBIN-35S-ASAt-DBF2 is the pBIN-35S-CaMVter vector in which the At-DBF2 cDNA was cloned in the antisense orientation from pYXAt-DBF2 in the BamHI-SmaI restriction sites, between the CaMV 35S RNA promoter and terminator. More details are described in Lee et al. (1999).

Example 8

Overexpression of At-DBF2 Sense and Antisense RNA in Plant Cells

Figure 12A:
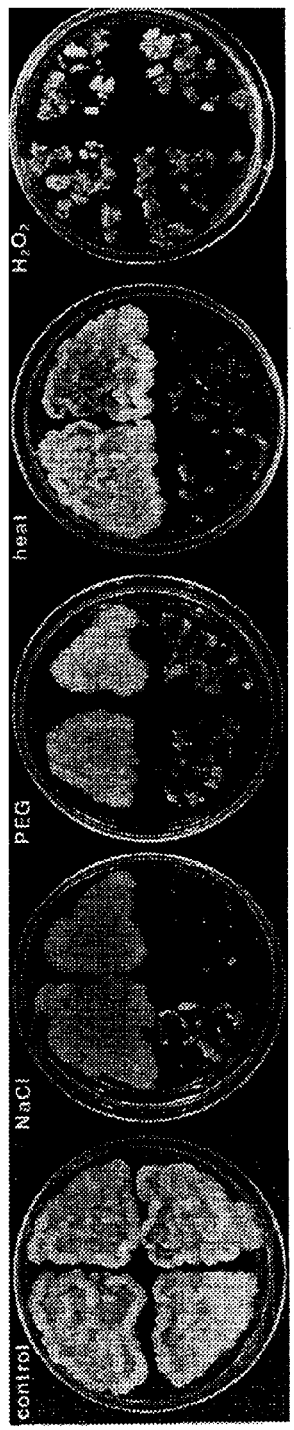
Figure 12C:
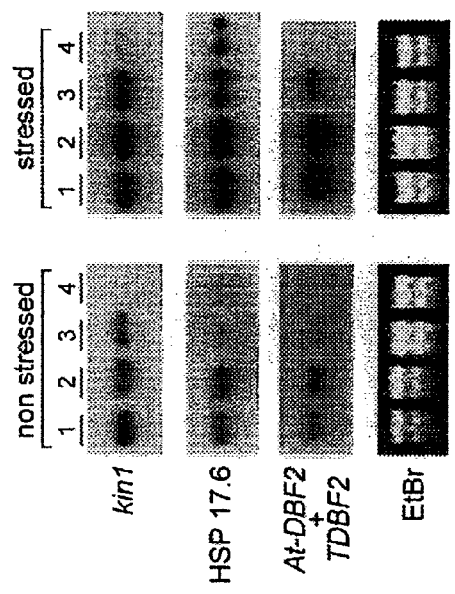
Figure 12B:
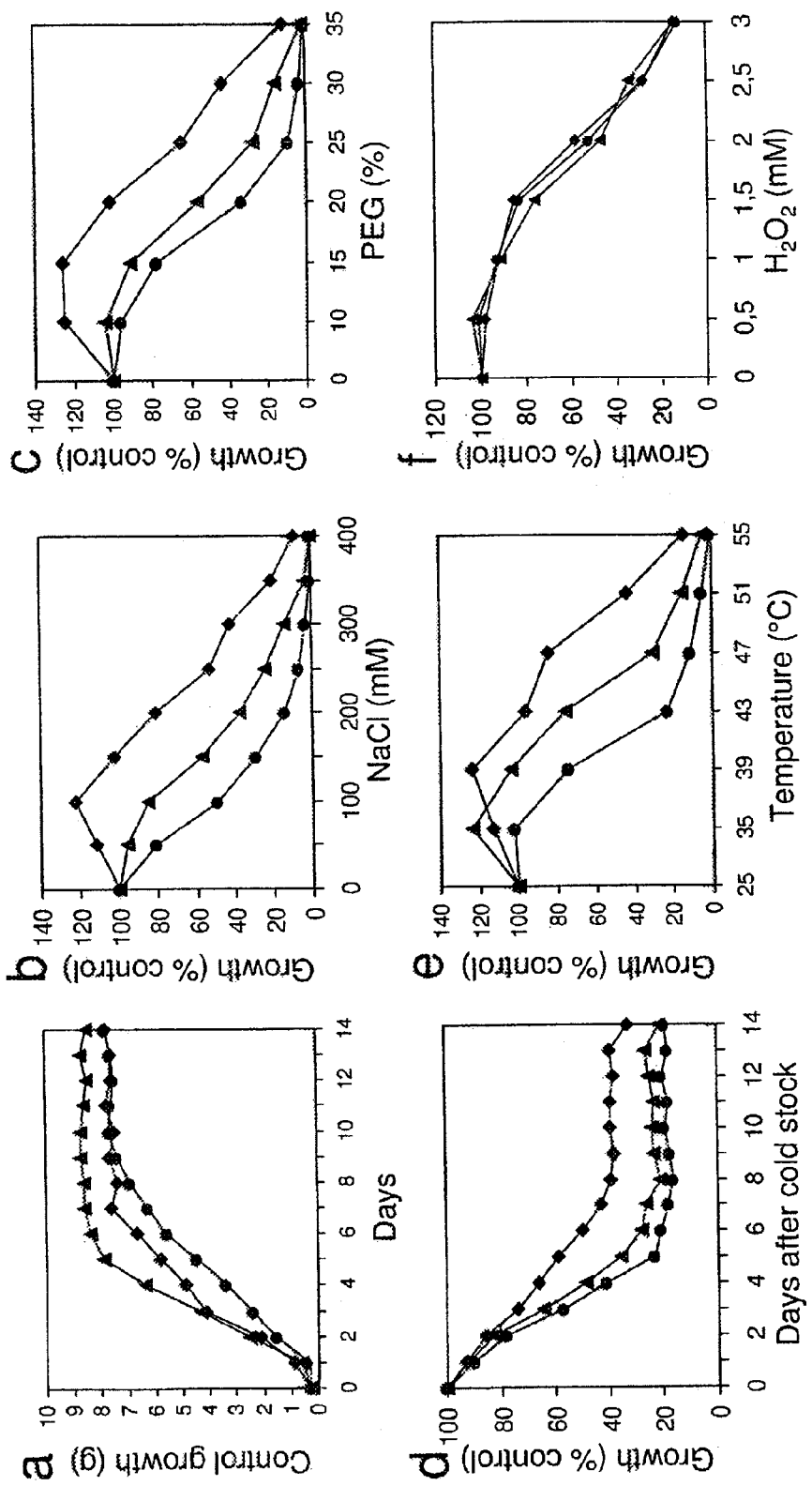

Transgenic plant cells overexpressing At-DBF2 were generated to test the role of this protein in stress tolerance in planta. Tobacco BY2 cells were stably transformed by A. tumefaciens carrying the At-DBF2 cDNA driven by the strong constitutive CaMV 35S RNA promoter. The antisense At-DBF2 RNA also was overexpressed under the control of the same promoter. Control lines were obtained by transforming tobacco BY2 cells with pBIN-35S-CaMVter. Three independently obtained At-DBF2-overexpressing tobacco transgenic cell lines have been selected with a high and similar At-DBF2 expression and analysed further. Three tobacco transgenic cell lines overexpressing antisense At-DBF2 were chosen that showed an undetectable tobacco DBF2 transcript level. Both the overexpression of At-DBF2 and the down-regulation of the endogenous gene by the antisense strategy did not result in significant differences in growth after 2 weeks (FIGS. 12A and 12B). On the contrary, marked differences in growth were observed after a 2-week treatment with NaCl, PEG-induced drought, cold, or high temperatures. Transgenic lines that overexpressed At-DBF2 were clearly more tolerant than control lines. Inhibition of the endogenous DBF2 expression was correlated with a higher sensitivity to those stresses. To understand the basis of stress tolerance in At-DBF2-overexpressing plant cells, expression of stress-induced genes was followed in control and stress conditions (FIG. 12C). Tobacco kin1 and HSP17.6A homologues already were induced in At-DBF2-overexpressing tobacco cells in control conditions to a level similar to that observed during stress conditions (PEG-induced drought), suggesting that At-DBF2 overexpression may mimic a stress signal.

Example 9

Arabidopsis Transformation and Recombinant T-DNA Vector Construction With Genes Conferring Tolerance to Environmental Stress Arabidopsis were stably transformed as described in Clarke, Wei and Lindsey (1992) by Agrobacterium tumefaciens C58C1RifR (pGV2260) strains carrying pBIN-35S-At-DBF2, pBIN-35S-At-HSP17.6A, pBIN-35S-At-c74 recombinant binary vectors. pBIN-35S-At-DBF2 is described in Lee et al. 1999. pBIN-35S-At-HSP17.6A recombinant binary vector was constructed as following: the EcoRI-XhoI fragment containing At-HSP17.6A cDNA in pYX-HSP17.6A (recombinant pYX212) was first cloned in pYES2 (Invitrogen) resulting in pYES-HSP17.6A. Than the BamHI-SphI fragment of pYES-HSP17.6A containing the At-HSP17.6A cDNA was cloned in the plant binary vector pBIN m-gfp4 in which the BamHI-SacI fragment containing the gfp receptor gene was deleted and replaced by the At-HSP17.6A cDNA. The 3' protruding ends generated by SacI and SphI were blunt ended by T4 DNA polymerase. pBIN-35S-c74 was constructed with a similar strategy as pBIN-35S-AtHSP17.6A with an intermediary pYES-Atc74 vector. The At-c74 cDNA was first amplified with PCR using the primers 5' AAA AAA CAC ATA CAG GAA TTC 3' (SEQ ID NO 122) and 5' AGT TAG CTA GCT GAG CTC GAG 3' (SEQ ID NO 123), then cloned "blunt ended" in the vector pYES2 cut with NotI and BstXI and blunt ended with T4 DNA polymerase. Subsequently, the BamHI-SphI fragment of pYES-c74 was cloned in pBINm-gfp4 as explained supra.

Example 10

Tolerance to Environmental Stress in Plant Cells

Transgenic calli were isolated from each of the transgenic Arabidopsis lines transformed with At-DBF2, At-HSP17.6A and At-c74. The growth of these transgenic calli during salt stress was measured and compared with control calli derived from transgenic Arabidopsis lines transformed with pBIN-35S-CaMVter. Callus pieces (25 for each transgenic line) of similar fresh weight (50 to 100 mg) were therefor grown on callus inducing medium (Clarke et al., 1992) supplemented with 200 mM NaCl. After two weeks, from visual inspection, it was clear that transgenic calli transformed with At-DBF2 or At-HSP17.6A or At-c74 looked much better than control transgenic calli transformed with pBIN-35S-CaMVter. The latter calli turned yellow and started dying. To confirm the observation, the fresh weight of the calli was measured. In comparison with the control transgenic calli, the fresh weight of the transgenic calli was for each of the three lines at least five times higher than the fresh weight of the control trangenic calli.

Example 11

Tolerance to Environmental Stress in Plants

Figure 6:
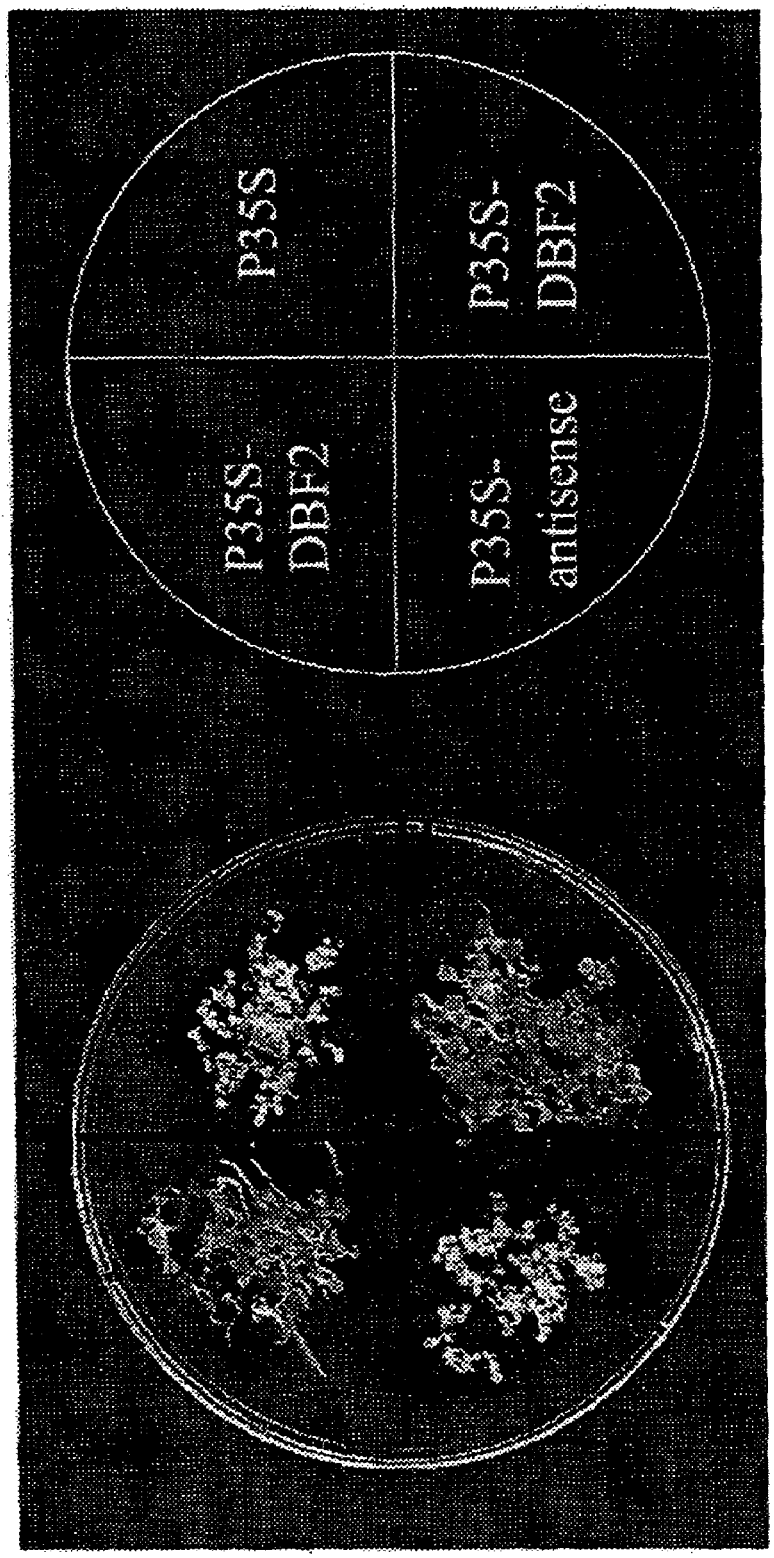

Seeds from transgenic Arabidopsis plants tranformed with pBIN-35S-At-DBF2, p-BIN-35S-At-c74, or pBIN- 35S-At-HSP17.6A, were sown in bulk on nylon filters (as described in Verbruggen et al. 1993) placed on solid K1 medium supplemented with kanamycin (75 micrograms/ml). For each recombinant pBIN binary vector at least five independent transgenic lines were tested for stress tolerance. In each of these lines overexpression of the transgene has been confirmed with Northern hybridisation experiments. Control plants were the ones transformed with pBIN-35S-CaMVter and transgenic plants transformed with pBIN-35S-AS+At-DBF2. After sowing, seeds were kept overnight at 4 degrees (to enhance germination). Growth was at 22 degrees, 60% humidity, 16 hours light/8 hours dark, 70 microeinsteins. After 9 days growth, filters were transferred to liquid K1 medium supplemented with 200 mM NaCl for overnight incubation. Plants were allowed to recover for 5 to 6 days by transferring the filters to solid K1 medium. Under these conditions, the control transgenic plants turned yellow, their growth was inhibited and eventually they died. On the contrary, the transgenic lines transformed with At-DBF2 or At-HSP17.6A or At-c74 survived very well (FIG. 6 and FIG. 11).

Figure 7:
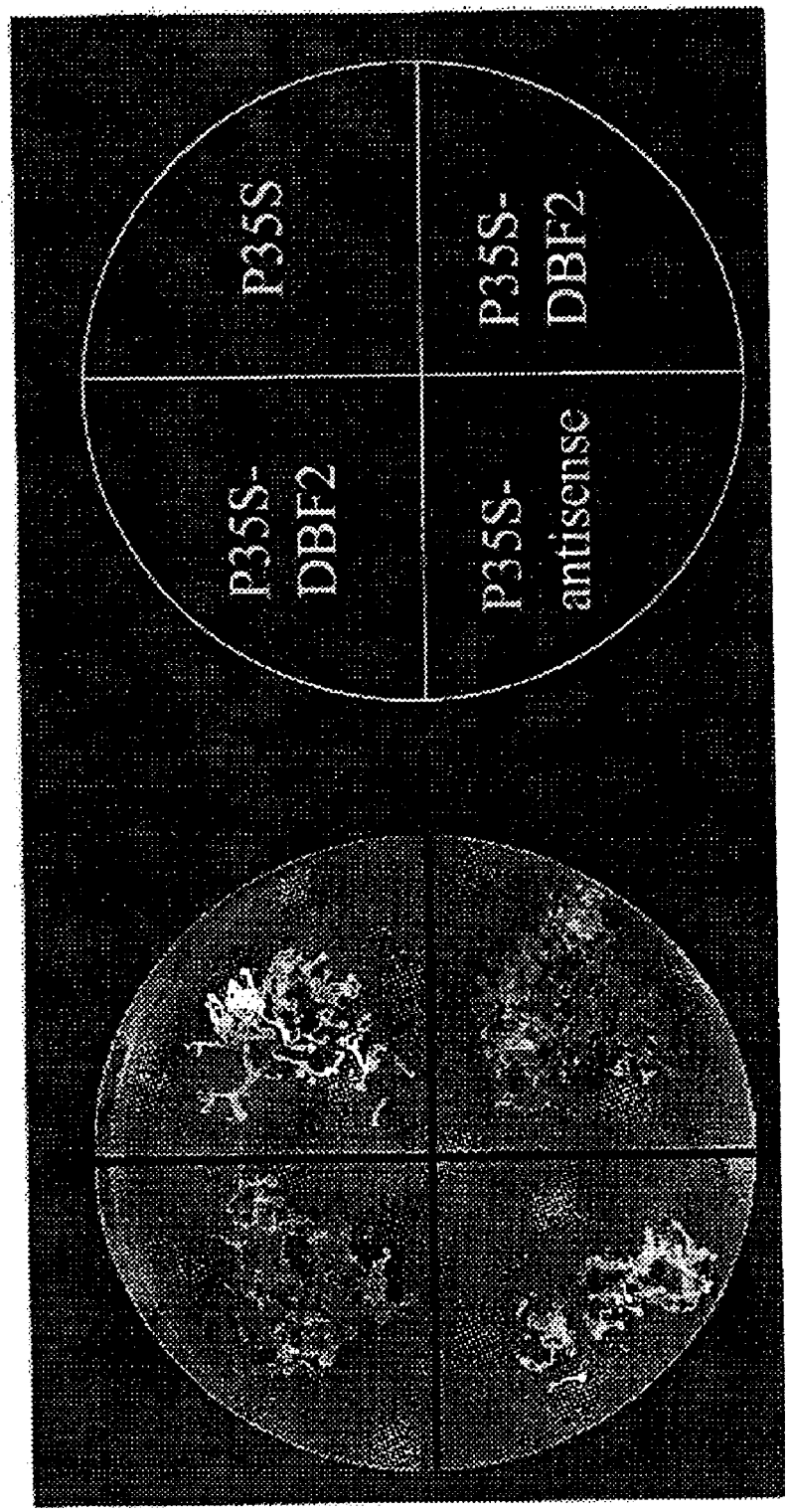
FIG. 7 shows the results of a comparison of the growth of *A. thaliana* plants transformed with the following constructs: P35S-At-DBF2 (upper left and bottom right section), P35S control (upper right section) and P35S-antisense At-DBF2 (bottom left section) upon applying an osmotic stress induced by 20% PEG overnight.

To further evaluate the scope of protection to environmental stress, transgenic plants were exposed to osmotic stress. Therefor seeds from transgenic *Arabidopsis* plants transformed with pBIN-35S-At-DBF2, pBIN-35S-At-c74 or pBIN-35S-At-HSP17.6A were sown in bulk on nylon filters (as described in Verbruggen et al. 1993) placed on solid K1 medium supplemented with kanamycin (75 micrograms/ml). For each recombinant pBIN binary vector at least five independent transgenic lines were tested for stress tolerance. In each of these lines overexpression of the transgene has been confirmed with Northern hybridisation experiments. Control plants were the ones transformed with pBIN-35S-CaMVter and transgenic plants transformed with pBIN-35S-ASAt-DBF2. After sowing, seeds were kept overnight at 4 degrees (to enhance germination). Growth was at 22 degrees, 60% humidity, 16 hours light/8 hours dark, 70 microeinsteins. After 9 days growth, filters were transferred to liquid K1 medium supplemented with 20% polyethylene glycol for overnight incubation. Plants were allowed to recover for 5 to 6 days by transferring the filters to solid K1 medium. Under these conditions, the control transgenic plants turned yellow, their growth was inhibited and eventually they died. On the contrary, the transgenic lines transformed with At-DBF2, At-HSP17.6A or At-c74 survived very well (see FIGS. 7 and 13). Their growth was comparable to growth on control medium without polyethylene glycol.

To further analyse the scope of protection to environmental stress, transgenic plants were exposed to high and low temperatures. Therefor seeds from transgenic plants transformed with pBIN-35S-At-DBF2 or pBIN-35S-At-c74 were sown in bulk on nylon filters (as described in Verbruggen et al. 1993) placed on solid K1 medium supplemented with kanamycin (75 micrograms/ml). For each recombinant pBIN binary vector at least five independent transgenic lines were tested for stress tolerance. In each of these lines overexpression of the transgene has been confirmed with Northern hybridisation experiments. Control plants were the ones transformed with pBIN-35S-CaMVter and transgenic plants transformed with pBIN-35S-ASAt-DBF2. After sowing, seeds were kept overnight at 4 degrees (to enhance germination). Growth was at 22 degrees, 60% humidity, 16 hours light/8 hours dark, 70 microeinsteins. After 9 days growth, for the experiments with high temperature stress, plants were exposed to 48° C. for two hours. For the experiments with low temperature stress, plants were exposed to gradually decreasing temperatures, down to -7° C. Plants were allowed to recover for 5 to 6 days by transferring the filters to solid K1 medium.

Figure 8:
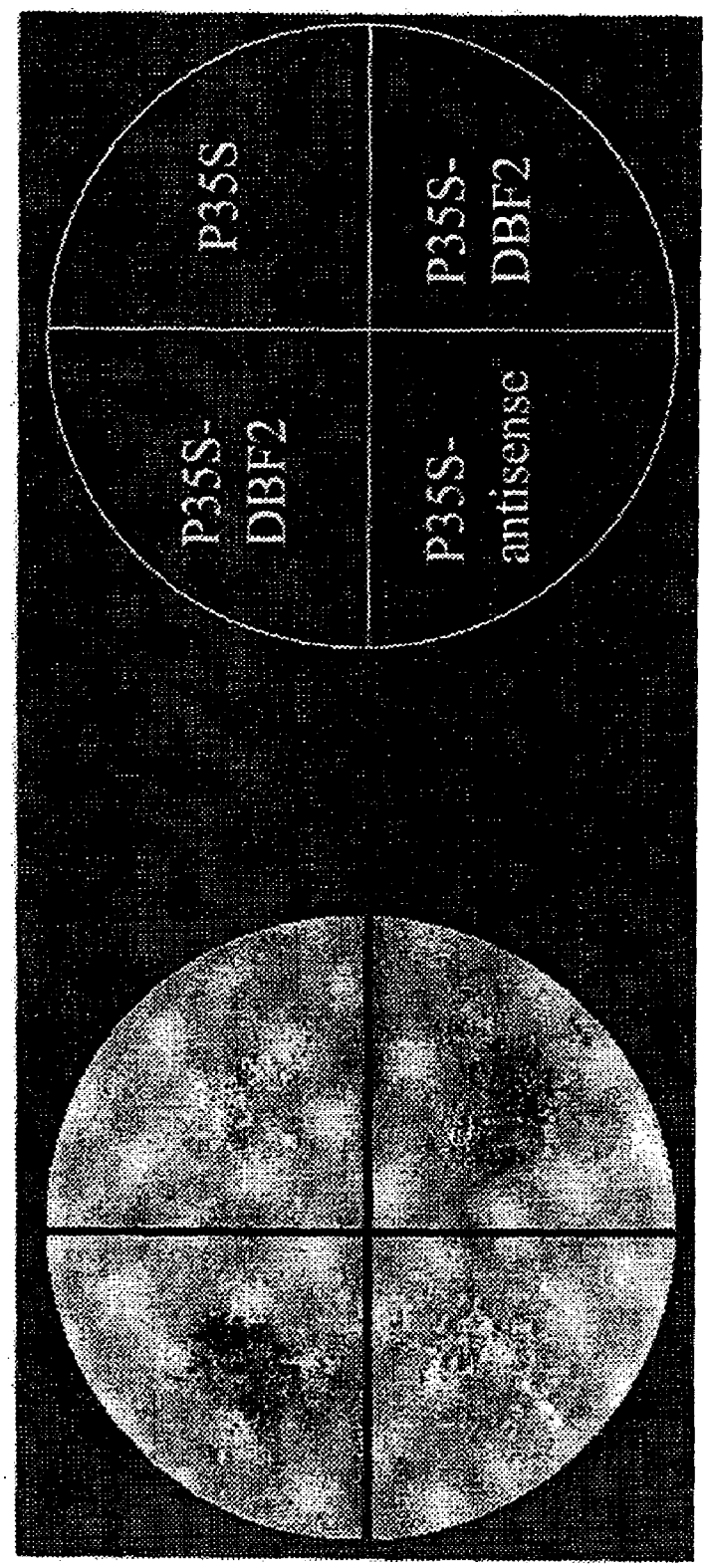
FIG. 8 shows the results of a comparison of the growth of *A. thaliana* plants transformed with the following constructs: P35S-At-DBF2 (upper left and bottom right section), P35S control (upper right section) and P35S-antisense At-DBF2 (bottom left section) upon applying a cold stress by gradually decreasing the temperature untill –7° C.
Figure 9:
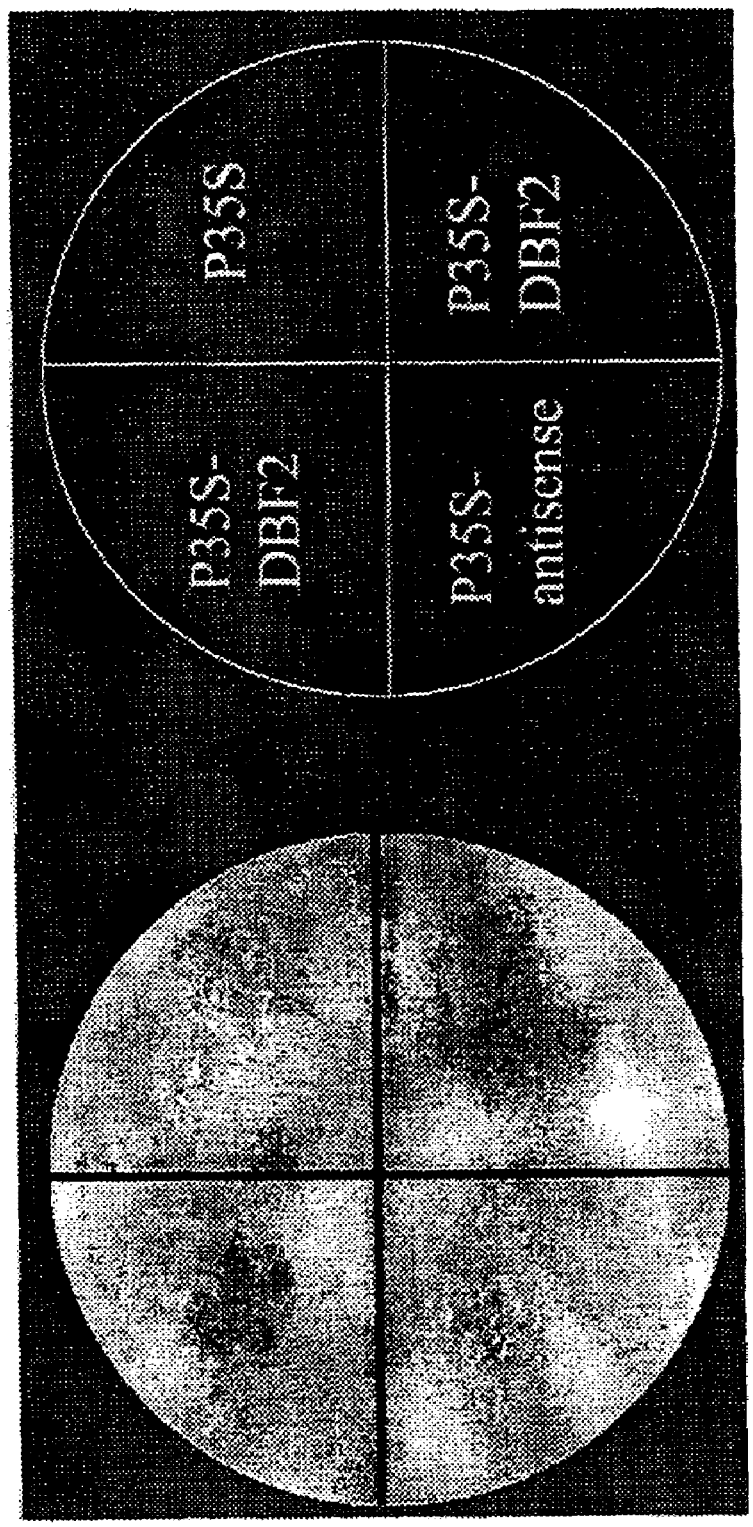
FIG. 9 shows the results of a comparison of the growth of *A. thaliana* plants transformed with the following constructs: P35S-At-DBF2 (upper left and bottom right section), P35S control (upper right section) and P35S-antisense At-DBF2 (bottom left section) upon applying a heat stress of 2 hours at 48° C.

Under both low temperature and high temperature stress, the growth of control transgenic plants was inhibited and eventually they died. The transgenic lines transformed with At-DBF2 or At-c74 survived very well. Their growth was comparable to growth under control conditions with normal temperature (see FIGS. 8 and 9).

To further analyse the scope of protection to environmental stress, transgenic plants were exposed to salt stress during germination. Sterilized mature seeds from transgenic plants transformed with pBIN-35S-At-DBF2 or pBIN-35S-At-c74 were placed on top of petri dishes containing MS (Murashige and Skoog) medium with 0.8% agar and 30 g $l^{-1}$ sucrose. Control plants were the ones transformed with pBIN-35S-CaMVter. Prior to germination and pH 5.7 adjustment, NaCl was added to a final concentration of 125 mM. Three petri dishes with a mean of 40-50 seeds per dish were used per treatment in every experiment. The complete experiment was repeated twice. Seed germination at 22° C. was followed. Seeds were considered to germinate after radical and green cotyledon emergency occurred.

On control medium (without 125 mM NaCl), germination of all transgenic lines was very similar to each other and to wild type plants. On medium supplemented with 125 mM NaCl, seeds from transgenic lines overexpressing At-DBF2 or At-c74 germinate significantly better than control transgenic lines. Less than 10% of the seeds from transgenic lines transformed with pBIN-35S-CaMVter germinate under these conditions. In contrast, more than 70% of the seeds from trangenic lines overexpressing At-DBF2 or At-c74 germinate on medium containing 125 mM NaCl (FIG. 14).

Example 12

Southern Hybridisation of At-DBF2 Genes in Other Plants

To investigate whether DBF2 homologues exist in other plant species, a Southern hybridisation analysis was performed using the full length At-DBF2 as a probe. Genomic DNA was extracted from tobacco, tomato and rice according to Dellaporta et al. (1983) and further purified by phenol:chloroform extractions. DNA (10 μg) was digested with restriction enzymes and separated on 1% (w/v) agarose gels using Lambda DNA digested with Hind III as molecular size standards. The DNA was transformed on to nylon membranes (Hybond N; Amersham, little Chalfont, UK) in 0.4 N NaOH. Filters were UV-cross-linked for 30 seconds, prehybridized for 3 hours at 56° C. in hybridization solution (2× SSPE, 0.1% (w/v) SDS, 5× Denhardt solution) using 200 gm$^{-3}$ denatured salmon sperm DNA, and hybridized overnight with radiolabelled probes. 1× SSPE was 0.15 M NaCl/0.01 M sodium dihydrogen phosphate/1 mM EDTA Filters were washed at 56° C. in 2× SSPE, 0.1% (w/v) SDS for 20 min, then 1× SSPE, 0.1% (w/v) SDS for 20 min, and finally in 0.1× SSPE, 0.1% (w/v) SDS for 20 min. Filters were exposed to X-ray film (Kodak X-AR; Kodak, N.Y., USA) in the presence of intensifying screens for 24 hours.

The results of the hybridisation experiments show that tobacco, tomato and rice have at least one homologue to At-DBF2.

TABEL 1

| puntative function in | Features of encoded protein | SEQ ID NO. | Growth on medium with 1.2 M NaCl | growth on medium with 2.0 M sorbitol |
|---|---|---|---|---|
| signalling | Similar to a yeast DBF2 cell cycle protein | 1 | ++++ | ++++ |
| metabolism | HSP17.6A | 3 | ++++ | ++++ |
| unknown | C74 | 5 | +++ | +++ |
| metabolism | Similar to ADH2 | 7 | + | ++++ |
| metabolism | Similar to *D. melanogaster* catalase/catalase 3 | 9 | ++++ | + |
| metabolism | Similar to the HSP90 heat shock protein family | 11 | ++++ | ++++ |
| metabolism | similar to phosphoenolpyruvate carboxylase | 13 | + | +++ |
| metabolism | pathogen related proteins, class 10 | 15 | + | ++++ |
| metabolism | Arabidopsis ascorbate peroxidase | 17 | ++++ | ++++ |
| metabolism | similar to phosphatase binding protein | 19 | ++++ | ++++ |
| metabolism | similar to phosphatase binding protein | 21 | ++++ | ++++ |
| metabolism | similar to retinol dehydrogenase | 23 | +++ | ++++ |
| metabolism | similar to retinol dehydrogenase | 25 | ++++ | ++++ |
| metabolism | ribosomal protein | 27 | ++++ | ++++ |
| metabolism | ribosomal protein | 29 | ++++ | ++++ |
| metabolism | similar to a protein transporter (kinase homolog) | 31 | ++++ | ++++ |
| metabolism | similar to a peptide transporter | 33 | ++++ | + |
| metabolism | similar to a wheat low affinity cation transporter LCT1 | 35 | ++++ | ++++ |
| metabolism | similar to yeast iso-1-cytochrome c (CYC-1) | 37 | ++++ | ++++ |
| metabolism | similar to yeast OSM1 | 39 | ++++ | ++++ |
| metabolism | similar to yeast copper uptake gene (CUP1) | 41 | ++++ | +++ |
| metabolism | similar to yeast UV-induced damage repair protein (RAD7) | 43 | ++++ | ++++ |
| metabolism | electron transporter, apocytochrome b | 45 | ++++ | ++++ |
| metabolism | similar to membrane lipoprotein LPPL1 | 47 | ++++ | ++++ |
| metabolism | similar to tobacco auxin binding protein | 49 | + | ++++ |
| metabolism | similar to tobacco cytokinin binding protein CBP 57 | 51 | +++ | ++++ |
| signalling | similar to calcium binding protein yeast calcineurin B | 53 | +++ | ++++ |
| signalling | similar to calcium binding protein glycine max calnexin | 55 | ++++ | +++ |
| signalling | similar to calcium binding protein *Dictyostelium discoideum calreticulin* | 57 | ++++ | ++++ |
| signalling | similar to calcium binding protein calmodulin 1 | 59 | ++++ | + |
| signalling | similar to calcium binding protein calmodulin 2 | 61 | + | ++++ |
| signalling | MAP kinase kinase, homologous to Dyctyostelium mekA (DdMek1) | 63 | ++++ | +++ |
| signalling | similar to human adenosine kinase | 65 | + | ++++ |
| signalling | similar to human tyrosine kinase | 67 | ++++ | ++++ |

TABEL 1-continued

| puntative function in | Features of encoded protein | SEQ ID NO. | Growth on medium with 1.2 M NaCl | growth on medium with 2.0 M sorbitol |
|---|---|---|---|---|
| signalling | similar to common ice plant tyrosine kinase | 69 | ++++ | ++++ |
| signalling | similar to the yeast protein kinase C receptor | 71 | ++++ | ++++ |
| signalling | similar to tobacco and Arabidopsis HAT7 homeotic protein | 73 | ++ | ++++ |
| signalling | similar to *E. coli* sigma factor regulator (RSEB) | 75 | + | ++++ |
| signalling | similar to human protein phosphatase 2C | 77 | ++++ | ++++ |
| metabolism | late embryogenesis abundant proteins, Arabidopsis LEA protein 10 & 14 | 79 | ++ | ++++ |
| metabolism | late embryogenesis abundant proteins, Arabidopsis LEA protein 10 & 14 | 81 | ++ | ++++ |
| metabolism | pathogen related proteins, class 10 | 83 | ++++ | ++++ |
| metabolism | cell wall peroxidase | 85 | ++++ | +++ |
| metabolism | ribosomal protein | 87 | +++ | ++++ |
| metabolism | salt stress induced protein, SAS 1 | 89 | ++++ | ++++ |
| metabolism | PR gene (AIG2) | 91 | ++++ | ++++ |
| metabolism | MT1c | 93 | ++++ | ++++ |
| metabolism | IPP2 (Isopentenyl diphosphate) | 95 | +++ | ++++ |
| metabolism | chlorophyll a/b binding protein | 97 | +++ | +++ |
| metabolism | glutathione transferase | 99 | ++ | ++++ |
| signalling | cold- and ABA inducible, calcium dependent - kinase, Kin1 | 101 | ++++ | ++++ |
| signalling | MAP kinase, Atmpkl | 103 | ++ | ++++ |
| signalling | Arabidopsis cell cycle protein histone H2A | 105 | ++++ | ++++ |
| unknown | chromosome 4 - sequence | 107 | +++ | ++++ |
| unknown | chromosome 4 - sequence | 109 | + | ++++ |
| unknown | chromosome 5 - sequence | 111 | ++++ | +++ |
| unknown | chromosome 5 - sequence | 113 | ++++ | ++ |
| unknown | chromosome 5 - sequence | 115 | ++++ | ++++ |
| unknown | chromosome 5 - sequence | 117 | + | ++++ |
| unknown | chromosome 5 - sequence | 119 | + | ++++ |
| signalling | similar to calcium binding protein centrin (caltractin) | 121 | ++++ | ++++ |

TABLE 2

EXEMPLARY PLANT-EXPRESSIBLE PROMOTERS FOR USE IN THE PERFORMANCE OF THE PRESENT INVENTION

| GENE SOURCE | EXPRESSION PATTERN | REFERENCE |
|---|---|---|
| α-amylase (Amy32b) | Aleurone | Lanahan et al (1992); Skriver et al. (1991) |
| cathepsin β-like gene | Aleurone | Cejudo et al. (1992) |
| *Agrobacterium rhizogenes* rolB | Cambium | Nilsson et al. (1997) |
| PRP genes | cell wall | http://salus.medium.edu/mmg/tierney/html |
| barley ltr1 promoter | Endosperm | |
| synthetic promoter | Endosperm | Vicente-Carbajosa et al. (1998) |
| AtPRP4 | Flowers | http://salus.medium.edu/mmg/tierney/html |
| chalene synthase (chsA) | Flowers | van der Meer et al. 1990 |
| apetala-3 | Flowers | |
| Chitinase | fruit (berries, grapes, etc) | Thomas et al. CSIRO Plant Industry, Urrbrae, South Australia, Australia; |

TABLE 2-continued

EXEMPLARY PLANT-EXPRESSIBLE PROMOTERS FOR USE IN THE PERFORMANCE OF THE PRESENT INVENTION

| GENE SOURCE | EXPRESSION PATTERN | REFERENCE |
|---|---|---|
| rbcs-3A | green tissue (eg leaf) | http://winetitles.com.au/gwrdc/csh95-1.html Larn et al. (1990); Tucker et al. (1992) |
| leaf-specific genes | Leaf | Baszczynski et al. (1988) |
| AtPRP4 | Leaf | http://salus.medium.edu/mmg/tierney/html |
| Pinus cab-6 | Leaf | Yamamoto et al. (1994) |
| SAM22 | Senescent leaf | Crowell et al. (1992) |
| *R. japonicum* nif gene | Nodule | U.S. Pat. No. 4,803,165 |
| *B. japonicum* nifH gene | Nodule | U.S. Pat. No. 5,008,194 |
| GmENOD40 | Nodule | Yang et al. (1993) |
| PEP carboxylase (PEPC) | Nodule | Pathirana et al. (1992) |
| Leghaemoglobin (Lb) | Nodule | Gordon et al. (1993) |
| *Tungro bacilliform* virus gene | Phloem | Bhattacharyya-Pakrasi et al. (1992) |
| sucrose-binding protein gene | plasma membrane | Grimes et al. (1992) |
| pollen-specific genes | pollen; microspore | Albani et al. (1990); Albani et al. (1991) |
| maize pollen-specific gene | Pollen | Hamilton et al. (1992) |
| sunflower pollen-expressed gene | Pollen | Baltz et al. (1992) |
| *B. napus* pollen-specific gene | pollen; anther; tapetum | Arnoldo et al. (1992) |
| root-expressible genes | Roots | Tingey et al. (1987); An et al. (1988); |
| tobacco auxin-inducible gene | root tip | Van der Zaal et al. (1991) |
| β-tubulin | Root | Oppenheimer et al. (1988) |
| Tobacco root-specific genes | Root | Conkling et al. (1990) |
| *B. napus* G1-3b gene | Root | U.S. Pat. No. 5,401,836 |
| SbPRP1 | Roots | Suzuki et al. (1993) |
| AtPRP1; AtPRP3 | roots; root hairs | http://salus.medium.edu/mmg/tierney/html |
| RD2 gene | root cortex | http://www2.cnsu.edu/ncsu/research |
| TobRB7 gene | root vasculature | http://www2.cnsu.edu/ncsu/research |
| AtPRP4 | leaves; flowers; lateral root primordia | http://salus.medium.edu/mmg/tierney/html |
| Seed-specific genes | Seed | Simon et al. (1985); Scofield et al. (1987); Baszczynski et al. (1990) |
| Brazil Nut albumin | seed | Pearson et al. (1992) |
| Legumin | Seed | Ellis et al. (1988) |
| Glutelin (rice) | Seed | Takaiwa et al. (1986); Takaiwa et al. |
| Zein | Seed | Matzke et al. (1990) |
| NapA | Seed | Stalberg et al. (1996) |
| Sunflower oleosin | seed (embryo and dry seed) | Cummins at al. (1992) |
| LEAFY | shoot meristem | Weigel et al. (1992) |
| *Arabidopsis thaliana* knat1 | shoot meristem | Accession number AJ131822 |
| *Malus domestica* kn1 | shoot meristem | Accession number Z71981 |
| CLAVATA 1 | shoot meristem | Accession number AF049870 |
| Stigma-specific genes | Stigma | Nasrallah et al. (1988); Trick et al. (1990) |
| Class I patatin gene | Tuber | Liu et al. (1991) |
| Blz2 | Endosperm | EP99106056.7 |
| PCNA rice | Meristem | Kosugi et al (1991); Kosugi and Ohashi (1997) |

TABLE 3

Stress inducible promoters

| Name | Stress | Reference |
|---|---|---|
| P5CS (delta(1)-pyrroline-5-carboxylate syntase) | salt, water | Zhang et al; Plant Science. Oct 28 1997; 129(1): 81-89 |
| cor15a | Cold | Hajela et al., Plant Physiol. 93: 1246-1252 (1990) |
| cor15b | Cold | Wilhelm et al., Plant Mol Biol. 1993 Dec; 23(5): 1073-7 |
| cor15a (−305 to +78 nt) | cold, drought | Baker et al., Plant Mol Biol. 1994 Mar; 24(5): 701-13 |
| rd29 | salt, drought, cold | Kasuga et al., Nature Biotechnology, vol 18, 287-291, 1999 |
| heat shock proteins, including artifical promoters containing the heat shock element (HSE) | Heat | Barros et al., Plant Mol Biol, 19(4): 665-75, 1992. Marrs et al., Dev Genet., 14(1): 27-41, 1993. Schoffl et al., Mol Gen Gent, 217(2-3): 246-53, 1989. |
| smHSP (small heat shock proteins) | heat | Waters et al, J Experimental Botany, vol 47, 296, 325-338, 1996 |
| wcs120 | Cold | Quellet et al., FEBS Lett. 423, 324-328 (1998) |
| ci7 | Cold | Kirch et al., Plant Mol Biol, 33(5): 897-909, 1997 Mar |
| Adh | cold, drought, hypoxia | Dolferus et al., Plant Physiol, 105(4): 1075-87, 1994 Aug |
| pwsi18 | water: salt and drought | Joshee et al., Plant Cell Physiol, 39(1): 64-72, 1998, Jan |
| ci21A | Cold | Schneider et al., Plant Physiol, 113(2): 335-45, 1997 |
| Trg-31 | Drought | Chaudhary et al., Plant Mol Biol, 30(6): 1247-57, 1996 |
| Osmotin | Osmotic | Raghothama et al., Plant Mol Biol, 23(6): 1117-28, 1993 |

REFERENCES

Adams et al. (1983), J. Am. Chem. Soc. 105:661

Aerne et al. (1998). Molecular Biology of the Cell, vol 9, 945-956.

Bray et al. (1997), Plant responses to water deficit. Trends Plant Sci. 2, 48-54

Carruthers et al. (1982), Cold Spring Harbor Symp. Quant. Biol. 47:411-418

Capecchi (1989), Science 244:1288-1292

Deblaere et al. (1985), Efficient octopine Ti plasmid-derived vectors for *Agrobacterium*-mediated gene transfer to plants, Nucl. Acids Res. 13, 4777-4788.

De Greve et al. (1982), J. Mol. Appl. Genet. 1(6):499-511
Dellaporta et al. (1983), A plant DNA minipreparation, version II. Plant Mol. Biol. Rep. 1, 19-22
Evans et al. (1983), Protoplasts Isolation and Culture, Handbook of Plant Cell Culture, pp. 124-176
Fowden et al. (1993), Plant Adaptation to Environmental Stress; ISBN: 0412490005
Fraley et al. (1983), Proc. Natl. Acad. Sci USA 80:4803
Fromm et al. (1985), Proc. Natl. Acad. Sci. USA 82:5824
Gietz and Schietsl, (1995) Methods in Molecular and Cellular Biology, 5, 255-269.
Grillo et al (1996), Physical Stresses in Plants: Genes and Their Products for Tolerance. Springer Verlag; ISBN: 3540613471
Hanks et al. (1988). Science, 241, 42-52.
Hansen et al. (1999), Trends in plant science reviews, Vol 4, No 6, 226-231
Haring et al. (1991), Plant Mol. Biol. 16:449-469
Haro et al. (1991). FEBS Lett, 291, 189-191.
Haseloff et al. (1988), Nature 334;585-591
Hemmerlin and Bach (1998). Plant Journal 14 (1) 65-74
Johnston et al. (1990). Mol. and Cell Biol. 10, no 4,1358-1366
Herrera-Estrella (1983), Nature 303:209-213
Holmberg & Bülow (1998), Improving stress tolerance in plants by gene transfer. Trends Plant Sci. 3, 61-66
Horsch et al., 1984), Science 233:496-498
Hull and Howell (1987), Virology 86:482-493
Ingram et al. (1996), The molecular basis of dehydration tolerance in plants. Ann. Rev. Plant Physiol. Plant Mol. Biol. 47, 377-403
Innis et al. (1990), A guide to methods and applications, Academic Press, San Diego
Jones et al (1989), Plants Under Stress: Biochemistry, Physiology and Ecology and Their Application to Plant Improvement (Society for Experimental Biology Seminar Serie), Cambridge Univ. Pr. (Short); ISBN: 0521344239
Johnston et al. (1995)
Kasuga et al. (1999), Nature Biotechnology 17, 287-291
Klee et al. (1987), Ann. Rev. of Plant Phys. 38:467-486
Klein et al. (1987), Nature 327:70-73
Komamitsky et al. (1998). Mol. and Cell Biol. 18, no.4, 2100-2107
Lee et al (1999). Proc. Nat. Acad. Sci. USA 1996, 5873-5877
Meyer et al. (1987), Nature 330:677
Millward et al. (1995). Proc. Nat. Acad. Sci. USA, 92, 5022-5026.
Nagata et al. (1992). Int. Rev. Cytol., 132, 1-30
Napoli et al. (1990), The Plant Cell 2:279-289
Needleman and Wunsch (1970), Mol. Biol. 48:443
Nilsen et al (1996), The Physiology of Plants Under Stress; Abiotic Factors. ISBN: 047131526
Odell et al. (1985), Nature 313:482-493
Paszkowski et al. (1984), EMBO j. 3:2717-2722
Pearson and Lipman (1988), Proc. Natl. Acad. Sci. (USA) 85:2444
Peassarakli et al, Handbook of Plant and Crop Stress. ISBN: 0824789873
Raton (1985), Binding, Regeneration of Plants, Plant Protoplasts, pp. 21-73, CRC Press
Reicheld et al. (1995). Plant Journal 7 (2) 245-252
Sambrook (1989), Molecular cloning, a laboratory manual, Cold Spring Harbor Press, 7.52.
Shaul et al. (1996). PNAS 93,4868-4872
Shinozaki et al. (1996), Molecular responses to drought and cold stress, Curr. Opin. Biotechnol. 7, 161-167
Shinozaki et al. (1997), Gene expression and signal transduction in water-stress response. Plant Physiol. 115, 327-334
Shinozaki et al. (1999), Drought, Salt, Cold and Heat Stress: Molecular Responses in Higher Plants (Biotechnology Intelligence Unit); ISBN: 1570595631
Schuller et al. (1994). Embo Journal, 13, 4382-4389.
Smith and Waterman (1981), Adv. Appl. Math. 2:482
Tomashow (1994), *Arabidopsis*(eds Meyrowitz, E & Somerville, C, 807-834 (Cold Spring Harbor Laboratory Press, Cold Spring Harbor, N.Y., 1994)
Toyn and Johnston, (1994). Embo Journal, 13, 1103-1113.
Verbruggen et al. (1993). Plant Phys. 103, 771-781
Walbot (1992), Ann. Rev. Plant Mol. Biol. 43:49-82
Weising et al; (1988), Ann; Rev. Genet. 22;421-477
Stalker, Science 242 (1988), 419
Vaek, Plant Cell 5 (1987),159-169
Powell, Science 232 (1986), 738-743
Pappu, World Journal of Microbiology & Biotechnology 11 (1995), 426-437
Lawson, Phytopathology 86 (1996) 56 suppl.
Van Camp, Biotech. 12 (1994), 165-168
Oeller, Science 254 (1991), 437-439
Stark, Science 242 (1992), 419
Visser, Mol. Gen. Genet. 225 (1991), 289-296
Voelker, Science 257 (1992), 72-74
Poirer, Science 256 (1992), 520-523
Meyer, Nature 330 (1987), 667-678
Duering, Molecular Breeding 2 (1996), 297-305
Strittmatter, Bio/Technology 13 (1995), 1085-1089
Estruch, Nature Biotechnology 15 (1997), 137-141
An, et al., *Plant Physiol.* 88: 547, 1998.
Albani, et al., *Plant Mol. Biol.* 15: 605, 1990.
Albani, et al., *Plant Mol. Biol.* 16: 501, 1991.
Arnoldo, et al., *J. Cell. Biochem.*, Abstract No. Y101, 204, 1992.
Baltz, et al., *The Plant J.* 2:713-721, 1992.
Baszczynski, et al., *Nucl. Acid Res.* 16: 4732, 1988.
Baszczynski, et al., *Plant Mol. Biol.* 14: 633, 1990.
Bhattacharyya-Pakrasi, et al, *The Plant J.* 4:71-79, 1992.
Cejudo, F. J., et al. *Plant Molecular Biology* 20:849-856, 1992.
Conkling, et al., *Plant Physiol.* 93: 1203, 1990.
Crowell, et al., *Plant Mol. Biol.* 18: 459-466, 1992.
Cummins, et al., *Plant Mol. Biol.* 19: 873-876, 1992.
Ellis, et al., *Plant Mol. Biol.* 10: 203-214, 1988.
Gordon, et al., *J. Exp. Bot.* 44:1453-1465, 1993.
Grimes, et al., *The Plant Cell* 4:1561-1574, 1992.
Hamilton, et al., *Plant Mol. Biol.* 18: 211-218, 1992.
Kosugi et al, Upstream sequences of rice proliferating cell nuclear antigen (PCNA) gene mediate expression of PCNA-GUS chimeric gene in meristems of transgenic tobacco plants, *Nucleic Acids Research* 19:1571-1576, 1991.
Kosugi S. and Ohashi Y, PCF1 and PCF2 specifically bind to cis elements in the rice proliferating cell nuclear antigen gene, *Plant Cell* 9:1607-1619, 1997.
Lam, E. et al., *The Plant Cell* 2:857-866, 1990.
Lanahan, M. B., et al., *Plant Cell* 4:203-211, 1992.
Liu et al., *Plant Mol. Biol.* 153:386-395, 1991.
Matzke et al *Plant Mol Biol*, 14(3):323-32 1990
Nasrallah, et al., *Proc. Natl. Acad. Sci. USA* 85: 5551, 1988.
Nilsson et al., *Physiol. Plant.* 100:456-462, 1997
Oppenheimer, et al., *Gene* 63: 87, 1988.
Pathirana, et al., *Plant Mol.Biol.* 20: 437-450, 1992.
Pearson, et al., *Plant Mol. Biol.* 18: 235-245, 1992.
Scofield, et al., *J. Biol. Chem.* 262: 12202, 1987.

Simon, et al., *Plant Mol. Biol* 5: 191, 1985.
Stalberg, et al, *Planta* 199: 515-519, 1996.
Suzuki et al., *Plant Mol. Biol.* 21:109-119, 1993.
Skriver, K., et al. *Proc. Natl. Acad. Sci.* (USA) 88: 7266-7270, 1991.
Takaiwa, et al., *Mol. Gen. Genet.* 208: 15-22, 1986.
Takaiwa, et al., *FEBS Letts.* 221: 43-47, 1987.
Tingey, et al., *EMBO J.* 6: 1, 1987.
Trick, et al., *Plant Mol. Biol.* 15: 203, 1990.
Tucker et al., *Plant Physiol.* 113: 1303-1308, 1992.
Van der Meer, et al., *Plant Mol Biol.* 15, 95-109, 1990.
Van der Zaal, et al, *Plant Mol Biol* 16, 983, 1991.
Vicente-Carbajosa et al, *Plant J.* 13: 629-640, 1998.
Weigel et al., *Cell* 69:843-859, 1992.
Yamamoto et al., *Plant Cell Physiol.* 35:773-778, 1994.
Yang, et al., *The Plant J.* 3: 573-585.
Clarke et al. (1992), Plant Molecular Biology Reporter Volume 10(2), 178-189
Ausubel et al. (1994),
Zhu et al. (1997),
Zhang et al; Plant Science. Oct. 28, 1997; 129(1): 81-89
Hajela et al., Plant Physiol. 93: 1246-1252 (1990)
Wilhelm et al., Plant Mol. Biol. December 1993; 23(5): 1073-7
Baker et al., Plant Mol. Biol. March 1994; 24(5): 701-13
Kasuga et al., Nature Biotechnology, vol 18, 287-291, 1999
Barros et al., Plant Mol. Biol, 19(4): 665-75, 1992.
Marrs et al., Dev. Genet., 14(1): 27-41, 1993.
Schoffl et al., Mol. Gen. Gent., 217(2-3): 246-53, 1989.
Waters et al, J. Experimental Botany, vol 47, 296, 325-338, 1996
Ouellet et al., FEBS Lett. 423, 324-328 (1998)
Kirch et al., Plant Mol. Biol., 33(5): 897-909, 1997
Dolferus et al., Plant Physiol., 105(4): 1075-87, 1994
Joshee et al., Plant Cell Physiol., 39(1): 64-72, 1998
Schneider et al., Plant Physiol., 113(2): 335-45, 1997
Chaudhary et al., Plant Mol Biol., 30(6): 1247-57, 1996
Raghothama et al., Plant Mol Biol., 23(6): 1117-28, 1993
Valvekens et al. (1988)
Porta et al. (1996), Mol Biol, 5(3):209-21

The invention claimed is:

1. A method for producing a plant with enhanced tolerance or resistance to osmotic stress or salt stress, said method comprising:

(a) transiently introducing into a plant cell a recombinant DNA comprising a polynucleic acid which is expressed in an amount effective to confer enhanced tolerance or resistance to osmotic stress or salt stress, wherein the polynucleic acid is selected from the group consisting of:

(i) a polynucleic acid of SEQ ID NO: 73 or the complementary strand thereof;

(ii) a polynucleic acid which is 95% identical to the polynucleic acid of SEQ ID NO: 73, wherein said polynucleic acid encodes a homeotic protein capable of conferring to a plant enhanced tolerance or resistance to osmotic stress or salt stress; or (iii) a polynucleic acid which comprises a sequence which is degenerate as a result of the genetic code to the sequence of the polynucleic acid of SEQ ID NO: 73; and (b) culturing the plant cell to regenerate a plant, thereby producing a plant with enhanced tolerance or resistance to osmotic stress or salt stress.

2. A method for producing a plant with enhanced tolerance or resistance to osmotic stress or salt stress, said method comprising stably introducing into a plant cell a recombinant DNA comprising a polynucleic acid which is expressed in an amount effective to confer enhanced tolerance or resistance to osmotic stress or salt stress, wherein the polynucleic acid is selected from the group consisting of:

(i) a polynucleic acid of SEQ ID NO: 73 or the complementary strand thereof;

(ii) a polynucleic acid which is 95% identical to the polynucleic acid of SEQ ID NO: 73, wherein said polynucleic acid encodes a homeotic protein capable of conferring to a plant enhanced tolerance or resistance to osmotic stress or salt stress; or (iii) a polynucleic acid which comprises a sequence which is degenerate as a result of the genetic code to the sequence of the polynucleic acid of SEQ ID NO: 73; and (b) culturing the plant cell to regenerate a plant, thereby producing a plant with enhanced tolerance or resistance to osmotic stress or salt stress.

3. The method of claim 1 or 2, comprising introducing into the genome of a plant cell one or more recombinant DNA molecules, said recombinant DNA molecules comprising: a plant expressible promoter and a polynucleic acid selected from the group consisting of:

(i) a polynucleic acid of SEQ ID NO: 73 or the complementary strand thereof;

(ii) a polynucleic acid which is 95% identical to the polynucleic acid of SEQ ID NO: 73, wherein said polynucleic acid encodes a homeotic protein capable of conferring to a plant enhanced tolerance or resistance to osmotic stress or salt stress; or (iii) a polynucleic acid which comprises a sequence which is degenerate as a result of the genetic code to the sequence of the polynucleic acid of SEQ ID NO: 73;

whereby said polynucleic acid is in the same transcriptional unit and under the control of said plant-expressible promoter.

4. A method for producing a transgenic plant, said method comprising:

(a) transiently introducing into a plant cell a recombinant DNA comprising a polynucleic acid and a plant expressible promoter, wherein the polynucleic acid is in the same transcriptional unit and under the control of the plant-expressible promoter, and wherein the polynucleic acid is selected from the group consisting of:

(i) a polynucleic acid of SEQ ID NO: 73 or the complementary strand thereof;

(ii) a polynucleic acid which is 95% identical to the polynucleic acid of SEQ ID NO: 73, wherein said polynucleic acid encodes a homeotic protein capable of conferring to a plant enhanced tolerance or resistance to osmotic stress or salt stress; or (iii) a polynucleic acid which comprises a sequence which is degenerate as a result of the genetic code to the sequence of the polynucleic acid of SEQ ID NO: 73; and (b) culturing the plant cell to regenerate a plant, thereby producing a transgenic plant.

5. The method of claim 3, wherein the plant expressible promoter is a constitutive promoter.

6. The method of claim 3, wherein the plant expressible promoter is a stress-inducible or organ- or tissue-specific promoter.

7. The method of claim 3, wherein the plant expressible promoter is the 35S promoter of CaMV.

8. The method of claim 4, wherein the plant expressible promoter is a constitutive promoter.

9. The method of claim 4, wherein the plant expressible promoter is a stress-inducible or organ- or tissue-specific promoter.

10. The method of claim 4, wherein the plant expressible promoter is the 35S promoter of CaMV.

* * * * *